United States Patent
Shen et al.

(10) Patent No.: US 10,072,271 B2
(45) Date of Patent: Sep. 11, 2018

(54) METHODS FOR IMPROVING CROP YIELD

(71) Applicant: HANGZHOU RUIFENG BIOTECHNOLOGY LIMITED INC., Hangzhou (CN)

(72) Inventors: Zhicheng Shen, Hangzhou (CN); Xianwen Zhang, Hangzhou (CN); Dongfang Wang, Hangzhou (CN); Jianhua Gao, Hangzhou (CN)

(73) Assignee: HANGZHOU RUIFENG BIOTECHNOLOGY LIMITED INC., Hangzhou, Zhejiang Province (CN)

( * ) Notice: Subject to any disclaimer, the term of this patent is extended or adjusted under 35 U.S.C. 154(b) by 167 days.

(21) Appl. No.: 14/367,450

(22) PCT Filed: Dec. 20, 2012

(86) PCT No.: PCT/CN2012/087069
§ 371 (c)(1),
(2) Date: Jun. 20, 2014

(87) PCT Pub. No.: WO2013/091563
PCT Pub. Date: Jun. 27, 2013

(65) Prior Publication Data
US 2016/0010100 A1    Jan. 14, 2016

(30) Foreign Application Priority Data
Dec. 23, 2011 (CN) .......................... 2011 1 0437868

(51) Int. Cl.
*A01H 5/00*    (2018.01)
*C12N 15/82*    (2006.01)
*C07K 14/415*    (2006.01)

(52) U.S. Cl.
CPC ........ *C12N 15/8261* (2013.01); *C07K 14/415* (2013.01)

(58) Field of Classification Search
None
See application file for complete search history.

(56) References Cited

U.S. PATENT DOCUMENTS 6,265,638 B1 * 7/2001 Bidney .............. C12N 15/8205
435/252.2
7,071,380 B1    7/2006 Lough et al.
2004/0123343 A1 * 6/2004 La Rosa .............. C07K 14/415
800/278
2004/0216190 A1    10/2004 Kovalic
2007/0039067 A1    2/2007 Feldmann et al.
2007/0044171 A1    2/2007 Kovalic et al.

FOREIGN PATENT DOCUMENTS

WO    WO 2010/086221 A1    8/2010
WO    WO 2010086221 A1 *  8/2010 ........... C07K 14/415

OTHER PUBLICATIONS

Doerks et al., (TIG, 14:248-250, 1998).*
Smith et al. (Nature Biotechnology, 15:1222-1223, 1997).*
Bork et al. (TIG, 12:425-427, 1996).*
Wells, Biochemistry 29:8509-8517, 1990.*
Ngo et al., (The Protein Folding Problem and Tertiary Structure Prediction, K. Merz., and S. Le Grand (eds.) pp. 492-495,1994).*
Keskin et al. (Protein Science, 13:1043-1055, 2004).*
Thornton et al. (Nature structural Biology, structural genomics supplement, Nov. 2000).*
Anderson et al., Plant Molecular Biology; 54:653-670, 2004.*
Kawakatsu et al. (Plant Cell, 18:612-625, 2006).*
Xiong et al. (Cell Research, 16:267-276, 2006).*
Paquet et al. (Journal of Experimental Botany, 56:1605-1614, 2005).*

* cited by examiner

*Primary Examiner* — Vinod Kumar
(74) *Attorney, Agent, or Firm* — Womble Bond Dickinson (US) LLP

(57) ABSTRACT

Compositions and methods for increasing plant growth and yield are provided. Compositions comprise the high yield gene TEL, promoters and enhancers to increase the expression of a TEL gene in a plant of interest. By enhancing the expression of at least one TEL gene in a plant, an improvement in plant growth and yield is achieved, resulting in an increase in crop yield in a field planted with such plants. A plant of interest may be transformed with a DNA construct comprising a promoter that is capable of driving expression in the plant operably linked to a coding sequence for a TEL gene. The DNA construct may comprise at least on enhancer that acts to increase expression of the TEL coding sequence. A promoter or enhancer can be inserted into the genome of the plant of interest at a site that increases the expression of the endogenous TEL coding sequence in the plant.

5 Claims, 12 Drawing Sheets
Specification includes a Sequence Listing.

METHODS FOR IMPROVING CROP YIELD

CROSS-REFERENCE TO RELATED APPLICATIONS

This application is the U.S. National Stage of International Application PCT/CN2012/087069 filed on Dec. 20, 2012, which designates the U.S. and was published by the International Bureau in English on Jun. 27, 2013, and which claims the benefit of Chinese Application No. 201110437868.4, filed Dec. 23, 2011, both of which are hereby incorporated by reference in their entirety.

FIELD OF THE INVENTION

This invention relates to the field of molecular biology. Methods for enhancing plant growth and yield are provided.

BACKGROUND OF THE INVENTION

The growing world population has made the improvement of crop yield an important goal of agriculture. Conventional means for crop and horticultural improvements utilize selective breeding techniques to identify plants having desirable characteristics. However, such selective breeding techniques have several drawbacks, namely that these techniques are typically labor intensive and result in plants that often contain heterogeneous genetic components that may not always result in the desirable trait being passed on from parent plants. Yield has been considered a multi-genic trait for many decades. Some progress has been made to enhance yield by traditional plant breeding. Such methods involve crossing closely or distantly related individuals to produce a new crop variety or line with desirable properties. Plant biotechnology has helped improve crop yield by developing plants that are resistant to disease and pests. Additionally, transgenic herbicide resistant plants have helped to increase yield in crops.

The domestication of many plants has correlated with dramatic increases in yield. Most phenotypic variation occurring in natural populations is continuous and is effected by multiple gene influences. The identification of specific genes responsible for the dramatic differences in yield, in domesticated plants, has become an important focus of agricultural research. Seed yield is a particularly important trait since the seeds of many plants are important for human and animal nutrition. Crops such as, corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain. The ability to increase plant yield would have many applications in areas such as agriculture, including in the production of ornamental plants, arboriculture, horticulture and forestry. Increasing yield may also find use in the production of algae for use in bioreactors (for the biotechnological production of substances such as pharmaceuticals, antibodies or vaccines, or for the bioconversion of organic waste) and other such areas.

Mei2 is an important gene in promoting meiosis in *Schizoacccharomyces pombe*. The presence of mei2-like genes in plants was first revealed by the identification and characterization of *Arabidopsis*-mei2-Like1 (AML1). AML1 is expressed in a number of tissues including leaves, roots, flowers, and siliques. An mei2-like gene has been isolated from maize and called the TERMINAL EAR1 (TE1) gene. Upon characterization, the maize gene was indicated in plastochron and leaf initiation in the meristem by negatively regulating the number and position of the sites of leaf initiation. Studies have revealed that mei2-like genes are widespread in plants where they constitute a diversified group. A Mei2 is a protein containing three RNA recognition motifs (RRM), and is capable of binding to RNAs. Homologues of Mei2 have also been identified in plants.

Increasing yield in crops is of great important for agriculture. To develop cultivars of enhanced yield has been one of the most important targets for cultivar developments of various crops. Although progress has been made in crop yield improvement by traditional breeding, new methods of improving crop yield are still highly desirable to further improve yield for various crops. Therefore, methods are needed for increasing yield.

SUMMARY OF INVENTION

Compositions and methods for increasing plant growth and yield are provided. Compositions comprise the high yield gene (Terminal earl-Like (TEL) gene), promoters, and enhancers to increase the expression of a TEL gene in a plant of interest. The invention recognizes that by enhancing the expression of at least one TEL gene in a plant results in an improvement in plant growth and yield, resulting in an increase in crop yield in a field planted with such plants. Any method for increasing the expression of a TEL gene in a plant is encompassed by the present invention. A plant of interest may be transformed with a DNA construct comprising a promoter that is capable of driving expression in the plant operably linked to a coding sequence for a TEL gene. Optionally, the DNA construct may comprise at least one enhancer that acts to increase expression of the TEL coding sequence. In another embodiment, a promoter or enhancer can be inserted into the genome of the plant of interest at a site that increases the expression of the endogenous TEL coding sequence in the plant.

Compositions of the invention include nucleic acid molecules encoding sequences for TEL polypeptides, sequences for promoters, and/or sequences for enhancers, vectors comprising those nucleic acid molecules, and host cells comprising the vectors. Compositions also include the TEL polypeptide sequences and antibodies to those polypeptides. The nucleotide sequences can be used in DNA constructs or expression cassettes for transformation and expression in plants of interest. The nucleotide or amino acid sequences may be synthetic sequences that have been designed for expression in a particular plant. Compositions also comprise transformed plants, plant cells, tissues, and seeds.

Thus, the present invention relates generally to the field of molecular biology and concerns a method for increasing plant yield relative to control plants. More specifically, the present invention concerns a method for increasing plant yield comprising modulating expression in a plant of a nucleic acid encoding the TEL gene or a homologue thereof. The present invention also concerns plants having elevated expression of a nucleic acid encoding the TEL gene, or a homologue thereof, which plants have increased yield relative to control plants. The invention also provides constructs useful in the methods of the invention.

In particular, methods are provided for enhancing the expression of a TEL coding sequence in a plant of interest. Such enhanced expression results in increased growth of the plant, increased seed production, and in increased yield. Methods and kits for detecting the TEL nucleic acids and polypeptides in a sample are also included.

The following embodiments are encompassed by the present invention:

1. A method for increasing plant growth and/or yield in a plant of interest, said method comprising increasing the expression of a TEL sequence in said plant.
2. The method of embodiment 1, wherein said method comprises transforming said plant with a DNA construct comprising a promoter that drives expression in a plant operably linked to a TEL nucleotide sequence wherein said TEL sequence encodes a protein that comprises an amino acid having at least one of the following characteristics:
    i) said amino acid sequence comprises an amino acid sequence that shares at least 58% sequence identity to SEQ ID NO:4;
    ii) said amino acid sequence comprises an amino acid sequence that shares at least 70% sequence identity to SEQ ID NO:4;
    iii) said amino acid sequence comprises an amino acid sequence that shares at least 80% sequence identity to SEQ ID NO:4;
    iv) said amino acid sequence comprises an amino acid sequence that shares at least 90% sequence identity to SEQ ID NO:4;
    v) said amino acid sequence comprises an amino acid sequence that has a TEL RNA Recognition motif (RRM3) in which at least 3 of the 4 residues Asn-His-Cys-Ile (SEQ ID NO:63) are conserved in said plant;
    vi) said amino acid sequence comprises an amino acid sequence that has a TEL specific conserved motif outside the C-terminus of the RRM3 domain and wherein at least 7 of the 10 residues in the following peptide are conserved: Lys/Arg-Phe-Pro/Ala-Cys-Asp/Glu-N-Asp/Glu-N-Tyr-Leu-Pro-Leu/Val (SEQ ID NO:64) (N represents any residue);
    vii) said amino acid sequence comprises an amino acid sequence that has at least about 60% sequence identity to the rice TEL protein;
    viii) said amino acid sequence comprises an amino acid sequence that has at least about 70% sequence identity to the rice TEL protein; and,
    ix) said amino acid sequence comprises an amino acid sequence that has at least about 80% sequence identity to the rice TEL protein.
3. The method of embodiment 2, wherein said DNA construct further comprises at least one enhancer that enhances expression of a gene in a plant operably linked to said promoter and TEL sequence.
4. The method of embodiment 3, wherein said at least one enhancer is a 35S enhancer from cauliflower mosaic virus (CaMV).
5. The method of any one of embodiments 1-4 wherein said TEL sequence is a synthetic sequence.
6. The method of any one of embodiments 2-5, wherein said promoter is a TEL promoter.
7. The method of any one of embodiments 2-6, wherein said TEL sequence has at least 58% identity with SEQ ID NO:4 and comprises at least one TEL motif.
8. The method of any one of embodiments 1-7, wherein the expression of a TEL sequence is increased at least two-fold to at least 50-fold.
9. An expression cassette comprising a DNA construct, said construct comprising a promoter that drives expression in a plant operably linked to a TEL nucleotide sequence and further operably linked to at least one enhancer that enhances expression in a plant, wherein said TEL sequence encodes a protein that comprises an amino acid having at least one of the following characteristics:
    i) said amino acid sequence comprises an amino acid sequence that shares at least 58% sequence identity to SEQ ID NO:4;
    ii) said amino acid sequence comprises an amino acid sequence that shares at least 70% sequence identity to SEQ ID NO:4;
    iii) said amino acid sequence comprises an amino acid sequence that shares at least 80% sequence identity to SEQ ID NO:4;
    iv) said amino acid sequence comprises an amino acid sequence that shares at least 90% sequence identity to SEQ ID NO:4;
    v) said amino acid sequence comprises an amino acid sequence that has a TEL RNA Recognition motif (RRM3) in which at least 3 of the 4 residues Asn-His-Cys-Ile (SEQ ID NO:63) are conserved in said plant;
    vi) said amino acid sequence comprises an amino acid sequence that has a TEL specific conserved motif outside the C-terminus of the RRM3 domain and wherein at least 7 of the 10 residues in the following peptide are conserved: Lys/Arg-Phe-Pro/Ala-Cys-Asp/Glu-N-Asp/Glu-N-Tyr-Leu-Pro-Leu/Val (SEQ ID NO:64) (N represents any residue);
    vii) said amino acid sequence comprises an amino acid sequence that has at least about 60% sequence identity to the rice TEL protein;
    viii) said amino acid sequence comprises an amino acid sequence that has at least about 70% sequence identity to the rice TEL protein; and,
    ix) said amino acid sequence comprises an amino acid sequence that has at least about 80% sequence identity to the rice TEL protein.
10. The expression cassette of embodiment 9, wherein said enhancer is a 35S enhancer from CaMV.
11. The expression cassette of any one of embodiments 9-10, wherein said TEL sequence is a synthetic sequence.
12. The expression cassette of any one of embodiments 9-11, wherein said promoter is a TEL promoter.
13. A plant transformed with the expression cassette of any one of embodiments 9-12.
14. A transformed seed of the plant of embodiment 13.
15. The method of embodiment 1, wherein said TEL sequence is an endogenous sequence.
16. The method of embodiment 15, wherein said plant of interest has at least one enhancer incorporated into its genome within about 30 kb of said TEL gene.
17. The method of embodiment 16, wherein said at least one enhancer is a 35S enhancer from CaMV.
18. The method of any one of embodiments 15-17, wherein the expression of said TEL sequence is enhanced at least two-fold to at least 50-fold.
19. A transformed plant that exhibits increased expression of a TEL sequence as compared to a control plant.
20. The transformed plant of embodiment 19, wherein said plant has stably incorporated into its genome a DNA construct comprising a promoter that drives expression in a plant operably linked to a TEL nucleotide sequence wherein said TEL sequence encodes a protein comprising an amino acid sequence having at least one of the following characteristics:
  i) said amino acid sequence comprises an amino acid sequence that shares at least 58% sequence identity to SEQ ID NO:4;
  ii) said amino acid sequence comprises an amino acid sequence that shares at least 70% sequence identity to SEQ ID NO:4;
  iii) said amino acid sequence comprises an amino acid sequence that shares at least 80% sequence identity to SEQ ID NO:4;
  iv) said amino acid sequence comprises an amino acid sequence that shares at least 90% sequence identity to SEQ ID NO:4;
  v) said amino acid sequence comprises an amino acid sequence that has a TEL RNA Recognition motif (RRM3) in which at least 3 of the 4 residues Asn-His-Cys-Ile (SEQ ID NO:63) are conserved in said plant;
  vi) said amino acid sequence comprises an amino acid sequence that has a TEL specific conserved motif outside the C-terminus of the RRM3 domain and wherein at least 7 of the 10 residues in the following peptide are conserved: Lys/Arg-Phe-Pro/Ala-Cys-Asp/Glu-N-Asp/Glu-N-Tyr-Leu-Pro-Leu/Val (SEQ ID NO:64) (N represents any residue);
  vii) said amino acid sequence comprises an amino acid sequence that has at least about 60% sequence identity to the rice TEL protein;
  viii) said amino acid sequence comprises an amino acid sequence that has at least about 70% sequence identity to the rice TEL protein; and,
  ix) said amino acid sequence comprises an amino acid sequence that has at least about 80% sequence identity to the rice TEL protein.
21. The transformed plant of embodiment 20, wherein said DNA construct further comprises at least one enhancer that enhances expression of a gene in a plant operably linked to said TEL sequence.
22. The transformed plant of embodiment 21, wherein said at least one enhancer is a 35S enhancer from CaMV.
23. The transformed plant of any one of embodiments 20-22 wherein said TEL sequence is a synthetic sequence.
24. The transformed plant of any one of embodiments 20-23, wherein said promoter is a TEL promoter.
25. The transformed plant of embodiment 24, wherein said TEL promoter is homologous to said TEL sequence.
26. The transformed of any one of embodiments 19-25 wherein the expression of the TEL sequence is increased at least two-fold to at least 50-fold.
27. The transformed plant of embodiment 19, wherein said TEL sequence is an endogenous sequence.
28. The transformed plant of claim 24, wherein said wherein said plant of interest has at least one enhancer incorporated into its genome within about 30 kb of said TEL gene.
29. The transformed plant of embodiment 28, wherein said at least one enhancer is a 35S enhancer from CaMV.
30. The transformed plant of any one of embodiments 27-29, wherein the expression of the TEL sequence is increased at least two-fold to at least 50-fold.
31. Transformed seed from the plant of any one of embodiments 19-30.
32. The transgenic plant of any one of embodiments 19-30, wherein said plant is selected from the group consisting of maize, sorghum, wheat, crucifers, cotton, rice, soybean, barley, sunflower, sugarcane, conifers, *Miscanthus*, switchgrass, and oilseed rape.

33. The plant of any one of embodiments 13, 14, and 20-32, wherein said plant is a monocot.
34. The plant of any one of embodiments 13, 14, and 20-34, wherein said plant is a dicot.

BRIEF DESCRIPTION OF THE FIGURES

FIG. 2: Alignment of the conservative motif of plant Mei2-like proteins. OsTE: TEL from *Oryza sativa* (SEQ ID NO: 2); GmTEL1: TEL from *Glycine max* (SEQ ID NO: 14); GmTEL2: TEL from *Glycine max* (SEQ ID NO: 16); AtTEL1: TEL from *Arabidopsis thaliana* (SEQ ID NO:22); AtTEL2: TEL from *Arabidopsis thaliana* (SEQ ID NO:24); PtaTEL1: TEL from *Populus tremula* x *Populus alba* (SEQ ID NO: 32); PtaTEL2: TEL from *Populus tremula* x *Populus alba* (SEQ ID NO: 34); VvTEL1: *Vitis vinifera* TEL1 (SEQ ID NO: 40); VvTEl2: TEL from *Vitis vinifera* (SEQ ID NO: 38); ZmTEL: TEL from *Zea mays* (SEQ ID NO: 6); SbTEL: TEL from *Sorghum bicolor* (SEQ ID NO: 8); SmTEL: TEL from *Selaginella moellendorffii* (SEQ ID NO: 36); RcTE: TEL from *Ricinus communis* (SEQ ID NO: 30); OtMei2L: Mei2-like gene from *Ostreococcus tauri* (SEQ ID No: 44); AlTEL1: TEL from *Arabidopsis lyrata* (SEQ ID NO: 26); BrTEL: TEL from *Brassica rapa* (SEQ ID NO:46); GhTEL1: TEL from *Gossypium hirsutum* (SEQ ID NO:18).

DETAILED DESCRIPTION

Figure 1:
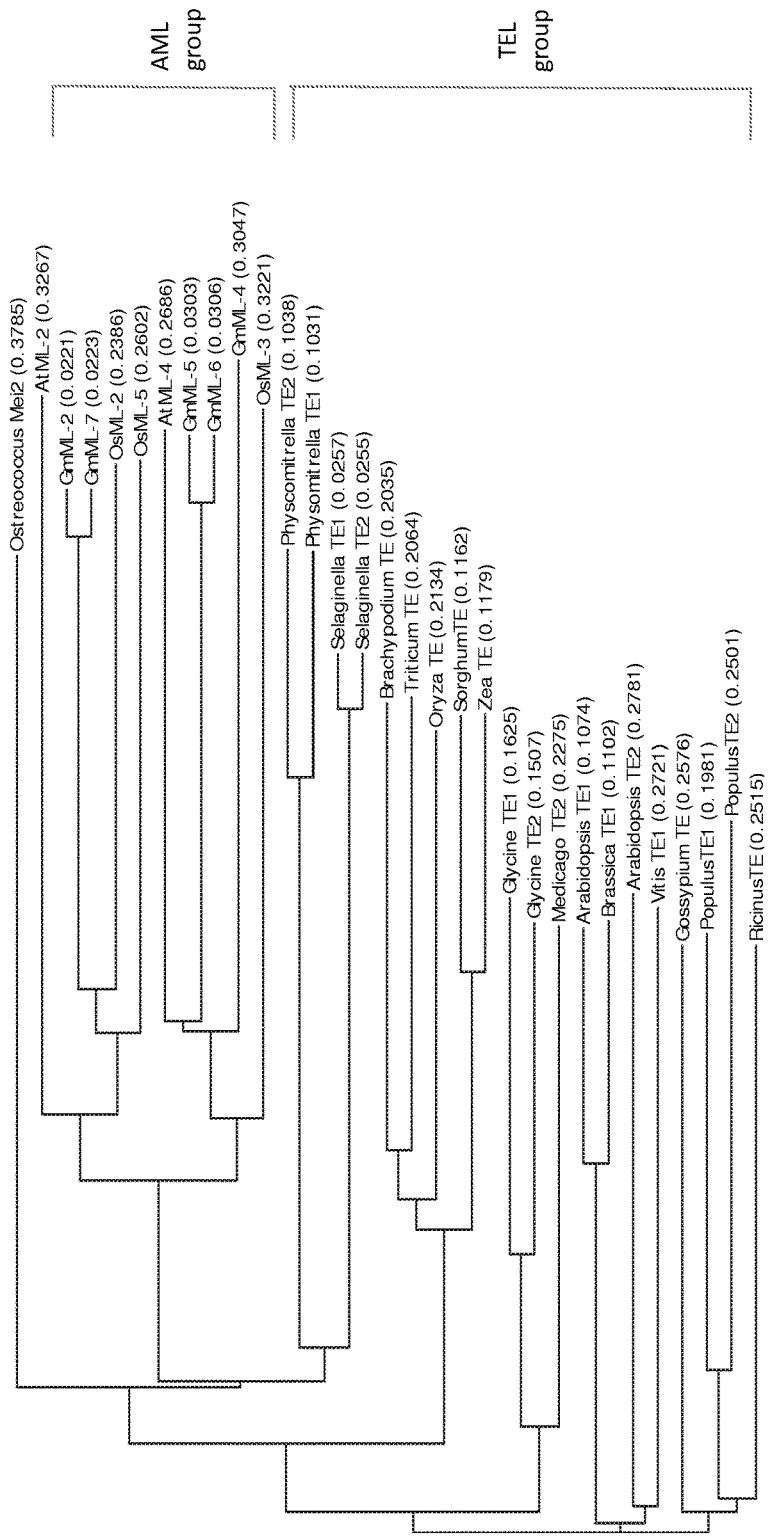
FIG. 1. Dendrogram of plant Mei2-like proteins. The sequence alignment and dendrogram building were carried out using a program provided by Vector NTi. The Mei2-like protein from unicellar green alge *Ostreococcus tauri* (SEQ ID NO: 44) was used as the root sequence. AtML-2 and AtML-4 are AML protein from *Arabidopsis thaliana*; GmML-2, GmML-4, GmML-5, GmML-6, and Gm1VIL-7 are AML protein from soybean (*Glycine max*); OsML-2, OsML-3 and OsML-5 (GenPept AP005651.3) are AML proteins from rice (*Oryza sativa*). *Physcomitrella* TE1 and *Physcomitrella* TE2 are TEL proteins from *Physcomitrella patens* (SEQ ID NO:42); Glycine TE1 and Glycine TE2 are the two TEL proteis from soybean (SEQ ID NO:14 and SEQ ID NO:16, respectively); *Ricinus* TE is the TEL protein from *Ricinus communis* (SEQ ID NO:30); *Populus* TE1 is the TEL protein from *Populus trichocarpa* (SEQ ID NO:32); *Populus* TE2 is the TEL protein from *Populus canescens* (SEQ ID NO:34); *Brassica* TE1 is the TEL gene from *Brassica rapa* (SEQ ID NO:46); *Arabidopsis* TE1 and *Arabidopsis* TE2 are the two TEL protein from *Arabidopsis thaliana* (SEQ ID NO:22 and SEQ ID NO:24, respectively); *Selaginella* TE1 (SEQ ID NO:36) and *Selaginella* TE2 are the TEL protein from *Selaginella moellendorffii*; Sorghum TE is the TEL from *Sorghum bicolor* (EES01930, SEQ ID NO:8); Zea TE is the TEL protein from *Zea mays* (AF047852, SEQ ID NO:6); Oryza TE is the TEL from *Oryza sativa* (SEQ ID NO:2); *Vitis* TE1 is a TEL protein from *Vitis vinifera* (XP 002271386, SEQ ID NO: 40); *Brachypodium* TE is the TEL from *Brachypodium* (SEQ ID NO:12); *Triticum* TE is the TEL from wheat *Triticum aestivum* L. (SEQ ID NO:10); *Gossypium* TE is a TEL from cottin *Gossypium hirsutum* (SEQ ID NO:18).

The present invention is drawn to methods for increasing the expression of a TEL gene or coding sequence in plants or plant cells. By increasing or enhancing the expression of a TEL sequence in the plant, the plant exhibits an improvement in plant growth and hence crop yield. By "TEL sequence" is intended a nucleic acid molecule that contains at least one of the following characteristics: encodes a protein comprising an amino acid sequence that shares at least 58% sequence identity to SEQ ID NO:4; encodes a protein comprising an amino acid sequence that shares at least 70% sequence identity to SEQ ID NO:4; encodes a protein comprising an amino acid sequence that shares at least 80% sequence identity to SEQ ID NO:4; encodes a protein comprising an amino acid sequence that shares at least 90% sequence identity to SEQ ID NO:4; encodes a protein comprising an amino acid sequence that comprises SEQ ID NO:4; encodes a protein comprising an amino acid sequence that has a TEL RNA Recognition motif (RRM3) in which at least 3 of the 4 residues Asn-His-Cys-Ile (SEQ ID NO:63)are conserved in said plant; encodes a protein comprising an amino acid sequence that has a TEL specific conserved motif outside the C-terminus of the RRM3 domain and wherein at least 7 of the 10 residues in the following peptide are conserved: Lys/Arg-Phe-Pro/Ala-Cys-Asp/Glu-N-Asp/Glu-N-Tyr-Leu-Pro-Leu/Val (SEQ ID NO:64) (N represents any residue); encodes a protein comprising an amino acid sequence that has at least about 60% sequence identity to the rice TEL protein; encodes a protein comprising an amino acid sequence that has at least about 70% sequence identity to the rice TEL protein; and, encodes a protein comprising an amino acid sequence that has at least about 80% sequence identity to the rice TEL protein.

That is, a TEL sequence of the invention comprises at least the RRM3 motif and at least about 15 additional amino acids, at least about 20 additional amino acids, at least about 25 additional amino acids, at least about 30 additional amino acids, at least about 40 additional amino acids, at least about 50 additional amino acids, up to the full length TEL sequence. In one embodiment, the TEL sequence encodes an amino acid sequence comprising the amino acid sequence: dtrttvmirnipnkysqklllnmldnhcilsnqqieascedeaqpfssydfly-lpidfnnkcnvgygfvnltspeaavrlykaf hkqpwevfnsrkicqvt-yarvqgldalkehfknskfpcdsdeylpvvfspprdgklltepvpl SEQ ID NO:62. In other embodiments, the TEL sequence comprises a sequence encoding an amino acid sequence having at least 40%, at least 50%, at least 60%, at least 70%, at least 80%, at least 90% or more sequence identity to SEQ ID NO:62.

The C-terminal RRM (RRM3) is unique to Mei2-like proteins and is the most highly conserved of the three RRMs. RRM3 also contains conserved sequence elements at its C-terminus not found in other RRM domains. See Jeffares et al. (2004) *Dev Genes Evol*. 214(3):149-58.

An increase in the expression of the TEL sequence results in an increase in plant growth, strength, vigor, and yield with no reduction in harvest index. Transformed plants are taller, have larger stems or stalks, grow faster, exhibit growth vigor, produce greater biomass, and have increased seed production. The plants contain larger and stronger roots. Planting a field of transformed plants of the invention will result in increased crop yield. By "crop yield" is intended the amount of a crop that is harvested per unit of land area. Crop yield is the measurement often used for a cereal, grain, or legume and is normally measured in metric tons per hectare (or kilograms per hectare). Crop yield also refers to the actual seed generation from the plant. By "plant growth" is intended plant size, height, circumference, strength, mass, number of seed produced, and the like.

The methods involve increasing or enhancing the expression of a TEL gene in a plant of interest. Any method for increasing the expression of a TEL gene in a plant is encompassed by the present invention. A plant of interest may be transformed with a DNA construct comprising a promoter that is capable of driving expression in the plant operably linked to a coding sequence for a TEL gene or a variant or truncation thereof. Optionally, the DNA construct may comprise at least one operably linked enhancer that acts to increase expression of the coding sequence. In another embodiment, a promoter or enhancer can be inserted into the genome of the plant of interest at a site that increases the expression of the native TEL coding sequence in the plant.

By enhancing or increasing the expression of a TEL sequence in plants, an increase in plant growth, seed production, and yield in general is observed. By "enhancing or increasing the expression of a TEL gene" is intended that the expression as measured by the production of mRNA or TEL protein is increased at least about two-fold, about five-fold, about 10-fold, about 20-fold, about 30-fold, about 40-fold, about 50-fold, about 60-fold, about 70-fold, about 80-fold or greater in the plant of interest as compared to a control plant. By "control plant" is intended a plant where the expression of a TEL sequence has not been altered or enhanced or that has not been transformed with an additional TEL sequence, i.e., a plant or plant cell genetically identical to the subject plant or plant cell but which is not exposed to conditions or stimuli that would induce expression of the TEL gene. That is, the modified plant of the invention exhibits enhanced expression of the TEL mRNA, the TEL protein, or both.

While not bound by any theory, it is believed that extreme over-production of the TEL protein may result in plants with undesirable phenotypes. Therefore, one can control expression by the selection of the promoters used to drive expression of a TEL sequence in a transformed plant. The TEL promoters provide good results in expressing the recombinant gene at desired levels. As discussed below, any promoter may be used, including strong constitutive promoters. However, in those instances where strong promoters are used, one can select a resulting plant based on the desired phenotype. Thus, the methods of the invention comprise selection of the desired phenotype of the transformed plant. Such desired plants will exhibit increased growth and vigor, increased strength with larger stems and roots or increased yield of grain or biomass. While desired transformed plants can be selected based on phenotypes, it is believed that such plants will show at least a two-fold to a 60-fold increase in TEL expression, at least a 10-fold to a 50-fold increase in expression, or at least a 20-fold increase, at least a 30-fold increase, or at least a 40-fold increase in expression.

Such desired plants can be grown and crossed with suitable plants to produce seed having the desired phenotype. That is, the recombinant TEL gene or the endogenous TEL gene whose expression has been increased by the insertion of at least one enhancer can be bred into plants of interest. Such plants will be grown and produce a crop with enhanced yield.

By "TEL gene" or TEL sequence" is intended a sequence that encodes the entire amino acid sequence of the TEL protein or variants or truncations of the TEL protein. Such truncations will comprise the RRM3 conserved region discussed above. The TEL genes used in transforming plants of interest may be homologous or heterologous to the plant. A number of TEL genes are known in the art and any can be used in the practice of the invention, including fragments and variants of known TEL genes as long as the fragments and variants retain the desired activity of promoting plant growth and increasing yield. The TEL genes are a group of genes from plants and fungi that share amino acid sequence similarity to the Mei2 of yeast (Watanabe and Yamamoto 1994, Cell 78:487-498). All plants have a large number of Mei2-like genes, and they may be divided into two groups based on their sequence similarity (Jeffares et al. 2004, Dev. Genes. Evol 214:149-158). One is the AML group, which is similar to the AML protein originally identified from *Arabidopsis thaliana* (Hirayama et al. (1997) *FEBS Lett.* 413: 16-20).

Figure 2:
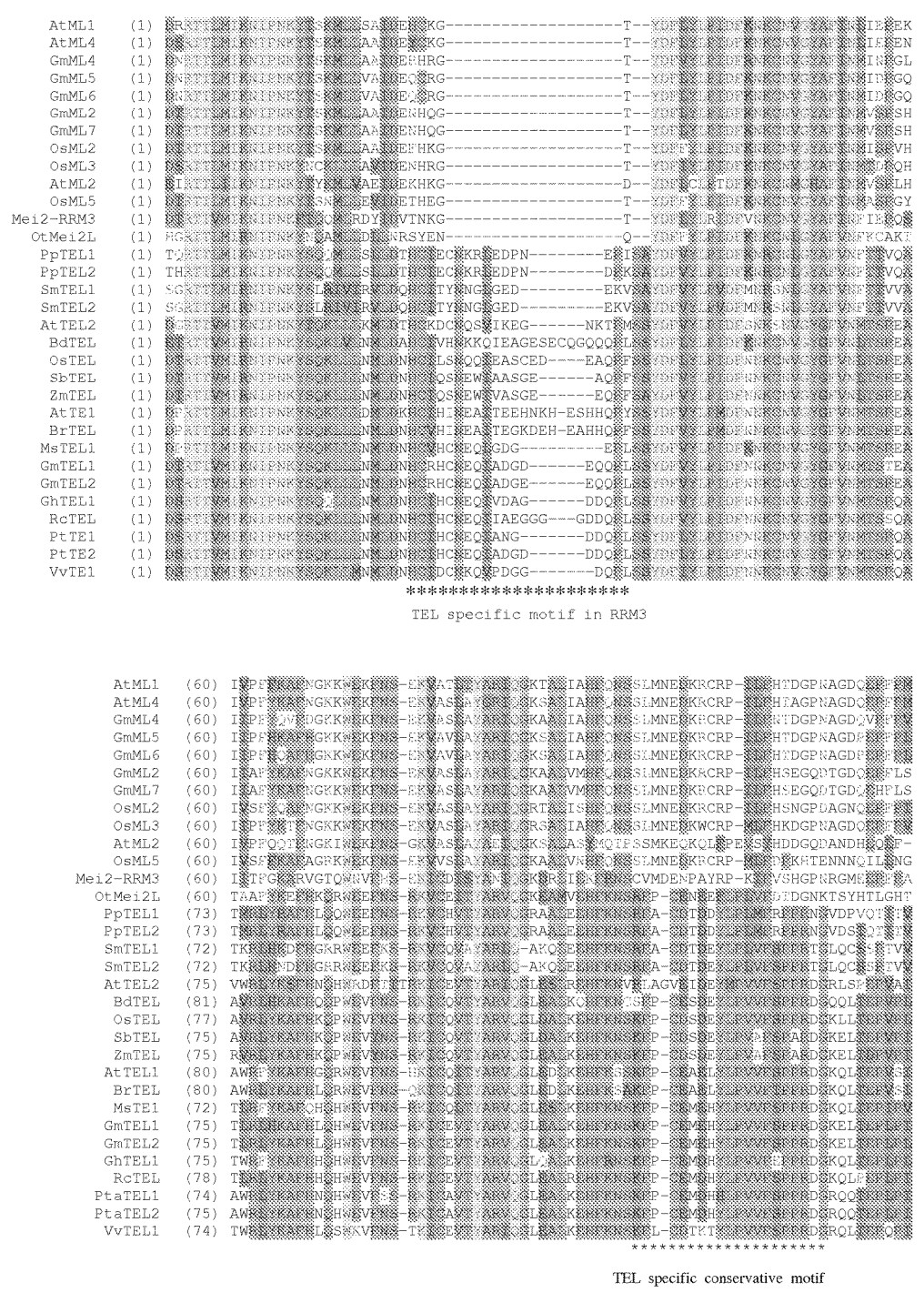

A second group of Mei2-like genes is the TEL group, which is similar to the Terminal Ear1 (TE1) gene from *Zea mays* (Veit et al. (1998) *Nature* 393:166-168). Whether or not a plant Mei2-like gene is a TEL or AML gene can be determined by an analysis of the encoded amino acid sequence. For instance, FIG. 1 shows the dendrogram of the various plant Mei2-like genes built by Vector NTI. In this dendrogram the plant Mei2-like genes were clearly clustered into two distinct groups, the AML group and the TEL group. A TEL-like protein usually contains two RNA Recognition Motifs (RRMs) at the N-terminal region and one RNA Recognition Motif (RRM3) at its C-terminal region. The RRM3 motif at the C-terminal is highly conserved among plants and may play an important role for the functions of the TEL proteins. Compared to AML proteins, a unique feature of TEL protein is an inserted TEL specific peptide inside the RRM3 motif (FIG. 2). All AML proteins are lack of this motif. Another unique feature of TEL proteins is the conserved region outside of the C-terminus of the RRM3 (FIG. 2). This is absence in all AML proteins. A TEL amino acid sequence of the invention shares at least about 60%, at least 70%, at least 80%, at least 90% or more sequence identity within this conserved region.

Thus, TEL or TEL-like proteins of the invention include those having at least one of the TEL motifs. A TEL or TEL-like protein of the invention include those having at least about 60%, at least 70%, at least 80%, at least 90% or more sequence identity to SEQ ID NO:4, the conserved region. To identify TEL sequences having the conserved region, the rice conserved motif can be used to blast the NCBI sequence database, using default parameters as discussed below. When the rice sequence is used, and the TEL sequences aligned, the sequences share about 60% or more sequence identity. Likewise, the TEL or TEL-like proteins include those having at least one of the TEL motifs and has at least 50%, at least 58% at least 60%, at least 70%, at least 80%, at least 90%, at least 91%, at least 92%, at least 93%, at least 94%, at least 95%, at least 96%, at least 97%, at least 98%, at least 99% sequence identity to a TEL protein of the invention. The TEL or TEL-like proteins include those having at least 60% sequence identity within the conserved region and has at least 50%, at least 58% at least 60%, at least 70%, at least 80%, at least 90%, at least 91%, at least 92%, at least 93%, at least 94%, at least 95%, at least 96%, at least 97%, at least 98%, at least 99% sequence identity to a TEL protein of the invention.

A number of TEL genes are disclosed herein and are known in the art and any of these TEL sequences, as well as variants and truncations thereof, can be used in any plant of interest. As discussed below, the sequences herein can be used to isolate other TEL genes that are useful in the practice of the invention. Nucleotide sequences encoding the TEL proteins of the present invention include the sequences set forth in SEQ ID NOs: 1, 3, 5, 7, 9, 11, 13, 15, 17, 19, 21, 23, 25, 27, 31, 33, 37, 39, 41, 43, 45, and variants, fragments, and complements thereof. Other sequences known in the art, and useful in the practice of the invention, include: *Arabidopsis thaliana* (e.g., NP_189242.1, BAB01438.1, NP_176943.1, BAA22374.1, NP_568946.1, NP_174902.1, NP_196346.1, ABE65689.1, BAF02107.1, AAG51742.1); *Zea mays* (e.g., NP_001104903.1, DAA56253.1, NP_001151419.1, DAA40614.1, NP_001132246.1, AFW58118.1, ACN26476.1, AFW86252.1, NP_001169543.1, AFW75193.1); *Vitis vinifera* (e.g., XP_002282117.1, XP_002271386.1, CBI17716.3, CBI16829.3, XP_003634410.1, CBI19075.3, CBI31752.3, CBI38012.3, XP_002279792.2); *Glycine max* (e.g., XP_003552800.1, XP_003537555.1, XP_003532096.1, XP_003551918.1, XP_003522450.1, XP_003546575.1); *Medicago truncatula* (e.g., XP_003601878.1, XP_003595582.1, XP_003595581.1, AAT38998.1, XP_003602750.1, XP_003630595.1); *Populus trichocarpa* (e.g., XP_002311749.1, XP_002314579.1, XP_002301014.1, XP_002328959.1, XP_002334130.1, XP_002297875.1); *Physcomitrella patens* (e.g., XP_001778423.1, AEN71547.1, XP_001764176.1, AEN71548.1, XP_001780082.1, XP_001765627.1); *Arabidopsis lyrata* subsp. *lyrata* (e.g., XP_002875310.1, XP_002887144.1, XP_002866463.1, XP_002871262.1, XP_002893925.1); *Ricinus communis* (e.g., XP_002515045.1, XP_002512974.1, XP_002513823.1, XP_002534743.1, XP_002511091.1); *Selaginella moellendorffii* (e.g., XP_002960552.1, XP_002969195.1, XP_002969607.1, XP_002965317.1, XP_002982799.1); *Sorghum bicolor* (e.g., XP_002456810.1, XP_002462714.1, XP_002437661.1, XP_002452169.1); *Brachypodium distachyon* (e.g., XP_003567374.1, XP_003576762.1, XP_003579645.1, XP_003569150.1); *Oryza sativa* Japonica Group (e.g., NP_001045139.1, EAZ14552.1, NP_001063754.1, NP_001172988.1); *Populus tremula* x *Populus alba* (e.g., ABR19818.1, ABR19817.1); *Hordeum vulgare* subsp. *vulgare* (e.g., BAJ85875.1, AAL85701.1); *Oryza sativa* Indica Group (e.g., A2WY46.1, EEC84932.1); *Solanum lycopersicum* (e.g., NP_001234547.1); *Triticum aestivum* (e.g., AAT39003.1); *Aegilops speltoides* (e.g., AAT39000.1); *Paramecium tetraurelia* strain d4-2 (e.g., XP_001432620.1, XP_001436478.1); *Citrus unshiu* (e.g., AAT39004.1) *Pinus taeda* (e.g., AAT38996.1); *Volvox carteri f. nagariensis* (e.g., XP_002957664.1); *Chlamydomonas reinhardtii* (e.g., XP 001700078.1); *Ostreococcus tauri* (e.g., XP_003079264.1); *Ostreococcus lucimarinus* CCE9901 (e.g., XP_001417970.1); *Chlorella variabilis* (e.g., EFN52088.1); *Picea sitchensis* (e.g., ABR16149.1); *Naegleria gruberi* (e.g., XP_002670292.1); *Tetrahymena thermophila* (e.g., XP_001032018.1); and *Albugo laibachii* (e.g., CCA21771.1). All of such sequences are herein incorporated by reference. By "complement" is intended a nucleotide sequence that is sufficiently complementary to a given nucleotide sequence such that it can hybridize to the given nucleotide sequence to thereby form a stable duplex.

Nucleic acid molecules that are fragments of these nucleotide sequences encoding TEL proteins are also encompassed by the present invention. By "fragment" is intended a portion of the nucleotide sequence encoding a TEL protein. A fragment of a nucleotide sequence may encode a biologically active portion of a TEL protein, or it may be a fragment that can be used as a hybridization probe or PCR primer useful for isolating other TEL-like sequences. Typically, truncations fragments of the nucleotide sequences of the present invention will encode protein fragments that comprise the RRM3 conserved region and retain the biological activity of the TEL protein and, hence, retain TEL activity. By "retains activity" is intended that the fragment will have at least about 50%, at least about 70%, 80%, 90%, 95% or higher of the TEL activity of the TEL protein. By "TEL activity" is intended increased plant growth or yield. Methods for measuring TEL activity include measuring levels of protein or mRNA levels as well as growing the altered plants for increased growth phenotype.

Variants of the TEL nucleic acid molecules may be made by various methods. These alterations may result in DNA sequences encoding proteins with amino acid sequences different than that encoded by a TEL protein of the present invention. Thus, the protein may be altered in various ways including amino acid substitutions, deletions, truncations, and insertions of one or more amino acids. Methods for such manipulations are generally known in the art. For example, amino acid sequence variants of a TEL protein can be prepared by mutations in the DNA. This may also be accomplished by one of several forms of mutagenesis and/or in directed evolution. In some aspects, the changes encoded in the amino acid sequence will not substantially affect the function of the protein. Methods include base misincorporation during DNA replication, such as XL-1 Red (Stratagene, La Jolla, Calif.); DNA shuffling (Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458); and the like. Alterations may be made to the protein sequence by insertion, deletion, or alterations introduced by molecular methods, such as PCR, mutagenesis, recombination, and the like. Such variants will possess the desired TEL activity. However, it is understood that the ability of a TEL protein to confer TEL activity may be improved by the use of such techniques upon the compositions of this invention.

Preferred TEL proteins of the present invention are encoded by a nucleotide sequence identical or having sequence identity to the nucleotide sequence of any of the TEL sequences listed herein or contained within the sequence listing. Variant amino acid or nucleotide sequences having at least about 50%, about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference TEL sequence using one of the alignment programs described herein using standard parameters are encompassed by the invention. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the percent identity is calculated across the entirety of the reference sequence. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to TEL-like nucleic acid molecules of the invention. BLAST protein searches can be performed with the BLASTX program, score=50, wordlength=3, to obtain amino acid sequences homologous to TEL protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Other mathematical algorithms may be used for the comparison of sequences including the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

As indicated, variant TEL nucleic acid molecules may be used in the practice of the invention. "Variants" of the TEL protein encoding nucleotide sequences include those sequences that encode the TEL proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the TEL proteins disclosed in the present invention as discussed below. Variant proteins encompassed by the present invention are biologically active, that is they continue to possess the desired biological activity of the native protein, that is, TEL activity.

The skilled artisan will further appreciate that changes can be introduced by mutation of the nucleotide sequences of the invention thereby leading to changes in the amino acid sequence of the encoded TEL proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more, predicted, nonessential amino acid residues. A "nonessential" amino acid residue is a residue that can be altered from the wild-type sequence of a TEL protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of similar or related proteins to the sequences of the invention (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related high yield proteins to the sequences of the invention (e.g., residues that have only conservative substitutions between all proteins contained in the alignment homologous proteins). However, one of skill in the art would understand that functional variants may have minor conserved or nonconserved alterations in the conserved residues. In one embodiment, changes in the amino acid sequence will not be made in the conserved motifs or in the region surrounding the motifs as set forth in FIG. 2.

Alternatively, variant nucleotide sequences can be made by introducing mutations randomly along all or part of the coding sequence, such as by saturation mutagenesis, and the resultant mutants can be screened for ability to confer TEL activity to identify mutants that retain activity. Following mutagenesis, the encoded protein can be expressed recombinantly, and the activity of the protein can be determined using standard assay techniques.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

In addition to the TEL proteins listed in this application, this invention also provides methods to clone and utilize new TEL genes other organisms, including plants, moss, and fungi. For example, by using the sequences provided herein, one can clone new TEL genes methods such as PCR and nucleic acid hybridization. PCR primers may be designed according to the conservative regions of the DNA sequences of TEL genes. Moreover, the conservative amino acid sequences may be used to design degenerate primers for PCR. A partially known gene from PCR can be used to clone a full-length gene using various known methods, such as Tail-PCR, 5'RACE, 3'RACE, etc. See, for example, Singer and Burke (2003) *Methods Mol Biol* 236:241-272; and commercially available kits. As described below, the genes provided in this invention and in other publications can be used to prepare probes to hybridize genomic or cDNA libraries to clone TEL genes. Once a TEL-like gene is cloned, its encoded amino acid sequence could be utilized to determine if that is an orthologue of TEL gene, as illustrated in FIG. 1.

With the rapid advancement of various sequencing projects, new TEL genes may be identified by searching various databases using the TEL amino acid sequences and/or nucleic sequences provided by this invention. Such databases include but not limited to databases of genome sequence, ETS, and cDNA sequences. BLAST method (Altschul et al. 1990 J. Mol. Biol. 215, 403-410) is a wide used. For example, Jeffares et al. identified 15 plant Mei-2 like gene from databases by searching, and several of which were further identified as members of the TEL group (Jeffares et al. 2004, *Dev. Genes. Evol.* 214:149-158).

To determine if a Mei2-like protein is a protein of the TEL group, its amino acid sequence can be examined. The TEL proteins of the invention have at least one of the following features to be useful for yield enhancement: comprises an amino acid sequence that shares at least 58% sequence identity to SEQ ID NO:4; comprises an amino acid sequence that shares at least 70% sequence identity to SEQ ID NO:4; comprises an amino acid sequence that shares at least 80% sequence identity to SEQ ID NO:4; comprises an amino acid sequence that shares at least 90% sequence identity to SEQ ID NO:4; comprises an amino acid sequence that has a TEL RNA Recognition motif (RRM3) in which at least 3 of the 4 residues Asn-His-Cys-Ile (SEQ ID NO:63) are conserved in said plant; comprises an amino acid sequence that has a TEL specific conserved motif outside the C-terminus of the RRM3 domain and wherein at least 7 of the 10 residues in the following peptide are conserved: Lys/Arg-Phe-Pro/Ala-Cys-Asp/Glu-N-Asp/Glu-N-Tyr-Leu-Pro-Leu/Val (SEQ ID NO:64) (N represents any residue); comprises an amino acid sequence that has at least about 60% sequence identity to the rice TEL protein; comprises an amino acid sequence that has at least about 70% sequence identity to the rice TEL protein; and, comprises an amino acid sequence that has at least about 80% sequence identity to the rice TEL protein.

Thus, using methods such as PCR, hybridization, and the like corresponding TEL sequences can be identified, such sequences having substantial identity to the sequences of the invention. See, for example, Sambrook and Russell (2001) *Molecular Cloning: A Laboratory Manual.* (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of a TEL nucleotide sequence disclosed herein can be used to screen cDNA or genomic libraries for additional TEL sequences for use in the invention. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known TEL protein-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, or 200 consecutive nucleotides of nucleotide sequence encoding a TEL protein of the invention or a fragment or variant thereof. Methods for the preparation of probes for hybridization are generally known in the art and are disclosed in Sambrook and Russell, 2001, supra herein incorporated by reference.

For example, an entire TEL nucleic acid sequence disclosed herein, or one or more portions thereof, may be used as a probe capable of specifically hybridizing to corresponding TEL-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding TEL sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m = 81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

As noted above, one method for increasing the expression of the TEL gene in plants is to transform a plant of interest with a DNA construct comprising a nucleic acid molecule that encodes a TEL sequence of the invention. General methods to introduce and express a TEL gene in a plant and hence crops are currently available. Generally transformation of a plant of interest includes the following steps: 1) Constructing an expression cassette for a TEL gene; (The polynucleotides used for construction can be a genomic fragment containing the coding sequence, or a full-length cDNA, or a DNA fragment synthesized artificially. Regulatory sequences, such as promoter, enhancer and terminator, can be operably linked to the coding DNA to create functional expression cassettes. Usually a promoter is linked to the 5' end of the coding DNA, while a terminator is linked to the 3' end of the coding DNA. The expression cassette may comprise a genomic TEL DNA fragment, including the native promoter, coding sequence and terminator). 2) Constructing transformation vectors with TEL expression cassettes; (For example, pCambia1300 or its modified versions can be used to clone TEL expression cassettes for *Agrobacterium*-mediated transformation). and, 3) Transforming target crops and selecting transgenic events. (Western analysis method can be used to detect the expression of the TEL transgenes).

Expression cassettes of native or endogenous TEL genes may be used in the practice of the invention. Such an expression cassette contains a promoter, a coding sequence and a terminator, all in one fragment of genomic DNA. The promoter of a TEL gene is usually located at the 5' end of the coding sequence and is up to 2-3 kb upstream of the start codon. The terminator is usually located at the 3' end of the coding sequence within about 1.0 kb. A polyA signal sequence such as AATAAA can be used at the end of the terminator.

Furthermore, this invention also provides a number of native TEL expression cassettes from various plant genomes. The nucleic acid sequences of these cassettes are listed in SEQ ID NOs:5, 7, 9, 13, 15, 17, 19, 21, 23, 27, 29, and 45. In order to enhance expression of these TELs in transgenic plants, enhancers can be inserted into these expression cassettes at upstream or downstream. One commonly used enhancer is the 35S enhancer of cauliflower mosaic virus (CaMV) (Benfey et al. 1990, EMBO J. 9:1685-1696).

As indicated, a TEL sequence of the invention may be provided in a DNA construct or an expression cassette for expression in a plant of interest. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain an enhancer to increase expression of the TEL coding sequence in the plant.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

"Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest. Constitutive or tissue-preferred promoters can be used in the practice of the invention. Many promoters are known and can be used including the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), the promoter from the rubisco small subunit, promoters derived from *Agrobacterium tumefaciens* T-DNA such as octopine synthase and nopaline synthase, and the like. Tissue-preferred promoters include meristem-specific promoters (Ito et al. (1994) *Plant Mol Biol* 24:863-878; Verma and Kumar (2005) *Indian J Biotechnology* 4:516-521; Shimizu et al (2009) *Plant Physiol* 149:841-850); green tissue specific promoters such as the maize (*Zea mays*) phophoenolpyruvate carboxylase (U.S. Pat. No. 5,856,177); etc. All of these references are herein incorporated by reference.

The promoter of a TEL gene can be used to drive the expression of the coding sequences of other TEL genes in a plant of interest. For example, the corn TEL gene promoter can be used to drive rice TEL gene expression in rice, wheat, sorghum, corn, etc. Promoters from various plants are provided in SEQ ID NOs:52-55. It is a well-known skill to isolate the promoter region from any gene that has been cloned.

Promoters used for control of gene expressions are well-studied. See, for example, Potenza et al. 2004, In. Vitro. Cell. Dev. Biol-Plant. 40:1-2). All promoters for constitutive expression and tissue specific expression may be used for driving the expression of TEL genes in plants for yield enhancement. Promoters used for directing the expression of TEL genes in this invention can be various heterogeneous promoters, such as tissue specific promoters (U.S. Pat. No. 5,880,330), ARSK1 root specific promoter, AP1 floral inflorescence promoter (Bai et al. 2008, Transgenic Res. 17:1035-1043). These promoters may provide tissue specific expression enhancement, which may result in tissue specific growth enhancements.

The DNA construct or expression cassette is provided with a plurality of restriction sites for insertion of the TEL sequence to be under the transcriptional regulation of the regulatory regions.

As indicated, enhancers may be used in the DNA construct to increase expression of the TEL coding sequence. Such enhancers include the 35S enhancer, the truncated 35S enhancer, and other transcription activators. One or more enhancer elements can be used in the construct, often at least two elements may be used. The enhancer may be 5' or 3' to the promoter driving expression of the TEL sequence and operably linked to the elements in the expression cassette.

The expression cassette will include in the 5'-3' direction of transcription, a transcriptional and translational initiation region (i.e., a promoter), a DNA sequence of the invention, and a translational and transcriptional termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Terminators used for TEL expression cassettes can be the TEL's native terminators, but also can be other terminators. Frequently used terminators include 35S terminator of CaMV. Other terminators include those disclosed in Guerineau et al. (1991) Mol. Gen. Genet. 262:141-144; Proudfoot (1991) Cell 64:671-674; Sanfacon et al. (1991) Genes Dev 5:141-149; Mogen et al. (1990) Plant Cell 2:1261-1272; Munroe et al. (1990) Gene 91:151-158; Ballas et al. (1989) Nucleic. Acids. Res. 17:7891-7903; and Joshi et al. (1987) Nucleic. Acids. Res. 15:9627-9640. Convenient termination regions are available from the T1-plasmid of *A. tumefaciens*, such as the octopine synthase and nopaline synthase termination regions.

Where appropriate, the gene(s) may be optimized for increased expression in the transformed host cell. That is, the genes can be synthesized using the specific plant-preferred codons for improved expression. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference. In order to enhance expression, the TEL genes to be used as a transgene can be modified. For example, the codon usage can be optimized, introns can be deleted, and premature polyA signals can be removed.

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

Transformation of plant cells can be accomplished by one of several techniques known in the art. The TEL gene of the invention may be modified to obtain or enhance expression in plant cells. Typically a construct that expresses such a protein would contain a promoter to drive transcription of the gene, as well as a 3' untranslated region to allow transcription termination and polyadenylation.

Typically this "plant expression cassette" will be inserted into a "plant transformation vector". This plant transformation vector may be comprised of one or more DNA vectors needed for achieving plant transformation. For example, binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the TEL gene may be located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection (Crossway et al. (1986) Biotechniques 4:320 334), electroporation (Riggs et al. (1986) Proc. Natl. Acad. Sci. USA 83:5602 5606, *Agrobacterium*-mediated transformation (U.S. Pat. Nos. 5,563,055 and 5,981,840), direct gene transfer (Paszkowski et al. (1984) EMBO J. 3:2717 2722), and ballistic particle acceleration (see, for example, U.S. Pat. Nos. 4,945,050; 5,879,918; 5,886,244; and, 5,932,782; Tomes et al. (1995) in Plant Cell, Tissue, and Organ Culture: Fundamental Methods, ed. Gamborg and Phillips (Springer-Verlag, Berlin); McCabe et al. (1988) Biotechnology 6:923 926); and Lecl transformation (WO 00/28058). Also see Weissinger et al. (1988) Ann. Rev. Genet. 22:421 477; Christou et al. (1988) Plant Physiol. 87:671 674; Datta et al. (1990) Biotechnology 8:736 740 (rice); Klein et al. (1988) Proc. Natl. Acad. Sci. USA 85:4305 4309; Klein et al. (1988) Biotechnology 6:559 563. See, also, U.S. Pat. Nos. 5,240,855; 5,322,783; 4,945,050; 5,324,646; U.S. Published Application No. 20010026941; 2002015066; and, International Publication No. WO 91/00915.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Following introduction of heterologous foreign DNA into plant cells, the transformation or integration of heterologous gene in the plant genome is confirmed by various methods such as analysis of nucleic acids and proteins associated with the integrated gene. Molecular techniques include PCR (Sambrook and Russell (2001) Molecular Cloning: A Laboratory Manual. Cold Spring Harbor Laboratory Press, Cold Spring Harbor, N.Y.), Southern blot analysis of genomic DNA, Northern blot analysis and Western blot (Sambrook and Russell, 2001, supra).

A number of selectable markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene). Methods for detecting the presence of a transgene in a plant, plant organ (e.g., leaves, stems, roots, etc.), seed, plant cell, propagule, embryo or progeny of the same are well known in the art.

Fertile plants expressing a TEL protein may be tested for TEL activity, and the plants showing optimal activity selected for further breeding. Methods are available in the art to assay for enhanced expression of a coding sequence. In this manner, plants can be screened and selected based on the level of expression of the TEL sequence. Furthermore, the transformed seed can be grown and selected based on the preferred phenotype.

As discussed, any method for enhancing the expression of a TEL sequence in a plant is encompassed by the invention. Another method to improve crop yield is to enhance the expression of the endogenous TEL gene or coding sequence in crops by other plant genetic engineering techniques. That is, instead of introducing a second TEL coding sequence by the use of an expression cassette, the expression of the endogenous TEL gene in the plant of interest can be enhanced. In this method, an enhancer (such as the 35S enhancer of CaMV) can be inserted in the vicinity of the endogenous TEL gene in the plant to increase expression of the endogenous sequence. The 35S enhancer has been found to be able to enhance gene expression when inserted at a region upstream or downstream of a gene, even when the enhancer is inserted 20 kb, 30 kb or greater from the gene of interest. (Jeong et al. 2006, *Plant J.* 45:123-132). Thus, an enhancer can be inserted in the area of the TEL sequence immediately upstream and/or downstream of the TEL gene. In other embodiments, an enhancer can be inserted in a region of the genome upstream and/or downstream of the TEL gene within about 1 kb, about 5 kb, about 10 kb, about 15 kb, about 20 kb, 30 kb or greater of the TEL gene. One of skill can determine when the enhancer is too far removed from the TEL sequence to have no enhancing effect. In one example, T-DNA containing at least one 35S enhancer was inserted about 5 kb downstream of the TEL gene and significantly enhanced the expression of TEL sequence and subsequently substantially increased yield.

Methods for site-specific targeting of nucleotide molecules into the genome are known and include TALEN-based integration (Li et al. (2012) *Nature Biotech* 30:390-392, Cermak et al. (2011) *Nucleic Acids Res Epub* 14 Apr. 2011; doi:10.1093/nar/gkr218, Bogdanove and Voytas (2011) *Science* 333:1843-1846, Miller et al. (2011) *Nature Biotech* 29:143-150, Scholze and Boch (2011) *Curr Opinion in Microbiol* 1447-53); Cre-lox site-specific recombination (Dale et al. (1995) *Plant J* 7:649-659, Lyznik et al. (2007) *Transgenic Plant J* 1:1-9); FLP-FRT recombination (Li et al. (2009) *Plant Physiol* 151:1087-1095); Bxb1-mediated integration (Yau et al. *Plant J* (2011) 701:147-166); zinc-finger mediated integration (Wright et al. (2005) *Plant J* 44:693-705, Cai et al. (2009) *Plant Mol Biol* 69:699-709); homologous recombination (Lieberman-Lazarovich and Levy (2011) *Methods Mol Biol* 701: 51-65, Puchta, H. (2002) *Plant Mol Biol* 48:173-182); etc. All of these references are herein incorporated by reference.

TALEN technology has been developed for sequence specific targeting in genetic engineering. TAL (transcription activator-like) effectors constitute a novel class of DNA-binding proteins with predictable specificity. Inside plant cells, TALs localize to the nucleus, bind to target promoters, and induce expression of plant genes. DNA-binding specificity of TALs is determined by a central domain of tandem repeats. Scholze and Boch supra. TALEN technology may be used to insert an enhancer sequence specifically into the vicinity of TEL gene. Therefore, using TALEN technology, at least one enhancer element can be inserted into desired locations into the genome downstream or upstream of the TEL gene. For example, using TAL technology, the 35S enhancer of CaMV may be inserted within 5 kb of the downstream of the rice TEL gene.

TEL expression may also be enhanced by the use of denovo-engineered transcription activator-like effector (TALE). TALEs from *Xanthomonas* are modular proteins that contain a DNA binding domain and a transcriptional activation domain (Boch and Bonas (2010) *Annu Rev Phytopathol* 48:419-436). The DNA binding domains of TALEs can be denovo-engineered to make them to bind to a specific DNA sequence. Such denovo-engineered TALEs may be used to activate the downstream gene of that specific sequence. This method of enhancing gene expression was successfully demonstrated in plants (Morbitzer et al. (2010), *Proc. Natl. Acad. Sci. USA* 107: 21617-21622). The promoter region of the TEL genes of rice, corn, wheat, and soybean are all known and provided in this application. TALEs could be modified to specifically bind to a site at the upstream close to the transcription initiation site. Transformation of such denovo-engineered TALEs in these plants will enhance the expression of their TEL genes, which will in turn enhance crop yields. In this manner, TALE mediated integration can be designed for a TEL gene in any plant of interest. The nucleotide sequence of the coding region for the TEL gene can be used to sequence DNA regions either downstream or upstream from the coding sequence. Such sequences can be used to target enhancers for integration using TALE technology.

Sequence specific insertion technology has been developed using Zinc-finger proteins (Urnov et al. (2010) *Nat. Rev. Genet.* 11: 636-646; Davis & Stokoe (2010) *BMC Med.* 8:42; Camenisch et al. (2008) *Mini Rev. Med. Chem.* 8: 669-676). Therefore, Zinc-finger methods may be used for sequence specific insertion of transcriptional enhancers to enhance the expression of TEL genes in plants and thus crops.

The methods of the invention may be used in any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, *Miscanthus*, switchgrass. Jatropha, etc.) and conifers.

Methods for increasing plant yield are provided. The methods comprise increasing or enhancing the expression of a TEL coding sequence in a plant which leads to increased plant growth, vigor, and yield. As defined herein, the "yield" of the plant refers to the quality and/or quantity of biomass and/or seed produced by the plant. By "biomass" is intended any measured plant product. An increase in biomass production is any improvement in the yield of the measured plant product. An increase in yield can comprise any statistically significant increase including, but not limited to, at least a 1% increase, at least a 3% increase, at least a 5% increase, at least a 10% increase, at least a 15% increase, at least an 18% increase, at least a 20% increase, at least a 30%, at least a 50%, at least a 70%, at least a 100% or a greater increase in yield compared to a plant not expressing the TEL sequence. Seed production in plants of interest can be increased by at least 10%, at least 20% increase, at least 30%, at least 50%, at least 70%, at least 80%, at least 100% or a greater compared to a control plant.

The following examples are offered by way of illustration and not by way of limitation.

EXPERIMENTAL

Example 1

Identification of Rice TEL Gene as a Yield Enhancement Gene (1) Molecular Characterization of a T-DNA Insertion Mutant of Rice with Higher Yield A transgenic rice line, named HSA-20, was identified having the unexpected, but highly desirable, agronomic trait of higher yield. Compared to the plants of the non-transgenic parental line "WYG-7", the most striking phenotype of the HSA-20 plants are their dramatically enlarged seeds. The 1,000-grain weight of the parental line used for transformation was 26.1 g, while the 1,000 grain weight of the HSA-20 line was 36.5 g, which is 39.8% higher. The HSA-20 seeds were approximately 20% longer and 7% wider than the seeds of the control plants. HSA-20 plants were also significantly taller and their culm diameter was also significantly bigger. The average height of the HSA-20 mature plants was 107 cm, compared to 97 cm for the non-transgenic plants. The seed number per main panicle was statistically the same between the HSA-20 and the control plants. The average weight of main panicles is 4.8 g compared to the 3.6 gram for the non-transgenic parental line. There was no significant difference in heading time between HSA-20 and the non-transgenic control.

Southern blot analysis of the T-DNA insertion of HSA-20 indicated that it was a transgenic event with only a single copy of T-DNA insertion. Examination of 200 plants of a segregated T1 population of HAS-20 by PCR detection showed that 100% of the plants with the phenotype of enlarged seeds were positive for the T-DNA insertion, while plants with regular sized seeds were all PCR negative, demonstrating that the insertion of the T-DNA is responsible to the phenotype of high yield.

(2) Characterization of the T-DNA Insertion Site

To characterize the T-DNA insertion site in HSA-20, the border sequences of the T-DNA in the rice genome was determined by TAIL-PCR method (Liu and Chen, 2007, BioTechniques 43:649-656). It was found that the T-DNA was inserted at the long arm of chromosome 1, and its border sequences of each sides were SEQ ID NO:50 and SEQ ID NO:51, respectively.

Figure 3:
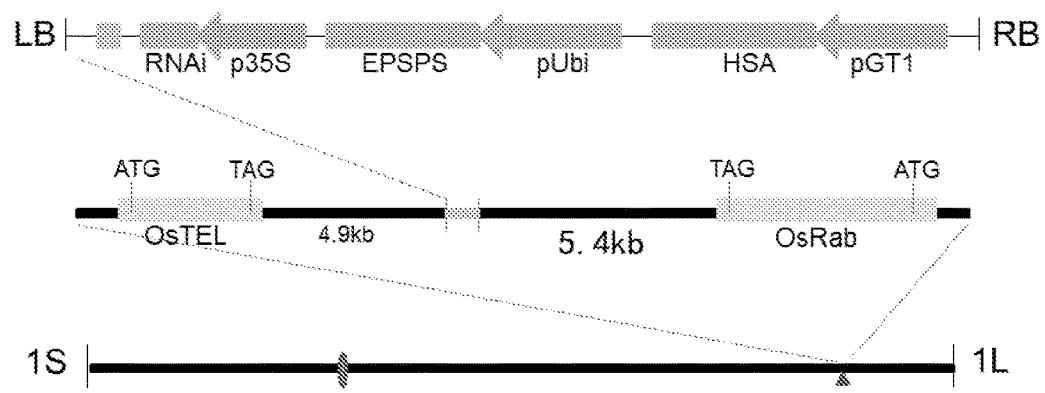
FIG. 3: Diagram of genomic structure around the T-DNA insertion of event HAS-20. The T-DNA insertion is located approximately 5 kb downstream of the OsTEL gene.

This insertion did not appear to be within any known or theoretical gene. It was inserted in the area between the terminal earl-like gene (OsTEL) and a putative gene encoding a RabGAP/TBC domain protein. The insertion is about 4.5 kb downstream of the OsTEL gene and 5.4 kb upstream of the putative gene encoding a RabGAP/TBC domain (FIG. 3).

(3) The Expression Enhancement of the OsTEL Gene in HSA-20 Plants

The mRNA levels of OsTEL and the putative gene encoding a RabGAP/TBC domain were compared between HSA-20plants and the non-transgenic parental line in one-month-old seedlings using RT-PCR analysis. The OsTE1 mRNA was found to be significantly higher in the HSA-20 plants than in the non-transgenic control plants, while the mRNA of the putative gene encoding a RabGAP/TBC domain protein was about the same. The enhanced expression of OsTEL in the HAS-20 plants was likely due to the CaMV 35S enhancer inside the T-DNA that was inserted 4.9 kb downstream from the OsTEL gene.

Example 2

Construction of OsTEL Expression Vectors for Rice Transformation

The transformation vector pCambia1300-355-G10 is a modified from pCambia1300. Specifically, the hygromycine resistant gene htpll was digested out from pCambia1300 by XhoI enzyme, and then replaced by an expression cassette of glyphosate tolerance gene G10evo (EPSP Synthase). The G10evo expression cassette is composed of a corn ubiquitin promoter, pUbi, the glyphosate resistant gene G10evo (EPSPS) and its down-stream terminator. The polynucleotide sequences of vector pCambia1300-355-G10 and EPSPS are shown as SEQ ID NO:47 and SEQ ID NO:48, respectively. The promoter p35S in vector pCambia1300-355-G10 provides an enhancer, which enhances the expression of rice OsTEL gene.

The full-length gene of OsTEL is composed of a putative promoter region, the coding sequence and a putative terminator (shown in SEQ ID NO:1). It was obtained by PCR amplification. The putative promoter of 1.8 kb and the coding region, including the terminator of about 4.0 kb, were obtained by PCR from genomic DNA isolated from rice (*Oryza stiva* spp. *japonica*) separately. The primers used for PCR were listed in Table1.

TABLE 1

PCR primers for cloning of OsTEL.

| Primers | Sequences | Restriction site |
|---------|-----------|------------------|
| p OsTEL-F: | 5'-<u>AAGCTT</u>GAAACTAGTACT AGACATTACTCTTCCAATGC (SEQ ID NO: 65) | HindIII |

TABLE 1-continued

PCR primers for cloning of OsTEL.

| Primers | Sequences | Restriction site |
|---|---|---|
| POsTEL-R: | 5'-<u>GGATCC</u>ACTTACCTACCC TACCAAGAACACCC (SEQ ID NO: 66) | BamHI |
| pOsTEL-MF: | 5'-ATCGCTATAGAGCATCCG AGCAAAAAACAGG (SEQ ID NO: 67) | |
| pOsTEL-MR: | 5'-CCTGTTTTTTGCTCGGAT GCTCTATAGCGAT (SEQ ID NO: 68) | |
| OsTELCod-F: | 5'-CA<u>GGATCC</u>AACAATGGAG GAAGGAGGTGGGAG (SEQ ID NO: 69) | BamHI |
| OsTELter-R : | 5'-CA<u>GGTACC</u>ACCTCATCCT TCAACCATAAAGAAATGCT (SEQ ID NO: 70) | KpnI |

To eliminate the BamHI site inside the promoter, two fragments of the promoter were amplified by primers pOsTEL-F/pOsTEL-MR and pOsTEL-R/pOsTEL-MF, respectively. These two fragments were then combined as the templates for next round of PCR using primers pOsTEL-F and pOsTEL-R to obtain the full-length promoter of OsTEL. A HindIII and a BamHI site were introduced at its 5' and 3' end, respectively. This promoter region DNA of 1.8 kb length was cloned into P-Easy vector (Transgene Inc., Beijing), and confirmed by sequencing, and named pOsTEL.

The fragment including the coding sequence and the putative terminator was obtained by PCR using primers OsTELcod-F and OsTELter-R. A BamHI and a KpnI site were introduced at its 5' and 3' end respectively. The 4.0 kb PCR product was cloned into P-Easy vector (Transgene Inc., Beijing), and confirmed by sequencing, and named as OsTEL-TER.

The PCR was carried out using high fidelity DNA polymerase Primer star and its companion reagents from TAKARA (Daliang, China). The PCR reaction conditions and procedures are as following:

PCR reaction mixture:

| | |
|---|---|
| Primer star | 1 ul |
| 2X Reaction buffer | 50 ul |
| Primer 1 | 2 ul |
| Primer 2 | 2 ul |
| dNTP mix (10 mM each) | 8 ul |
| Plant genome DNA | 100 ng |
| H2O | up to 100 ul |

PCR reaction program:

| | |
|---|---|
| Step 1: 98° C. | 3 min |
| Step 2: 98° C. | 20 s |
| Step 3: proper Tm ° C. | 20 s |
| Step 4: 72° C. | 3.5 min |
| 35 cycles of Step 2 to 4 | |
| Step 5: 72° C. | 10 min |

Construction of vector harboring T-DNA with the native OsTEL gene and 35S enhancer:

The two PCR products cloned in T-Easy vector were digested out of the vector by double enzyme digestions, HindIII/BamHI and BamHI/KpnI, respectively. The two resulting fragments were simultaneously cloned into pCambia1300-35S-G10 between its HindIII and KpnI sites, generating vector pCambia1300-35S-G10-OsTEL (shown in FIG. 4A), which has a 35S promoter (p35S) at the downstream of OsTEL gene. The full-length polynucleotide sequence of the cloned rice OsTEL gene is shown as SEQ ID NO:1.

Figure 4:
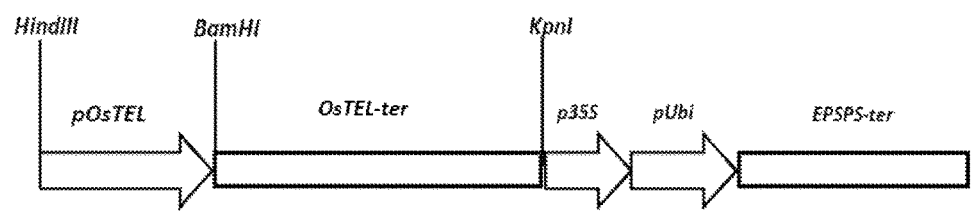
FIG. 4: Diagram of T-DNA used for plant transformation. The native OsTEL gene expression cassette composes of the promoter (pOsTEL), the protein coding sequence and the terminator (OsTEL-ter), and its whole polynucleotide sequence is shown as SEQ ID NO: 1. In specifics, p35S represents 35S promoter of CaMV; pUbi represents corn ubiquitin promoter; EPSPS-ter represents the glyphosate tolerance gene G10evo (EPSPS) and its terminator. (A): pCambia1300-355-G10-OsTEL; (B): pCambia1300-G10-OsTEL; (C): pCambia1300-G10-p35S-OsTEL. The polynucleotide sequences of the vectors pCambia1300-35s-G10 and pCambia1300-G10 are shown as SEQ ID NO: 47 and SEQ ID NO: 49, respectively.
Figure 4:
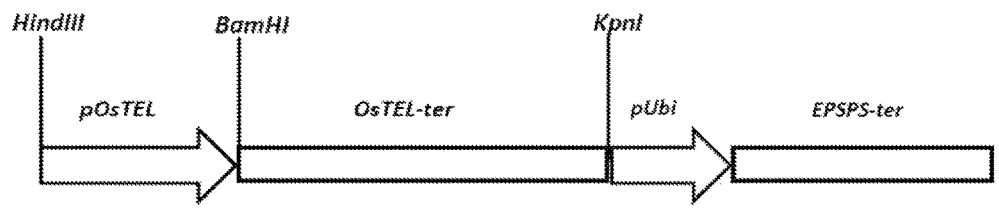
Figure 4:
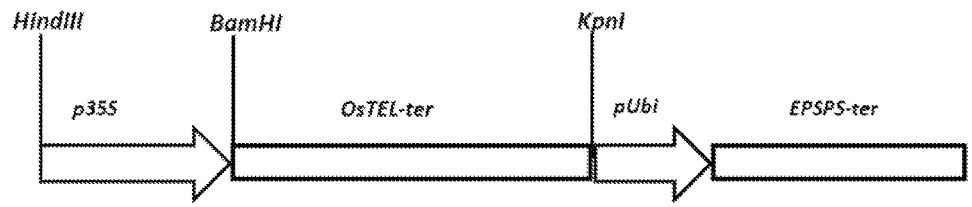

Construction of vector harboring T-DNA with the native OsTEL gene but lacking the 35S enhancer:

Both the 35S promoter and the hptII gene were removed from plasmid pCambia1300 by digestion it with EcoRI and XhoI. Then the glyphosate tolerance expression cassette pUbi-EPSPS, anchored with digestion sites of EcoRI and XhoI on the appropriate ends, was ligated into digested pCambia1300 DNA as described above. The resulting vector pCambia1300-G10 (sequence is shown as SEQ ID NO:49) lacks p35S promoter compared to the vector pCambia1300-355-G10 (as described in the first paragraph of Example 2). pCambia1300-G10 was digested by HindIII and KpnI, and then ligated to the fragment of the OsTEL gene obtained by digesting pCambia1300-35S-G10-OsTEL also with HindIII and KpnI. The resulting vector is pCambia1300-G10-OsTEL. The T-DNA structure of this vector is shown in FIG. 4B.

Construction of vector using p35S to drive the expression of OsTEL: The 35S promoter of CaMV was modified by PCR to have a HindIII and a BamHI site on its 5' and 3' ends respectively. This promoter was ligated to the OsTEL-TER fragment digested with BamHI and KpnI. The 35S promoter and the OsTEL-TER were then ligated into pCambia1300-G10 predigested with HindIII and KpnI, producing the transformation vector pCambia1300-G10-p35S-OsTEL (FIG. 4C).

Transformation vector construction for corn ZmTEL

The corn native ZmTEL gene, including its promoter and terminator, was obtained by PCR amplification. The sequences of PCR primers used are shown in TABLE 3.

TABLE 3

PCR primers used for PCR amplification of ZmTEL gene PCR primers used for ZmTEL cloning in corn

| Primer | Sequence |
|---|---|
| ZmTE-A-F: | 5'-GG<u>AAGCTT</u>GGCGCTTTTTCTGAGTGCCAATCACT* (SEQ ID NO: 71) |
| ZmTE-A-R: | 5'-CAGGCTGGG<u>AAGCTT</u>GTGTGTGTTCTTGCA* (SEQ ID NO: 72) |
| ZmTE-B-F: | 5'-TGCAAGAACACACAC<u>AAGCTT</u>CCCAGCCTG* (SEQ ID NO: 73) |
| ZmTE-B-R: | 5'-GTGAAAAGCATGGCCGAAGTCACTACTGCCTC (SEQ ID NO: 74) |
| ZmTE-C-F: | 5'-CTTCGGCCATGCTTTTCACAGATCCGTAGC (SEQ ID NO: 75) |
| ZmTE-C-R: | 5'-GT<u>GGTACC</u>GAGGTTTGAATTACCCCCCTATTTAAGA# (SEQ ID NO: 76) |

*The underlined part represents HindIII site;
the underlined part represents the KpnI site.

Figure 5:
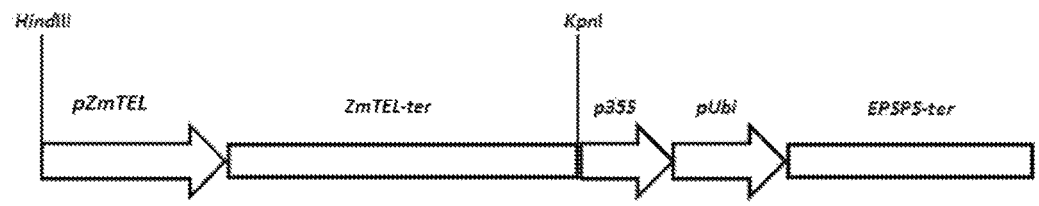
FIG. 5: Diagram of T-DNA of vector pCambia1300-355-G10-ZmTLE for corn transformation. The corn ZmTEL gene includes the promoter (pZmTEL), the protein coding sequence and the terminator (ZmTEL-ter), and its whole polynucleotide sequence is shown as SEQ ID NO: 5.

First, three DNA fragments of corn ZmTEL gene, named as ZmTEL-A, ZmTEL-B and ZmTEL-C, were amplified from the corn genome by PCR with primer pairs ZmTE-A-F abd ZmTE-A-R, ZmTE1-B-F and ZmTE-B-R and ZmTE1-C-F and ZmTE-C-R, respectively. Then, a combined fragment of ZmTEL-B and ZmTEL-C was created by PCR using the combined first round PCR products ZmTEL-B and ZmTEL-C as the template and ZmTE-B-F and ZmTE-C-R as primers. This combined fragment was digested by HindIII and KpnI, and together with the fragment ZmTEL-A digested with HindIII, ligated into plasmid pCambia1300-35S-G10 which had been predigested with HindIII and KpnI. A clone with ZmTEL-A linked to the vector in the correct orientation was selected and named pCambia1300-35S-G10-ZmTEL (FIG. 5). The polynucleotide sequence of corn ZmTEL gene is shown as SEQ ID NO:5.

Example 3

Rice Transformation

Rice transformation via *Agrobacterium*-mediated method is well known in the art. See, for example, Hiei et al. (1997) *Plant Mol Biol* 35:205-218; Hiei et al. (1994) *Plant J* 6:271-282; Nishimura et al. (2007) *Nature Protocols* 1:2796-2802; all of which are herein incorporated by reference.

The four vectors constructed as described in EXAMPLE 2 were transformed into rice "Xiushui 134" using the *Agrobacterium*-mediated transformation method (Lu & Gong (1998) Chinese Bulletin of Life Sciences 10: 125-131 and Liu et al. (2003) Molecular Plant Breeding 1: 108-115). The procedure was slightly modified to accommodate the glyphosate tolerance gene as the selection marker. The calli induced from the mature seeds of "Xiushui 134" were used as the recipient. The single clones of EHA4404 containing the binary vectors of pCambia1300-35S-G10-OsTEL, pCambia1300-G10-OsTEL, pCambia1300-G10-p35S-OsTEL and pCambia1300-35S-G10-ZmTEL1, respectively, were separately cultured for infecting calli. The prepared calli were soaked in the bacteria cell suspension (OD595≈0.4) containing 100 μM of acetosyringone, and co-cultured for 30 min (with occasional shaking) Then, the calli were transferred to the co-culture medium and incubated in dark for 2~3 days at 28° C. After co-cultivation, the calli were rinsed with the sterile water and then cultured in the selective medium with an appropriate concentration of hygromycin for two months at 28° C. in dark (successively cultured once in the middle time). After selection, the vigorously growing transgenic calli were transferred to the pre-differentiation medium for an incubation of about 10 days. Then, the pre-differentiated calli were transferred to the differentiation medium and incubated for differentiating and sprouting at 30° C. with a photoperiod of 16 h. After 2~3 weeks, the resistant regenerating plantlets were transferred to the rooting medium containing 0.1 mg/L glyphosate for seedling invigorating and rooting. The well-grown regenerated plantlets were washed to remove the agar and transplanted to water in a greenhouse for identification. The specific ingredients of the media mentioned in this part are shown in APPENDIX I.

Example 4

Analysis of Transgenic Rice for Yield Enhancement

T-DNA vectors pCambia1300-35S-G10-OsTEL, pCambia1300-G10-OsTEL, pCambia1300-G10-p35S-OsTEL, and pCambia1300-35S-G10-ZmTELwere used to transformed rice XS134 (*O. sativa japonica*) using *Agrobacterium*-mediated transformation. At least 100 independent transgenic events for each construct were obtained. There were events for each construct that showed one or more of the following phenotypes: higher plant height, larger seeds, fewer tiller numbers, and wider curt diameter. Many events produced seeds whose average weight was 30%, 40%, 50%, and even 60% more than the average weight of seeds from control plants. Table 4 summarizes the phenotypes observed among different constructs.

TABLE 4

Phenotypes of transgenic rice expressing OsTEL and ZmTEL.. Parental line for transformation an elite of japonica cultivar "XS-134" developed by Zhejiang Jiaxing Agriculture Academy, Jiaxing, Zhejing, China.

| Vector | Number of Events created | Phenotypes observed |
| --- | --- | --- |
| pCambia1300-35S-G10-OsTEL | 480 | 410 |
| pCambia1300-G10-OsTEL | 300 | 71 |
| pCambia1300-G10-p35S-OsTEL | 200 | 46 |
| pCambia1300-35S-G10-ZmTEL | 270 | 230 |

The results demonstrated that OsTEL can enhance yield when its expression is under the control of various promoters. Both the native promoter and constitutive promoters worked. Furthermore, a CaMV 35S enhancer downstream of the OsTEL or ZmTEL gene increases the frequency of phenotypes in the transgenic events. Also, the expression of the heterologous TEL gene from *Zea mays* in rice can enhance rice yield as well as the endogenous promoter from rice.

The event named OsX-2, transformed with pCambia1300-35S-G10-OsTEL, showed an 18.6% yield increase compared with the non-transgenic control plants under the same agricultural planting conditions and planting density.

Example 5

Corn Transformation and Analysis of Transgenic Corn

1) Corn Transformation

Corn transformation via *Agrobacterium*-medicated method is well established (Frame et al. 2002, Plant Physiol. 129: 13-22. Glyphosate was used as the selection agent in this experiment. Briefly, *Agrobacterium tumefaciens* strain LBA4404, containing T-DNA construct pCambia1300-35S-G10-ZmTEL and pCambia1300-35S-G10-OsTEL respectively, was prepared to transform corn embryos 8-10 days after fertilization (1.0-1.5 mm in length). The embryos were incubated with *Agrobacterium* for 2-3 days at 22° C., and then moved to callus induction media containing Timentin at 200 mg/L). After dark culture for 10-14 days at 28° C., the calli were moved to selection media containing 2 mM glyphosate, and continued to be culture for 2-3 weeks at 28° C. After another 2-3 weeks culture on renewed glyphosate selection media, the surviving calli were moved to regeneration media, and cultured for 10-14 days then moved to fresh regeneration media for another 10-14 days. The shoots generated were then moved to rooting media containing 0.1 mM glyphosate. The surviving plantlets were moved to a greenhouse for growth and to produce seeds.

2) Analysis of Transgenic Corn

Figure 12:
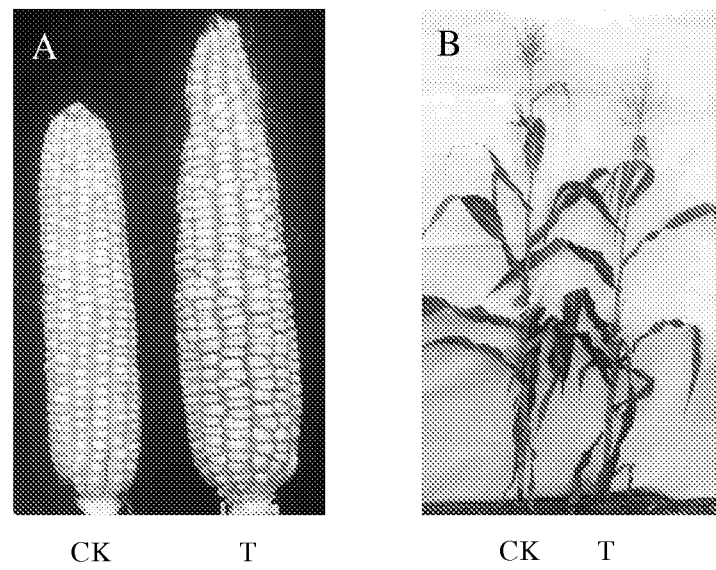
FIG. 12: A comparison of the phenotypes of the transgenic corn (T) with ZmTEL gene and the non-transgenic parental line in EXAMPLE 5. Compared to the control plants (CK), the transgenic lines (T) showed significant increased plant height (see B), and enlarged seeds and cobs (see A).

About 120 events were obtained each from pCambia1300-35S-G10-ZmTEL and pCambia1300-35S-G10-OsTEL. About 80 events from both constructs showed one or more of the following phenotypes: Faster and more robust growth, taller plant height, larger ears, and bigger kernels (FIG. 12).

Events TE13 and TE31, transformed with pCambia1300-35S-G10-ZmTEL, showed 25.5% and 21.9% more weight per ear than the control corn plants. Real-time PCR analysis of ZmTEL gene expression indicated that the expression of ZmTEL was significantly enhanced in both TE13 and TE31. The amount of mRNA of ZmTEL in both TE13 and TE31 was about 40 times the level found in control plant leaves at the flowering stage.

Example 6

Cloning and Vector Construction of TEL Genes from Different Plant Species

Based on analysis of genes homologous to TEL found searching databases of genes of different plants, PCR primers for cloning of the TEL gene homologues were designed (shown in Table 5). Using the genomes of different plants as the templates and the proper primers, the full length TEL genes, including the promoter region, the coding sequence, and the terminator, were separately amplified through PCR from various plants. The technique of plant genome extraction is described before (Allen G C et al. 2006, Nat. Protoc. 1:2320-2325). The PCR reactions were carried out following standard procedures, essentially as described as in EXAMPLE 1.

TABLE 5

Primers used for cloning of TEL genes of various plants PCR primers used for TEL cloning in different plants

| Primer | Sequence* | Enzyme digestion site |
|---|---|---|
| GhTEL1-F | CTGCAGGACATTAGAGTTAGG ACCTTATGGAACATGA (SEQ ID NO: 77) | PstI |
| GhTEL1-R | GGTACCACGAGCTAATCTCTA TCTGTTAACCAGA (SEQ ID NO: 78) | KpnI |
| GhTEL2-F | AAGCTTCTAAGCACAAATTTG ACTTAG (SEQ ID NO: 79) | HindIII |
| GhTEL2-R | GGTACCTCACCAACTAGTTGA ATTAATGGTGACA (SEQ ID NO: 80) | KpnI |
| AtTEL1-F | GGGGTACCCCCGAAAAGAATC ATACTTGTAGAACA (SEQ ID NO: 81) | KpnI |
| AtTEL1-R | GGGGTACCATAAGATTAAAGT TGTAGTCAACCATCACTATC (SEQ ID NO: 82) | KpnI |
| AtTEL2-F | GGAAGCTTGGTCGAGACATGG TACTGAGTAAAACCCTA (SEQ ID NO: 83) | HindIII |
| AtTEL2-R | GGAAGCTTAACCTGAACAAGC AAAAAAACACTCACATC (SEQ ID NO: 84) | HindIII |

TABLE 5-continued

Primers used for cloning of TEL genes of various plants PCR primers used for TEL cloning in different plants

| Primer | Sequence* | Enzyme digestion site |
|---|---|---|
| BrTEL-F | AAGCTTGAACGATTAGGCTGT TGTAGG (SEQ ID NO: 85) | HindIII |
| BrTEL-MR | GGATCCGATGGAGATAGTCCG TACGACG (SEQ ID NO: 86) | BamHI |
| BrTEL-MF | GGATCCAAGAATGTTCACGTT CTTTAATATCCC (SEQ ID NO: 87) | BamHI |
| BrTEL-R | GGTACCTAAATGAATTTGTGT TGTTGGATTTGG (SEQ ID NO: 88) | KpnI |
| TaTEL-F | AAGCTTGTGCAGTGAGTTGGA GAGCAACTTTGC (SEQ ID NO: 89) | HindIII |
| TaTEL-MR | GAGGTCAAAGAAGTGCACTGT GGCCACG (SEQ ID NO: 90) | ApaLI |
| TaTEL-MF | CGTGGCCACAGTGCACTTCTT TGACCTC (SEQ ID NO: 91) | ApaLI |
| TaTEL-R | GGTACCCATCACCCGCATGAT ATATTTTCATACTACG (SEQ ID NO: 92) | KpnI |
| GmTEL1-F | GTCGACTTAACACCAAAACAA ACATGCAGTATCT (SEQ ID NO: 93) | SalI |
| GmTEL1-R | GTCGACCATGTTTATTACCTA AATCTCCTACATCGA (SEQ ID NO: 94) | SalI |
| GmTEL2-F | AAGCTTGGAAATGGAAATCTA AGGGATAAAGCAG (SEQ ID NO: 95) | HindIII |
| GmTEL2-R | GTCGACGTGAGAATCATAATA CAGCTAGGATTTCTCTA (SEQ ID NO: 96) | SalI |

*The underlined parts represent the enzyme digestion sites. Cloning of the TEL homologous genes from cotton.

Two homologous genes of TEL were found from the genome of *Gossypium raimondii* published online through sequence alignment. Two pairs of primers, GhTEL1-F/GhTEL1-R and GhTEL2-F/GhTEL2-R (see TABLE 5), were designed based on the sequences of these two genes. Using the genomic DNA of the local cotton species *Gossypium hirsutum* as template, two TEL DNA fragments of GhTEL1 and GhTEL2 were amplified through PCR with primer pairs GhTEL1-F/GhTEL1-R and GhTEL2-F/GhTEL2-R, respectively. The obtained DNA fragments including promoter, coding region, and terminator, were named pGhTEL1-GhTEL1-ter and pGhTEL2-GhTEL2-ter respectively (sequences are shown in SEQ ID NO:17 and SEQ ID NO:19).

Figure 6:
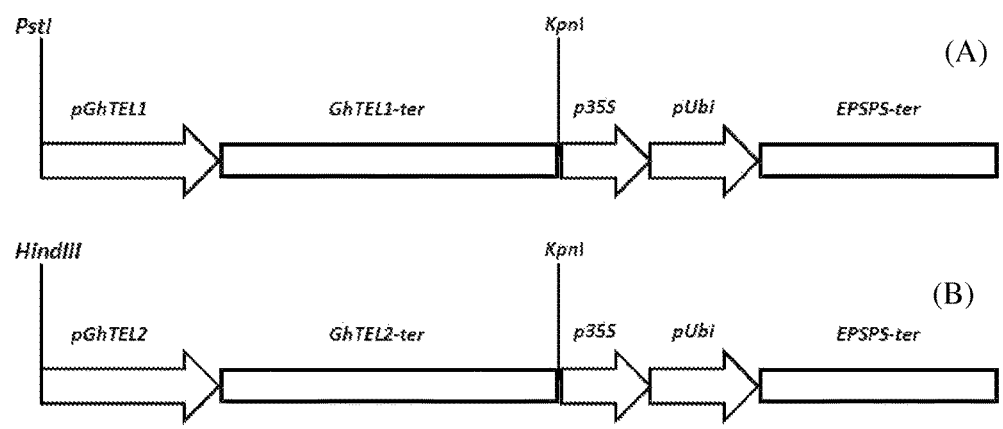
FIG. 6: Diagram of T-DNA structure for cotton transformation. A: pCambia1300-35S-G10-GhTLE1; B: pCambia1300-35S-G10-GhTEL2. Both GhTEL1 and GhTEL2 genes include a promoters (pGhTEL1 and pGhTEL2), the protein coding sequence and a terminator s(GhTEL1-ter and GhTEL2-ter). The whole polynucleotide sequences of the two expression cassette are shown as SEQ ID NO: 17 and SEQ ID NO: 19, respectively.

The ends of pGhTEL1-GhTEL1-ter were separately anchored with a PstI and a KpnI sites through PCR. Similarly, a HindIII and a KpnI sites were added onto the ends of pGhTEL2-GhTEL2-ter. The pGhTEL1-GhTEL1-ter fragment was cut by PstI and KpnI double-enzyme digestion and then cloned into the plasmid pCambia1300-35S-G10 between its PstI and the KpnI sites, generating a new plasmid named pCambia1300-35S-G10-GhTEL1, the T-DNA structure of which was shown in FIG. 6(A). Similarly, using HindIII and KpnI, the pGhTEL2-GhTEL2-ter fragment was double-digested and then cloned into the HindIII and the KpnI sites of pCambia1300-35S-G10, generating vector pCambia1300-35S-G10-GhTEL2 with its T-DNA structure shown in FIG. 6(B).

Cloning of the TEL genes from *Arabidopsis thaliana*.

Two homologous genes of TEL were found from the genome of *Arabidopsis thaliana* (published online) through sequence alignment. Two pairs of primers, AtTEL1-F&AtTEL1-R and AtTEL2-F&AtTEL2-R (see TABLE 5), were designed based on the sequences of these two genes. The genome DNA of *Arabidopsis thaliana* was used as template. Two TEL-1 like genes of AtTEL1 and AtTEL2 were amplified through PCR with primer pairs of AtTEL1-F&AtTEL1-R and AtTEL2-F&AtTEL2-R, respectively. The resulting DNA fragments including promoter, coding region, and terminator, were separately called as pAtTEL1-AtTEL1-ter and pAtTEL2-AtTEL2-ter, whose sequences were shown in SEQ ID NO:21 and SEQ ID NO:23.

Figure 7:
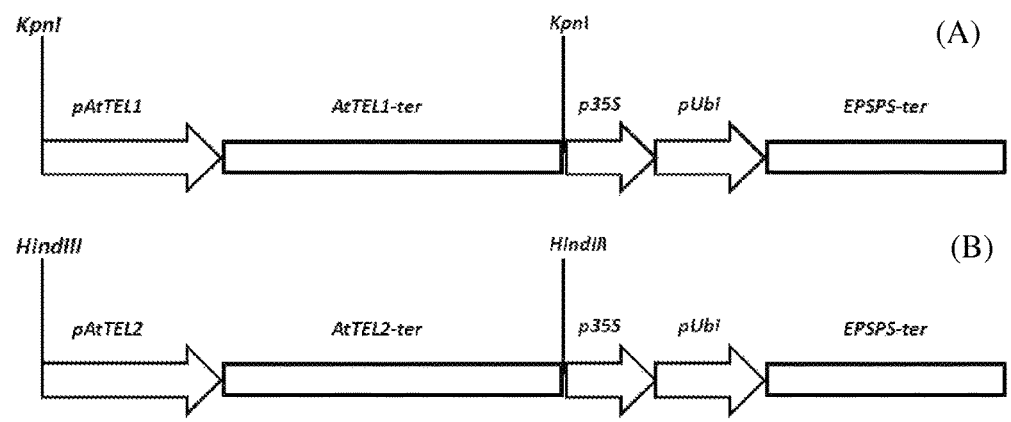
FIG. 7: Diagram of T-DNA structure of the vectors pCambia1300-35S-G10-AtTLE1(A) and pCambia1300-35S-G10-AtTEL2(B) for canola transformation. The *Arabidopsis thaliana* AtTEL1 and AtTEL2 genes both include the promoters (pAtTEL1 and pAtTEL2), the protein coding sequences and the terminators (AtTEL1-ter and AtTEL2-ter), and their whole polynucleotide sequences are shown as SEQ ID NO: 21 and SEQ ID NO: 23, respectively.

The ends of pAtTEL1-AtTEL1-ter were both anchored with a KpnI sites through PCR. The pAtTEL1-AtTEL1-ter fragment was digested by KpnI and then inserted into the plasmid of pCambia1300-35S-G10 at its KpnI site. A new plasmid named pCambia1300-35S-G10-AtTEL1 was generated, the T-DNA structure of which is shown in FIG. 7(A). Similarly, a HindIII site was added on both ends of pAtTEL2-AtTEL2-ter. The HindIII digested fragment pAtTEL2-AtTEL2-ter was inserted into plasmid pCambia1300-355-G10 at its HindIII site. The resulting vector was pCambia1300-355-G10-AtTEL2 and its T-DNA structure was shown in FIG. 7(B).

Cloning of the TEL gene from *Brassica*.

One TEL gene was found from the genome of *Brassica rapa* through sequence blast search. The BrTEL gene was divided into two parts for PCR cloning, one (named as BrTEL-A) includes the promoter and a partial coding region, and the other one (named as BrTEL-B) includes the rest part of the coding region and the terminator. Two pairs of primers, BrTEL-F/BrTEL-MR and BrTEL-MF/BrTEL-R (TABLE 5), were designed based on the sequences of the BrTEL gene. BrTEL-A and BrTEL-B were separately amplified from the genome DNA of *Brassica rapa* with primer pairs of BrTEL-F/BrTEL-MR and BrTEL-MF/BrTEL-R, respectively.

Figure 8:
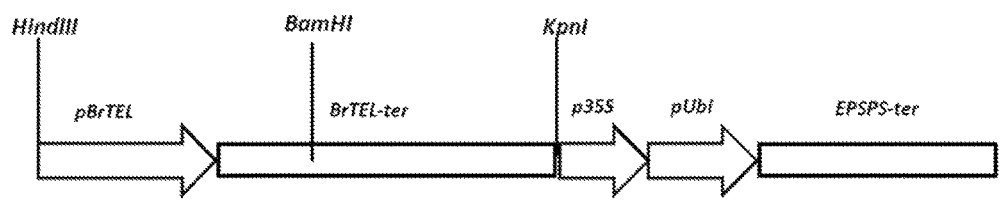
FIG. 8: T-DNA structure of vector pCambia1300-355-G10-BrTEL for canola transformation. The BrTEL gene includes the promoter (pBrTEL), the protein coding sequence and the terminator (BrTEL-ter), and its whole polynucleotide sequence is shown as SEQ ID NO:45.

By PCR, the ends of BrTEL-A were anchored with a HindIII and a BamHI site, respectively. At the same time, the BrTEL-B was anchored with a BamHI and a KpnI sites on its ends, respectively. The HindIII/BamHI double-digested BrTEL-A and BamHI/KpnI double-digested BrTEL-B were then cloned in a three-way ligation into the plasmid of pCambia1300-35S-G10 between site HindIII and KpnI. The vector pCambia1300-355-G10-BrTEL was constructed, and its T-DNA structure was shown in FIG. 8. The whole nucleotide sequence of the cloned BrTEL gene was shown as SEQ ID NO:45.

Cloning of the TEL gene from wheat.

The methods of the TEL gene searching and PCR primer designing in wheat were the same as those described above. The *Triticum aestivum* TaTEL gene was divided into two parts for PCR amplification, one (named as TaTEL-A) includes the promoter and partial coding region, and the other one (named as TaTEL-B) includes the rest part of the coding region and the terminator. Two pairs of primers, TaTEL-F/TaTEL-MR and TaTEL-MF/TaTEL-R (TABLE 5), were designed to amplify TaTEL-A and TaTEL-B separately from the genome of *Triticum aestivum* with primer pairs of TaTEL-F/TaTEL-MR and TaTEL-MF/TaTEL-R, respectively.

Figure 9:
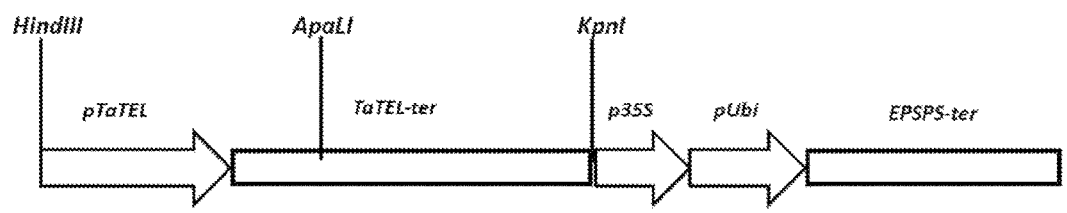
FIG. 9: T-DNA structure of wheat transformation vector pCambia1300-35S-G10-TaTEL. The wheat TaTEL gene includes the promoter (pTaTEL), the protein coding sequence and the terminator (TaTEL-ter), and its whole polynucleotide sequence is shown as SEQ ID NO:9.

Using PCR, the ends of TaTEL-A were anchored with a HindIII and an ApaLI sites, respectively. At the same time, the TaTEL-B was anchored with an ApaLI and a KpnI sites on its ends, respectively. The TaTEL-A double-digested by HindIII and ApaLI and TaTEL-B double-digested by ApaLI and KpnI were then cloned in a three way ligation into plasmid pCambia1300-35S-G10 between HindIII and KpnI sites. The resulting vector pCambia1300-35S-G10-TaTEL was constructed; its T-DNA structure is shown in FIG. 9. The whole nucleotide sequence of the cloned TaTEL gene is shown as SEQ ID NO:9.

Cloning of the TEL genes from soybean.

There are two TEL genes in the soybean (*Glycine max*) genome. The two genes were amplified from genomic DNA of *Glycine max* using PCR with primer pairs of GmTEL1-F/GmTEL1-R, and GmTEL2-F/GmTEL2-R (see TABLE 5), respectively. The acquired DNA fragments, including their promoter regions, coding regions, and terminators, were separately named pGmTEL1-GmTEL1-ter and pGmTEL2-GmTEL2-ter, and their entire nucleotide sequences are shown in SEQ ID NO:13 and SEQ ID NO:15.

Figure 10:
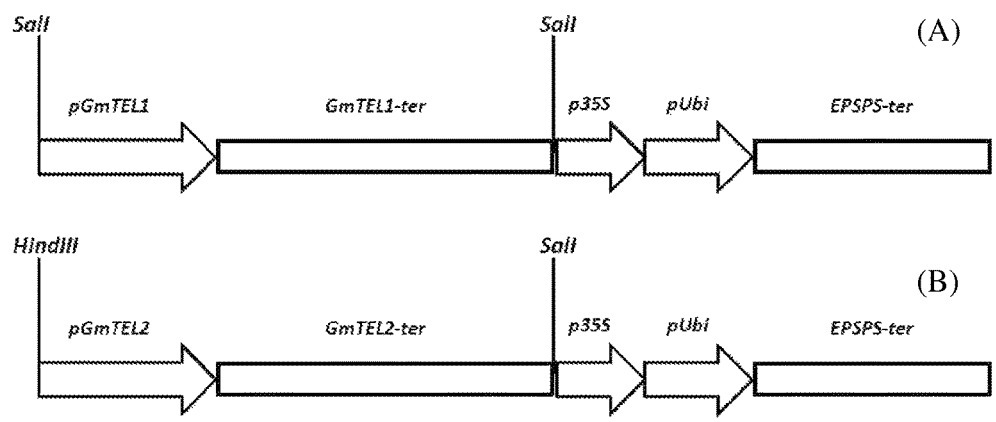
FIG. 10: T-DNA structures of soybean transformation vectors pCambia1300-35S-G10-GmTLE1 (A) and pCambia1300-35S-G10-GmTEL2 (B). The soybean GmTEL1 and GmTEL2 genes both include the promoters (pGmTEL1 and pGmTEL2), the protein coding sequences and the terminators (GmTEL1-ter and GmTEL2-ter), and their whole polynucleotide sequences are shown as SEQ ID NO:13 and SEQ ID NO:15, respectively.
Figure 11:
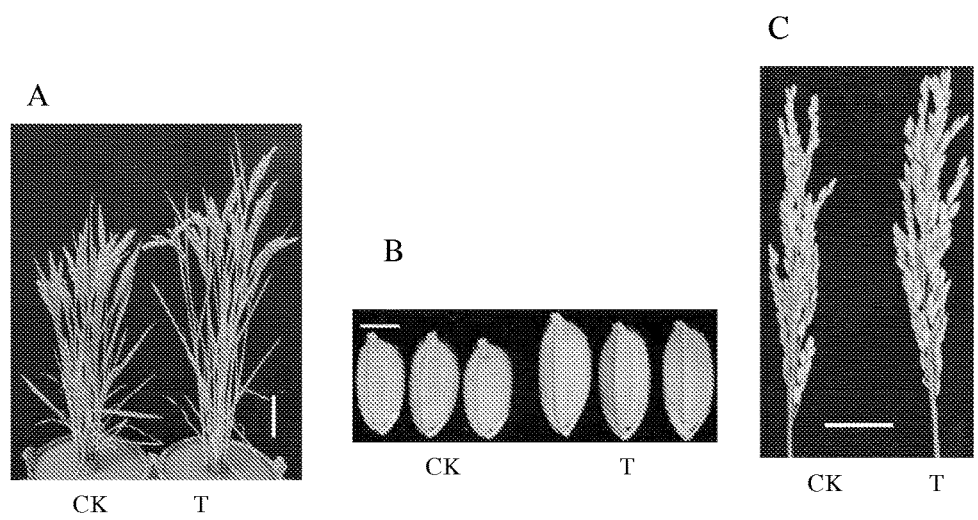
FIG. 11: A comparison of the phenotypes of the transgenic rice (T) with OsTEL-1 gene and the non-transgenic parental line "Xiushui 134" (CK). Compared to the control plants (CK), the transgenic lines (T) showed significant increased plant height(see A), and enlarged seeds(see B) and panicles (see C).

The ends of both fragments were anchored with a SalI site through PCR. The fragment pGmTEL1-GmTEL1-ter was digested by SalI and then inserted into the plasmid pCambia1300-35S-G10 at its SalI site. The resulting plant transformation vector pCambia1300-35S-G10-GmTEL1 was constructed, the T-DNA structure of which was shown in FIG. 10(A). Similarly, a HindIII site and a SalI site were added onto the ends of pGmTEL2-GmTEL2-ter, respectively. The HindIII/SalI double-digested fragment pGmTEL2-GmTEL2-ter was inserted into plasmid pCambia1300-35S-G10 between its HindIII and SalI sites. The resulting vector was pCambia1300-35S-G10-GmTEL2 and its T-DNA structure is shown in FIG. 10(B).

Using technical procedures outlined above, or comparable procedures known in the art, TEL gene homologues can be isolated and characterized from any plant species, including, but not limited to, monocots, dicots, angiosperms, and gymnosperms. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, apple, pear, peach, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape., etc.).

Energy crops, including but not limited to switchgrass, *Arundo*, Camelina, Jatropha, and miscanthus.

Example 7

Sequence Analysis of TEL Genes from Plants

By searching the databases and using PCR based cloning, putative Mei2-like genes from various plant species were obtained. The encoded amino acid sequences of these TEL genes are listed in SEQ ID NOs:2, 6, 8, 10, 12, 14, 16, 18, 20, 22, 24, 26, 28, 30, 32, 34, 36, 38, 40, 42, 44, and 46. As listed above, there are many AML genes from various plants that can be identified in databases. A dendrogram was constructed by Vector NT based on amino acid sequence alignment of the selected AML proteins and TEL proteins (FIG. 1). There are two distinct groups in the dendrogram, the AML group, and the TEL group. Therefore, the TEL genes and the AML genes from plants can be distinguished by phylogenetic analysis based on their amino acid sequences.

The TEL proteins discovered from various plant species share significant similarity to each other. However, the most conserved part of the TEL proteins from plants is the RRM3 region (FIG. 2). Compared to the AML proteins, two of the most striking features of the TEL proteins are the additional region of TEL-specific motif inside the RRM3 domain (FIG. 2) and the conserved element outside the C-terminus of RRM3 (FIG. 2). The AML proteins and the yeast Mei2 protein do not have either of these two features. Interestingly, the Mei2-like protein from *O. tauri* contains a conserved C-terminal TEL sequence motif while it does not have the TEL-specific motif inside the RRM3 domain. *O. tauri* is a unicellular species of marine green alga, belonging to the Prasinophyceae, an early-diverging class within the green plant lineage. Likely, the Mei2-like protein from *O. tauri* represents a common ancestor to both of the TEL and the AML proteins of modern plants.

The motif composing of part of the RRM3 and its C-terminal outside conservative region (SEQ ID NO:4 in rice TEL) is highly conserved among different plant TEL proteins. The sequence identity of this motif among different TEL proteins from different plant species is 68% or higher. This motif from rice TEL shares 59% identity with the motif from the 0. tauri Mei2-like protein. However, this motif shares amino acid sequence identity of less than 58% with any motif from any plant AML proteins.

The RRM3 domain of the yeast Mei2 protein is the critical domain for functions 0. Thus, the RRM3 of plant TEL proteins may also play an important role in enhancing yield. However, the RRM3 only does not retain TEL function in transgenic rice study. Thus, in addition to the RRM3 domain, the conserved region outside the C-terminus of RMM3 may be also critical for its biological functions.

Example 8

Generation of Antibodies Against Plant TEL Proteins and their Use for TEL protein detection The cDNA encoding the full-length of the OsTEL protein was obtained by RT-PCR using primers OsTEL-f (5' GGATCCATGGAGGAAGGAGGTGGGAGTGGC) (SEQ ID NO:97) and OsTEL-r (5' CTCGAGCTAGTCAGTGTAGCCTAGGCGCTGTAGC) (SEQ ID NO:98). The PCR product was cloned into pET32b (Novagen) using restriction enzyme sites BamHI and XhoI, resulting in expression vector pET32b-OsTEL. The cDNA sequence was fully determined (SEQ ID NO:56), and then use for expression in *E. coli*. The expressed protein was then purified and used to immunize rabbits by an antibody service company in Hangzhou. Antiserum was collected from the immunized rabbits.

The obtained antiserum was used to detect OsTEL protein in both transgenic rice expressing the additional OsTEL gene and non-transgenic rice with only the endogenous OsTEL expression. Significantly more OsTEL protein was detected in transgenic rice lines.

Example 9

Genetic Transformation of Canola

The technique of rape transformation is well known in the art. The cotyledon, hypocotyl, and stem of rape have all been used as target tissue for transformation by various researchers. For example, Moloney et al. (1989) found that the cut end of cotyledon petioles was easily transformed using *Agrobacterium* binary vectors. Pua et al. (1987) developed a regeneration system of stem sections with a rate of transformation up to 10%. Moloney et al (1989) raised the rate of transformation to 55% using the petiole as target tissue.

The detailed procedure for rape transformation used herein was as following. The seed of rape was sterilized using 0.5% mercuric chloride for 10 minutes, then washed with sterile water 3-4 times, and incubated on MS medium (30 g/L sucrose and 6 g/L agar). After incubating in dark for two days, the seed was transferred to an incubator with a photoperiod of 16 h light: 8 h dark. After 6-8 days, the hypocotyl of the sterile seedling was cut down as receptor for genetic transformation. The hypocotyl was transformed onto pre-incubating solid MS medium (1.0 mg/L 2, 4-D, 1.0 mg/L 6BA, 30 g/L sucrose, and 6 g/L agar) for 72 h in dark. The pre-incubated hypocotyl was immersed into a cell suspension of *Agrobacterium* containing the plasmid of pCambia1300-35S-G10-BrTEL for 8-10 minutes, and then transferred onto solid MS medium (1.0 mg/l 2, 4-D, 1.0 mg/l 6BA, 100 M As, 30 g/l sucrose, and 6 g/l agar) (after the excess *Agrobacterium* suspension was absorbed using sterile absorbent paper) and subsequently cultured for 48 h in the dark.

After being washed by sterile water containing 500 mg/l cephaloglycin, the co-incubated hypocotyl was transferred onto selective solid MS medium (1.0 mg/L 2, 4-D, 1.0 mg/L 6BA, 12 mM glyphosate, 500 mg/L cephaloglycin, 30 g/L sucrose, and 8 g/L canakeo) for at least 14 days in light, and then subcultured on the differentiation solid MS medium (2.0 mg/L ZT, 4.0 mg/L 6BA, 5 mg/L AgNO3, 12 mM glyphosate, 500 mg/L cephaloglycin, 30 g/L sucrose, and 8 g/L canakeo) in light, successively transferred every two weeks until resistant seedlings grew. The resistant seedlings were transferred onto the stem-differentiation solid MS medium (2.0 mg/L ZT, 3.0 mg/L 6BA, 5 mg/L AgNO3, 2 mM glyphosate, 500 mg/L cephaloglycin, 30 g/L sucrose, and 8 g/L canakeo) and incubated in light. When the stem grew up to 1 cm, it was cut off and put on the rooting solid MS medium (0.2 mg/L IBA, 30 g/L sucrose, and 8 g/L canakeo) for a 7-day incubation till the roots of the stem grew.

Example 10

Soybean Transformation

The procedure to obtain transgenic soybeans used here is the existing technology (Deng et al., 1998, Plant Physiology Communications 34: 381-387; Ma et al., 2008, Scientia Agricultura Sinica 41: 661-668; Zhou et al., 2001, Journal of Northeast Agricultural University 32: 313-319). The healthy, plump and mature soybeans were selected, disinfected in 80% ethanol for 2 minutes, cleaned by bacteria free water, and sterilized in a dryer filled with chlorine (generated by the chemical reaction of 50 ml NaClO and 2 ml concentrated HCl) for 4-6 hours. The sterile soybeans were sowed into B5 medium in a bechtop and incubated at 25° C. for 5 days with a light intensity of 90-150 µmol photons m-2 s-1. When the cotyledon turned green and the seed husk cracked, the sterile bean sprout was picked out. The epicotyl and hypocotyl removed bean sprout was longitudinally cut in fifty-fifty, resulting into two pieces of explant with both cotyledon and epicotyl. The explant was scratched at the node of cotyledon and epicotyl for 7-8 cuts and used as the target tissue for infection.

Single colonies of *Agrobacterium* containing vector pCambia1300-35S-G10-GmTEL1 and pCambia1300-35S-G10-GmTEL2, respectively, were separately cultured for use. The prepared explants were soaked in the *Agrobacterium* cell suspension for 30 min. Then the infected tissues were transferred to the 1/10 B5 co-culture medium after the excess cell suspension was removed using a clean sterile filter paper, and incubated at 25° C. for 3-5 days in the dark.

The co-cultured tissues were washed by B5 liquid medium to remove the *Agrobacterium*, and then put on the solid B5 medium for an incubation of 5 days at 25° C. for sprouting. The induced plumule tissues were transferred to selective B5 medium containing 0.1-0.5 mM glyphosate and incubated at 25° C. in the light for 4 weeks, with the medium changed every 2 weeks. The selected plumule tissues were transferred to the solid MS medium for seedling culture at 25° C. with light. Then, the transgenic seedlings were transferred to ½ B5 medium for root induction. Finally, the generated plantlets were washed to remove the agar and planted in the greenhouse for further characterization.

Example 11

Enhancement of TEL Gene Expression by Insertion of Enhancers Near Endogenous Genes In genetics, an enhancer is a short region of DNA that can be bound with proteins (namely, the trans-acting factors, much like a set of transcription factors) to enhance transcription levels of genes (hence the name) in a gene cluster. While enhancers are usually cis-acting, an enhancer does not need to be particularly close to the genes it acts on, and sometimes need not be located on the same chromosome. (Spilianakis et al. (2005) *Nature* 435 (7042): 637-45. doi: 10.1038/nature03574. PMID 15880101) An enhancer may be located upstream or downstream of the gene it regulates. Furthermore, an enhancer need not be located near to the transcription initiation site to affect transcription, as some have been found located in several hundred thousand base pairs upstream or downstream of the start site. Enhancers do not act on the promoter region itself, but are bound by activator proteins. These activator proteins interact with the mediator complex, which recruits polymerase II and the general transcription factors which then begin transcribing the genes. Enhancers can also be found within introns. An enhancer's orientation may even be reversed without affecting its function. Additionally, an enhancer may be excised and inserted elsewhere in the chromosome, and still affect gene transcription.

The region downstream of the TEL gene of *Zea mays* was selected to insert an expression cassette containing a double 35S enhancer by TALEN method. The targeted region was: Ctgtttatacaagagccctatcaatgatggcctaaatacggagactactagat-caactaac (SEQ ID NO:58). Other nearby regions would also suffice for enhancer insertion. The expression cassette of a G10evo gene (EPSPS, SEQ ID NO:48) has a double 35S promoter, which contains two 35S enhancers. The G10evo EPSP synthase provides glyphosate tolerance as a selectable marker for transformation, while the 35S promoter provides an enhancer element to enhance expression of the TEL gene that is located in an adjacent region.

To construct a transformation vector, a DNA fragment composed of the G10evo expression cassette and the sequences flanking each side of the target sequence in corn was constructed (SEQ ID NO: 59). This fragment has a XhoI site and KpnI site at its ends and was cloned into pCambia1300 predigested with the same two enzymes, XhoI and KpnI. The resulting vector is named pCambia1300-355-G10-Rec.

The targeted sequence in the maize genome (SEQ ID NO: 58) is about 3 kb downstream of TEL gene. Based on this target sequence, a pair of designer TALENs, TALEN-F and TALEN-R, are designed and synthesized. The expression cassettes of TALEN-F and TALEN-R are constructed using the CaMV 35S promoter and rice actin promoter respectively. The DNA sequences of the expression cassettes containing TALEN-L and TALEN-R are shown in SEQ ID NO:60 and SEQ ID NO:61, respectively. The DNA fragment of TALEN-F cassette, which has a HindIII and EcoRI restriction site at its ends, and the DNA fragment of TALEN-R cassette, which has an EcoRI and KpnI restriction site at its ends, are ligated in a three-way ligation into pCambia1300-355-G10-Rec predigested by HindIII and KpnI. The resulting vector pCambia1300-355-G10-Rec-TALEN-FR contains both expression cassettes of TALEN-F and TALEN-R (Fig X).

pCambia1300-35S-G10-Rec-TALEN-FR is transformed into *Agrobacterium tumefaciens* LBA4404 and used to transform corn. Selection media containing 2 mM glyphosate is used for callus culture selection. The resulting transgenic corn plants are screened for events that have been correctly inserted in the target area by PCR method.

Other methods of targeted gene insertion known in the art can be used to introduce a transcriptional enhancer into the region near the TEL gene of a desired plant species. In this manner, the expression of the endogenous gene can be increased over normal endogenous levels, resulting in enhanced plant vigor and increased yield. This methods of enhancing yield can be used alone or in conjunction with heterologous genes to produce plants with increased vigor and/or yield.

The following sequences are included in the sequence listing:

| SEQ ID NO: | Gene/Protein ID | DNA/ mRNA/ protein |
|---|---|---|
| 1 | Oryza sativa TELGene | DNA |
| 2 | Oryza sativa TEL | Protein |
| 3 | Conserved Oryza sativa TEL motif | cDNA |
| 4 | Conserved Oryza sativa TEL motif (91 aa) | Protein |
| 5 | Zea mays TEL (genomic sequence with promoter and NA terminator) | DNA |
| 6 | Zea mays TEL | Protein |

| SEQ ID NO: | Gene/Protein ID | DNA/ mRNA/ protein |
|---|---|---|
| 7 | Sorghum Bicolor TEL (genomic) | DNA |
| 8 | Sorghum Bicolor TEL | Protein |
| 9 | Triticum aestivum TaTEL (genomic sequence with promoter and terminator) | DNA |
| 10 | Triticum aestivum TEL | Protein |
| 11 | Brachypodium distachyon TEL | cDNA |
| 12 | Brachypodium distachyon TEL | protein |
| 13 | Glycine max GmTEL1 (genomic sequence with promoter and terminator) | DNA |
| 14 | Glycine max TEL1 | protein |
| 15 | Glycine max GmTEL2 (genomic sequence with promoter and terminator- | DNA |
| 16 | Glycine max TEL2 | Protein |
| 17 | Gossypium herbaceum GhTEL1 (genomic sequence with promoter and terminator) | DNA |
| 18 | Gossypium herbaceum GhTEL1 | protein |
| 19 | Gossypium herbaceum GhTEL2 (genomic sequence with promoter and terminator) | DNA |
| 20 | Gossypium herbaceum TEL2 | protein |
| 21 | Arabidopsis thaliana AtTEL1 (genomic sequence with promoter and terminator) | DNA |
| 22 | Arabidopsis thaliana s TEL1 | Protein |
| 23 | Arabidopsis thaliana AtTEL2 (genomic sequence with promoter and terminator | DNA |
| 24 | Arabidopsis thaliana TEL2 | Protein |
| 25 | Arabidopsis lyrata TEL | cDNA |
| 26 | Arabidopsis lyrata TEL | Protein |
| 27 | Medicago truncatula TEL | cDNA |
| 28 | Medicago truncatula TEL | Protein |
| 29 | Ricinus communis TEL | cDNA |
| 30 | Ricinus communis TEL | Protein |
| 31 | Populus tremula x Populus alba TEL1 | DNA |
| 32 | Populus tremula x Populus alba TEL1 | Protein |
| 33 | Populus tremula x Populus alba TEL2 | DNA |
| 34 | Populus tremula x Populus alba TEL2 | Protein |
| 35 | Selaginella moellendorffii TEL | cDNA |
| 36 | Selaginella moellendorffii TEL | Protein |
| 37 | Vitis vinifera TEL2 | cDNA |
| 38 | Vitis vinifera TEL2 | Protein |
| 39 | Vitis vinifera TEL1 | cDNA |
| 40 | Vitis vinifera TEL1- | Protein |
| 41 | Physcomitrella patens TEL1 | DNA |
| 42 | Physcomitrella patens TEL1 | protein |
| 43 | Ostreococcus tauri Mei2L | cDNA |
| 44 | Ostreococcus tauri Mei2L | protein |
| 45 | Brassica rapa TEL (BrTEL genomic sequence with promoter and terminator) | DNA |
| 46 | Brassica Rapa TEL | Protein |
| 47 | pCambia 1300-35S-G10 (modified pCambia1300 vector) | Vector |
| 48 | G10evo (EPSPS for glyphosate tolerance) | DNA |
| 49 | pCambia 1300-G10 (without p35S) | Vector |
| 50 | Left border sequence of T-DNA of HAS-20 | T-DNA |
| 51 | Right border sequence of T-DNA of HAS-20 | T-DNA |
| 52 | Oryza sativa TEL promoter | DNA |
| 53 | Zea mays TEL promoter | DNA |
| 54 | Triticum aestivum TEL promoter | DNA |
| 55 | Sorghum Bicolor TEL promoter | DNA |
| 56 | cDNA of OsTEL | cDNA |
| 57 | cDNA of ZmTEL | cDNA |
| 58 | The targeted sequence by TALEN | DNA |
| 59 | Expression cassette of EPSPS with 35S promoter, and flanking with corn sequence at each side for sequence specific recombination | DNA |
| 60 | TALEN-L (expression cassette) (35S promoter + CDS + 35S terminator) | DNA |
| 61 | TALEN-R (expression cassette) ( rice actin promoter + TALEN-R + 35S terminator) | DNA |

The invention used many techniques in molecular biology, biochemistry and tissue culture. These techniques are available in the art. Detailed methods of the techniques can be referenced in Current Protocols in Molecular Biology (ed. by Ausubel, John Wiley and Sons Pres) and Molecular Cloning: A Labortory Manual, 3rd ED (ed. by J. Sambrook, Cold Spring Harbor Laboratory Press (2001).

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for increasing seed yield in a monocot plant, said method comprising:
   (a) transforming monocot plants with a DNA construct comprising a heterologous promoter that drives expression in a monocot plant operably linked to a Terminal Earl-Like (TEL) nucleotide sequence, wherein said TEL nucleotide sequence encodes a protein comprising an amino acid sequence having at least 95% amino acid sequence identity to the SEQ ID NO: 2; and
   (b) selecting a monocot plant obtained from step (a) transformed with said DNA construct which overexpresses said protein, and exhibits increased seed yield in the selected transgenic monocot plant as compared to a wild type monocot plant of the same species which is grown under the same growth conditions,
   wherein expression of said TEL nucleotide sequence in said selected monocot plant increases the production of TEL mRNA by 5-fold to 50-fold when compared to a control monocot plant of the same monocot plant species lacking said DNA construct and grown under the same conditions, wherein said selected transformed monocot plant is rice or corn, wherein said selected transformed rice or corn plant exhibits seed yield of at least 5% to 30% more than a control rice or corn plant lacking said DNA construct and grown under the same conditions.

2. The method of claim 1, wherein said DNA construct further comprises at least one enhancer that enhances expression of a gene in a monocot plant, and wherein said enhancer is operably linked to said heterologous promoter and said TEL nucleotide sequence.

3. The method of claim 2, wherein said at least one enhancer is a 35S enhancer from cauliflower mosaic virus (CaMV).

4. The method of claim 2, wherein said heterologous promoter is a TEL promoter.

5. The method of claim 2, wherein said TEL nucleotide sequence encodes a protein comprising an amino acid sequence that has at least 97% amino acid sequence identity with the SEQ ID NO: 2.

* * * * *

SEQUENCE LISTING

<160> NUMBER OF SEQ ID NOS: 98

<210> SEQ ID NO 1
<211> LENGTH: 5915
<212> TYPE: DNA
<213> ORGANISM: Oryza sativa
<220> FEATURE:
<221> NAME/KEY: misc_feature
<222> LOCATION: (0)...(0)
<223> OTHER INFORMATION: Oryza sativa TELGene

<400> SEQUENCE: 1

```
aagcttgaaa ctagtactag acattactct tccaatgcaa acaccactat tccatactta      60
aatttaatgc tatttatatc acatgatgtc ttggatgttg tgtagaaact atatctcatg     120
caagacatga tttccttctc tttcctcatt tatttacttg ccacatcatt tttcatccta     180
ggtgacaact tatttaatgc tatggacact atcctagtca ttgggttggg aatggcctta     240
```

```
ctccctccat tccaaaatag cacaactact cttaacccaa aaaacaaaaa ataattatta    300
tcatattata gtttgaatga tcctaataaa tataatgcat atatccaata tgattagata    360
acatgagagt gaaggattta aaaataataa taatttaatg gagaagatgc catagttaat    420
tgtatacttg catgcatgcc ttatattatg gaacatctaa gaaaattggt tgtgctttat    480
attatgcaat ggagggagtg tcttaaaaaa tatactccag tttgtaattc taacatatta    540
ccatgttaat tggataaaaa ttatatatgt tagatggtgg tggattgaaa ttataatggt    600
tgatataatt atattcgaaa cacaaatagc atatgtggag attgaagcta aagatgtat    660
ttcaaataga atcctactta aatctactgt atgcaaatgt atctttggaa aaagctacga    720
attacattaa gaaaatgtat tttctaatat acactttctc tatcgtaaaa tatagctatc    780
tatagcattt aaaaattatc ataaaatata acaacttcta taccaatcac aaccttcgac    840
attcaaattc tccacctagt ccttcttaac caaacatttc ttttctcatt taattttatc    900
tactttttta atcccttata tccaaactta aaactttcta tttagaatgg aggtaattct    960
gtatatagat taccaaaagg tacaagagct aagaatcgtg catcaaattc acttcggaaa   1020
attacataag aaaaacattt gctagtttgt tctacataaa tctcgagaat tttcacaacg   1080
gaacacgaag ctaggagaat ttcacatttt ataaactttt tataaaatga ttaaaaaata   1140
ttgaaaaata aattaaaaaa atctaaagtc aacttcaaat taaaaaatta aaattaaaat   1200
tttggctaat aaacatagca aaagccgaaa gatgagactg aaagctaccc agatcaaaca   1260
gttctatcgc tatagaggat ccgagcaaaa acagggccg gccggccggc agaagaacac    1320
accacaccac tccccagtcc ccagcccacc cccaccccc ccctcgtgg cactgtagcc      1380
agtgtactat actgccctgc ccttcaccac tttcacctcc ctcctcgagt cttctcctct   1440
cgtctccccc tctccctctc ctctccgcca ccacgccacc gtgcttccct cccctttgtt   1500
cctgtagcgt tccgaataaa agcccacctg cttttccttc ccgcgaccat taccataaaa   1560
agagcttgct cccaccgcct ctctctctat ctccccgtcg ctagctacca gcagcaacaa   1620
gtacactccc cccactcctc ccccacacgc cgcgtacaac tagctaagca gaggagaggg   1680
agagagagag aggtggggtt ttgatggaag tacaattcta gctatgttct tgatcggggc   1740
catgatcgcg gatctctaga aagttctaga tcttccgtgc gtggtgggcg ggtggggtg    1800
ttcttggtag ggtaggtaag tgctgctgca atggaggaag gaggtgggag tggcgtgggt   1860
gggatgcagg gagcggcgtc gaatcttctg gacgccggag ctcaggcgtt ctaccctgcc   1920
gtcggcgcgc cgttcccgtt ccagcagctt ccgcaccagc tgtactgccc gcagccgccg   1980
ccgccgccgt accaggtcat gccggtgccg ccgccgccgc cgccggtggg cttgcctgta   2040
ccgccgctgc cggcgacgat ggcgccgcag ccgggctact gcgtgccggc ggccgcgacg   2100
gtggtggacg gtccggccag ccgcgccgtc gtgctgagcc tggtgccgcc gcacgcgccg   2160
gaggacgaga tcgcccgcgc gatggctccg ttcggtgcgg tgcgcgccgt ggacgcgtcg   2220
gcggtggcgt ccgagggcgt cgcgaccgtc tacttcttcg atctccgctc cgccgagcac   2280
gccgtcacgg gggtccgcga gcagcacatc cggcagcagt gccggctcgg ccagctctac   2340
gccgccgccg ccgccgccgc cgcctcgtcc ccgacctggc ccccgccggc gtgggactgg   2400
ccccacgacg acaaccgcgg gctcgtcctc ggccaggccg tctgggccca cttcgccgcc   2460
gcctccaccg tccccgacga cggcgccagc cgcggctccc tcgtcgtgct caattccctc   2520
ccgccatgt ccgtgttcga actccgcgaa atcttccaag catacggtac atacaccacc    2580
accgcacgct ttcttccgcg aattcctcca tgtttcgctt cttgtgtttc caaccaattc   2640
```

```
attctcttgg tcgggtcgcc tcgtcgtgtg tttgcaggtg acgtgaagga cgtgagggag    2700
tcggcgctgc ggccgagcaa caagttcgtc gagttcttcg acacgcgcga cgccgaccgc    2760
gcgctccacg agctcaacgg caaggagctc ttcggccgcc gcctcgtcgt cgagtacacg    2820
cgccctcccc tccccggccc acgcaggtaa aagaattcac cgtcgtgtta attcccatcg    2880
aaaacgcacg gtaaaactaa tttggctgtg gttggcaggc gcgggcacgt gtcgcaccag    2940
cccttggccc cgacgccgcc gaggctgcag gcggcttggc ggccggcgcc ggcgccgtcg    3000
cagtctgcgc agccgtcgtc gtctggctcc ggcaaggcga gggaaggcgt ggtgcttctg    3060
cgcaggagct ccgggaaagg tagctcgggt agccagtcca agggcggtgg caatgctggc    3120
cacgagcgga agagcaaggg cggcaagagc gccgcggcgg cgtgttcgac ggcggcttca    3180
gcatcgtcgt ctaccgcaac ggcgcccagc aagcaaagcc agaaaggcgg cggcggcggc    3240
ggcggccgtg gcgggagctg agaggccag aagagcgggt gggaggctcg cttcctgttc     3300
aaagaacccg aggccgcggc cgccgccgcc ggcgacgctg ccgcctccga dacgcatgag    3360
ccggcgagct gcaaggacac gagaaccacc gtgatgatca ggaacatccc aaacaagtac    3420
aggtcactcc gctagcttcc acgttgttga cgaaatgcta tatttcatgg gcgccgcgag    3480
cccagaattg cctgcctcgc attgcgagct tggcactgat gcctgagctt gtcgtctgtt    3540
gcttgttcgc agccagaagc tgctgctcaa catgctggac aaccactgca tcctctccaa    3600
ccagcagatc gaggcgagct gcgaagacga agcccagcca ttctcctcct acgatttcct    3660
ctacctcccc atagatttca agtgagtcag ctcccgatat gctgtattta tattttatgg    3720
tgcccaatgc aagaacactg cggcacacac tgtccacgcc caatgacaat gacggcctcc    3780
atgcttcatt tccgactgag aattcagtcc tagaaaacta attaattta tgattcttga     3840 ggggaattgt gcaatggaat tgcattgccg tgtgaaggaa ggacaaaggt atatgaaagg    3900
ggcttggaaa tgtactggga gatgaatggg tagttgggag ctctagctgc tggtagtgat    3960
gtgtgagctt gtggatcgag ttatctttgg gctgggtagt actagcatgt tactgcactg    4020
tactgctagt ctgcaacaca tatggacgcc tactctggtg ccatggctgt aatagcccaa    4080
atggaaagga aattggcagt ccaagggaga tcacaccaga tccttctcgt tttgatgcat    4140
caaatccttt tgttgcatgc aatcctctga tcatgagcat ctgttcacat gtctaccttt    4200
cttgcgcacc tgcctctagg atctcctgcc tgccttgctc tctttcttgc ttgcttgcgc    4260
tgtcttgacc tgcacttcca tagcaaagtc caacgcaaaa aggagggct agacgtcatg     4320 gagtagcggt gaaaaggtgc atcaatgcaa aagcgttttc aattttgaca tgtagtaata    4380
tatttctttt cctgagaaaa aggtatggtg accaatgcat aattaagcac tttcttttca    4440
ctggagtacc aactttatc tttgcacgaa ccaagttgag aaaagaccta tcaaatgccc     4500
caatgactag cgtgcattgt ggaatcaaaa ggtagctcca caacaaaaat atgatagaaa    4560
tattgttgtg caagtttata gttccccgag cttctgactt cgaaggcctc aattccaaga    4620
atatttgtgt tcttgacctt gacaagtcgt ttgttatcat tcataactca tttttggtca    4680
cccggttctt tatcgcttct ctacttgttg agaagttttt aaattcaggc attaaattat    4740
cttttcggct gtgctaacct gctaaaatat gaggccatgc agcaacaagt gcaacgtggg    4800
ctatggcttc gtcaacctca cctcgccgga ggctgccgtg cggctgtaca aggcgttcca    4860
caagcaaccg tgggaggtgt tcaactcgcg caagatttgc caagtgacat acgcacgcgt    4920
gcaagtacga gcgccgttaa atctctccca attgtgctga taaatctaga ccgatcatca    4980
```

-continued

```
tgtgtggcaa gtgctaaacc cgtgcatgcg cgcagggcct ggacgcgctc aaggagcact    5040
tcaagaactc caagttcccg tgcgacagcg acgagtacct gcccgtggtg ttctcgccgc    5100
cgcgggacgg caagctgctc acggagccgg tgccgctggt cggccgctcg ccggcaccgt    5160
cgtcggcgtc cggggcgtcg tcgccgccca agagctgcgc cgcgagcgtc gacccactcg    5220
cgcaggagct catgacagcg ccgtcttcct ccggcgacgg cgcctcctcc gcctcctcgt    5280
ccaatgccca cgccgacgag gatgacgtcc atggcgaaac cggtggtgac cgtggcgacg    5340
acgcggggct cgatctggag ctacagcgcc taggctacac tgactagctg gcgtctggcg    5400
gctttgcttc gagaggtggt ggcaatgatg gtggctacgg ctgctgcatg caagcaaggg    5460
aagtgaagtg aacaggtgat tcatttatg ctttaagca gagataggag taggaaagaa     5520
ctcgagaaaa gaagcgattt gatgttattt tgagaggagt agcagtagta gtggtggtgg    5580
tattcgttgg tagctgcaga tgggagtcgt gttcttttg gttttaagtt ccttctttg     5640
aaacttggag ctagctaggg ggccggggg ggggggggg agctagctag ggggccgggg     5700
ggggggggg caaaactatt cttcttggtc atgcgttcgt ttgttacatt aattacaact    5760
tacaacactc caaatttcga gtctgtgtga tgactgatac tagatttgaa gagatctccc    5820
aaatctttt ctcaaactgt cctcgtcgga gtactccagt atataagcat ttctttatgg    5880
ttgaaggatg aggtagcacg gagaatacgg gtacc                               5915
```

<210> SEQ ID NO 2
<211> LENGTH: 683
<212> TYPE: PRT
<213> ORGANISM: Oryza sativa
<220> FEATURE:
<223> OTHER INFORMATION: Oryza sativa TEL

<400> SEQUENCE: 2

```
Met Glu Glu Gly Gly Gly Ser Gly Val Gly Gly Met Gln Gly Ala Ala
 1               5                  10                  15

Ser Asn Leu Leu Asp Ala Gly Ala Gln Ala Phe Tyr Pro Ala Val Gly
            20                  25                  30

Ala Pro Phe Pro Phe Gln Gln Leu Pro His Gln Leu Tyr Cys Pro Gln
        35                  40                  45

Pro Pro Pro Pro Pro Tyr Gln Val Met Pro Val Pro Pro Pro Pro Pro
    50                  55                  60

Pro Val Gly Leu Pro Val Pro Pro Leu Pro Ala Thr Met Ala Pro Gln
65                  70                  75                  80

Pro Gly Tyr Cys Val Pro Ala Ala Ala Thr Val Val Asp Gly Pro Ala
                85                  90                  95

Ser Arg Ala Val Val Leu Ser Leu Val Pro Pro His Ala Pro Glu Asp
            100                 105                 110

Glu Ile Ala Arg Ala Met Ala Pro Phe Gly Ala Val Arg Ala Val Asp
        115                 120                 125

Ala Ser Ala Val Ala Ser Glu Gly Val Ala Thr Val Tyr Phe Phe Asp
    130                 135                 140

Leu Arg Ser Ala Glu His Ala Val Thr Gly Val Arg Glu Gln His Ile
145                 150                 155                 160

Arg Gln Gln Cys Arg Leu Gly Gln Leu Tyr Ala Ala Ala Ala Ala Ala
                165                 170                 175

Ala Ala Ser Ser Pro Thr Trp Pro Pro Ala Trp Asp Trp Pro His
            180                 185                 190

Asp Asp Asn Arg Gly Leu Val Leu Gly Gln Ala Val Trp Ala His Phe
```

```
                195                 200                 205
Ala Ala Ala Ser Thr Val Pro Asp Asp Gly Ala Ser Arg Gly Ser Leu
210                 215                 220

Val Val Leu Asn Ser Leu Pro Ala Met Ser Val Phe Glu Leu Arg Glu
225                 230                 235                 240

Ile Phe Gln Ala Tyr Gly Asp Val Lys Asp Val Arg Glu Ser Ala Leu
                245                 250                 255

Arg Pro Ser Asn Lys Phe Val Glu Phe Phe Asp Thr Arg Asp Ala Asp
            260                 265                 270

Arg Ala Leu His Glu Leu Asn Gly Lys Glu Leu Phe Gly Arg Arg Leu
        275                 280                 285

Val Val Glu Tyr Thr Arg Pro Ser Leu Pro Gly Pro Arg Arg Arg Gly
290                 295                 300

His Val Ser His Gln Pro Leu Ala Pro Thr Pro Pro Arg Leu Gln Ala
305                 310                 315                 320

Ala Trp Arg Pro Ala Pro Ala Pro Ser Gln Ser Ala Gln Pro Ser Ser
                325                 330                 335

Ser Gly Ser Gly Lys Ala Arg Glu Gly Val Val Leu Leu Arg Arg Ser
            340                 345                 350

Ser Gly Lys Gly Ser Ser Gly Ser Gln Ser Lys Gly Gly Asn Ala
        355                 360                 365

Gly His Glu Arg Lys Ser Lys Gly Gly Lys Ser Ala Ala Ala Cys
370                 375                 380

Ser Thr Ala Ala Ser Ala Ser Ser Ser Thr Ala Thr Ala Pro Ser Lys
385                 390                 395                 400

Gln Ser Gln Lys Gly Gly Gly Gly Gly Gly Arg Gly Gly Ser Trp
                405                 410                 415

Arg Gly Gln Lys Ser Gly Trp Glu Ala Arg Phe Leu Phe Lys Glu Pro
            420                 425                 430

Glu Ala Ala Ala Ala Ala Gly Asp Ala Ala Ser Glu Thr His
        435                 440                 445

Glu Pro Ala Ser Cys Lys Asp Thr Arg Thr Thr Val Met Ile Arg Asn
450                 455                 460

Ile Pro Asn Lys Tyr Ser Gln Lys Leu Leu Leu Asn Met Leu Asp Asn
465                 470                 475                 480

His Cys Ile Leu Ser Asn Gln Gln Ile Glu Ala Ser Cys Glu Asp Glu
                485                 490                 495

Ala Gln Pro Phe Ser Ser Tyr Asp Phe Leu Tyr Leu Pro Ile Asp Phe
            500                 505                 510

Asn Asn Lys Cys Asn Val Gly Tyr Gly Phe Val Asn Leu Thr Ser Pro
        515                 520                 525

Glu Ala Ala Val Arg Leu Tyr Lys Ala Phe His Lys Gln Pro Trp Glu
530                 535                 540

Val Phe Asn Ser Arg Lys Ile Cys Gln Val Thr Tyr Ala Arg Val Gln
545                 550                 555                 560

Gly Leu Asp Ala Leu Lys Glu His Phe Lys Asn Ser Lys Phe Pro Cys
                565                 570                 575

Asp Ser Asp Glu Tyr Leu Pro Val Phe Ser Pro Arg Asp Gly
            580                 585                 590

Lys Leu Leu Thr Glu Pro Val Pro Leu Val Gly Arg Ser Pro Ala Pro
        595                 600                 605

Ser Ser Ala Ser Gly Ala Ser Pro Pro Lys Ser Cys Ala Ala Ser
610                 615                 620
```

Val Asp Pro Leu Ala Gln Glu Leu Met Thr Ala Pro Ser Ser Ser Gly
625                 630                 635                 640

Asp Gly Ala Ser Ser Ala Ser Ser Ser Asn Ala His Ala Asp Glu Asp
            645                 650                 655

Asp Val His Gly Glu Thr Gly Gly Asp Arg Gly Asp Ala Gly Leu
        660                 665                 670

Asp Leu Glu Leu Gln Arg Leu Gly Tyr Thr Asp
        675                 680

<210> SEQ ID NO 3
<211> LENGTH: 273
<212> TYPE: DNA
<213> ORGANISM: Oryza sativa
<220> FEATURE:
<221> NAME/KEY: misc_feature
<222> LOCATION: (0)...(0)
<223> OTHER INFORMATION: Conserved Oryza sativa TEL motif

<400> SEQUENCE: 3
tacgatttcc tctacctccc catagatttc aacaacaagt gcaacgtggg ctatggcttc      60
gtcaacctca cctcgccgga ggctgccgtg cggctgtaca aggcgttcca caagcaaccg     120
tgggaggtgt tcaactcgcg caagatttgc caagtgacat acgcacgcgt gcaaggcctg     180
gacgcgctca aggagcactt caagaactcc aagttcccgt gcgacagcga cgagtacctg     240
cccgtggtgt tctcgccgcc gcgggacggc aag                                 273

<210> SEQ ID NO 4
<211> LENGTH: 91
<212> TYPE: PRT
<213> ORGANISM: Oryza sativa
<220> FEATURE:
<223> OTHER INFORMATION: Conserved Oryza sativa TEL motif

<400> SEQUENCE: 4

Tyr Asp Phe Leu Tyr Leu Pro Ile Asp Phe Asn Asn Lys Cys Asn Val
1               5                   10                  15

Gly Tyr Gly Phe Val Asn Leu Thr Ser Pro Glu Ala Ala Val Arg Leu
            20                  25                  30

Tyr Lys Ala Phe His Lys Gln Pro Trp Glu Val Phe Asn Ser Arg Lys
        35                  40                  45

Ile Cys Gln Val Thr Tyr Ala Arg Val Gln Gly Leu Asp Ala Leu Lys
    50                  55                  60

Glu His Phe Lys Asn Ser Lys Phe Pro Cys Asp Ser Asp Glu Tyr Leu
65                  70                  75                  80

Pro Val Val Phe Ser Pro Pro Arg Asp Gly Lys
                85                  90

<210> SEQ ID NO 5
<211> LENGTH: 6114
<212> TYPE: DNA
<213> ORGANISM: Zea mays
<220> FEATURE:
<221> NAME/KEY: misc_feature
<222> LOCATION: (0)...(0)
<223> OTHER INFORMATION: Zea mays TEL1 (genomic sequence with promoter
      and NA terminator)
<220> FEATURE:
<221> NAME/KEY: misc_feature
<222> LOCATION: 5574
<223> OTHER INFORMATION: n = A,T,C or G

<400> SEQUENCE: 5

-continued

```
aagcttgcat gcctgcaggt cgacgattca tatgagtgcc aatcactgcg tgagaaccga    60
cggcggtgct cactgcacag gcgcggacgg tccgcggtca ggggccgaac gatccgcgac   120
ctggcgcagg gcttaggatt tcctgcctga cggtcggaca gtccgcgtct acaggccgga   180
cggtccgcgc gtgcgcaggg gcggcgaagg tcgccggcga cgcctggatc tcgccccgag   240
agggaccccg tcggggagga gagatcttag gtgttgtcta ggcttggtag gccgacctag   300
acttctctaa tcgacgtaga gtcgaagaga agcagagaat ttggggattg gaaggctaaa   360
ctcgaactag actagaacta aatacgagat aaactggtat tgattcgatt gatgatgttt   420
aatcggctgt attcctctgt atttatagag gaggggctg gacccgttag agacagattt    480
tccgagctaa ttccgtgaat cttgccaaca actatagcaa gaaactcgga actctaactg   540
gttctacgtg cgcgcggacc gtccggacca gcgatgcggg ccgtctggcc ctctatttgg   600
tgctcaccgg aaccatgtct taccaatgtg ttgaaattgt tttatggcga acataaaaat   660
ctaaagttgt aattttaaa ataaagccct cctaaacaga acattaattt ttataattga    720
tattcaaata ttttagtccg gtaaccaaac gcccagtaat ttgaagaata tggtctttat   780
ttgtagccgg cggcatctcg aaaagctaga tctaactccg aaaacaaaca cgcaaaatct   840
accggaaaaa tctcccccag caaagaagca gacgtggggc ctgtcatgta cgcacggggc   900
atgactcgtg caagagcaac aagtgctgtc gttgcagagg atccgagcta aacaatcca    960
gcacacggcc actctcgtct ctcctcttcc tcctcttccc tccgtaccgc ccgcccttca  1020
cctcctcgac tcttctccac cgccccctcc ctcctcgcgt ctctctcccc ctttgtccct  1080
gtagagctcc aaataaaacc ccaccggttt tcttttcccg cggcaattac cataaaaaga  1140
gctcccaatc tctctctcct ctctccggcc cctctctctc gtttctggca ggagtggtgc  1200
ggtactacca ccgctctctc actccacaca cacacaccga gtatacggct aagcaggaga  1260
gagaacggga gagtgagact gagacggggt cccaagtaca attctcgcct ggttcttgat  1320
cgaaggcatg atcaagaatc accagaaagt tctagatctt tagacggcag tcttccttgg  1380
actcctcggt ttcttttgtt ctgagctcta gccatggagg gtgggggagg gagtggaatg  1440
ggtgggttcc cggaagccac gggtaacctt ctcgatgccg cagctcagga gttccaccct  1500
acggtctgtg cccctatcc tctacagccg cttccgcaac agctatactg cccccaccca   1560
tatccagcca tgccggtgcc tccgccgccg caaatagcca tgttacagcc agtgcctccg  1620
atggcgatgg ccatggcgcc gcagccgggg tacaccttgc caacgacgac gccggtggtc  1680
aatgcccgt cgagccgcgt cgtggtgctg ggccttgtcc cgccgcacgc gcaggaggcc   1740
gacgtggcgc aggcgatggc gccattcggc gcgatccgct cggtcgacgc gtgcgcggtg  1800
gcgtccgagg gcgtggccac cgtccatttc ttcgacatcc gcgccgccga gctcgccttg  1860
acctgcgtcc gggagcagca catgcgccag cagagccgcc tcgggcagct ctacgcggcg  1920
gccgccgtag ccccggcgtg ggctcctgca ccgacgcccc aggcctggga ctggcctcac  1980
cccaacgacg acggccgcgg cctcgtcctc gggcacgccg tctgggccca cttcgccacc  2040
ggcgccgacg acggcgacaa ccgcggctcc ctggtggtcc tgagcccct gcccggcgtc   2100
tcggtcgctg acctccgcca agtcttccag gccttcggta cgcgccaccg accgagccga  2160
ccaaccaggc atttcgtttt cccacgctcg tttcttgtgt ttcccgcagc aattgtattg  2220
gcccgtcctc gtgttcgcag gggacttgaa ggatgtgagg gagtcggcgc agcggccag   2280
ccacaagttc gtggacttct tcgacacgcg cgacgccgcg cgcgcgctcg ccgagctcaa  2340
```

```
cggccaggag cttttcggcc gccgcctcgt cgtcgagttc acgcgccctt ccggccccgg    2400
gccccgcagg taaacaacaa cgcaatttca gtcagctagc cttcccatca ccctgtgggc    2460
ggctgaattt ttgccgtgtg cctgtcggtc ctaggcgcgg gtacgcaccc caccagcacc    2520
ggcccaccgc gccgactccg ccgaggcttc aagcgacgtg gcgaccgtcc caaccgacgt    2580
cgtctcagcc gccggcatcc tcgtcgtcgt ccggttccgt aagggcgagg aaggagtgg    2640 tgcttctgag gaggagctcc tgtaaggcta gcgcgggcag cgaccagtcg tccaagggag    2700
gcaatgccgg aacgagccat gagcgcaaga ccaagggcgg caagatcgtg gtggcggcgg    2760
cggcggcggt gtcctcgtcg accccgacag cgtccgggaa gcaaacccag aaaggcgtcg    2820
ggagcagcgg cggcgggagc tggaaaggac gaaagagcgg gtgggaggcg cgcttcctgt    2880
tcaaggagcc cgaggccggc ggcggcgccg acacgcaggc aacgccggct tcggagatgg    2940
acacgaggac caccgtcatg atcaggaaca taccgaacaa gtacaggtat ccctgccaat    3000
ctccacgttt gttgcaacaa tgctatattt catgggcgac gcacagaatt gcgattctgc    3060
tagctgatgc ccgaggcgtt tgggtcgcag ccagaagctg ctgctcaaca tgctggacaa    3120
ccactgcatc caatccaacg agtggatcgt ggcgagcggc gaggagcagc ccttctccgc    3180
ctacgatttc gtctacctcc ccatagattt caagtgagtt gcgcgctcgg cttccttctc    3240
acataattgc atttagctgt tcgcattgac ttatatttta tggtgcccaa tgcaagaaca    3300
cacacgcaca cacaagcttc ccagcctgaa ttcggttgtt ttcctgggaa tttgttgcct    3360
tgaaaaatgg ttggagtggg aaatgtgggc ggggggtggg tggcgaggag ctggctggaa    3420
gcgtgagctt caggatcgag gtatcttatc tttgggtggg tagagtacag tgcagcaggc    3480
atagatgggc tatggcgtta ctagcccaaa tggaaataaa tttggcagcg gcaagcgaga    3540
ccatgccaga tccttctcgt tttgatgccc cccatggatt ctttggttgc atgcgcgcat    3600
ctgctggctg ctgctgccgc tgccgctgct gatggcgagg gagccggcct gccttccttt    3660
ctcgcggctg ctgccgcccc tgggatcgcc tccctgcctg cctttcttgc tttgcacagc    3720
cgtgcacttc cataacgagg ccaacacata caaaaggtgc ggcaccgatg gggttgtagt    3780
gttgagacta gacagtagag atagacgctt agctatggag atggagctgt gaaaaaaaaa    3840
gagttgcatg agtatgaaaa gggggaaaaa gtcagcactt tcgttctaaa gagaaaattt    3900
gaacttcaga tcaaagtagt tttctatatg caaacaaaat gtatggtttc aagtttgctt    3960
atttaaagca cttgctttta tataccgcc cggcagcttt tctcttgcac gaagcaagtt    4020
tgagaaaaga cctatcaatg cccaatgacg agaggacatt agtggctgtc aaaaggcatg    4080
cagcttcaaa catactcatg tgtaaagcag ctgcagcata atgccaaagt ttttttttgat    4140 tgcaagtctt tttagttatt gttcctccat gccattacca ttctgaattt cttgcccttg    4200
catgaaatga gaattttttct tccttatgca aaaacaaaaa aaatgcagc aacaagtgta    4260 atgtgggcta cggcttcgtc aacctgacat cgccggaggc tgccgtgcgg ctgtacaagg    4320
cgttccacaa gcagccatgg gaggtgtaca actcgcgcaa gatctgccaa gtgacatacg    4380
cgcgcgtaca agtacgtact ccactcctgc agctgccctt ctcctacatc tacatccgcc    4440
aaagacattt taatactacg tacgtactta ttgctcacat gtcaatgtta caattgtgcg    4500
gcggcgcagg gcctggaagc gctgaaggag cacttcaaga actccaagtt cccgtgcgac    4560
agcgacgagt acctgcccgt ggcgttctcg ccggcgcgcg acggcaagga gcttacggat    4620
ccagtgccca tcgtgggccg ctcgcccgcg ggtcgtccg cgtcgtcgcc tcccaagagc    4680
cgggcggcca gcgtggaccg gcttgggcag gagctgatgc cggcgccctc gtcatccgcg    4740
```

-continued

```
gacggcgcgt cgtcgaccac tacgtccacc cacgcgccgt ccgaacacga cgacgaggag    4800
gagggagaca tcaggctcgc aggcgagctg cggcggcttg gctacgacga ctagctggct    4860
ccgatcctag ctgcagctag gcgggcgggg cctagctcag caacgatcgg cacggcgtgg    4920
cgtcgcttcg agaagcgcgg aggcagtagt gacttcggcc aagcttttca cagatccgta    4980
gcgctcgctc ctgcacgcgc aggcgaagca agtgaagtgg actgggactt gactttggag    5040
aagcaaaagt gagctgatgt tcgttggttc gtagacgctg cgcacagcag gtgtggagtc    5100
gtgttctttt ggattttggt ttgaagtttc ctactacttg tttctttgaa acttggagct    5160
atagctagct taggcttagc taggactgct gggaggggaa agggcatgca ggggactatc    5220
aattcgtggt tcgtcatgcg ctcgttcttt acattaaaat aagattgtta ttagtacagc    5280
tttacaatac ttctgcatat tcggagagag actctgatct catatcatca cgagttgcta    5340
gatttcgtcg gatctcttcg attgatgcga accaacagat ctttctctat cgctgcacgg    5400
ctccaccgcg ctatctttgc agactcacac tgtcctctcc tttgtagact ctagtcttct    5460
catccttcta tttttctcaa tttacatttc tatttgttca atttacattt agtagcccat    5520
cgatctgtgc tcactcgtgc taaaaaacaa agatgtaagc gttgcgtaat attnagacag    5580
tacaagcata tatctagaaa attcaaatta tcttgtgatt tgaaatggaa aactgtctca    5640
ctaataaaaa gatatttgta tcaaatatat attttatatt tttatttatt tcctaacata    5700
atagatataa taggtactat atagtttata tctatttatc aaaacttatt gtcgtttatt    5760
taaaaacaat atatatttat ccatatatat attttttcca tgcatggcat ctctatatat    5820
ttaaatatgt aattattttg aaatcttacc cttaatcatg gtgcctcttc ttgcatcatg    5880
tgtcctcagt catgaatgaa tctatttcct ctctcctcaa gttaagtcga gactcctgag    5940
tttattgtat ctttcattaa ctctagtttt ttgtattttc ttataaataa atattttagg    6000
ttatagaata agttcttaag tactacaata tcataaaacc attgttttaa aaacatgtat    6060
catattattc aaaataagtc atagagcttg aagtgagatc ttaaataggg tacc          6114
```

<210> SEQ ID NO 6
<211> LENGTH: 655
<212> TYPE: PRT
<213> ORGANISM: Zea mays
<220> FEATURE:
<223> OTHER INFORMATION: Zea mays TEL1

<400> SEQUENCE: 6

```
Met Gly Gly Phe Pro Glu Ala Thr Gly Asn Leu Leu Asp Ala Ala
 1               5                  10                  15

Gln Glu Phe His Pro Thr Val Cys Ala Pro Tyr Pro Leu Gln Pro Leu
                20                  25                  30

Pro Gln Gln Leu Tyr Cys Pro His Pro Tyr Pro Ala Met Pro Val Pro
            35                  40                  45

Pro Pro Pro Gln Ile Ala Met Leu Gln Pro Val Pro Pro Met Ala Met
        50                  55                  60

Ala Met Ala Pro Gln Gly Tyr Thr Leu Pro Thr Thr Thr Pro Val Val
65                  70                  75                  80

Asn Gly Pro Ser Ser Arg Val Val Leu Gly Leu Val Pro Pro His
                85                  90                  95

Ala Gln Glu Ala Asp Val Ala Gln Ala Met Ala Pro Phe Gly Ala Ile
            100                 105                 110

Arg Ser Val Asp Ala Cys Ala Val Ala Ser Glu Gly Val Ala Thr Val
```

-continued

```
            115                 120                 125
His Phe Phe Asp Ile Arg Ala Ala Glu Leu Ala Leu Thr Cys Val Arg
    130                 135                 140
Glu Gln His Met Arg Gln Gln Ser Arg Leu Gly Gln Leu Tyr Ala Ala
145                 150                 155                 160
Ala Ala Val Ala Pro Ala Trp Ala Pro Ala Pro Thr Pro Gln Ala Trp
                165                 170                 175
Asp Trp Pro His Pro Asn Asp Asp Gly Arg Gly Leu Val Leu Gly His
                180                 185                 190
Ala Val Trp Ala His Phe Ala Thr Gly Ala Asp Asp Gly Asp Asn Arg
                195                 200                 205
Gly Ser Leu Val Val Leu Ser Pro Leu Pro Gly Val Ser Val Ala Asp
    210                 215                 220
Leu Arg Gln Val Phe Gln Ala Phe Gly Asp Leu Lys Asp Val Arg Glu
225                 230                 235                 240
Ser Ala Gln Arg Pro Ser His Lys Phe Val Asp Phe Phe Asp Thr Arg
                245                 250                 255
Asp Ala Ala Arg Ala Leu Ala Glu Leu Asn Gly Gln Glu Leu Phe Gly
                260                 265                 270
Arg Arg Leu Val Val Glu Phe Thr Arg Pro Ser Gly Pro Gly Pro Arg
                275                 280                 285
Arg Arg Gly Tyr Ala Pro His Gln His Arg Pro Thr Ala Pro Thr Pro
    290                 295                 300
Pro Arg Leu Gln Ala Thr Trp Arg Pro Ser Gln Pro Thr Ser Ser Gln
305                 310                 315                 320
Pro Pro Ala Ser Ser Ser Ser Gly Ser Val Arg Ala Arg Glu Gly
                325                 330                 335
Val Val Leu Leu Arg Arg Ser Ser Cys Lys Ser Ser Ala Gly Ser Asp
                340                 345                 350
Gln Ser Ser Lys Gly Gly Asn Ala Gly Thr Ser His Glu Arg Lys Thr
    355                 360                 365
Lys Gly Gly Lys Ile Val Val Ala Ala Ala Ala Ser Ser Ser Thr
    370                 375                 380
Pro Thr Ala Ser Gly Lys Gln Thr Gln Lys Gly Val Gly Ser Ser Gly
385                 390                 395                 400
Gly Gly Ser Trp Lys Gly Arg Lys Ser Gly Trp Glu Ala Arg Phe Leu
                405                 410                 415
Phe Lys Glu Pro Glu Ala Gly Gly Ala Asp Thr Gln Ala Thr Pro
                420                 425                 430
Ala Ser Glu Met Asp Thr Arg Thr Thr Val Met Ile Arg Asn Ile Pro
    435                 440                 445
Asn Lys Tyr Ser Gln Lys Leu Leu Leu Asn Met Leu Asp Asn His Cys
    450                 455                 460
Ile Gln Ser Asn Glu Trp Ile Val Ala Ser Gly Glu Glu Gln Pro Phe
465                 470                 475                 480
Ser Ala Tyr Asp Phe Val Tyr Leu Pro Ile Asp Phe Asn Asn Lys Cys
                485                 490                 495
Asn Val Gly Tyr Gly Phe Val Asn Leu Thr Ser Pro Glu Ala Arg Val
                500                 505                 510
Arg Leu Tyr Lys Ala Phe His Lys Gln Pro Trp Glu Val Tyr Asn Ser
    515                 520                 525
Arg Lys Ile Cys Gln Val Thr Tyr Ala Arg Val Gln Gly Leu Glu Ala
    530                 535                 540
```

```
Leu Lys Glu His Phe Lys Asn Ser Lys Phe Pro Cys Asp Ser Asp Glu
545                 550                 555                 560

Tyr Leu Pro Val Ala Phe Ser Pro Ala Arg Asp Gly Lys Glu Leu Thr
                565                 570                 575

Asp Pro Val Pro Ile Val Gly Arg Ser Pro Ala Ser Ser Ala Ser
            580                 585                 590

Ser Pro Pro Lys Ser Arg Ala Ala Ser Val Asp Arg Leu Gly Gln Glu
        595                 600                 605

Leu Met Pro Ala Pro Ser Ser Ser Ala Asp Gly Ala Ser Ser Thr Thr
    610                 615                 620

Thr Ser Thr His Ala Pro Ser Glu His Asp Glu Glu Glu Glu Gly
625                 630                 635                 640

Asp Ile Arg Leu Ala Gly Glu Leu Arg Arg Leu Gly Tyr Asp Asp
                645                 650                 655

<210> SEQ ID NO 7
<211> LENGTH: 3476
<212> TYPE: DNA
<213> ORGANISM: SORGHUM BICOLOR
<220> FEATURE:
<221> NAME/KEY: misc_feature
<222> LOCATION: (0)...(0)
<223> OTHER INFORMATION: Sorghum Bicolor TEL genomic DNA

<400> SEQUENCE: 7
atggagggtg ggggagggag tggaataggt gggttccgg  gagccccggg taaccttctc      60
gatgccgcag ctcaggagtt ccaccctacg gtctgtgccc cctaccctct acagccgctc     120
ccgcaccagc tatactgccc ccacacatat ccagccatgc cgccgccgcc gcaaatggcc     180
atgttgcagc ctgtgcctcc gatggcgatg cccatggcgc cgcagccggg gtacaccttg     240
cccacgacgg cgccggtggt cgacggcccg tccagccgcg tcgtggtgct gtgcctggtg     300
ccgccgcacg cgcaggagcg cgacgtggcg caggcgatgg cgccgttcgg cgcgatccgc     360
tcggccgacg cgtgcgcggt ggcgtccgag ggcgtggcca ccgtccattt cttcgacatc     420
cgcgccgccg agctcgccgt ggcctgcgtc gcgagcagc  acatgcggca gcagagccgg     480
ctcgggcagc tctacgcggc ggccgccgtg ccccggcgt  gggctcctgc accaccgacg     540 gcgcccagg  cctgggactg gccccacccc aacgacgacg gccgcggcct cgtcctcggg     600
caagtcgtgt gggcccactt cgcccccggc gccgacgacg gcgagaaccg cggctccctg     660
gtggtcctga gccccctgcc cggcgtctcg gtcgctgacc tccgccaagt cttccaggcc     720
ttcggtacgc gccaccgacc gagccgacca accaggcatt tcgttttccc acgtcgtttt     780
cttgtgtttc ccgcagcaat tgtattggcc cgtcctctcg tcttcgcagg ggacttgaag     840
gatgtgaggg agtcggcgca ccggcccagc acaagttca  tcgacttctt cgacacccgc     900
gacgccgcgc gcgcgctcgc cgagctcaac ggccaggagc tcttcggccg ccgcctcgtc     960
atcgagttca cgcgcccttc cggccccggg ccccgcaggt aacacaacac caacaccca    1020 attttcagtt cagtcagcta gccttcccat caccctgtgg gcggctgaat ttttgccgtg    1080
tgcctgtcgg tcctaggcgc gggtacgcgc cccaccaccg gccaccgcg  ccgactccac    1140 cgaggcttca acaagcgacg tggcgaccgg cccagacgac gtcgtctcag ccgccggcat    1200
cctcctcgtc gtcgtccgtc tccgtaaggg ccagggaagg agtggtgctt ctgaggaggc    1260
cgagcgatca ggccaaggga ggcaatgccg gcacgagaca agagcgcaag agcaagggcg    1320
gcaagaacgt ggcgtcgtcg gcgtcggcgc cggcgtcctc gtcgaccccg acagcgtccg    1380
```

-continued

```
ggaagcaagc ccagaaaggt gccgggagca gcggcggcgg tggtgctggc ggtggcggcg      1440
ggaactggaa aggacgaaag agcggctggg aggcgcgctt cctgttcaag gatcccgagt      1500
ccgccggcga cgccgacacg cagtcgtcgc cggcttcgga gagggacacg aggaccaccg      1560
tcatgatcag gaacataccc aacaagtaca ggtatccctg ccaatctcca cattgttgca      1620
acaatataat gctatatttc atgggcggcg cacgcccaga attgcgattc tgctgacgct      1680
cgaggccgtt ggggtcgcag ccagaagctg ctcctcaaca tgctggacaa ccactgcatc      1740
caatccaacg agtggatcgc ggcgagcggc gaggcgcagc ccttctcctc ctacgatttc      1800
gtctacctcc ccatagattt caagtgagtt gcgcccggct cccctcgcac acaattttgc      1860
aattagcagt ttgcattaac ttatatttta tggtgcccga tgcaagaaca cacgcttggc      1920
agcctgaatt cggttgtttt tttctgggaa tttggtgcct tgaaaatggt tggaatggga      1980
aatgtggggg gtggaagcgt gagcttctgg atcgaggtat cttatctttg ggtgggtaga      2040
gtacagtgta gcagatggct atggcgttac tagcccaaat ggaaataaat ttggcagcgg      2100
cccaagggag accgcgccag atccttctcg ttttgatgcc cccatggttt ctttggttgc      2160
atgcgcgcgc gcatctgctg ggtgctggtg ttggctgctg ctgccgatgc cgatgccgag      2220
ggggcctcct gccttccttt ctcgccgctg ctgccgcccc tgtgatcgcc tccctgcctg      2280
cctttctagc tttgcacagt cgtgcccttc cataacaagg ccaacacata caaaaggagc      2340
ggcaccgtcc ggtgggaggt gtagtgtagt agagacagac accagcagct atggaatgga      2400
gttgtgaaca aaaagaaca gttgcatcag tatatgaaaa ggaaaaaggt caacactttc      2460
attctaaaga gaaaaaaat tgagctttgg ataaaagttt atacatgcaa ccaggatatt      2520
ctttcaagtg aagcacttgc tttatactcc tatataccag cagcttttct ctagcacgaa      2580
gcaagttgag aaaagaccta tcaatgccca atgacgagaa gacattagtg gctgtcaaaa      2640
gtatactcca tgtaaagcag ctgcagcatc atgccaaagc tttttttttt ttgttattgt      2700
tgctctaaaa gtctctaggt gttgttcatc catgccatac cattctgaat ttcttgctct      2760
agcatgaaat gagaaatttg tcgtgctttg cctgacactg ggtttcttct tatgcaaaaa      2820
tgtaaaaaat aaaaaactaa aaattgcagc aacaagtgca atgtgggcta cggcttcgtc      2880
aacctgacct cgccggaggc cgccgtgcgg ctgtacaagg cgttccacaa gcagccatgg      2940
gaggtgtaca actcgcgcaa gatctgccaa gtcacatacg cgcgcgtaca agtacctact      3000
gcatttcacc tgcccttcta gtcctactag gccaccaaag atatttacta ctacgtactt      3060
ggctcacatg ttaatgttac aaatgtgtgg cttccgccac gctcacgttg tgtggccttt      3120
gcgcggcgca gggcctggac gcgctgaagg agcacttcaa gaactccaag ttcccgtgcg      3180
acagcgacga gtacctgccc gtggcgttct cgccggcgcg cgacggcaag gagctcacgg      3240
aaccggtgcc catcgtgggc cggtcgcccg cgtccggcgc gtcgtcgcct cccaagagcc      3300
gggcggccag cgtggacctg cttgggcagg agctgatgcc ggcgccgtcg tcgtccgcgg      3360
acggcgcgtc gtcgaccacc acgtccaccc acgcgctgtc cgaacacgcc gacgacgacg      3420
acaacgacga agacatcagg ctcgccggcg agctgcggcg cctaggctac gccgac         3476
```

<210> SEQ ID NO 8
<211> LENGTH: 666
<212> TYPE: PRT
<213> ORGANISM: SORGHUM BIOCOLOR
<220> FEATURE:
<223> OTHER INFORMATION: Sorghum Bicolor TEL

<400> SEQUENCE: 8

```
Met Glu Gly Gly Gly Ser Gly Ile Gly Gly Phe Pro Gly Ala Pro
 1               5                  10                  15

Gly Asn Leu Leu Asp Ala Ala Gln Glu Phe His Pro Thr Val Cys
             20                  25                  30

Ala Pro Tyr Pro Leu Gln Pro Leu Pro His Gln Leu Tyr Cys Pro His
         35                  40                  45

Thr Tyr Pro Ala Met Pro Pro Pro Gln Met Ala Met Leu Gln Pro
     50                  55                  60

Val Pro Pro Met Ala Met Pro Met Ala Pro Gln Pro Gly Tyr Thr Leu
 65                  70                  75                  80

Pro Thr Thr Ala Pro Val Val Asp Gly Pro Ser Ser Arg Val Val
                 85                  90                  95

Leu Cys Leu Val Pro Pro His Ala Gln Glu Arg Asp Val Ala Gln Ala
                100                 105                 110

Met Ala Pro Phe Gly Ala Ile Arg Ser Ala Asp Ala Cys Ala Val Ala
            115                 120                 125

Ser Glu Gly Val Ala Thr Val His Phe Phe Asp Ile Arg Ala Ala Glu
130                 135                 140

Leu Ala Val Ala Cys Val Arg Glu Gln His Met Arg Gln Gln Ser Arg
145                 150                 155                 160

Leu Gly Gln Leu Tyr Ala Ala Ala Val Pro Pro Ala Trp Ala Pro
                165                 170                 175

Ala Pro Pro Thr Ala Pro Gln Ala Trp Asp Trp Pro His Pro Asn Asp
            180                 185                 190

Asp Gly Arg Gly Leu Val Leu Gly Gln Val Val Trp Ala His Phe Ala
        195                 200                 205

Pro Gly Ala Asp Asp Gly Glu Asn Arg Gly Ser Leu Val Val Leu Ser
210                 215                 220

Pro Leu Pro Gly Val Ser Val Ala Asp Leu Arg Gln Val Phe Gln Ala
225                 230                 235                 240

Phe Gly Asp Leu Lys Asp Val Arg Glu Ser Ala His Arg Pro Ser His
                245                 250                 255

Lys Phe Ile Asp Phe Phe Asp Thr Arg Asp Ala Ala Arg Ala Leu Ala
            260                 265                 270

Glu Leu Asn Gly Gln Glu Leu Phe Gly Arg Arg Leu Val Ile Glu Phe
        275                 280                 285

Thr Arg Pro Ser Gly Pro Gly Pro Arg Arg Gly Tyr Ala Pro His
    290                 295                 300

His Arg Pro Thr Ala Pro Thr Pro Pro Arg Leu Gln Ala Thr Trp
305                 310                 315                 320

Arg Pro Ala Gln Thr Thr Ser Ser Gln Pro Ala Ser Ser Ser Ser
                325                 330                 335

Ser Ser Val Ser Val Arg Ala Arg Glu Gly Val Val Leu Leu Arg Arg
            340                 345                 350

Pro Ser Asp Gln Ala Lys Gly Gly Asn Ala Gly Thr Arg Gln Glu Arg
        355                 360                 365

Lys Ser Lys Gly Gly Lys Asn Val Ala Ser Ser Ala Ser Ala Pro Ala
    370                 375                 380

Ser Ser Ser Thr Pro Thr Ala Ser Gly Lys Gln Ala Gln Lys Gly Ala
385                 390                 395                 400

Gly Ser Ser Gly Gly Gly Ala Gly Gly Gly Gly Asn Trp Lys
                405                 410                 415
```

```
Gly Arg Lys Ser Gly Trp Glu Ala Arg Phe Leu Phe Lys Asp Pro Glu
            420                 425                 430

Ser Ala Gly Asp Ala Asp Thr Gln Ser Ser Pro Ala Ser Glu Arg Asp
        435                 440                 445

Thr Arg Thr Thr Val Met Ile Arg Asn Ile Pro Asn Lys Tyr Ser Gln
    450                 455                 460

Lys Leu Leu Leu Asn Met Leu Asp Asn His Cys Ile Gln Ser Asn Glu
465                 470                 475                 480

Trp Ile Ala Ala Ser Gly Glu Ala Gln Pro Phe Ser Ser Tyr Asp Phe
                485                 490                 495

Val Tyr Leu Pro Ile Asp Phe Asn Asn Lys Cys Asn Val Gly Tyr Gly
            500                 505                 510

Phe Val Asn Leu Thr Ser Pro Glu Ala Ala Val Arg Leu Tyr Lys Ala
        515                 520                 525

Phe His Lys Gln Pro Trp Glu Val Tyr Asn Ser Arg Lys Ile Cys Gln
    530                 535                 540

Val Thr Tyr Ala Arg Val Gln Gly Leu Asp Ala Leu Lys Glu His Phe
545                 550                 555                 560

Lys Asn Ser Lys Phe Pro Cys Asp Ser Asp Glu Tyr Leu Pro Val Ala
                565                 570                 575

Phe Ser Pro Ala Arg Asp Gly Lys Glu Leu Thr Glu Pro Val Pro Ile
            580                 585                 590

Val Gly Arg Ser Pro Ala Ser Gly Ala Ser Ser Pro Pro Lys Ser Arg
        595                 600                 605

Ala Ala Ser Val Asp Leu Leu Gly Gln Glu Leu Met Pro Ala Pro Ser
    610                 615                 620

Ser Ser Ala Asp Gly Ala Ser Ser Thr Thr Thr Ser Thr His Ala Leu
625                 630                 635                 640

Ser Glu His Ala Asp Asp Asp Asn Asp Glu Asp Ile Arg Leu Ala
                645                 650                 655

Gly Glu Leu Arg Arg Leu Gly Tyr Ala Asp
            660                 665

<210> SEQ ID NO 9
<211> LENGTH: 5994
<212> TYPE: DNA
<213> ORGANISM: Triticum aestivum
<220> FEATURE:
<221> NAME/KEY: misc_feature
<222> LOCATION: (0)...(0)
<223> OTHER INFORMATION: Triticum aestivum TEL1 -- genomic sequence with
      promoter and terminator

<400> SEQUENCE: 9
aagcttgtgc agtgagttgg agagcaactt tgcagtccat cgtggcatgt tccactactg      60
atgccaatta tatggctatt tccgaggcat gcaaagaagc tatttgattg tgaggtttat     120
acactcggct ttgtggagat tcatcttgcc ctactgtatt tagtggaagt gctatatatc     180
ttacaaaaaa tctaatgtat catgagacaa caaagcacat tgatatcaga tatcactata     240
ttcgagatgt tgctgaaggt tatttgaagg tatgaaagat aagtactcat aataatcctg     300
ctgatatgat gacaaagcca gtttctacca ataagtttga gcaaatgtag gcgctctcgc     360
tgcccagccg cctgcgccac ccaagcccgc aaccatgcag tgcgctttgc tgcaaagcac     420
cgctcacgcc ctcatccccg tccgcgcgcc cctgtgtgct cacgacgagt tgcgtcgttg     480
aggtatttgg ggaaccaatt gtaatctagc tatcgatttt agggtgtgtt gtgctatttt     540
```

```
gtatggacct tgttataaat tcaactagtg actagtgggc tgccgtgtga gactggtcgt    600
aatggtagta tcatagttag tatcatgcat gccaactaga caattttaat gaggtgtcat    660
agcattaaat aaagaaagag atgatagagc atcacatcat gacaccgtat cataataaat    720
gatactccct ccgtccgggt ttattaggcc taaagacaac ttttcttaga ccaagacaca    780
tagtaatttg atcacattaa ttcttccatt ccactcccaa tgcactctct cacatgcatg    840
cagccaatga aaaagcacac atgaagtgta ttaactttc agccatggca caacaacaa    900 tagctttcaa tacaaccaat gaaatggttg catgcatgca tccttccaac gccgggcctt    960
ataaaagggg gcatgcttgt gatgctgaga ggcctaataa acccgacgg agggagtatg    1020 ctactttgtg tcatgcatga caataaataa aatagtacat gatactaata tatgatacta    1080
tgcattagag aggtactatt attcactagt atcatatgca tgatactagc atatgatact    1140
ctccattaca accaggctga ccgaaatagt ctttacagga tcagtttcgc ccgatgccac    1200
atggtaccac aaatccattt tagggcgagc cgtatactgt ttttgtagag gcgttttttg    1260
cggtataacc tagagctgtc taaagttgca atatcgagct tttacatttt ccctaaaac    1320 agggtttgat ttttacagca gagagtttct tacagtgaac gtagtatcta agcagtggca    1380
gcagctagaa gatccgtgca acatgagaca caagagctct aacaaactcc cggaatcatc    1440
catgtccccg aaagatgaac acgttctggc gtcacagaag atccgagcca acagggccgg    1500
ccagccgcac aacacaacac cccgcagcgg gcgcaggagg cagcgcttct tcctcccgag    1560
accagccagc cgctctccct ccctccccct tgttcctgta gacttccaaa taaaagccca    1620
cctgctttct tttcccgcga ccatttccat aaaaagagct ccccgcccct ctctctcctc    1680 ctcccccag ccccaggtac ccctccaccc aacccagtcc acagctaagc aagaaggggc    1740
aggcgggcga gggagagaga gagagaggga ccgctcaagt acaattctag cctagtttct    1800
tgatcgcggt ttgcagccac gacccagaat taatcccaag aatgttctag atcttccgcc    1860
tagcgccgcc gccgccgctg ctccaattcg gcctgcacgt gccatggacg gggtggagg    1920 aggcggtggt ggcatggccg gcatgccggg catgccggga gcgcctcaaa acatcctgga    1980
cgccggagct cagaagtact accctagtgc tggcgcgccc tacccgcccc cgcccttcct    2040
gtcgatcccg caccagctct actgcccgcc gccgttcccg gtcatgccgc cgccgacggc    2100
catgcccatg cccatgccca tgccacagcc gcagaccgtc gcgattcagc gcagattgg    2160 gctccccgtg ccgacggtag ccgcgacggc ggtcgacggt ccggcgagcc gcgcggtcgt    2220
gctcagcctg ctgccgccac acacgccgga gatcgaggtg gcgcgcgcga tggcgccctt    2280
tggcgacgtg cgcacggtgg acgcgccggc gctggcgtcc gagggcgtgg ccacagtgca    2340
cttctttgac ctccgcgccg ccgagaacgc cgtcaccgcg gtgcgcgagc agcacatgcg    2400
gcagcagtgc cgcctcagcc agctgtacgc cgccacgacc gcctggccac cccagccgcc    2460
ggcgtgggac tggcaccagg acgactgccg gggcctcgtc ctcggccagg ccgtatgggc    2520
tcacttcgcc gctgcctcca ccctcccga cgacggcgcc aaccgcggct ccctcgtcgt    2580
gctcaattcc ctcccggacg tctccctctc cgagctccgc caggccttcc aagcctacgg    2640
tacgcaccca ccaccgaacc gagccaccga acacttctcg ccacaattct cctctaatgc    2700
ccgaccggtg tttgtttgca ggtcccttga aggatgtgag ggagtccgcg cagcggccga    2760
accacaaatt cgtggagttc ttcgacacgg ccatgccgc cgggcgctc gccgagctca    2820 acggccggga cttcttcggc caccgcttca tcctcgagtt cacgcgccct tctgtccccg    2880
```

```
gcgtacgcag gtaattcttg cgcaccgcct tgccctcact tgcccatcga tccagtccgt   2940
cgactaaaat actatgtgaa ttgcacgcag gcgcgggttc gtgtcgccgc gacccatcgt   3000
cccgacgccg cccaggctgc aagcggcgtg gcgtcccttg ccgtctccgg cgaaacagcc   3060
gtcgtcgtcg tcgaccggca ctggcaaggc caggggagag gtggttacca cgagcaggtg   3120
ctcctccaag tctaacgcgg gcgatcggtc caagggtggc acaagccatg aacggaaggg   3180
caagggcaag ggcgggaaga aagccacaat tgtcgttgac acgacgtcgt cgtctccggc   3240
ctcggcttcc gaggcggcgg cgaccgcgtc ggcgtccggc aagcagcagc cgcagaaagg   3300
agtcgtccgc gtgggggagct ggagaggccc aagagctgg agaggcgggt gggagacgcg   3360
cttcgagttc aaacagcccg acgccgcccg ctccgacagc aacgccacca ccgccgccga   3420
cacgacacg caagaaccgg agacgaggac caccgtgatg atcaggaaca taccgaacaa   3480
gtacaggtcg tcatcctccg cgtttgccgc aacaatgcta ctactactag tactatattt   3540
catgggcgca tgctatgcta caattgtgag aaggatttgc ctagctcatg ctcggccttg   3600
tgtgcctgac cttgtgatct cttgttcgtt gcagccagaa gctgctgctc aacatgctgg   3660
acaaccactg catcgagtac aacaataaga tcgacgccgg cgaaggcggc ggcgagccct   3720
tctcctccta cgatttcctc tacctcccca tagatttcaa gtgagtcctc caactataag   3780
ctgctgcatt cgttcatatt tcatggagct cattcccacg aacacacact caatttactc   3840
aatttgcaaa ttaaaattgt atgagaagtt ggttcaattg aggtagaaaa atgtgaaggc   3900
tacaaaatta caaaattggt agaaaccagg acaagttctt ggccattagc cggccggctg   3960
tttgagcttg tgtggggtga aggggggcat cttcggtac tactaccacg ccctgtactg   4020
cctggtctgc gccagcattg ttgtgccatg gtcttattag cccaaatgga aaagaaattg   4080
gagatggcac cggatccttt tcgttttgat gcaatgaatt ctttggttgc atgcatcgcc   4140
tggcccggct gatcgatcag aaagggggcct gtgttcgcct gtctttcttt tctcgcacat   4200
ctgctgcctc tctaggatcc tcctccctcc ctccctgcca attgcttttc ttgctttgca   4260
cagccctcac tgctggcatg ccatgcgctt ccatatcaag gccagcacga catggataaa   4320
agcaaacctt tgggtgagag aatcatggag tagcggtgaa aagttgcatc atatgcaaaa   4380
gcgttcatgt attttgtggt gttcaaagta tgaaaattgg tgttggctaa tttcaagcac   4440
actttctttt ttgtgtcttg tttggctgcc aactttccgc ttgcacgaag caaaggctga   4500
gaaaagacct gccatcagtg cccaatgaca agaggaactt tggtgcgctt ctgcccaaag   4560
ccagcttcac atctatagta aaaaaattct actggtagct ccaaaagctt ttgacctctc   4620
caactagtag tgtagctctt gcttggctga ttactccaag gttttggtag tagtactagc   4680
tctaaattaa tcagtggtat tatatcttca tcttttttgc ggggaagtgg tattatatct   4740
tcaaatgaac gtctaaattt tgttgtggca tgcagcaaca agtgcaacgt ggggtacggg   4800
ttcgtgaacc tcaccacgcc ggaggcggcc gtgcggctgt acaaggcgtt ccacaagcag   4860
ccatgggagg tgtacaactc cgcaagatc tgccaagtca cgtacgcacg cgtgcaggta   4920
cgtactctcg tgtaccgcat ctgcatgcca tgaatcttga caagttcctc ctatgccacc   4980
cacagcagta cgtagctcgc cgtgttaatt aaccaacgag cgtgatgcgc agggcctgga   5040
ggcgctcaag gaccacttca agaactccaa gttcccctgc gacagcgacg agtacctgcc   5100
ggtgatcttc tcgccgccgc gcgacggcag gcagctcacc gagccggagc tcctcgtgcc   5160
gcgctcgccc atgccgtcgc cgtcctgccc gcggaagggc caggccgcgg gcttggaccc   5220
gctggcgctg gagctcatgg cgccgccctc gtcgtccggc gacggcgcgt cctcaacgat   5280
```

-continued

```
gtccacccac gccgacgagg acgcccacgg cgcgagcggc ggcagcgacg acgacgacga    5340
cggtgggctc ggcgaggagc tacagcgcct aggctacacc gactaggtat aggcacgcgg    5400
cgagccagcc agccagccta gcatttgctt cgagaagtgg ccgagcaatg atggtggttg    5460
ctgcatggca tatctctggg gcggatctgc gagtgaagcg aagggtcaca caacatttat    5520
ggcatgtgaa tggagattga acgacgacag gagtgtggga gatgaaatga ctcgagaaaa    5580
gaagcgattt gatgtgtgtg gtttcgatcg agagaggtac tatcatcatc gccgtcgtca    5640
ttcattcgta ctagctggac gcatgcagca ggcggagtcg tgttcttgtg gtttttagat    5700
ttgaagttaa gtttctctct ttgaaacttg gagctagcca gctagctaga ctattcttct    5760
tcatgccttc tttcgttcgt tacattaatt acaagtttta cgtactccga atttcgttct    5820
tcatgtgatg gtaatgatag atttgatcag atctcaccat ctctctctct gccgaattac    5880
caactctatg ttttccattt tgtttacttg gccctaattt gcattcatgt tcccttaaga    5940 ttttattcg cccatttcgt agtatgaaaa tatatcatgc gggtgatggg tacc            5994
```

<210> SEQ ID NO 10
<211> LENGTH: 682
<212> TYPE: PRT
<213> ORGANISM: Triticum aestivum
<220> FEATURE:
<223> OTHER INFORMATION: Triticum aestivum TEL

<400> SEQUENCE: 10

```
Met Asp Gly Val Gly Gly Gly Ala Gly Met Ala Gly Met Pro Gly
 1               5                  10                  15

Met Pro Gly Ala Pro Gln Asn Ile Leu Asp Ala Gly Ala Gln Glu Tyr
                20                  25                  30

Tyr Pro Ser Ala Gly Ala Ser Tyr Pro Pro Pro Phe Leu Ser Leu
             35                  40                  45

Pro His Gln Leu Tyr Cys Pro Pro Leu Pro Val Met Pro Pro
         50                  55                  60

Met Ala Met Pro Met Pro Met Pro Met Pro Gln Pro Gln Thr
65                  70                  75                  80

Val Ala Ile Gln Pro Gln Ile Gly Leu Pro Val Pro Thr Val Ala Ala
                 85                  90                  95

Thr Ala Val Asp Gly Pro Ala Ser Arg Ala Val Val Leu Ser Leu Leu
            100                 105                 110

Pro Pro His Thr Pro Glu Leu Glu Val Ala Arg Ala Met Ala Pro Phe
        115                 120                 125

Gly Asp Val Arg Thr Val Asp Ala Ser Ala Leu Ala Ser Glu Gly Val
    130                 135                 140

Ala Thr Val His Phe Phe Asp Leu Arg Ala Ala Glu Asn Ala Val Thr
145                 150                 155                 160

Ala Val Arg Glu Gln His Met Arg Gln Gln Cys Arg Leu Ser Gln Leu
                165                 170                 175

Tyr Ala Ala Thr Thr Ala Trp Pro Pro Gln Pro Pro Ala Trp Asp Trp
            180                 185                 190

Gln Gln Asp Asp Cys Arg Gly Leu Val Leu Gly Gln Ala Val Trp Ala
        195                 200                 205

His Phe Ala Ala Ala Ser Thr Val Pro Asp Asp Gly Ala Asn Arg Gly
    210                 215                 220

Ser Leu Val Val Leu Asn Ser Leu Pro Asp Val Ser Leu Ser Glu Leu
225                 230                 235                 240
```

-continued

Arg Gln Ala Phe Gln Ala Tyr Gly Pro Leu Lys Asp Val Arg Glu Ser
            245                 250                 255

Ala Gln Arg Pro Asn His Lys Phe Val Glu Phe Asp Thr Arg His
        260                 265                 270

Ala Ala Arg Ala Leu Ala Glu Leu Asn Gly Arg Asp Phe Phe Gly His
        275                 280                 285

Arg Phe Ile Leu Glu Phe Thr Arg Pro Ser Ile Pro Gly Ala Arg Arg
        290                 295                 300

Arg Gly Phe Val Ser Pro Arg Pro Ile Val Pro Thr Pro Pro Arg Leu
305                 310                 315                 320

Gln Ala Ala Trp Arg Pro Leu Pro Ser Pro Ala Lys Gln Pro Ser Ser
                325                 330                 335

Ser Ser Thr Gly Thr Gly Lys Ala Arg Gly Glu Val Val Thr Thr Ser
            340                 345                 350

Arg Cys Ser Ser Lys Ser Asn Ala Gly Asp Arg Ser Lys Gly Gly Thr
        355                 360                 365

Ser Gln Glu Arg Lys Gly Lys Gly Lys Gly Lys Lys Ala Thr Ile
    370                 375                 380

Val Val Asp Thr Thr Ser Ser Pro Ala Ser Ala Ser Glu Ala Ala
385                 390                 395                 400

Ala Thr Ala Ser Ala Ser Gly Lys Gln Gln Pro Gln Lys Gly Val Val
            405                 410                 415

Arg Val Gly Ser Trp Arg Gly Pro Lys Ser Trp Arg Gly Gly Trp Gly
                420                 425                 430

Asp Ala Phe Arg Val Gln Thr Ala Arg Arg Arg Ser Asp Ser Asn
        435                 440                 445

Ala Thr Thr Ala Ala Asp Thr Asp Thr Gln Glu Ala Glu Thr Arg Thr
    450                 455                 460

Thr Val Met Ile Arg Asn Ile Pro Asn Lys Tyr Ser Gln Lys Leu Leu
465                 470                 475                 480

Leu Asn Met Leu Asp Asn His Cys Ile Glu Tyr Asn Lys Ile Asp
                485                 490                 495

Ala Gly Glu Gly Gly Glu Pro Phe Ser Ser Tyr Asp Phe Leu Tyr
            500                 505                 510

Leu Pro Ile Asp Phe Asn Asn Lys Cys Asn Val Gly Tyr Gly Phe Val
        515                 520                 525

Asn Leu Thr Thr Pro Glu Ala Ala Val Arg Leu Tyr Lys Ala Phe His
    530                 535                 540

Lys Gln Pro Trp Glu Val Tyr Asn Ser Arg Lys Ile Cys Gln Val Thr
545                 550                 555                 560

Tyr Ala Arg Val Gln Gly Leu Glu Ala Leu Lys Asp His Phe Lys Asn
                565                 570                 575

Ser Lys Phe Pro Cys Asp Ser Asp Glu Tyr Leu Pro Val Ile Phe Ser
        580                 585                 590

Pro Pro Arg Asp Gly Arg Gln Leu Thr Glu Pro Glu Leu Leu Val Pro
        595                 600                 605

Arg Ser Pro Met Pro Ser Pro Ser Pro Arg Lys Gly Gln Ala Ala
610                 615                 620

Gly Leu Asp Pro Leu Ala Leu Glu Leu Met Ala Pro Pro Ser Ser Ser
625                 630                 635                 640

Gly Asp Gly Ala Ser Ser Thr Met Ser Thr His Ala Asp Glu Asp Ala
            645                 650                 655

His Gly Ala Ser Gly Gly Ser Asp Asp Asp Asp Gly Gly Leu Gly
            660             665             670

Glu Glu Leu Gln Arg Leu Gly Tyr Thr Asp
        675             680

<210> SEQ ID NO 11
<211> LENGTH: 2058
<212> TYPE: DNA
<213> ORGANISM: Brachypodium distachyon
<220> FEATURE:
<221> NAME/KEY: misc_feature
<222> LOCATION: (0)...(0)
<223> OTHER INFORMATION: Brachypodium distachyon TEL cDNA

<400> SEQUENCE: 11

| | | | | |
|---|---|---|---|---|
| atggagggaa | gaggtgctgg | catgggcggg | atgccgggag | ctcccccaat catcctggac | 60 |
| gctggagctc | aggagtacta | ccctgcagtc | gttggcggcg | ccgccgccta cccgccattc | 120 |
| ctgccgctta | ccccgcagca | gctctactgc | ccgccgccat | accaggccat gccgcctccg | 180 |
| ccgccgccga | tggccctgcc | cttgccgctg | ccgatgccaa | tgccgattcc gattccgcag | 240 |
| cagattgggc | cgacggccgc | ggcggcggcg | gcggcggttg | acgcgccggc gagccgcgcg | 300 |
| gtggtgctga | gcctggtgcc | gccgcacgcg | caggagggcg | acgtggcgcg cgccatggcg | 360 |
| gcattcggcg | cggtgcgcgc | cgtggacgcg | tccgcggtgc | cgtccgagcg cgtggccacc | 420 |
| gtgcacttct | tcgacctccg | cgccgccgag | ctcgccgtgg | ccgccgtgcg cgcgcagcac | 480 |
| atgcggcagc | agtgccgcct | cagccagctc | tacgccgcca | cggtctcctg gcctccgtcg | 540 |
| gcggcggggc | caggcccagc | tcctgctgcc | tgggactggc | cccacgacga catcctgggc | 600 |
| ctcgtcctcg | ggcaggccgt | ctgggcccag | ttcgccgccg | cctccacgct ccccgacgac | 660 |
| ggcttcagcc | gcggctccct | cgtcgtgctc | aattccctcc | ggacgacgt ctccctcctc | 720 |
| gagctccgcc | aggccttcca | agctttcggt | gacttgaagg | atttgaggca gtcgccgcat | 780 |
| cggccgagcc | acaagttcgt | ggagttcttc | gacacccgcg | acgccgcccg cgcgctcgcc | 840 |
| gagctcaacg | gccaggactt | cttcggccac | cgcctcgtcc | tcgagttcac gcgcccctcg | 900 |
| accccgggct | tccgcaggcg | cgggtacgtg | ctgcagcagc | agcccatggc cccgatcccg | 960 |
| ccgaggctgc | aacaggcatg | gcgtccgacg | tttccacagg | cgtcgtcatc gtcctcaggg | 1020 |
| accggcaggg | ggagggaagg | cgtggtgctc | atgaggagat | caagctctgc gaaatctagc | 1080 |
| ggctcaggtg | atcgatccaa | gggaggcaac | aacaacaaca | caatggcgc cggcaggagc | 1140 |
| catgagcgga | agggcaaggg | cgggaagaag | cccaccatcg | tcgtcgtggc gtcatcatcc | 1200 |
| gcttcgtcgt | cgtccacgac | ggaggcgacc | accgcgtcgt | cgtctggcaa gcagcagtgc | 1260 |
| gtcaagtcgg | tcggccgtgc | cgggagcggg | cggagccaca | ggggctggaa aggccggttc | 1320 |
| gacaagcaat | tcgagttcaa | agagccggaa | gccgccgccg | ccgacgacac cgacacgcaa | 1380 |
| gagccggaga | gcgggaccac | ggtgatgatc | aggaacatac | ccaacaagta cagccagaag | 1440 |
| ctggtactca | acatgctgga | tcgcactgc | atcgtccaca | caagaagca gatcgaggcc | 1500 |
| ggcgaaagcg | aatgccaggg | gcagcagcag | cccttatcct | cctacgactt cctctacctc | 1560 |
| cccatcgatt | tcaaaaacaa | gtgcaacgtg | gctacggct | tcgtgaacct cacctcgccg | 1620 |
| gaggctgccg | tgcgtctgca | caaggcattc | caccagcagc | cgtgggaggt cttcaactcg | 1680 |
| cgcaagatct | gccaggttac | atacgcacgc | gtgcagggcc | tggaggcgct gaagcagcac | 1740 |
| ttcaagaact | gctcgttccc | gtgcgagagc | gacgagtacc | tgccggtggt gttctcgccc | 1800 |
| ccgcgtgacg | gccagcagct | caccgagcca | gtgcccctgg | tccagccctc gctgcgcgcc | 1860 |

```
ccgacctcaa acgtcgaccc gctggcgctg gacctcatgg cagccgcgcc ttcgtcgacg    1920
tcgggcgacg gcgcatcctc caccatgtcc acccacgccg acgagggcca cggcgcaagc    1980
tgcagcaacg atgatgatga cgacaacgac gacgagggac tcgccgagga gctacagcgc    2040
ctaggctaca ccgactag                                                  2058
```

<210> SEQ ID NO 12
<211> LENGTH: 685
<212> TYPE: PRT
<213> ORGANISM: Brachypodium distachyon
<220> FEATURE:
<223> OTHER INFORMATION: Brachypodium distachyon TEL

<400> SEQUENCE: 12

```
Met Glu Gly Arg Gly Ala Gly Met Gly Gly Met Pro Gly Ala Pro Pro
 1               5                  10                  15

Ile Ile Leu Asp Ala Gly Ala Gln Glu Tyr Tyr Pro Ala Val Val Gly
             20                  25                  30

Gly Ala Ala Ala Tyr Pro Pro Phe Leu Pro Leu Thr Pro Gln Gln Leu
         35                  40                  45

Tyr Cys Pro Pro Pro Tyr Gln Ala Met Pro Pro Pro Pro Pro Pro Met
 50                  55                  60

Ala Leu Pro Leu Pro Leu Pro Met Pro Met Pro Ile Pro Ile Pro Gln
 65                  70                  75                  80

Gln Ile Gly Pro Thr Ala Ala Ala Ala Ala Ala Val Asp Ala Pro
                 85                  90                  95

Ala Ser Arg Ala Val Val Leu Ser Leu Val Pro Pro His Ala Gln Glu
            100                 105                 110

Gly Asp Val Ala Arg Ala Met Ala Ala Phe Gly Ala Val Arg Ala Val
        115                 120                 125

Asp Ala Ser Ala Val Pro Ser Glu Arg Val Ala Thr Val His Phe Phe
    130                 135                 140

Asp Leu Arg Ala Ala Glu Leu Ala Val Ala Ala Val Arg Ala Gln His
145                 150                 155                 160

Met Arg Gln Gln Cys Arg Leu Ser Gln Leu Tyr Ala Ala Thr Val Ser
                165                 170                 175

Trp Pro Pro Ser Ala Ala Gly Pro Gly Pro Ala Pro Ala Ala Trp Asp
            180                 185                 190

Trp Pro His Asp Asp Ile Leu Gly Leu Val Leu Gly Gln Ala Val Trp
        195                 200                 205

Ala Gln Phe Ala Ala Ala Ser Thr Leu Pro Asp Asp Gly Phe Ser Arg
    210                 215                 220

Gly Ser Leu Val Val Leu Asn Ser Leu Pro Asp Asp Val Ser Leu Leu
225                 230                 235                 240

Glu Leu Arg Gln Ala Phe Gln Ala Phe Gly Asp Leu Lys Asp Leu Arg
                245                 250                 255

Gln Ser Pro His Arg Pro Ser His Lys Phe Val Glu Phe Asp Thr
            260                 265                 270

Arg Asp Ala Ala Arg Ala Leu Ala Glu Leu Asn Gly Gln Asp Phe Phe
        275                 280                 285

Gly His Arg Leu Val Leu Glu Phe Thr Arg Pro Ser Thr Pro Gly Phe
    290                 295                 300

Arg Arg Arg Gly Tyr Val Leu Gln Gln Gln Pro Met Ala Pro Ile Pro
305                 310                 315                 320
```

```
Pro Arg Leu Gln Gln Ala Trp Arg Pro Thr Phe Pro Gln Ala Ser Ser
            325                 330                 335

Ser Ser Ser Gly Thr Gly Arg Gly Arg Glu Gly Val Val Leu Met Arg
        340                 345                 350

Arg Ser Ser Ser Ala Lys Ser Ser Gly Ser Gly Asp Arg Ser Lys Gly
            355                 360                 365

Gly Asn Asn Asn Asn Asn Gly Ala Gly Arg Ser His Glu Arg Lys
    370                 375                 380

Gly Lys Gly Gly Lys Lys Pro Thr Ile Val Val Ala Ser Ser Ser
385                 390                 395                 400

Ala Ser Ser Ser Thr Thr Glu Ala Thr Thr Ala Ser Ser Ser Gly
            405                 410                 415

Lys Gln Gln Cys Val Lys Ser Val Gly Arg Ala Gly Ser Gly Arg Ser
            420                 425                 430

His Arg Gly Trp Lys Gly Arg Phe Asp Lys Gln Phe Glu Phe Lys Glu
        435                 440                 445

Pro Glu Ala Ala Ala Asp Asp Thr Asp Thr Gln Glu Pro Glu Thr
    450                 455                 460

Arg Thr Thr Val Met Ile Arg Asn Ile Pro Asn Lys Tyr Ser Gln Lys
465                 470                 475                 480

Leu Val Leu Asn Met Leu Asp Ala His Cys Ile Val His Asn Lys Lys
                485                 490                 495

Gln Ile Glu Ala Gly Glu Ser Glu Cys Gln Gly Gln Gln Pro Leu
                500                 505                 510

Ser Ser Tyr Asp Phe Leu Tyr Leu Pro Ile Asp Phe Lys Asn Lys Cys
        515                 520                 525

Asn Val Gly Tyr Gly Phe Val Asn Leu Thr Ser Pro Glu Ala Ala Val
        530                 535                 540

Arg Leu His Lys Ala Phe His Gln Gln Pro Trp Glu Val Phe Asn Ser
545                 550                 555                 560

Arg Lys Ile Cys Gln Val Thr Tyr Ala Arg Val Gln Gly Leu Glu Ala
                565                 570                 575

Leu Lys Gln His Phe Lys Asn Cys Ser Phe Pro Cys Glu Ser Asp Glu
        580                 585                 590

Tyr Leu Pro Val Val Phe Ser Pro Pro Arg Asp Gly Gln Gln Leu Thr
    595                 600                 605

Glu Pro Val Pro Leu Val Gln Pro Ser Leu Arg Ala Pro Thr Ser Asn
    610                 615                 620

Val Asp Pro Leu Ala Leu Asp Leu Met Ala Ala Pro Ser Ser Thr
625                 630                 635                 640

Ser Gly Asp Gly Ala Ser Ser Thr Met Ser Thr His Ala Asp Glu Gly
            645                 650                 655

His Gly Ala Ser Cys Ser Asn Asp Asp Asp Asp Asn Asp Glu
            660                 665                 670

Gly Leu Ala Glu Glu Leu Gln Arg Leu Gly Tyr Thr Asp
        675                 680                 685

<210> SEQ ID NO 13
<211> LENGTH: 6312
<212> TYPE: DNA
<213> ORGANISM: Glycine max
<220> FEATURE:
<221> NAME/KEY: misc_feature
<222> LOCATION: (0)...(0)
<223> OTHER INFORMATION: Glycine max TEL1 -- genomic sequence with
      promoter and terminator
```

<400> SEQUENCE: 13

```
ggatcctcta gagattattg tcgacttaac accaaaacaa acatgcagta tcttatttag      60
aagaggacaa caaagatgg agggagcaag caggaaacaa gaaagaacgt agtcccttct     120
taaaaatggt gaagaggcag ggaaacatcg ctttcactta cttttagtgc cacatcaaac     180
gggttttgtt tgtttagtgg caactgccaa acaagagata gagtcattca tagagggcta     240
gagattagag aagtcacggt tggctgctgg cctgttcaaa tggtacgaat aatgtggaac     300
aatttaaaca acatgttaca ttttttcta tattttccta taaatctttt taatagttca     360
tacaaaatat aaataaaaaa tataaataaa aaataaatat gttcaatatc ttagatacat     420
aaaaaaaatg cctaatagta cttttatct aacaagttag ataattaata agaatttttt     480
atagaaaaat taaaaagtaa atgggattaa tgaactaata tttttttta ataactaaaa     540
tcaaatttaa ctatattgtc agaaactaaa aatatatttt gctcataaat ttatataact     600
gataatttac ttacttatta cttaattcta tatttaatca taaacattaa agttacaaac     660
atcttaatta attgtaggta atttattagt taaatgagat taatatattt agttaatatg     720
gaaaaggttg tgtaaaatta acatgtatta ggaaaagtgt gtgagaaatt agtgaaagaa     780
acaaaaaata cttgcatgga gattagaaaa ggatgggaca atgagagacg tggaagatgg     840
aggcagtgtc attcatgcaa agaatcaaat gcttagaata aaatagcatt ggtgtggtgt     900
tgaggctagg agagcttcaa aacttgagaa atctcacctt tcactgcaga ttggaatcct     960
aactcaactc aatgagacaa ttattaaact tattgtaagg ctatcaccaa ccccccgtca    1020
tctctcccag tatctttaac cacagtgaca atgggaactg aaattcgttt ttcttatta    1080
ataatccaac cactatttgc agaagagcca tccggagttg tctgcacata acaagacaaa    1140
taatatacca atacaaatta ttgggaaaaa cttaattact accaataatc aaacgcaagg    1200
caacttgtgg ctatgttttg ggcctaaatt aaattaataa tgagatgaga aggagagca    1260
gtgaaaatag ctagataaga aaaactgtca caaaattctg tgtgtgtaag gaagtgttca    1320
cagatgaagc attatgagca gtagaaaaat acaaaaacat gaaatagtac ggtacccagg    1380
ctgccaagca ggcaccggag ccatttattg ttgtcctctt ttggcatttg ttgtttttat    1440
acagaattgc aaattcaacg ttgaatgaaa attgcctaaa tagttggatt aatcatcatg    1500
gttttaaaat gtgaatgaaa aggtgttaca ggaaattata tttgcagact caaatggaag    1560
atatgaccct agtcaaacag tccatttact gggttctgat tgactattg gacttgttaa    1620
agaaatagac ttgatattct tttaaatact aggatgatat ttgaaaaaaa taatactagc    1680
tataactcaa aacatattga atacacctca ttggatgttt gtttagaata gtctaaatta    1740
taacaaataa ttatttgtat tttaagtctc tttcaaaaag ctaacaagaa tatgaactct    1800
ttttcccctc aaaataaagc tcatgccaaa taacttaact ttttcttaaa aataataata    1860
aatattgttt atgttttgaa tatgaagaat gctttaatat ctgacaattt ttttattaa    1920
aattaattaa tactagatta agtggtgaca taaattaaaa ctattttttt tagatgagtg    1980
ataggaacac actttataat atagtctttt taatatattt ttttattgat taatttatta    2040
aaactataaa atcaagaaaa ataattatta ataaaatat gagacgtatt gaattttatg    2100
atttcctata aatttaagtt atgatattca tatacatcat ttttggatga aataaaagag    2160
agagagaaag aaaaaaaga atagaaagag aaaataataa atgtgataaa tgatatgata    2220
aaaggaaag agaaagatag agaaataatt ggaggaaagg tggaatgaaa gagaaaataa    2280
```

```
aatatttttg tatttatcta actaatatgt ttatatttag ccaattgttt gaagacatta    2340
gttaaagaac ctaaaataaa aataatttat tggaaaaaaa ttgaattatt cataatctat    2400
cttatatttt cttataattt agataataaa tatatttaga taagtatttg tagcatataa    2460
ataaagaatg aaaatgacaa tgaagcaaaa ccaccaaaat ggtgagtcct tagtcagtag    2520
ctgtggtgtg caagggagaa aagagaggg gtaataaagt aaaaggggat ggggcatta     2580 ggtgggaaag tactttttga gtaagttttt gggttaggaa agtagagaat gaggaaaaga    2640
ggcgagtgag tgagatttga atgggagaaa ccgggatcat tgtcagcttc cagggtaact    2700
tagacccgag agcagaggag ttcagacccc tcaatcttca atgccaatgg tatcctcttc    2760
ctcttcccac acccctctcc acctcctcca cccgctccct cctcctcact ccgctcccat    2820
tcacctccca ctccgccctc cgcgcagaac tccaggcctt cggcgacatc agagccctcc    2880
aaaccgactc cctccgccac ggcatcctca ccgtccactt cttcgacctc cgccatgcag    2940
agtccgcctt cgccgccatc cgctccatgc acctccattt ccctcaattc ctcctctcgg    3000 cccacccat ctccgcccac tacgtcctcc cttcctccaa cgccttcccc gacgcccaca     3060
accaaggcac cctcgtcatc ttcaacctcc accccaacct ctccaccgtc caactccgtc    3120
gtctcttcca acctttcggt accctacttc tctctctttt ctttattatt attgttattt    3180
ttttgttcgc tagctgttag cggaggaaat cgtgtccgca cctgttttct cttctcttct    3240
ctcttaattc atacatgttg gaggaacttt ttaaggtgat gtttggtggg atgatactaa    3300
taataatagg attgtcatgt ctttgtcttg gacttttttct gtctccactt tttattttaa   3360
ataaaatttg ttggtggttg gttcaatcaa aatccatata taggtcccat aaaggaattg    3420 agagatatccc catggaaaaa gaatcagaga tttgtggagt tcttcgacat aagagacgcc    3480
gccaaggcct tgaagcacat gaacggcaag gaaattcacg gcaaacaggt tgtgattgag    3540
ttcagtagac ccggtggtca cacccgcaag ttcttccatc attctcctcc ttccgaaacc    3600 acaccttttca acgttcctcc gccaccacca ccgtttcctc cttccccgcg acgtcgtttt   3660
gctgctcctc gcttgcattc ctctcaaaag aaatcaccgg gaagccacaa gagtacggga   3720
tctattgatg cggaaatggg atcaatgagt ttgaccggag aagttgaagt tcagcattct    3780
tcacatggcc ccacacagag gaatcttagc agaaagcaca attgcgatac cactgtagta    3840
gtaggaacca ccaccaagca gcagcagcag caacaacaac aacaacaagt acctagaagt    3900
aggcactgga agggaaaaca agcgaagaaa caagaaacta ggtttctaat caaagagggt    3960
gccattgtag aatctggtcc caaagatact agaactactg tcatgatcaa aaacattccc    4020
aacaagtata ggtccgtttt tcatttcttt atatttactt ctatacattg cttcattttc    4080
ttcttctatt cgtgctcctg ttactagaaa ctagaaaagg gtgagtttga gcaatatgac    4140
caatcgagct tctctctctc tctctcgcta tgaagatacc cttttctctct ctataaccaa    4200 acaaacaaaa cagtgcataa aagcttcaag agagagagag agagaaaggc actgtaaagt    4260
gagctaaagt atgatgatag tataaaaaat gagtatgaaa ttaaattaaa gtataatgta    4320
gtatctgaga actatataat gtagtataaa aagttttggt tttgacttgt tgcagtcaga    4380
agttgctatt aaacatgctg gataaccact gcagacactg caacgagcag attgcagacg    4440
gcgatgagca gcagcctcta tcctcctacg acttcgtgta ccttcccatt gatttcaagt    4500
attttttcca tttccatgcg tgcaatccca cttatttaac taattaattg atttacccac    4560
caagcaaaat gtatcaatta ttattatgtt ttgaaacagc aacaagtgca acgtgggata    4620
tggttttgtg aacatgactt ccacggaggc aacactcagg ctccacaagg ccttccatct    4680
```

```
tcaacattgg gaggttttca attcaagaaa aatctgcgaa gtcacctatg ctagagttca    4740
ggtactacta tttcgctatt catattagta cataggaaaa aaaaaatacc tttcttaat     4800 ctcaaatata agaaaattgt aattaacttt tatttattta atgttattat ctctaaaata    4860
ttttttttat taaattgaag tttcagtttc aataataata cattttattt ccttacatta    4920
atttccaata aaggataaaa aaaattatca gcgtgaatat tttcttgttc ttttatttga    4980
taatttgaga tgtaagtatt aattgttaag tgtgacatac agtattatat attaatgagt    5040
aatgccaaat tctcgtgtta tattctcatg catattttcc tactattttt ttatgtattg    5100
gatgaaaaat aaaagcattt attgtcttga aaatataaaa tatatttaaa acttatcata    5160
aaagataaca ggagaattta ttggaggata taataggaat attaaagaat tattattttt    5220
caatgaaaaa tatttttatt ttaagatttt taactaatat tcttaagata ttagttagca    5280
tttctcgtaa gtatatactg gaattagtac aataaattca tattgttgat ttaaaagcaa    5340
atgaataatg aaatgaaggg attggaagca ttgaaagagc acttcaagaa ctcaaagttc    5400
ccatgcgaga tggagcatta cttaccagtg gtgttttcgc cgcctcgaga tgggaaagaa    5460
ctgacggagc cacttccaat agtggggaac aagcaacaac aacaagccat atcaagtggc    5520
ggcggcggca gcggcagcgt aggtgatgat gatgagacaa atgaagaagt gggtagtagt    5580
gttgtgattc tgaaagacag catttaaggt ggttgagcaa cgagccacac ctgtgttcgt    5640
cttcgtgcct taaccagcca accaacctac ctacaactac agcaaccatt tctctatctc    5700
tcaactgaac ctgttgctgc tcactgctca cctttcctcc aatatctctt cacttttttt    5760
tttataaata ttttcgtttc ctgcttttgt ctagtgaaat tgaatttgtc gcttttttc    5820 ttttttcttt tcaatcactt gtttgtagac ttgtagttgt aggttctgct gcttcagatg    5880
tactgtagta gtatttagtt tgcctattta attttcaaga atttcgatgt atcattttt     5940 ttatagatag aaaactttaa agagaacata gaaactttag ttagttcttg acgattacta    6000
ggtttagact gggtttgatt gtgtagtaga gaaaagagc agaaaagaat taagaaaat      6060 atttaaatta aagtagtaga taagagaag aatggaattc cacctttttt tttttttca      6120 tgaatagtat tttctcccett acaaccaaac taaatattaa gctagtagta actaggagtg    6180
gaatggaaag gtttcatgaa catatacgat tgtgtcttac tgtagataat aaacatctat    6240
ttgaatagga tcgatgtagg agatttaggt aataaacatg gtcgacgaat ctctagagga    6300
tccccgggta cc                                                        6312
```

<210> SEQ ID NO 14
<211> LENGTH: 497
<212> TYPE: PRT
<213> ORGANISM: Glycine max
<220> FEATURE:
<223> OTHER INFORMATION: Glycine max TEL1

<400> SEQUENCE: 14

Met Gly Glu Thr Gly Ile Ile Val Ser Phe Gln Gly Asn Leu Asp Pro
1               5                   10                  15

Arg Ala Glu Glu Phe Arg Pro Leu Asn Leu Gln Cys Gln Trp Tyr Pro
                20                  25                  30

Leu Pro Leu Pro Thr Pro Leu Ser Thr Ser Thr Arg Ser Leu Leu
            35                  40                  45

Leu Thr Pro Leu Pro Phe Thr Ser His Ser Ala Leu Arg Ala Glu Leu
        50                  55                  60

-continued

```
Gln Ala Phe Gly Asp Ile Arg Ala Leu Gln Thr Asp Ser Leu Arg His
 65                  70                  75                  80

Gly Ile Leu Thr Val His Phe Phe Asp Leu Arg His Ala Glu Ser Ala
                 85                  90                  95

Phe Ala Ala Ile Arg Ser Met His Leu His Phe Pro Gln Phe Leu Leu
            100                 105                 110

Ser Ala His Pro Ile Ser Ala His Tyr Val Leu Pro Ser Ser Asn Ala
        115                 120                 125

Phe Pro Asp Ala His Asn Gln Gly Thr Leu Val Ile Phe Asn Leu His
130                 135                 140

Pro Asn Leu Ser Thr Val Gln Leu Arg Arg Leu Phe Gln Pro Phe Gly
145                 150                 155                 160

Pro Ile Lys Glu Leu Arg Asp Thr Pro Trp Lys Lys Asn Gln Arg Phe
                165                 170                 175

Val Glu Phe Phe Asp Ile Arg Asp Ala Ala Lys Ala Leu Lys His Met
            180                 185                 190

Asn Gly Lys Glu Ile His Gly Lys Gln Val Val Ile Glu Phe Ser Arg
        195                 200                 205

Pro Gly Gly His Thr Arg Lys Phe Phe His His Ser Pro Pro Ser Glu
210                 215                 220

Thr Thr Pro Phe Asn Val Pro Pro Pro Pro Pro Phe Pro Pro Ser
225                 230                 235                 240

Pro Arg Gln Ile Thr Gly Lys Pro Gln Glu Asn Leu Ser Arg Lys His
                245                 250                 255

Asn Cys Asp Thr Thr Val Val Gly Thr Thr Thr Lys Gln Gln Gln
            260                 265                 270

Gln Gln Gln Gln Gln Gln Val Pro Arg Ser Arg His Trp Lys Gly
        275                 280                 285

Lys Gln Ala Lys Gln Glu Thr Arg Phe Leu Ile Lys Glu Gly Ala
290                 295                 300

Ile Val Glu Ser Gly Pro Lys Asp Thr Arg Thr Val Met Ile Lys
305                 310                 315                 320

Asn Ile Pro Asn Lys Tyr Ser Gln Lys Leu Leu Leu Asn Met Leu Asp
                325                 330                 335

Asn His Cys Arg His Cys Asn Glu Gln Ile Ala Asp Gly Asp Glu Gln
            340                 345                 350

Gln Pro Leu Ser Ser Tyr Asp Phe Val Tyr Leu Pro Ile Asp Phe Asn
        355                 360                 365

Asn Lys Cys Asn Val Gly Tyr Gly Phe Val Asn Met Thr Ser Thr Glu
370                 375                 380

Ala Thr Leu Arg Leu His Lys Ala Phe His Leu Gln His Trp Glu Val
385                 390                 395                 400

Phe Asn Ser Arg Lys Ile Cys Glu Val Thr Tyr Ala Arg Val Gln Gly
                405                 410                 415

Leu Glu Ala Leu Lys Glu His Phe Lys Asn Ser Lys Phe Pro Cys Glu
            420                 425                 430

Met Glu His Tyr Leu Pro Val Val Phe Ser Pro Pro Arg Asp Gly Lys
        435                 440                 445

Glu Leu Thr Glu Pro Leu Pro Ile Val Gly Asn Lys Gln Gln Gln Gln
450                 455                 460

Ala Ile Ser Ser Gly Gly Gly Ser Gly Ser Val Gly Asp Asp
465                 470                 475                 480

Glu Thr Asn Glu Glu Val Gly Ser Ser Val Val Ile Leu Lys Asp Ser
```

485        490        495

Ile

<210> SEQ ID NO 15
<211> LENGTH: 5479
<212> TYPE: DNA
<213> ORGANISM: Glycine max
<220> FEATURE:
<221> NAME/KEY: misc_feature
<222> LOCATION: (0)...(0)
<223> OTHER INFORMATION: Glycine max TEL2 -- genomic sequence with
      promoter and terminator

<400> SEQUENCE: 15

| | |
|---|---|
| aagcttggaa atggaaatct aagggataaa gcagggtgct caatagccgt gaaaattttc | 60 |
| aacgttgatg aaactgtatt ttttgacaag acgacaataa agcaacaaac aagaaagaaa | 120 |
| gaggtcgatt gatgaattgc caaacaaatc cgaacgtcaa tgtgctttgt tagaaacgta | 180 |
| gtcccttctt aaaattgctc aagaggcagg gaaacatcgc tttcactcac ttttggtgcc | 240 |
| acatcaaacg ggttttcttt gtttaatgcc aacggccaaa caaacaagaa atagagaggg | 300 |
| gcagagaagt catgcttggc tactctcctg tgcaaatgct acaatttaag caacactaat | 360 |
| gttacatttt tagtttttat ctaacaagtt agataattaa taagaaattt tgtataaaaa | 420 |
| tttaaaaagt aaatgggaaa aatgtaaaag taattagggt gatcacaagt ttaactaata | 480 |
| tttatttttt taataaataa ctaaaatcaa atttagctat attgacaaaa actgaaaaca | 540 |
| tattttaatt tcctcatata tttatacaat tgatgattta cttgattgtt actttgttat | 600 |
| atatttaatt ataaatatta acgttacata actcttaatt agttaaaggt aatttattga | 660 |
| ttaaatgaga ttaatatatt tagttaatat ggaaaagttg tgtaaaacat gtattaggaa | 720 |
| aagtatgaga aattagtgaa ggaacaaaaa aaatacttgc atggagacta ggaaaggaca | 780 |
| atgagagacg tggaagatgg aggcagtgcc attcatgcaa ataattaatt aaatactcgg | 840 |
| aataaaatag ctttggtgtg gtgttgaggc taattggaat cctaactcaa ctcaatggga | 900 |
| actgaaattc gttttctctc attaatcatc caaccactat ttacataaga gccatccaga | 960 |
| gttgtctgca tataacaaga ccctttgag tgccttttt ggattttaat taagatgcat | 1020 |
| attattttaa atttttcact ttatatgcct tgacgactaa tataccaata caattatta | 1080 |
| tgggcctaaa tgaaatgaat atgatgagaa aagggagcag tgaaaatagc taagaaaaac | 1140 |
| tgaatcacaa aattcagtgt gtaaggaagt gttcacagat aaagcactat gagcagtaga | 1200 |
| aaatacaaaa acatgaaata gtacggtacc caagctgcca agcaggcatc ggagccattt | 1260 |
| attgctgtcc tcttttggca tctgttgctt ttatacagca ttgtaagtgc aacgttgaat | 1320 |
| ggaaaataac ctaaataatt gattaatcag catggtttt aaatgtgaat gaaaaggtgt | 1380 |
| tacaggaaat tatatttgca aactcaaatg gaagtcaaac agtccattta ttgggttctg | 1440 |
| atttgactat gggacttgtt taaaaacatc acttgtattt ttaaattaaa tactagaatg | 1500 |
| atataatcaa aagttggtat aatgatggaa tattttattg tattcatatg agtgaaaata | 1560 |
| atatatttaa tgtgttagtt tggaatatat tcttttgta taggttaaaa tttattaaaa | 1620 |
| aaattataaa ataaaaaaaa taattattaa ataagatgtg aaaattttta aattttttta | 1680 |
| tcaataaatt ttaactagta aaaatagtg tatttcaagt atttttttt cttttgcaaa | 1740 |
| accagcaaaa attaatacgg ttagtaagaa ttgagttcat atatcttaag accataaatt | 1800 |
| tgagtcttaa tgtcaaatgt aagaattttt ttaatagata atctttcaag aaattattaa | 1860 |

```
ataatctaga attactaggt gaccatattt tcaaccattg tttatactac tataacacat    1920
ttgaaattaa caattaacca aaataataat aaattttag tatatgtcat atgaaaatta     1980
attaagatca taaaaatttt gatgtatcta attattttc gtgaggagtg ttagaaatat     2040
atcttcagta agctcctcca aacatgcatt atctaattgg ttaaaattta tgaaaaatta    2100
tagaattagg aagaaaaaaa gttattaaat ataatgcaag acacactaaa ttttattatt    2160
tttaataaat ttcaagaaaa tataaaaaga tgtgtattct taaccgttct ttctcaattt    2220
ttcataatat gtaagtagca gtggaaaagt tatttattaa gcagtttgaa acaataactt    2280
ggccatagtc actaccaata tttatattta tgagagacat ggttcaactt ttgaatttgt    2340
gagaactaat taatactggc cagttatata gtatgcagta gtgtaaaaat gaatgaaaat    2400
cataatgatc caaacagag ccagcactgg ctaactcagc tcatggtgtg gtgtggggag     2460
gggtaataaa gtaaaatagg gttgtggcat taggtgggaa agtacatttt tagcaacttt    2520
gggttggata ggaaagtaga gaatgaggag tcctctgtcc ttccagctct ccttgagaga    2580
aagagagaag agaatgggag aaaccggtat cattctcagc ttccccggaa acttagaccc    2640
gagagcagaa gagttcagac ccaacaccat aaatattcaa tgccaatggt accctcttcc    2700
tcttcctctt cctcttccac ttcccatacc cctccctcct cctaacctca ccacctcctc    2760
cacccgctcc ctcctcctca ccccggtccc tctcacctcc cactccgccc tccgagccga    2820
gctccaggcc ttcggagaca tcagagccct ccaaaccgaa gccctccgcc acggcattct    2880
caccgtccac ttcttcgacc tccgccatgc acaatccgcc ttcgccgcca tccgctccat    2940
gcaactccac ttccaccca accctggcct cctctctgcc cactacgtcc tccctaactc     3000
caactccctc cccgactccc acaaccaagg caccctcgtc atcttcaacc tccaccccaa    3060
cctctcctcc gaccaactcc gtcgtctctt ccaacctttc ggtactctta acctcattcc    3120
tttctttatt attgtttctg aactttttc attcttttg ttgtttgttg tttgttcaat      3180
caaaaatcca tacatattag gtcccataaa ggaattgaga gatacccccat ggaaaaagaa   3240 tcaaagattc gtggagttct tcgacataag agacgccgcc aaggccttga aacacatgaa    3300
cggcaaggaa attgacggca aacaggttgt tattgagttc agtagacccg gtggtcacac    3360
ccgtaagttc ttccatcatc attccaaaac cacagtacct cctctcaatt tcaatgctcc    3420
tcgcttgcat tcctctcaga agaaatcacc gggaagtccc agcaatagta cgggatctat    3480
tgatgcggaa atggggtcaa tgagtttgac cggaggagaa gttgaagagc agcattcttc    3540
ttcacaaggc cccacgcgga ggaatcttgg cagaaagcac accacactag tagtaggaaa    3600
caccaagcaa caacaagtac ctagaagtag gcactggaag ggaaaacaag cgaagaaaca    3660
cgaaactcgg tttctaatca agaggacgc cattgtagaa tctggtccca aagatactag     3720
aactactgtc atgatcaaaa acattcccaa caagtacagg tccgtttttt cattctttat    3780
tatttacttc tattgcttca cttttcttctt ctattcgtgt ttctgtgact agaaaacgtg    3840
agtttgagct atgaccaaga gagatgacca attgagcttc catttctctc tctctctttt    3900
tgaagatacc ctttctctct cttaaatcat tcaaacaaaa cactgtataa agccgagag     3960 agagagagag aaaggcgctg caaaatacta aaatgtgcta agtataatg atatatagtg      4020 taaatgagta tgaaataaat ttaagtataa tgtagcagaa tagtattttt tttttcatt     4080 tgaaatgaaa tatttgagga ttttatatat aatataattc tgagtgtgtt gtgttttgac    4140
ttgttgcagc cagaagttgc tattaaacat gctggataac cattgcagac actgcaacga    4200
gcagattgca gacggcgaag agcagcagcc tctgtcctcc tacgacttcg tgtacctccc    4260
```

```
cattgatttc aagtattttt cccatttcca ttccatgcgt gcaatcttat tatttaacta    4320
attaattacc cagcaaaatg ggtcaattat tattattatt attattatta ttaattatgt    4380
ttttgaaaca gcaacaagtg caacgtggga tatgggtttg tgaacatgac atccccggag    4440
gcaacactca ggctctacaa ggccttccat cttcaacatt gggaggtttt caattcaaga    4500
aaaatctgcg aagtcaccta tgctagagtt caggtattac tatttcgcta ttcagagtat    4560
taattgctaa gtgtgacatt tatgtatata ctagctagta ctagtgatac aatttatata    4620
ttcatattat tgatttaaaa gtaaacaaca atgaagggtt tggaagcatt gaaagagcac    4680
tttaagaact caaagttccc atgtgagatg gagcattact tgccagtggt gttttcaccg    4740
cctcgagatg ggaagaact gacggagcca cttccactag tggggaacaa gcagcagcag    4800
cagcaacaag ccattccaat tccaatctca agtggcggtg atggtgacgt ggctagcagc    4860
aaaagtggcg gcgtaggtgg tgatgatgag acaaatgaag aagaagtggc ctagtgagtt    4920
ctcaagggta gtgttgtgat tgtgaatcag tgttagcagg agaaccagac agacagcatt    4980
taaggtggtt gagcaacgac ccacacctct gttccaacca acctacaact acagcaacca    5040
tttctcaatc tctctcatca actcaacctt tcctccatta tctttatttt ttctttttta    5100
tattttcgtt tcctgctttt gtctagtgaa atttaatttc tagtttttt tttttctttc    5160 ttttctttca atcacttgtt tttgtttgta ttgtagttgt aggttctgac gcttcagatg    5220
tactgtagta gtatttagtt tgcctgttaa attttcaaga atttcgatag aaaacttat     5280 agatatcata gaaaaacttg agttggtgct tggccattac tactacgttt agagatgctg    5340
atgaaccact gagcaaatta agcggatgtg attgtgttaa ccgggtgcac ttctcgagga    5400
attaatactg gaaactagga tcagtaggaa ggatttcatg ctagagaaat cctagctgta    5460
ttatgattct cacgtcgac                                                 5479
```

<210> SEQ ID NO 16
<211> LENGTH: 511
<212> TYPE: PRT
<213> ORGANISM: Glycine max
<220> FEATURE:
<223> OTHER INFORMATION: Glycine max TEL 2

<400> SEQUENCE: 16

```
Met Gly Glu Thr Gly Ile Ile Leu Ser Phe Pro Gly Asn Leu Asp Pro
 1               5                  10                  15

Arg Ala Glu Glu Phe Arg Pro Asn Thr Ile Asn Ile Gln Cys Gln Trp
             20                  25                  30

Tyr Pro Leu Pro Leu Pro Leu Pro Leu Pro Ile Pro Leu Pro
         35                  40                  45

Pro Pro Asn Leu Thr Thr Ser Ser Thr Arg Ser Leu Leu Thr Pro
     50                  55                  60

Val Pro Leu Thr Ser His Ser Ala Leu Arg Ala Glu Leu Gln Ala Phe
 65                  70                  75                  80

Gly Asp Ile Arg Ala Leu Gln Thr Glu Ala Leu Arg His Gly Ile Leu
                 85                  90                  95

Thr Val His Phe Phe Asp Leu Arg His Ala Gln Ser Ala Phe Ala Ala
            100                 105                 110

Ile Arg Ser Met Gln Leu His Phe His Pro Asn Pro Gly Leu Leu Ser
        115                 120                 125

Ala His Tyr Val Leu Pro Asn Ser Asn Ser Leu Pro Asp Ser His Asn
    130                 135                 140
```

Gln Gly Thr Leu Val Ile Phe Asn Leu His Pro Asn Leu Ser Ser Asp
145                 150                 155                 160

Gln Leu Arg Arg Leu Phe Gln Pro Phe Gly Pro Ile Lys Glu Leu Arg
            165                 170                 175

Asp Thr Pro Trp Lys Lys Asn Gln Arg Phe Val Glu Phe Phe Asp Ile
        180                 185                 190

Arg Asp Ala Ala Lys Ala Leu Lys His Met Asn Gly Lys Glu Ile Asp
            195                 200                 205

Gly Lys Gln Val Val Ile Glu Phe Ser Arg Pro Gly Gly His Thr Arg
        210                 215                 220

Lys Phe Phe His His His Ser Lys Thr Thr Val Pro Pro Leu Asn Phe
225                 230                 235                 240

Asn Ala Pro Arg Leu His Ser Ser Gln Lys Lys Ser Pro Gly Ser Pro
            245                 250                 255

Ser Asn Ser Thr Gly Ser Ile Asp Ala Glu Met Gly Ser Met Ser Leu
        260                 265                 270

Thr Gly Gly Glu Val Glu Glu Gln His Ser Ser Ser Gln Gly Pro Thr
            275                 280                 285

Arg Arg Asn Leu Gly Arg Lys His Thr Thr Leu Val Val Gly Asn Thr
290                 295                 300

Lys Gln Gln Val Pro Arg Ser Arg His Trp Lys Gly Lys Gln Ala
305                 310                 315                 320

Lys Lys His Glu Thr Arg Phe Leu Ile Lys Glu Asp Ala Ile Val Glu
            325                 330                 335

Ser Gly Pro Lys Asp Thr Arg Thr Thr Val Met Ile Lys Asn Ile Pro
        340                 345                 350

Asn Lys Tyr Ser Gln Lys Leu Leu Leu Asn Met Leu Asp Asn His Cys
            355                 360                 365

Arg His Cys Asn Glu Gln Ile Ala Asp Gly Glu Glu Gln Pro Leu
    370                 375                 380

Ser Ser Tyr Asp Phe Val Tyr Leu Pro Ile Asp Phe Asn Asn Lys Cys
385                 390                 395                 400

Asn Val Gly Tyr Gly Phe Val Asn Met Thr Ser Pro Glu Ala Thr Leu
            405                 410                 415

Arg Leu Tyr Lys Ala Phe His Leu Gln His Trp Glu Val Phe Asn Ser
        420                 425                 430

Arg Lys Ile Cys Glu Val Thr Tyr Ala Arg Val Gln Gly Leu Glu Ala
            435                 440                 445

Leu Lys Glu His Phe Lys Asn Ser Lys Phe Pro Cys Glu Met Glu His
        450                 455                 460

Tyr Leu Pro Val Val Phe Ser Pro Pro Arg Asp Gly Lys Glu Leu Thr
465                 470                 475                 480

Glu Pro Leu Pro Leu Val Gly Asn Lys Gln Gln Gln Gln Gln Gln Ala
            485                 490                 495

Ile Pro Ile Pro Ile Ser Ser Gly Gly Asp Gly Asp Val Ala Ser
        500                 505                 510

<210> SEQ ID NO 17
<211> LENGTH: 5058
<212> TYPE: DNA
<213> ORGANISM: Gossypium herbaceum
<220> FEATURE:
<221> NAME/KEY: misc_feature
<222> LOCATION: (0)...(0)
<223> OTHER INFORMATION: Gossypium herbaceum TEL1 -- genomic sequence with promoter and terminator

<400> SEQUENCE: 17

```
ctgcaggaca ttagagttag gaccttatgg aacatgaata taaatgtata tagttcatct      60
tcttcctcat tttgacttgt ctagataaat actattattg tgatgcatag aaggaattat     120
atttgtaatg atataaaacc accatgattt ttagtagtta cttatttaat taagtatagt     180
ttgatcatta ttgtaattaa agtgcataca tctaaaaaga ctcatgtgac catttggcaa     240
agtgagagaa tgttggaatt tgtggccttt atggctacat aaaagattat tgagggaatt     300
tttgatcttt gaggagactg tggcacccgt cctaccaatt caacccatat atgctatagg     360
acagggtttc aaatcttact aaacacaaaa tatgaatttg catggtaggt aaaggtactt     420
cccttcatg aactcgacac aaaattttga tggaggcaat agacaaaatt tagaattaaa     480
attgagcata aacactctta agcctaatac taaacatgct aagaggactc acagcttctt     540
attaataggt taaaaatccc ttcaatgcta agaggactca cagcttctta ttaataggtt     600
aaaaatccct tcaacaacca tgttgacgaa agtaatgtac tatgcacatt agacattaat     660
aggtacattg actaaaatca tgtatcttta aagtacatat attgaatttt actaggtaca     720
ttaaccaaat tatgcatctt taatgactaa tatatgatta tggttaatta ctttggatta     780
attgtatcac attaaaataa ttcatgtact tgtacaatta tataccaaag gaggaagaat     840
aggcatctac attaagaagg tggtgtttta tggaagtata atgtgcaaat gttaaaagtt     900
taattttttga tacaatatat aaatgttaaa attttaaatt ttaaaacttt aaattattat     960
tatgttaatt ttaaaaactc caagttaact tttagtaatc atttattgat cgatgatgaa    1020
aatatttaaa taattaaata attatttat aagttttgat gattggatga taaaaaaaat    1080
cttaataatt gaatatctca atttaattta ttaattatcg ggagaataac acatagatgc    1140
ggatgtgaaa gaataaatga gggtgcactg cactgtgcta aaaataaaag cagaggtgga    1200
gaagcgatta gtctgtccga gtctgactgt ctctgattag tcaaaaatac caaagatgaa    1260
aagaaaaaaa agtaatactc acatgcagca atgcttatta ttactcaacc cgcaccacac    1320
atttcatttg tgtggccacg tgcacgctcc aaattcttaa tcaaccccg aattactacg    1380
aggatcatga tcaaaatcca aaaacaaaaa cccagaaagt aagggttttt attcactcta    1440
aaaaaagtca tcatctttcc catgaggtgg caattcggga gacgacgaca cttttggcaa    1500
cctttcttg tttcctggaa accaagtata tagcgaaaag gaagggaaa aaaaaccaaa    1560
accctcccaa tccattctct cctttcgtt tttacttaca cttcgactac caactttaat    1620
gagttttct tggacatgga aaacgacaac aatacaaaca aagaaaatgt tttcttgggc    1680
ttttaatttc ccaagctgaa ctcagataaa agagaacagc tttctcataa atatactttc    1740
tcggctcctt tttatctagt tgaagaaaag ctttttttttc cctttgagt ggtggactac    1800
tggttctccg ccctgaaaca gccatggggg aaaccgggac ggtccggttc cctggaaacc    1860
ttgacccgac ggcacaagaa ttttggcccg cccaaaacgt agtttgccaa ccccaatttc    1920
ctctctacag accccccaa ctttactacc cgtacgctgc gtctccaacg gtaccgtttt    1980
gcagcggcgg cgtaccgcag ttccatgctg ccctgcctct acatgcacct gtagctatac    2040
ctgcaccagc gccttgcgtc actacagcgt ccatggtggt tgcaccgcag ctgccacttc    2100
cacctccgac tgcggcggcg acgagggctt tggtgttaac gttggttcca tgcgatgtga    2160
gcgagtcaaa ggtgaggaaa gaattggaag tgttcgggga agtacgcggg gtccagatgg    2220
aaagagtccg agaagggatc gtgaccgtcc atttctacga tctgagacat gcggagaaag    2280
```

```
cgttgaaaga aatacgcgag cagcacatgc aagagcaagc cagggttcga gaccagtaca    2340
ctgcggctgc taccgggtgc gaaccaggtg tgtccaacgc ttgtgttcca ctcccttctg    2400
cgcgtggact catagccggg aggcctgtct gggcccactt cactattccg gcaagcaatg    2460
ctgtccctga ggggaataat caaggaactg ttgtggtatt caatttggac accggcgttt    2520
caatttcgca actcaaagaa atcttccaag cttatggtaa gtttcggttc atttcttgtc    2580
ttttatgttc gcttgctttg tttgggtttt tgttgttcaa tctattttgt tttactcttt    2640 tgcgggggg gggagttga tactttgatt agcagtcaaa gatattttca tgctttgtta    2700
caaaattttg caacctggtt tgttgtttag gcccagtgaa ggaactgaga gaaacaccat    2760
tgaagaaaca ccaaaagttt gtggagtttt atgacgtaag ggatgcggct aaggctttga    2820
gagaaatgaa tggaaaagaa attaatggga agcaagttgt aattgaattt agtcgacccg    2880
gaggatatag caggaagctc ttcaatagtg ataacaacgt taacaaaatt aacgctttta    2940
cggctttcac tgataaatat aatccccata cgagaaatcc caagtactca tcttctcccc    3000
cacctccccc gccgctgcct cgtaaattct ctgctagatt ttcttccaac gatataccte    3060 gttctttttct cctcgaaac caatcgccta ctgtgaaacc tttgaattct agtaaaggaa    3120
accctaatat gaataatgac agcaagtgtt ccgccgttga aacggcggtg gttaaagata    3180
aggtcgggag tggtggaggt ccaaaaaaga ctgtaaagaa gaaccaaagc aactcatcaa    3240
cggtagctaa gcacaaccag cagctatgtc ggggcaggcc gtggaaaggt agacagtcga    3300
agaaatttga tcctcgtttc cttataagcg aagatgctat ggtgggatct gattctaaag    3360
attccaggac cactgtcatg atcaagaaca tacccaacaa gtataggttg gtctttttca    3420
ccaactaccg cttaaaagta gctaataaaa tgattgcatt ttcggtttct tgttggaaat    3480
tcggggaagt tttcatcttt taattttgca tgttgcagtc aaaaattgtt gttgaacatg    3540
ttggacaatc actgcattca ctgtaacgag caaatagctg aggacgacga tcagcccttta   3600 tcttcctatg atttcgtcta cctccccatc gattttaagt aattttcttt cctttctttc    3660
ctttttttta ttattatctc aatttgtaag agcattgcat aattcattaa catttttttg    3720
gtttaaacaa aacagcaaca agtgtaatgt aggatatgga tttgtgaaca tgacatctcc    3780
gcaagcaaca tggaggcttt acaaggcatt tcatcatcaa cattgggaag ttttcaactc    3840
cagaaaaatc tgtgaagtaa cttatgcgag agttcaggtt ttttttttct tcgttttctt    3900
ctaatatttt catttgttgg atcaaattaa aactataaga ttgattgttg gtatagggat    3960
tggaggcgtt gaaagaacat tttagaaact caaaattccc atgcgaaatg gaacactatc    4020
taccagttgt attttcgcca cctcgagacg gaaaacaact gactgagcca cttcctatag    4080
ttggtcaaaa gcagcgatcc cccaacagtg gtccctcagc caaagacagt gaagaagacg    4140
aagatgatta taatcactac gaccattgcg gtgaagagag ttgtaacgaa aatccgcttg    4200
ctgatgataa tactgcaaat tctgctcaag aagaaaataa tgtcaacagt accaatcatt    4260
taaaatactg ggattccgat gatacggttg accagcacga agaattccct cagcaatcac    4320
tgtagcctaa tgccaaggaa aaagaaaaaa caagaaaaaa aggattgtag ctgttgtaag    4380
catgaacagt agtgaaaagg ttaaaacgct gaagcaaaat attatctctg tgattttct    4440 tacgactatt acatttgttt tgggacttgc tacttccaac tacatggacg cattgtcatg    4500
aagtagtgaa tgaattcaaa gtaatcttag tttactgcaa ccaaggaagg cagtgtggat    4560
tcacagctgt taaaactggc cgcaccatcc aatggccaat ggtttgttga gcaccgagcc    4620
```

-continued

```
ctctctttca tttagctgac caaccccaa cgccagcctg aaccttgctg tcattctctt    4680
tctatctttc aggctatcat ctggggctat ccatcatctc catttacttc cgtcccttc    4740 gaacctctta cctgttgctt tcttgatgga tcttaattac catgataaag ctattaagtc    4800
taaatattgt agattcagaa aattcacaaa tcggattttg ggtctaatta aattcttctt    4860
taacatgtac atgaaaaaaa agaaaaactg aagcatctgt ttatataata gtttattaag    4920
gaggagggaa gaaagagacc aatggataaa gagaaggttt cttgattctt catcttctac    4980 cgtcttatt tgttggaaag aacaggattt cttttcttct tccttctggt taacagatag     5040
agattagctc gtggtacc                                                  5058
```

<210> SEQ ID NO 18
<211> LENGTH: 679
<212> TYPE: PRT
<213> ORGANISM: Gossypium herbaceum
<220> FEATURE:
<223> OTHER INFORMATION: Gossypium herbaceum TEL1

<400> SEQUENCE: 18

```
Met Gly Glu Thr Gly Thr Val Arg Phe Pro Gly Asn Leu Asp Pro Thr
  1               5                  10                  15

Ala Gln Glu Phe Trp Pro Ala Gln Asn Val Val Cys Gln Pro Gln Phe
             20                  25                  30

Pro Leu Tyr Arg Pro Pro Gln Leu Tyr Pro Tyr Ala Ala Ser Pro
         35                  40                  45

Thr Val Pro Phe Cys Ser Gly Gly Val Pro Gln Phe His Ala Ala Leu
     50                  55                  60

Pro Leu His Ala Pro Val Ala Ile Pro Ala Pro Ala Pro Cys Val Thr
 65                  70                  75                  80

Thr Ala Ser Met Val Val Ala Pro Gln Leu Pro Leu Pro Pro Pro Thr
                 85                  90                  95

Ala Ala Ala Thr Arg Ala Leu Val Leu Thr Leu Val Pro Cys Asp Val
            100                 105                 110

Ser Glu Ser Lys Val Arg Lys Glu Leu Glu Val Phe Gly Glu Val Arg
        115                 120                 125

Gly Val Gln Met Glu Arg Val Arg Glu Gly Ile Val Thr Val His Phe
    130                 135                 140

Tyr Asp Leu Arg His Ala Glu Lys Ala Leu Lys Glu Ile Arg Glu Gln
145                 150                 155                 160

His Met Gln Glu Gln Ala Arg Val Arg Asp Gln Tyr Thr Ala Ala Ala
                165                 170                 175

Thr Gly Cys Glu Pro Gly Val Ser Asn Ala Cys Val Pro Leu Pro Ser
            180                 185                 190

Ala Arg Gly Leu Ile Ala Gly Arg Pro Val Trp Ala His Phe Thr Ile
        195                 200                 205

Pro Ala Ser Asn Ala Val Pro Glu Gly Asn Asn Gln Gly Thr Val Val
    210                 215                 220

Val Phe Asn Leu Asp Thr Gly Val Ser Ile Ser Gln Leu Lys Glu Ile
225                 230                 235                 240

Phe Gln Ala Tyr Gly Pro Val Lys Glu Leu Arg Glu Thr Pro Leu Lys
                245                 250                 255

Lys His Gln Lys Phe Val Glu Phe Tyr Asp Val Arg Asp Ala Ala Lys
            260                 265                 270

Ala Leu Arg Glu Met Asn Gly Lys Glu Ile Asn Gly Lys Gln Val Val
        275                 280                 285
```

```
Ile Glu Phe Ser Arg Pro Gly Gly Tyr Ser Arg Lys Leu Phe Asn Ser
290                 295                 300

Asp Asn Asn Val Asn Lys Ile Asn Ala Phe Thr Ala Phe Thr Asp Lys
305                 310                 315                 320

Tyr Asn Pro His Thr Arg Asn Pro Lys Tyr Ser Ser Pro Pro
                325                 330                 335

Pro Pro Pro Leu Pro Arg Lys Phe Ser Ala Arg Phe Ser Ser Asn Asp
            340                 345                 350

Ile Pro Arg Ser Phe Leu Pro Arg Asn Gln Ser Pro Thr Val Lys Pro
                355                 360                 365

Leu Asn Ser Ser Lys Gly Asn Pro Asn Met Asn Asn Asp Ser Lys Cys
370                 375                 380

Ser Ala Val Glu Thr Ala Val Val Lys Asp Lys Val Gly Ser Gly Gly
385                 390                 395                 400

Gly Pro Lys Lys Thr Val Lys Lys Asn Gln Ser Asn Ser Ser Thr Val
                405                 410                 415

Ala Lys His Asn Gln Gln Leu Cys Arg Gly Arg Pro Trp Lys Gly Arg
                420                 425                 430

Gln Ser Lys Lys Phe Asp Pro Arg Phe Leu Ile Ser Glu Asp Ala Met
            435                 440                 445

Val Gly Ser Asp Ser Lys Asp Ser Arg Thr Thr Val Met Ile Lys Asn
450                 455                 460

Ile Pro Asn Lys Tyr Ser Gln Lys Leu Leu Leu Asn Met Leu Asp Asn
465                 470                 475                 480

His Cys Ile His Cys Asn Glu Gln Ile Ala Glu Asp Asp Gln Pro
                485                 490                 495

Leu Ser Ser Tyr Asp Phe Val Tyr Leu Pro Ile Asp Phe Asn Asn Lys
            500                 505                 510

Cys Asn Val Gly Tyr Gly Phe Val Asn Met Thr Ser Pro Gln Ala Thr
                515                 520                 525

Trp Arg Leu Tyr Lys Ala Phe His Gln His Trp Glu Val Phe Asn
530                 535                 540

Ser Arg Lys Ile Cys Glu Val Thr Tyr Ala Arg Val Gln Gly Leu Glu
545                 550                 555                 560

Ala Leu Lys Glu His Phe Arg Asn Ser Lys Phe Pro Cys Glu Met Glu
                565                 570                 575

His Tyr Leu Pro Val Val Phe Ser Pro Pro Arg Asp Gly Lys Gln Leu
            580                 585                 590

Thr Glu Pro Leu Pro Ile Val Gly Gln Lys Gln Arg Ser Pro Asn Ser
                595                 600                 605

Gly Pro Ser Ala Lys Asp Ser Glu Glu Asp Asp Tyr Asn His
            610                 615                 620

Tyr Asp His Cys Gly Glu Ser Cys Asn Glu Asn Pro Leu Ala Asp
625                 630                 635                 640

Asp Asn Thr Ala Asn Ser Ala Gln Glu Glu Asn Val Asn Ser Thr
                645                 650                 655

Asn His Leu Lys Tyr Trp Asp Ser Asp Asp Thr Val Asp Gln His Glu
                660                 665                 670

Glu Phe Pro Gln Gln Ser Leu
                675

<210> SEQ ID NO 19
<211> LENGTH: 5567
```

<212> TYPE: DNA
<213> ORGANISM: Gossypium herbaceum
<220> FEATURE:
<221> NAME/KEY: misc_feature
<222> LOCATION: (0)...(0)
<223> OTHER INFORMATION: Gossypium herbaceum TEL2 -- genomic sequence
      with promoter and terminator

<400> SEQUENCE: 19

| | | | | | |
|---|---|---|---|---|---|
| aagcttctaa | gcacaaattt | gacttagtta | atttcttgca | tagttcaaga | taggcccgtg | 60 |
| gtaggtttcg | acaaagatga | cgttgtgaga | attcgtgtca | atgtggagat | tgttagagtt | 120 |
| tgtgacccaa | attattgtta | ataagagat | tgcttgcaaa | tcaagttaaa | caatatttat | 180 |
| tttctttcta | gaagatttaa | tatttactag | tacaatatat | ttagtattta | ttagcataat | 240 |
| ttatttgacc | tacgaattta | gcctataaat | actcttttac | aactttagaa | aatacactta | 300 |
| ttaaaagatt | agatcttata | acactttttgg | agattttttgt | gtttacgttt | ttagagtttt | 360 |
| tttttgagtt | tcggggttta | gttttcatct | ctgtctttta | tactcttttat | ttttttctat | 420 |
| tataataaaa | ttatctttac | ccgtgatttt | ttatcctctt | tgaagaaatt | ttttcacgtt | 480 |
| aaatttatat | tcaatttctt | aattttttaa | gctatttta | ttttttatta | cttaatcaag | 540 |
| tcaatcccag | caagtatatt | taaaattaga | ataattcaat | gcaaatctat | tagacttgat | 600 |
| aaacacaata | tgtagataaa | tttataaaaa | tttactccgc | agaaaaccaa | catgaaaagt | 660 |
| aacatgtccg | tgcgggtttt | ggcaatttgg | caatgacaac | cccacaatat | ttgtcctatt | 720 |
| gccacgtata | cgttgattct | tcatcaatca | tcatcccaaa | taaaaatcaa | aacaaaaggg | 780 |
| ttaatatgaa | atttggcccc | tgcgcttgtc | tatttgtact | taatttggtt | tataaaattt | 840 |
| tttgaatcta | gttagtagag | gtgttcatgg | gccgagcggc | ccggcccggc | ccgatggccc | 900 |
| gctcaaaata | tgggagggtt | tgggtaaaaa | tataggcccg | aaatatgggc | ttggacaaaa | 960 |
| aaacgaggct | cgattaaaaa | ataggccggg | cctcgggcac | cacttttttg | gcccgggccg | 1020 |
| gcccggcccg | aataataaat | attttttatta | ttttttatttt | tttatttttaa | aatacttttta | 1080 |
| aaatactttt | tttaaattttt | tttaatttta | aaattttttt | aaaatttttt | taaaatactt | 1140 |
| tttttaatttt | taaaatatttt | ttaaaatact | ttttaaaatt | tttattttaa | ttttaaaat | 1200 |
| aaatttttgg | tatttatttta | aaaacgggcc | gggccgggcc | cgagcttatg | aattttttccc | 1260 |
| gggcctagga | cccgggccaa | aatctttttt | gggcacggcc | tggcccggcc | catgaacacc | 1320 |
| tctactagtt | agtacatgaa | cttgtatttc | gtcaaccaac | tcggtaccttt | cgcattaaca | 1380 |
| ttgctagtta | tgttgacctg | gcattattag | ccaatctgat | ggtgccacat | ggtaacttct | 1440 |
| ccatataaca | catgacaaac | ataaattaaa | aactataata | taaatatata | aattatattt | 1500 |
| gtcatgtggc | actctaagag | gctaccactt | ggcatcacca | tatttgttag | aaatgtcaca | 1560 |
| taagtacaaa | ctaacggtgt | tggtgtggag | ggatcaactt | ggttgataga | atagaagttt | 1620 |
| agagaccaac | tcggtctaaa | aaatttagt | gaccaactgg | gtacaaatag | agaagttcaa | 1680 |
| gggctaaatt | atatattata | ccaaaaccaa | atggcttcac | tggtaaattc | atgtcttcaa | 1740 |
| tgaggtggta | attggcaatc | ggcatttata | gcaacctttg | tcttggaaac | tatgtatata | 1800 |
| tgcatgtatt | gtaaaacaaa | ggacaaggcc | aaaacaccaa | aatcactcct | tttcttctac | 1860 |
| atttatgcta | gcgagtttca | agtttctcaa | ctctgtctgt | agaacacttt | tgggagatgg | 1920 |
| aaaacaacaa | acaacaagc | aaaaaatttg | attacttggg | ttttaactc | aataaacaca | 1980 |
| gttcctcgta | gataaatttt | cagttttttc | tttaaagca | aagcaaagca | aaggtttatc | 2040 |
| cttttttagct | tttctttttt | gggtactgtt | tctcagctct | gagacagcca | tggcggaaac | 2100 |

```
cgggccggca cggttcactg gaaattacct agacccgtct gcacaagaat tttggcccgc   2160
ccaaaacact ctattccaac cccaaattcc tctcttcaga ccgtcccaac tttactaccc   2220
ctacgccgca cccttaacgt tgtcgttttc tggtggtggc gtagcacagt tccatgtggc   2280
ggtacctgta cctgcacctt tgccagcagc gtacgttaca ggttccacga tggttttacc   2340
cgaaccgccg cgttctcttc cgcctccagc tgcgacggcg acgagggctt tagtgttgac   2400
atccgttcca tgcgatgtga gcgagtgtaa agtgagggaa gaactggaag tgttcgggga   2460
aatacgcggg gtccagatgg aaagggtggg agaaggaatc gtgacggttc atttctatga   2520
tgtgagacat gcggagcgag cgttgaatgt aatacgagag aagcacatgc aacaagaagc   2580
caggggtggt gcagccgggt ccgaaccagg ggagaccaac gcctatactc ctgagactgg   2640
actgatatcg aggagagctg tttgggccca ctttattatt ccggccacta atgctttgcc   2700
tgacgggaat aatcaaggaa gtcttgtagt tttcaatctg gaccccggtg cttccacttc   2760
taaactcaaa gaattttcc atgcttatgg taagttaagt gtttcgcctt tcctatatga    2820
aaaacacagt caaaagggt ttgattggtt ggtacttagg ctgccttgtt ttataaattt    2880
gttgataggt cccgtgaagg aactgagaga acgccgttg aagaagcacc aaaagttctt    2940
ggagttttat gatgtaagag atgcggctaa agccttacga gaaatgaatg gaaaagaaat   3000
caatgggaag caagttgtca ttgaattcag tcgacccgga gggtataaca gcaagttctt   3060
caatgctaat attgccaacc atgttaagcc tttcaaacct tgcactccca atatttcatt   3120
cactgccagt aaatataatc acccttcttc ttcaccgtcg ttagcttgta gattctccgg   3180
ttccggtaga tattctgcca acatccctcc tcgttctttt ctttctcgaa gccaatcccc   3240
taccgagaac ctgtctgatt ctcgcaaggg aagccctaat gagattaagg aaagcaagaa   3300
gagttcagtt gcaacggcgg tcgttggtgg tggagcagct gcaaacaagg ttgcgaagaa   3360
ccaaaacaac cagtccccac agaggattag caacggggtt aagcagcagc aatgtagggg   3420
aaggccatgg aaaggcaaac aagggaggaa atttgatcct cgtttcttaa taagcgaaga   3480
tgctatggcg gaatcgaact gtaaagattc aaggactacc gtcatgatta agaacatacc   3540
caataaatat aggtttgtct tttttaccaa ctgttactta aatagaaaat aacacgattg   3600
catttctttt tgttatttca tatttttatg tgcctttgaa tatggcattt tgcagtcagc   3660
agttgttgtt gaacatgctt gacaatcact gtattcactg caacgagcaa attgtcgacg   3720
cccggcgatg atcagccttt atcttcttac gatttcgtct acctcccgat tgatttcaag   3780
taattttctt ttccgccccc ccttttcct tgagtttgta catagatcct atatataaat    3840
ccgttgatag tgtattgaaa tcaagattat tgtatgtaag attcattgtt gcacattttt   3900
tctttgaatt taaaaaatcc agcaacaagt gtaatgtggg atatggattt gtgaacatga   3960
catccccgca agcaacttgg agattttaca aggccttcca ccatcaacat gggaagtttt   4020
tcaactcaag aaaaatctgt gaagtcactt atgccagagt tcaggttttt aatataaat    4080 tagcctcatg ttgaccaaaa atcattaggt tcattcatt catcatttat atgggtctaa    4140
tttgtttatg aaatgattaa aatagggatt gcaggcgttg aaagaacatt ttagaaactc   4200
aaagttccca tgcgaaatgg atcactatct tccagtagtt tttgagccgc ctcgagacgg   4260
gaaacaactg actgagccac ttccacttcc tgtagttggt gaaaagcaga actccatcgg   4320
tggtccctcg ccaaaaccca atgaaaaaca agatgattac gatgaacata gcgatagcgt   4380
cgataagtgt cataatgata catcgcttga ggatggaggt ggtgcaagtt cgtacggtgg   4440
```

```
agaaaataat gccatcatca atcacttcaa ctagtgtgct ccagttgacc agtaggaggg    4500
ggaagttcac agtaacagcg tcagccaaag gccaaacgac ggcgatgttg gttcatgatc    4560
aaagaaagaa tcattgctct tatggcctga acagtgacac cctgaacaga aattatatat    4620 atttttgtg acttactact agtagtacta ctttgcatgg acaagagtca tggaaaattt     4680
gaatgaaata gaatataata ttcgtttttg atgcaaccaa ggcagccctc attcacgctt    4740
cacagctgtt tttggtgtta gaaatagctg caccaaccaa tgcccaatgg tgttgatgtt    4800
gatcaccgag cctctcatat aggtgcccaa agtcccgaac ccgccgctag cctaaggtgc    4860
gctctctctc tttcaggtta gctggggccg accacaatca catccattta ctgctctcac    4920
caccacctct tctctgcccc tccatttcct cctaaaatca ctggattcga ttagttcaga    4980
atgcagtcta atcaaattac aaatggtgaa cagttttttt cccctttaaa ataatttaaa    5040
acttgattca tttataaaca attttttat aatttaaaaa aaaatcaatt aaatcctaaa     5100
taatttttaa aaattaatta aaattttggt aaattactat aataattatc caactatttta   5160 taattttttg tcaccaattg attaactatg atatatttt ttaaaattaa tataataata     5220
tttttaattt ttaatatttta tacattatat cgaaatatat aacctttaat atgcagtgtg   5280
taattaagtt tttctttaca atcttttcat ttaaaaagtt aaaaaaataa atttatcaat    5340
taaatttaat taaaaaatat ataaaaaatg gaatatttta aaatagaaat tcttattaaa    5400 gaaaattat aaaaatatag aattaaaatt acacaatagg taaatattga gtgttatatt     5460
ttttaaaatt aataaattaa cacaatatat aaatattgag agttatagtt attattatgc    5520
taatttcaaa aattgtcacc attaattcaa ctagttggtg aggtacc                  5567
```

<210> SEQ ID NO 20
<211> LENGTH: 673
<212> TYPE: PRT
<213> ORGANISM: Gossypium herbaceum
<220> FEATURE:
<223> OTHER INFORMATION: Gossypium herbaceum TEL2

<400> SEQUENCE: 20

```
Met Ala Glu Thr Gly Pro Val Arg Phe Thr Gly Asn Tyr Leu Asp Pro
 1               5                  10                  15

Ser Ala Gln Glu Phe Trp Pro Ala Gln Asn Thr Leu Phe Gln Pro Gln
            20                  25                  30

Ile Pro Leu Phe Arg Pro Ser Gln Leu Tyr Tyr Pro Tyr Ala Ala Pro
        35                  40                  45

Leu Thr Leu Ser Phe Ser Gly Gly Gly Val Ala Gln Phe His Val Ala
    50                  55                  60

Val Pro Val Pro Ala Pro Leu Pro Ala Ala Tyr Val Thr Gly Ser Thr
65                  70                  75                  80

Met Val Leu Pro Glu Pro Pro Leu Ser Leu Pro Pro Ala Ala Thr
                85                  90                  95

Ala Thr Arg Ala Leu Val Leu Thr Ser Val Pro Cys Asp Val Ser Glu
            100                 105                 110

Cys Lys Val Arg Glu Glu Leu Glu Val Phe Gly Glu Ile Arg Gly Val
        115                 120                 125

Gln Met Glu Arg Val Gly Glu Gly Ile Val Thr Val His Phe Tyr Asp
    130                 135                 140

Val Arg His Ala Glu Arg Ala Leu Asn Val Ile Arg Glu Lys His Met
145                 150                 155                 160

Gln Gln Glu Ala Arg Gly Gly Ala Ala Gly Ser Glu Pro Gly Glu Thr
```

```
                165                 170                 175
Asn Ala Tyr Ala Pro Glu Thr Gly Leu Ile Ser Arg Arg Ala Val Trp
                    180                 185                 190

Ala His Phe Ile Ile Pro Ala Thr Asn Ala Leu Pro Asp Gly Asn Asn
                    195                 200                 205

Gln Gly Thr Leu Val Val Phe Asn Leu Asp Pro Gly Val Ser Thr Ser
                    210                 215                 220

Lys Leu Lys Asp Ile Phe Gln Ala Tyr Gly Pro Val Lys Glu Leu Arg
225                 230                 235                 240

Glu Thr Pro Leu Lys Lys His Gln Lys Phe Leu Glu Phe Tyr Asp Val
                    245                 250                 255

Arg Asp Ala Ala Lys Ala Leu Arg Glu Met Asn Gly Lys Glu Ile Asn
                    260                 265                 270

Gly Lys Gln Val Val Ile Glu Phe Ser Arg Pro Gly Gly Tyr Asn Ser
                    275                 280                 285

Lys Phe Phe Asn Ala Asn Thr Ala Asn His Val Lys Pro Phe Lys Pro
                    290                 295                 300

Cys Thr Pro Asn Ile Ser Phe Thr Ala Ser Lys Tyr Asn His Pro Ser
305                 310                 315                 320

Ser Pro Pro Ser Leu Ala Cys Arg Phe Ser Gly Ser Gly Arg Tyr Ser
                    325                 330                 335

Pro Asn Ile Pro Pro Arg Tyr Phe Leu Ser Arg Ser Gln Ser Pro Thr
                    340                 345                 350

Glu Asn Leu Ser Asp Ser Arg Lys Gly Ser Pro Asn Glu Ile Lys Glu
                    355                 360                 365

Ser Lys Lys Ser Ser Val Ala Thr Ala Val Val Gly Gly Gly Ala Ala
370                 375                 380

Ala Asn Lys Val Ala Lys Asn Gln Asn Asn Gln Ser Pro Gln Arg Ile
385                 390                 395                 400

Ser Asn Gly Val Lys Gln Gln Gln Cys Arg Gly Arg Pro Trp Lys Gly
                    405                 410                 415

Lys Gln Gly Arg Lys Phe Asp Pro Arg Phe Leu Ile Ser Glu Asp Ala
                    420                 425                 430

Met Ala Glu Ser Asn Cys Lys Asp Ser Arg Thr Thr Val Met Ile Lys
                    435                 440                 445

Asn Ile Pro Asn Lys Tyr Ser Gln Gln Leu Leu Leu Asn Met Leu Asp
                    450                 455                 460

Asn His Cys Ile His Cys Asn Glu Gln Ile Val Asp Ala Gly Asp Asp
465                 470                 475                 480

Gln Pro Leu Ser Ser Tyr Asp Phe Val Tyr Leu Pro Ile Asp Phe Asn
                    485                 490                 495

Asn Lys Cys Asn Val Gly Tyr Gly Phe Val Asn Met Thr Ser Pro Gln
                    500                 505                 510

Ala Thr Trp Arg Phe Tyr Lys Ala Phe His His Gln His Trp Glu Val
                    515                 520                 525

Phe Asn Ser Arg Lys Ile Cys Glu Val Thr Tyr Ala Arg Val Gln Gly
                    530                 535                 540

Leu Gln Ala Leu Lys Glu His Phe Arg Asn Ser Lys Phe Pro Cys Glu
545                 550                 555                 560

Met Asp His Tyr Leu Pro Val Val Phe Glu Pro Pro Arg Asp Gly Lys
                    565                 570                 575

Gln Leu Thr Glu Pro Leu Pro Leu Pro Val Val Gly Glu Lys Gln Lys
                    580                 585                 590
```

```
Ser Ile Gly Gly Pro Ser Pro Lys Pro Asn Glu Lys Gln Asp Asp Tyr
        595                 600                 605

Tyr Glu His Ser Asp Ser Val Glu Glu Cys His Asn Asp Thr Ser Leu
    610                 615                 620

Glu Asp Gly Gly Gly Ala Ser Ser Tyr Gly Gly Glu Asn Asn Ala Ile
625                 630                 635                 640

Phe Asn His Phe Lys His Cys Ala Pro Val Asp Gln Gln Gly Glu
                645                 650                 655

Val His Ser Asn Ser Val Ser Gln Arg Pro Asn Asp Gly Asp Phe Gly
            660                 665                 670

Ser

<210> SEQ ID NO 21
<211> LENGTH: 5315
<212> TYPE: DNA
<213> ORGANISM: Arabidopsis thaliana
<220> FEATURE:
<221> NAME/KEY: misc_feature
<222> LOCATION: (0)...(0)
<223> OTHER INFORMATION: Arabidopsis thaliana TEL1   --genomic sequence
      with promoter and terminator

<400> SEQUENCE: 21 ggtaccccg aaaagaatca tacttgtaga acaaataaga gattgaatta cgtggtaagc      60
aagaagtggt atttaggtaa attattactt taccttgaaa aaaatagaaa acgaaaacca    120
agattatggt ttttggtcgt tggtttttgg ggagtcttct tctcgaaccg agattttcat    180
gtgcacgtgc gtttggtcac tacttcgtgt ttaacaaaca ctttccttca ctatactagt    240
atccacatta aacaatgata ttgcttttta aagataattt gattctaata tcattaaaac    300 cttttttgtat gaattttaaa ctaatgattt cgtgaatgtg tgtaataatg taccctcctt    360
ggacagttgg actcgcgata atgtatcctt aagagttaag tctttttttt tcttctgttt    420
ttgggtgcaa cctaagagtt aagtctctag ctaacttta accaaaaata gaaagtctcc    480
agctaactat tgctagaact taaatgtttt ggagattaga cacataaaga aaagaaaaca    540
cacacacaca cactagatat tttgatattg gagatgctaa aaaatatact cacctcctca    600
acatatgaca aaatgaacga aaaggaggga aaaaaaacac aaagcaaaaa agctcaattg    660
cgactaaata caaagtgtat gagtactaag ccgcagacaa accctaagct acattttgtg    720
gtgaactata cgtctatacg tctatacgtc taaaccgaaa gcccaaaggt ttatgtggat    780
ttaattttga tctttatttc ataaggtttt gttttgtttt ccttctatga tgtgagattc    840
cttttcgagt cgaacttacc tctttaaatt acctcaattt aaaaggtttt atgcggacta    900
tactaccaat ctttacctat cacataaact ttagatccca aactaaagtt tcgcttgcgt    960
agctccaaga ccagctttgg ttactatttt tttgttatga tgtctgtcta tagaattagt   1020
agctggtatt catatggttt gcttgataat ttatagtcgt tgtggttaaa gttcaactga   1080
ttattggtcc accaaataat attttctacg ataagttgag aaatttattt agacaatgca   1140
gcatgtggtg aaaatatagt taagagttttt agacggttaa aaattacaaa ctatttggaa   1200
aactacaaaa aaaaaaaaaa tgtttcatat tctccattaa aatttaattt tatcgtttaa   1260
acgctaaaat gttgtcaatc gaaatatttt agaaccgtat cgtcgttaat cgaaaaaaac   1320
tctattatgt taccgctata gtatacttta cattgatacg atacgacgat gtataacaaa   1380
caatgaaaag tgagattcgg agtacgaatg ccatatataa gatactgcaa attatgagtg   1440
```

```
agacaaaaga aaatccaaca aaacaatcaa aaagtaaaat tctccgatag tccaaaaaag   1500
tcttcccata ataatcctcc gatatattac cataaggtcc ataaccattt tttccttatc   1560
aatttatttc taatcacatt caattagtag cttttcttta cactgtttta aaaatacta    1620
atcgaaactt aaagatgaac attttccacg tactcagtat tcgtgtcgcg tagggacttt   1680
ctatattacg cctcgtaaaa ccaaagaacc caaagcctac aacaaaaagt gcgtaggggt   1740
attaacgtaa cttaacaaga ggatagtaat aataaattcg atttaacata aaacagtca    1800
ttttcgagaa acttaaatgc ttacaacaca aaaaataaaa catttgttct cttccactgt   1860
cttgtctgta ataagagcaa agacagagag agacgacgtt acagtatctc tctctcacac   1920
gatcaagaga aacttcatca ttcgtcggaa aatatcaact ctggtattaa tggaagactc   1980
cagactttt ccgttcgtcg gaaacttaga ccctcgtgct caagagttta taccattcaa    2040
ccctatctcc tccggttttc actttccgta cactcctcct cctccacagc ttcctcctcc   2100
gttacctccg tcgtcgtacg gattatctcc gacggagcca agagttttca cattcttcaa   2160
tatcccacca catccgatga tgttttctcc tcctcctcct caaccaccac caccaccacc   2220
gcgtccatgt ttcaacggcg tttcggcagc tcaacggctt cctctgccgt caaatactcc   2280
gacgcgatct ctctctttga tctccgtacc acgtgacgta accgagtcta cggtgagacg   2340
tgacttggag gtttacggcg acgttcgtgg cgtgcaaatg gagagaatct ctgaaggaat   2400
cgtgaccgtc catttctacg atatacgtga cgctaaaaga gcggtacgtg aagtttgtgg   2460
tagacacatg cagcaacaag ctagaggtgg aagcgtctgg agctcacctt ctacttcatc   2520
ggcgcgtggg tttgtttccg gtagacctgt gtgggctcag ttcgtagttc cggcgactag   2580
tgccgttccc ggaggttgta accaaggaac gttagtaata tttaacttag ccctgaggt    2640
ctcttccatt actctcagac agattttcca agtttacggt actgttcttt ttttttttt    2700
tctaatttct atgtcttgat ttagtttact ttgtttcctc gatttgtgga tatgtcagga   2760
attaaaacat tttacaaaga ctttaaaatg ttaagctatg gtataaatta cattattatt   2820
tacatgaatc atggattcat tgtttgcatg ctatgaaaca tctttagctt ttgaatatag   2880
attatattgg accgtttgtt tatgtgagaa tctatgtttc aggtccgatc aaagagttga   2940
gagagacacc gtacaaaaaa catcaaaggt tcgttgagtt ttatgatgtg agagacgcgg   3000
cgagagcgtt tgatcgaatg aatggtaaag agattggtgg gaagcaagtt gtgatcgaat   3060
ttagtcgacc tggtggaatt aagaacaggt tcaggtcatc taggcaaccg cagctaccat   3120
ttcaaccgct tcgagagcca ccaatcctaa ttcctccttt gaggcggcca gtatctttca   3180
tcaaagataa aaacaagaat gtgagcccta aaatggagt tattgctgtt gatgcttcta    3240
tgcgttcctt atgtatcatc gatgctgacg ataataagac tcgaggaacc cgaggaacgg   3300
aatccgaatg cgcggagaca aaaagcaaga atgtggctaa gtgggggaag aaaagacaga   3360
tgaagaacat ggaactaagt cagtttctta tcagtgaaga aaccatggaa gatccgagtt   3420
gcagagatcc acgtaccact ttgatgatca agaacatacc aaacaagtac aggttgggct   3480
ttataatcta atttatttag tatattataa tatttgaaag ttttcaatt attctctaag    3540
aaactaaaga ctaaatcttt ctaatcttca ataaagtaat tatatggatt taaagttcga   3600
agcttttgca cactctagga tgaataaaga tttagatctt tcattaaaat attcacatgg   3660
attcgtgtgc tatattcaaa gttttatatt ctagataaaa ttctccaatg ttatgttcaa   3720
tcaaactttt aattatattc ttgttttgat catacccttaa ttgactaaca ttatccctta  3780
ggattcttgt aggttttta ttttatgaga ttccatgtgt gaattttcta aggttttcag    3840
```

```
tgttttttgtt tatatagtca aaagctactg ttggatatgt tggacaagca ttgcattcac    3900
ataaacgaag caatcaccga ggagcacaat aaacatgagt ctcatcatca gccgtattct    3960
tcttatgatt tcgtgtatct ccccatggat ttcaagtaat cgagcatcga aattcaatga    4020
catatagttt ttttttttt  gtcaaaattc aatgacatat agtatttgtt atatttatag    4080
ctaaaatcat aactcttttc tttgttgtga tattagcaac aagtgcaatg ttggttatgg    4140
gtttgtgaac atgacatctc cggaagcagc ttggaggttt tacaaggcat tcatggtca    4200 gcgttgggag gttttaatt  cgcataagat ttgccaaatc acatatgcga gagttcaggt    4260
ataatataca cattaatgtt ttgaaatggc aaactaaata aacttgaaat ggtcacaatg    4320
tgtttatttt gttaaaccaa cgtcttgaat tttatgataa gtatgatgat atggtcacaa    4380
ttgtgtttgc ttgacaaaaa aaaaaggtca caattgtgtt tattttgtta cttttgatcg    4440
ccaataaagg gtttggagga tctaaaggaa cacttcaaga gctcgaaatt tccatgcgag    4500
gctgagctat acctgccggt ggtcttctcg cctccacgag atgggaagca gttaacagaa    4560
cctgtctcca tcaacataac catcaacggc tgcaccagac ttaatcataa tcattttgag    4620
caaacagtcg gtcaagatca ctttctgagt ggatcatgtt gtgacagtga ccatgataac    4680
agtcatgaag atggattttc cggcagtagc gtagactgtg gccggagtat caccgtggaa    4740
ggagaaacat ctttctaggt gttatctgta atgtgtatca tcatcataag atataacaaa    4800
gtgtaagtag acatcatttt ggttagaatt tgtatctttt tttttttttt tttttttgta    4860
tgtctgaatc taaagttctt tttggtcatg acatgaatta aattacgcat gcaaagttct    4920
ttttggttat caacatgaat taaacgactc ctgcaaagtt ctaaaaggtc acatctggat    4980
aactcttttt cttttctttt gatataatga aagtgtagta atatttagat ttaagttctt    5040 acttttaaa  tacggatata aaattgatag gagaccgaaa ttgggttgac ctagggtaag    5100
agttcttttt caggcaatac catctttgtt ctagtgttag ctgtcttatt cagtgacctg    5160
tgaaagggac aatagaggac tctgtgctag tgatgatcac attctgtatc tccctctgat    5220
tcatggggca ctgacacgtg gtctgatatc caccttactt ggtgcatggc agtgttgata    5280
gtgatggttg actacaactt taatcttatg gtacc                               5315
```

<210> SEQ ID NO 22
<211> LENGTH: 615
<212> TYPE: PRT
<213> ORGANISM: Arabidopsis thaliana
<220> FEATURE:
<223> OTHER INFORMATION: Arabidopsis thaliana TEL1

<400> SEQUENCE: 22

```
Met Glu Asp Ser Arg Leu Phe Pro Phe Val Gly Asn Leu Asp Pro Arg
 1               5                  10                  15

Ala Gln Glu Phe Ile Pro Phe Asn Pro Ile Ser Ser Gly Phe His Phe
            20                  25                  30

Pro Tyr Thr Pro Pro Pro Gln Leu Pro Pro Leu Pro Pro Ser
        35                  40                  45

Ser Tyr Gly Leu Ser Pro Thr Glu Pro Arg Val Phe Thr Phe Phe Asn
    50                  55                  60

Ile Pro Pro His Pro Met Met Phe Ser Pro Pro Pro Gln Pro Pro
65                  70                  75                  80

Pro Pro Pro Pro Arg Pro Cys Phe Asn Gly Val Ser Ala Ala Gln Arg
                85                  90                  95
```

```
Leu Pro Leu Pro Ser Asn Thr Pro Thr Arg Ser Leu Ser Leu Ile Ser
                100                 105                 110

Val Pro Arg Asp Val Thr Glu Ser Thr Val Arg Arg Asp Leu Glu Val
            115                 120                 125

Tyr Gly Asp Val Arg Gly Val Gln Met Glu Arg Ile Ser Glu Gly Ile
        130                 135                 140

Val Thr Val His Phe Tyr Asp Ile Arg Asp Ala Lys Arg Ala Val Arg
145                 150                 155                 160

Glu Val Cys Gly Arg His Met Gln Gln Gln Ala Arg Gly Gly Ser Val
                165                 170                 175

Trp Ser Ser Pro Ser Thr Ser Ser Ala Arg Gly Phe Val Ser Gly Arg
            180                 185                 190

Pro Val Trp Ala Gln Phe Val Val Pro Ala Thr Ser Ala Val Pro Gly
        195                 200                 205

Gly Cys Asn Gln Gly Thr Leu Val Ile Phe Asn Leu Asp Pro Glu Val
        210                 215                 220

Ser Ser Ile Thr Leu Arg Gln Ile Phe Gln Val Tyr Gly Pro Ile Lys
225                 230                 235                 240

Glu Leu Arg Glu Thr Pro Tyr Lys Lys His Gln Arg Phe Val Glu Phe
                245                 250                 255

Tyr Asp Val Arg Asp Ala Ala Arg Ala Phe Asp Arg Met Asn Gly Lys
            260                 265                 270

Glu Ile Gly Gly Lys Gln Val Val Ile Glu Phe Ser Arg Pro Gly Gly
        275                 280                 285

Ile Lys Asn Arg Phe Arg Ser Ser Arg Gln Pro Gln Leu Pro Phe Gln
        290                 295                 300

Pro Leu Arg Glu Pro Pro Ile Leu Ile Pro Pro Leu Arg Arg Pro Val
305                 310                 315                 320

Ser Phe Ile Lys Asp Lys Asn Lys Asn Val Ser Pro Lys Asn Gly Val
                325                 330                 335

Ile Ala Val Asp Ala Ser Met Arg Ser Leu Cys Ile Ile Asp Ala Asp
            340                 345                 350

Asp Asn Lys Thr Arg Gly Thr Arg Gly Thr Glu Ser Glu Cys Ala Glu
        355                 360                 365

Thr Lys Ser Lys Asn Val Ala Lys Trp Gly Lys Lys Arg Gln Met Lys
        370                 375                 380

Asn Met Glu Leu Ser Gln Phe Leu Ile Ser Glu Glu Thr Met Glu Asp
385                 390                 395                 400

Pro Ser Cys Arg Asp Pro Arg Thr Thr Leu Met Ile Lys Asn Ile Pro
                405                 410                 415

Asn Lys Tyr Ser Gln Lys Leu Leu Leu Asp Met Leu Asp Lys His Cys
            420                 425                 430

Ile His Ile Asn Glu Ala Ile Thr Glu Glu His Asn Lys His Glu Ser
        435                 440                 445

His His Gln Pro Tyr Ser Tyr Asp Phe Val Tyr Leu Pro Met Asp
        450                 455                 460

Phe Asn Asn Lys Cys Asn Val Gly Tyr Gly Phe Val Asn Met Thr Ser
465                 470                 475                 480

Pro Glu Ala Ala Trp Arg Phe Tyr Lys Ala Phe His Gly Gln Arg Trp
                485                 490                 495

Glu Val Phe Asn Ser His Lys Ile Cys Gln Ile Thr Tyr Ala Arg Val
            500                 505                 510

Gln Gly Leu Glu Asp Leu Lys Glu His Phe Lys Ser Ser Lys Phe Pro
```

```
              515                 520                 525
Cys Glu Ala Glu Leu Tyr Leu Pro Val Val Phe Ser Pro Pro Arg Asp
    530                 535                 540

Gly Lys Gln Leu Thr Glu Pro Val Ser Ile Asn Ile Thr Ile Asn Gly
545                 550                 555                 560

Cys Thr Arg Leu Asn His Asn His Phe Glu Gln Thr Val Gly Gln Asp
                565                 570                 575

His Phe Leu Ser Gly Ser Cys Cys Asp Ser Asp His Asp Asn Ser His
            580                 585                 590

Glu Asp Gly Phe Ser Gly Ser Ser Val Asp Cys Gly Arg Ser Ile Thr
        595                 600                 605

Val Glu Gly Glu Thr Ser Phe
    610                 615

<210> SEQ ID NO 23
<211> LENGTH: 4413
<212> TYPE: DNA
<213> ORGANISM: Arabidopsis thaliana
<220> FEATURE:
<221> NAME/KEY: misc_feature
<222> LOCATION: (0)...(0)
<223> OTHER INFORMATION: Arabidopsis thaliana TEL2  -- genomic sequence
      with promoter and terminator

<400> SEQUENCE: 23
aagcttggtc gagacatggt actgagtaaa accctaaatc gttagaaatg gcagattcgt    60
aaatcaaatt gtttgaagaa agagctaaga ataatatgca ctacgtgggc ctttggctta   120
tggcccaata tgcctatttt tcttttactc tcattagccc aaccggtctc gtggtaaggt   180
caagtaacca tgggatcgaa caaataaaag tttgatattt cgtttcaatc actaattggc   240
tcattgcata ccaaccattc tcaattttat tttttaaaag tggaaaatca tataaacatt   300
cattttaaat tttgaataaa taacacataa aaaatcacta aaataattta ctaaccaaaa   360
gttgataaaa ttttgaagt ataacttcat gtcttcatca ttatgatcac atcatgatga   420
atcaacaaag tttcttcata atttattctt aacttttgta gctgaattct gaaataatat   480
atagaagata ttcacgtttt cacactttt ttattattag ctagagaatg tagtttatgt   540
aataaatgaa ggatatggta taaacatgac aaaaacaaat gacagcccaa acaaggaag   600 taggtaacaa taacattcct taaaacaagg aattgccctg gtcccatttt ggtcctaccc   660
tcgaactata actatattta catgacatgc gtttattata tgtacataga cagatattac   720
gtatgtcaaa ctccatagct ccaaaccatt acgtatctga cctagagggc ctccctaatc   780
cttcttttgt gataggagat tgtagaaaac ttataaaaat ctatgaaaca aaaggctaga   840
ttaggctaat atgggctaaa tgtaatgtaa tgtctatgtg ggtgagattt attcgttgtt   900
tttacgtcaa aggaatgtt gtcactatac atttatggaa cataaacaat actacagatt   960
atttagaaat gtataggctt agatagttta cactttgcat tgagatggag agagacacga  1020
caaatcggcc catgcacttt tgcggtgaaa ttggggaaca cgacattacg aactattgca  1080
cccaaataca aattctatat agtatgatac atggataatg gtaccoaact aatcgaaaat  1140 tgtgttccta ggcataaaat ctaactatga tatttgtttt aaacaagaaa aattctttcg  1200
taaataatgt tttagagaaa acatgatttt gattatctta aaaactaaat caacatagaa  1260
aaatgaatga gactttgtta tgtaacctat gttcttctcg tgattattaa caaaaaaacc  1320
tctacaattg tttgaatact ctgcattttc catcagtcca ttgcaatgaa accctctcaa  1380
```

-continued

```
aggacaaaat ggtaaattgc tcgaacgagt tagtacacca ttaaattaaa gaaccttgac      1440
ttgttttgtt agtaaacaaa aattgggaaa taataataga aatctctgca gaataaaaac      1500
aaaaccaaca aaaattccac ttttgtgctc tctccctctc cctcccttg gcaccaaata       1560 aagaggtaga gagagacgaa atagtacgat cactgaagaa tatcaaacgt ccatagtcat      1620
tacctgtcac cggaaaaacc agttcccaac tcatcacctc tccctctaaa ccaacaatgt     1680
ctgtcaccgg accattcagt cacccaacaa accttaaccc aacagctccg gcgttctttc     1740
cggcgataaa ccaacaccaa aaccaaaacc cctccttaat tccgacaaga ttcttcctcc     1800
ctcatccccc tcctcctcct cctcctccgc cgccgccgct atacttttct tatttctctc    1860
tccctcctcc tcctcctcct cctcatcttc caccgacttc agtaacacca accagagccg    1920
tgatgttatt acaagtccca gctaccgtca ctgagacatc tctaagacga gacatggaac    1980
tattcggtga agtccgtgga gtccaaatgg aaagagcaca tgaaggaatc gtgattttcc    2040
atttctacaa tctaataaac tcacaaagag cttttaacga gatacgttac cgtcacatgc    2100
aacaacagga acaacaacaa catttccact tcacgacggc gcgtggactc gtctccggtc    2160
attctctttg ggcccatttc gtgtttcctc aactcaatgc tgttcctgaa ggaaacaatc    2220
aaggctctct tgtcattatg aacttagaac ccaccgtctc ttcctcaact ctccgtcaca    2280
ttttccaagt ttatggtaaa gtttcaattt ttaacgagat aaacaaataa agttgcaaac    2340
tttatgctaa ttagtgttac gaaaatcatt gtaggagaag tgaagcaggt gagagagacg    2400
ccgtgtaaga gagaacaaag atttgtggag ttttttgacg ttagagacgc tgcaaaagct    2460
ctccgtgtaa tgaacggaaa agttatctcc ggtaaaccaa tggttatcca gtttagtcgt    2520
cccggtggtt taaccaagaa actcttcttc gcttcacact tccataaaaa cttcatcttt    2580
aacaacgaac accattatta tccaccgcca ccaccaccat cacgaatggt gaagtcggat    2640
attctaatgt acaagcaaca acaaaagaag aagaagaaga agtatgtaaa gaagaatctt    2700
ggtgatcctt atttcatgat aaacgaaaac gctataccg gcggagagtt cagagacgga     2760
agaaccaccg tgatgatcaa gaacatccct aacaagtaca cgtaagtaaa aaaaaaagca    2820
tgcatctttt tcattatagc ttagtgattg tgataggcat gtgcttcttg attctcttgt    2880
tagtccgata ttgtcctaaa acgaggaatt gcttttgttc tgttttttga ttttgggtt     2940 tgacaaaaag tcaacaagac ctaatggata atagtaatga gaacaagcta tttgtattca    3000
tatgtttact attttgtgt atattctggt cccatggaga ttaacaaata tcgactagtc     3060
aattttatag tattgtttct atttacagac agaagctgct tttgaagatg ttggacacac    3120
attgtaaaga ttgtaaccaa agtgtaatca aagaagggaa caaaactcct atgtcttctt    3180
atgactttgt ctacctcccc attgatttca ggtaattaat tgattacccg ttttctatgt    3240
gattaatagt atattagtga tgagtgtgct aattaaattt ggtgttttgt tagcaacaaa    3300
agcaatgtgg gatatgggtt tgtgaacatg acatcaccag aagcagtgtg gagactttac    3360
aagagctttc acaatcaaca ttggagagat ttcaccacca ctagaaagat ctgtgaggtc    3420
acttatgctc gtatccaggt aaagaaaaac aagaaagatc ttcatgaatc tcttgtttag    3480
tcacgctgga ataataaaaa gctgtttttt ttataagggt cttgagtcat aagggaaca     3540 tttcaagaac gttaggctag caggagtaga gatagacgag tacatgccgg ttgttttctc    3600
gccgccgcgt gatggacggt tgtcaccgga gcctgtggct attgttgacc cttgggataa    3660
accagtggat gatgaagaca gatgttgtaa gtcacgagac gggtttgttg tgtccgacaa    3720
gaagatggta ggaagtgatg gttgtggttt ttgtcttagt gagagaatcg aaaacggcgg    3780
```

```
cgtttgagat  dacgtaagga  ggagaaacag  taaatgaaaa  ttaatgatgg  tttcggcttt    3840
taggcggcga  tctatataat  acgtagctgt  atccatcatg  tcttatcatc  ttctgtataa    3900
ccatcttctt  cttcatctct  ctcttactct  gtctctctct  atcttttctt  tttgtgggtt    3960
ttgtttggat  atgtaaaacg  ttgttcaact  tttgtattga  agtatttggc  aacttttttt    4020
aattagaaaa  caaaacttta  atgttgtaca  aatgctatgt  aagaaccttt  tgtcatcaaa    4080
acttgaggtt  gtacagaaaa  aagagagtca  gtttaggtg   gtgtcttttg  ttttttttgtt   4140 ctttctattt  ctctatcact  atattattaa  aatgctatgg  tctttaagtt  gtttaactga    4200
aaagagtgat  taaccacctt  atttagtata  gctcttccta  aatttatcaa  ttaaaaaacg    4260
tagtcacctt  agactttaac  ttttcataaa  tcttgtcaca  tgtctttact  gctttgaaaa    4320
aagtatacta  ccaaaagttc  taaattctaa  tcactagttt  ttcgataatt  ttttggtgat    4380
gtgagtgttt  ttttgcttgt  tcaggttaag  ctt                                    4413

<210> SEQ ID NO 24
<211> LENGTH: 527
<212> TYPE: PRT
<213> ORGANISM: Arabidopsis thaliana
<220> FEATURE:
<223> OTHER INFORMATION: Arabidopsis thaliana TEL2

<400> SEQUENCE: 24

Met Ser Val Thr Gly Pro Phe Ser His Pro Thr Asn Leu Asn Pro Thr
 1               5                  10                  15

Ala Pro Ala Phe Phe Pro Ala Ile Asn Gln His Gln Asn Gln Asn Pro
            20                  25                  30

Ser Leu Ile Pro Thr Arg Phe Leu Pro His Pro Pro Pro Pro
        35                  40                  45

Pro Pro Pro Pro Pro Leu Tyr Phe Ser Tyr Phe Ser Leu Pro Pro
    50                  55                  60

Pro Pro Pro Pro Pro His Leu Pro Pro Thr Ser Val Thr Pro Thr Arg
65                  70                  75                  80

Ala Val Met Leu Leu Gln Val Pro Ala Thr Val Thr Glu Thr Ser Leu
                85                  90                  95

Arg Arg Asp Met Glu Leu Phe Gly Glu Val Arg Gly Val Gln Met Glu
            100                 105                 110

Arg Ala His Glu Gly Ile Val Ile Phe His Phe Tyr Asn Leu Ile Asn
        115                 120                 125

Ser Gln Arg Ala Phe Asn Glu Ile Arg Tyr Arg His Met Gln Gln Gln
    130                 135                 140

Glu Gln Gln Gln His Phe His Phe Thr Thr Ala Arg Gly Leu Val Ser
145                 150                 155                 160

Gly His Ser Leu Trp Ala His Phe Val Phe Pro Gln Leu Asn Ala Val
                165                 170                 175

Pro Glu Gly Asn Asn Gln Gly Ser Leu Val Ile Met Asn Leu Glu Pro
            180                 185                 190

Thr Val Ser Ser Ser Thr Leu Arg His Ile Phe Gln Val Tyr Gly Glu
        195                 200                 205

Val Lys Gln Val Arg Glu Thr Pro Cys Lys Arg Glu Gln Arg Phe Val
    210                 215                 220

Glu Phe Phe Asp Val Arg Asp Ala Ala Lys Ala Leu Arg Val Met Asn
225                 230                 235                 240

Gly Lys Val Ile Ser Gly Lys Pro Met Val Ile Gln Phe Ser Arg Pro
```

```
                    245                 250                 255
Gly Gly Leu Thr Lys Lys Leu Phe Phe Ala Ser His Phe His Lys Asn
                260                 265                 270

Phe Ile Phe Asn Asn Glu His His Tyr Tyr Pro Pro Pro Pro Pro Pro
            275                 280                 285

Ser Arg Met Val Lys Ser Asp Ile Leu Met Tyr Lys Gln Gln Gln Lys
        290                 295                 300

Lys Lys Lys Lys Lys Tyr Val Lys Lys Asn Leu Gly Asp Pro Tyr Phe
305                 310                 315                 320

Met Ile Asn Glu Asn Ala Ile Thr Gly Gly Glu Phe Arg Asp Gly Arg
                325                 330                 335

Thr Thr Val Met Ile Lys Asn Ile Pro Asn Lys Tyr Thr Gln Lys Leu
            340                 345                 350

Leu Leu Lys Met Leu Asp Thr His Cys Lys Asp Cys Asn Gln Ser Val
        355                 360                 365

Ile Lys Glu Gly Asn Lys Thr Pro Met Ser Ser Tyr Asp Phe Val Tyr
370                 375                 380

Leu Pro Ile Asp Phe Ser Asn Lys Ser Asn Val Gly Tyr Gly Phe Val
385                 390                 395                 400

Asn Met Thr Ser Pro Glu Ala Val Trp Arg Leu Tyr Lys Ser Phe His
                405                 410                 415

Asn Gln His Trp Arg Asp Phe Thr Thr Arg Lys Ile Cys Glu Val
            420                 425                 430

Thr Tyr Ala Arg Ile Gln Gly Leu Glu Ser Leu Arg Glu His Phe Lys
        435                 440                 445

Asn Val Arg Leu Ala Gly Val Glu Ile Asp Glu Tyr Met Pro Val Val
    450                 455                 460

Phe Ser Pro Pro Arg Asp Gly Arg Leu Ser Pro Glu Pro Val Ala Ile
465                 470                 475                 480

Val Asp Pro Trp Asp Lys Pro Val Asp Asp Glu Asp Arg Cys Cys Lys
                485                 490                 495

Ser Arg Asp Gly Phe Val Val Ser Asp Lys Lys Met Val Gly Ser Asp
            500                 505                 510

Gly Cys Gly Phe Cys Leu Ser Glu Arg Ile Glu Asn Gly Gly Val
        515                 520                 525

<210> SEQ ID NO 25
<211> LENGTH: 1812
<212> TYPE: DNA
<213> ORGANISM: Arabidopsis lyrata
<220> FEATURE:
<221> NAME/KEY: misc_feature
<222> LOCATION: (0)...(0)
<223> OTHER INFORMATION: Arabidopsis lyrata TEL

<400> SEQUENCE: 25
atggaagatt ctagactttt tccgttcgcc ggaaacttag accctcgtgc tcaagagttt      60
ataccactta accctaccct ctccggtttt tacttcccgt tcactcctcc ttcaccgctt     120
cctccgccgt tacatccgtc gtcggagcca agagttttca cattcttcaa catcccacca     180
catccggtga tgttttctcc tcctcctcct caaccaccac catcaccacc accgcgtccg     240
tgttttaacg gcgtttcggc agctcaacga cttcctccgc cgtcaaattc tccgacgcga     300
tctctctcat tgatctccgt accgcgtgac gtcaccgagt ctacagtgag acgtgacttg     360
gaggtttacg gcgacgttcg tggcgtgcaa atggagagaa tctctgaagg aatcgtgacc     420
```

```
gtccatttct acgatatccg tgacgctaaa agagcggttc gagaagtttg tggtagacac    480
atgcagcaac aagccagagg tggaagcgtt tggagctcac cttctacttc atcggcgcgt    540
gggtttgttt ccggtagacc tgtgtgggct cagttcgtag ttccggccac tagcgccgtt    600
cccggaggtt gtaaccaggg aacgttagtt atatttaact tagaccctga agtctcttcc    660
attactctca gacagttttt ccaagtttac ggtccgatca aagagttgag agagacaccg    720
tacaagaaac atcaaaggtt cattgagttt tatgatgtaa gagatgcggc gagagcgttt    780
gatcgaatga atggtgaaga gatcggtggg aagcaagttg tgatcgaatt tagtcgacct    840
ggtggaatta agaacaagtt caggtcatct aggcaaccgc agctaccgtt caaccgctt     900 caacagccac caattctatt tcctcctttg aggcggccag taactctcat gaaagataaa    960
aacaagaatg tgagccctaa aaatggaatt attgctgttg gtgcttctat gcgttcgtta    1020
tgtatcattg gtgatgacga taataagacc cgaggaacgg aatccgaatg tgcggagaca    1080
aagagcaaga atgtggctaa gtgggggaag aaaagacaga tgaagaacat ggaactaagt    1140
cagtttctta tcagtgaaga aaccatggaa gatccgagtt gcagagatcc acgtactact    1200
ttgatgatca agaacatacc aaacaagtac agtcaaaagc tactcttgga tatgctagac    1260
aatcattgca ttcacatcaa caaagcaatc accgaggagc acgatgaaca tgagtctcat    1320
catcagccgt attcttctta tgatttcgtg tatctcccca tggatttcaa caataagtgc    1380
aatgttggtt atgggtttgt gaacatgaca tctccggaag cagcttggag gttttacaag    1440
gcgtttcatc atcaacgttg ggaggttttt aattcgcgta agatttgcca gatcacatat    1500
gcaagagttc agggtttgga ggatctaaag gaacacttca agagctctaa gtttccgtac    1560
gaggctgagc tatacctgcc agtggtcttc tcgcctccac gagacgggaa gaggttaaca    1620
gaacctgtct ccatcaacat caacggctgc accagactta atcatcttga gcgaatggac    1680
ggtcaagatc actctctgag tagatcatat tgtgatagtg accatgataa tagtcacgaa    1740
gatggatttt ccggcagtag tagcatagac tgtggccggt gtatcacatt ggaaggagaa    1800
acatctttct ag                                                       1812
```

<210> SEQ ID NO 26
<211> LENGTH: 603
<212> TYPE: PRT
<213> ORGANISM: Arabidopsis lyrata
<220> FEATURE:
<223> OTHER INFORMATION: Arabidopsis lyrata TEL

<400> SEQUENCE: 26

```
Met Glu Asp Ser Arg Leu Phe Pro Phe Ala Gly Asn Leu Asp Pro Arg
 1               5                  10                  15

Ala Gln Glu Phe Ile Pro Leu Asn Pro Thr Ser Ser Gly Phe Tyr Phe
                20                  25                  30

Pro Phe Thr Pro Pro Ser Pro Leu Pro Pro Leu His Pro Ser Ser
            35                  40                  45

Glu Pro Arg Val Phe Thr Phe Phe Asn Ile Pro His Pro Val Met
        50                  55                  60

Phe Ser Pro Pro Pro Ser Gln Pro Pro Ser Pro Pro Arg Pro
65                  70                  75                  80

Cys Phe Asn Gly Val Ser Ala Ala Gln Arg Leu Pro Pro Ser Asn
                85                  90                  95

Ser Pro Thr Arg Ser Leu Ser Leu Ile Ser Val Pro Arg Asp Val Thr
            100                 105                 110
```

Glu Ser Thr Val Arg Arg Asp Leu Glu Val Tyr Gly Asp Val Arg Gly
            115                 120                 125

Val Gln Met Glu Arg Ile Ser Glu Gly Ile Val Thr Val His Phe Tyr
        130                 135                 140

Asp Ile Arg Asp Ala Lys Arg Ala Val Arg Glu Val Cys Gly Arg His
145                 150                 155                 160

Met Gln Gln Gln Ala Arg Gly Gly Ser Val Trp Ser Pro Ser Thr
                165                 170                 175

Ser Ser Ala Arg Gly Phe Val Ser Gly Arg Pro Val Trp Ala Gln Phe
                180                 185                 190

Val Val Pro Ala Thr Ser Ala Val Pro Gly Gly Cys Asn Gln Gly Thr
            195                 200                 205

Leu Val Ile Phe Asn Leu Asp Pro Glu Val Ser Ser Ile Thr Leu Arg
        210                 215                 220

Gln Phe Phe Gln Val Tyr Gly Pro Ile Lys Glu Leu Arg Glu Thr Pro
225                 230                 235                 240

Tyr Lys Lys His Gln Arg Phe Ile Glu Phe Tyr Asp Val Arg Asp Ala
                245                 250                 255

Ala Arg Ala Phe Asp Arg Met Asn Gly Glu Glu Ile Gly Gly Lys Gln
            260                 265                 270

Val Val Ile Glu Phe Ser Arg Pro Gly Gly Ile Lys Asn Lys Phe Arg
        275                 280                 285

Ser Ser Arg Gln Pro Gln Leu Pro Phe Gln Pro Leu Gln Gln Pro Pro
        290                 295                 300

Ile Leu Phe Pro Pro Leu Arg Arg Pro Val Thr Leu Met Lys Asp Lys
305                 310                 315                 320

Asn Lys Asn Val Ser Pro Lys Asn Gly Ile Ile Ala Val Gly Ala Ser
                325                 330                 335

Met Arg Ser Leu Cys Ile Ile Gly Asp Asp Asp Asn Lys Thr Arg Gly
            340                 345                 350

Thr Glu Ser Glu Cys Ala Glu Thr Lys Ser Lys Asn Val Ala Lys Trp
        355                 360                 365

Gly Lys Lys Arg Gln Met Lys Asn Met Glu Leu Ser Gln Phe Leu Ile
    370                 375                 380

Ser Glu Glu Thr Met Glu Asp Pro Ser Cys Arg Asp Pro Arg Thr Thr
385                 390                 395                 400

Leu Met Ile Lys Asn Ile Pro Asn Lys Tyr Ser Gln Lys Leu Leu Leu
                405                 410                 415

Asp Met Leu Asp Asn His Cys Ile His Ile Asn Lys Ala Ile Thr Glu
            420                 425                 430

Glu His Asp Glu His Glu Ser His His Gln Pro Tyr Ser Ser Tyr Asp
        435                 440                 445

Phe Val Tyr Leu Pro Met Asp Phe Asn Asn Lys Cys Asn Val Gly Tyr
    450                 455                 460

Gly Phe Val Asn Met Thr Ser Pro Glu Ala Ala Trp Arg Phe Tyr Lys
465                 470                 475                 480

Ala Phe His His Gln Arg Trp Glu Val Phe Asn Ser Arg Lys Ile Cys
                485                 490                 495

Gln Ile Thr Tyr Ala Arg Val Gln Gly Leu Glu Asp Leu Lys Glu His
            500                 505                 510

Phe Lys Ser Ser Lys Phe Pro Tyr Glu Ala Glu Leu Tyr Leu Pro Val
        515                 520                 525

Val Phe Ser Pro Pro Arg Asp Gly Lys Arg Leu Thr Glu Pro Val Ser

```
                530              535              540
Ile Asn Ile Asn Gly Cys Thr Arg Leu Asn His Leu Glu Arg Met Asp
545              550              555              560

Gly Gln Asp His Ser Leu Ser Arg Ser Tyr Cys Asp Ser Asp His Asp
                565              570              575

Asn Ser His Glu Asp Gly Phe Ser Gly Ser Ser Ile Asp Cys Gly
                580              585              590

Arg Cys Ile Thr Leu Glu Gly Glu Thr Ser Phe
            595              600
```

<210> SEQ ID NO 27
<211> LENGTH: 1575
<212> TYPE: DNA
<213> ORGANISM: Medicago truncatula
<220> FEATURE:
<221> NAME/KEY: misc_feature
<222> LOCATION: (0)...(0)
<223> OTHER INFORMATION: Medicago truncatula TEL2 Genomic

<400> SEQUENCE: 27

```
atgggagaaa ccttaaaccc tactgctcca gagtttaatc caaacagcta cattcccatt      60
ccagtcgccg tcggtattcc ctaccccat ccacccacg ccgtcacacc gccgccgcac      120
ctttccacaa tacccacccg ctctattctc tcagtcccg ccctcccac ccctgaaact      180
gacctccgaa aagaccttc agctttcggt gaagtgagag ccgttcaaac ggactcattc      240
cgtaacggag tcataactgc tcattactat gatcttagac acgcagagac ggcgtttgcc      300
gctattcgga ctcatcacgt cctctgcgct gcctatttca accctctatc ttattcccaa      360
attttcccca cgccactacc tccgccgcca ccgggtctcg tcgccggtgc accgctgtgg      420
gcccattatg tactctccga tgctcagaat caaggaaccc tagttgtttt caacttagat      480
gacgacgttt cttctgatca gctgcaacaa gttttcggag cttttggagc aattaaggaa      540
gtgagggata caccatggaa gaaaaggaat caaagttttg ttgagttttt cgacataaga      600
gatgctgaaa aagctttgaa agaattgaat ggcaaagaga ttaatggaaa accaattgct      660
attgagttta gtaaaccaaa attatttcat tctgaaccca atgcttatat ctctaataag      720
cctttttaatt acaaccttaa tccacctcct tccccgcgac gtcattttgc ttcacaacct      780
cattcaccac aattatctca aagagtttg acatttaacc gggtaaacca aataggat       840
ggttcaatgg gttcattgaa gggtgaagag aggtatcctt tgttagagt tcaaagtaga      900
gagagttttg gggaaagtgc ttggagttgg aaggggaagt tagcaaagag acatgaaaat      960
cgttttctaa tcaagaaga tgccattgtt gaatctgatc ctagaaccac tctcatgatc     1020
aaaaacatac ccaacaaata cagtcagaag ttactgttga atatgctgga caaccactgt     1080
gtacactgca atgagcagct aggcgacggc gagcctctct cctcctatga ctttgtgtat     1140
cttcctatag attttaagaa caatgcaac gtgggatatg gattcgtgaa tatgacatct     1200
cctgaggcaa cgctaagatt ctacaaggcc ttccagcacc aacattggga ggtcttcaat     1260
tctagaaaaa tttgccaact cacatacgca agagttcagg gtttggaatc gttgaaagag     1320
cattttaaga actcaaagtt cccgtgtgag atggagcatt acctgccagt ggtgttttca     1380
ccgcctcgag atggaaaaca attgacggag ccaattccag tggcggggaa catgctacaa     1440
attggtgctg ctccttctgt agctgatgag atggaaggtc aagatcatag agtaggtagt     1500
ggtggctgtg acgtgatcag cagaaaaagt ggcggcatag gtgatgatga tgatgataaa     1560
acagatgtga agtga                                                     1575
```

<210> SEQ ID NO 28
<211> LENGTH: 524
<212> TYPE: PRT
<213> ORGANISM: Medicago truncatula
<220> FEATURE:
<223> OTHER INFORMATION: Medicago truncatula TE2

<400> SEQUENCE: 28

```
Met Gly Glu Thr Leu Asn Pro Thr Ala Pro Glu Phe Asn Pro Asn Ser
 1               5                  10                  15

Tyr Ile Pro Ile Pro Val Ala Val Gly Ile Pro Tyr Pro Tyr Pro Pro
            20                  25                  30

Tyr Ala Val Thr Pro Pro His Leu Ser Thr Ile Pro Thr Arg Ser
            35                  40                  45

Ile Leu Leu Ser Pro Ala Pro Pro Thr Pro Glu Thr Asp Leu Arg Lys
 50                  55                  60

Asp Leu Ser Ala Phe Gly Glu Val Arg Ala Val Gln Thr Asp Ser Phe
 65                  70                  75                  80

Arg Asn Gly Val Ile Thr Ala His Tyr Tyr Asp Leu Arg His Ala Glu
                 85                  90                  95

Thr Ala Phe Ala Ala Ile Arg Thr His His Val Leu Cys Ala Ala Tyr
            100                 105                 110

Phe Asn Pro Leu Ser Tyr Ser Gln Ile Phe Pro Thr Pro Leu Pro Pro
            115                 120                 125

Pro Pro Pro Gly Leu Val Ala Gly Ala Pro Leu Trp Ala His Tyr Val
            130                 135                 140

Leu Ser Asp Ala Gln Asn Gln Gly Thr Leu Val Val Phe Asn Leu Asp
145                 150                 155                 160

Asp Asp Val Ser Ser Asp Gln Leu Gln Gln Val Phe Gly Ala Phe Gly
                165                 170                 175

Ala Ile Lys Glu Val Arg Asp Thr Pro Trp Lys Lys Arg Asn Gln Ser
            180                 185                 190

Phe Val Glu Phe Phe Asp Ile Arg Asp Ala Glu Lys Ala Leu Lys Glu
            195                 200                 205

Leu Asn Gly Lys Glu Ile Asn Gly Lys Pro Ile Ala Ile Glu Phe Ser
            210                 215                 220

Lys Pro Lys Leu Phe His Ser Glu Pro Asn Ala Tyr Ile Ser Asn Lys
225                 230                 235                 240

Pro Phe Asn Tyr Asn Leu Asn Pro Pro Ser Pro Arg Arg His Phe
                245                 250                 255

Ala Ser Gln Pro His Ser Pro Gln Leu Ser His Lys Ser Leu Thr Phe
            260                 265                 270

Asn Arg Val Asn His Asn Arg Ile Gly Ser Met Gly Ser Leu Lys Gly
            275                 280                 285

Glu Glu Arg Tyr Pro Phe Val Arg Val Gln Ser Arg Glu Ser Phe Gly
            290                 295                 300

Glu Ser Ala Trp Ser Trp Lys Gly Lys Leu Ala Lys Arg His Glu Asn
305                 310                 315                 320

Arg Phe Leu Ile Lys Glu Asp Ala Ile Val Glu Ser Asp Pro Arg Thr
                325                 330                 335

Thr Leu Met Ile Lys Asn Ile Pro Asn Lys Tyr Ser Gln Lys Leu Leu
            340                 345                 350

Leu Asn Met Leu Asp Asn His Cys Val His Cys Asn Glu Gln Leu Gly
            355                 360                 365
```

```
Asp Gly Glu Pro Leu Ser Ser Tyr Asp Phe Val Tyr Leu Pro Ile Asp
        370                 375                 380

Phe Lys Asn Lys Cys Asn Val Gly Tyr Gly Phe Val Asn Met Thr Ser
385                 390                 395                 400

Pro Glu Ala Thr Leu Arg Phe Tyr Lys Ala Phe Gln His Gln His Trp
                405                 410                 415

Glu Val Phe Asn Ser Arg Lys Ile Cys Gln Leu Thr Tyr Ala Arg Val
            420                 425                 430

Gln Gly Leu Glu Ser Leu Lys Glu His Phe Lys Asn Ser Lys Phe Pro
        435                 440                 445

Cys Glu Met Glu His Tyr Leu Pro Val Val Phe Ser Pro Pro Arg Asp
    450                 455                 460

Gly Lys Gln Leu Thr Glu Pro Ile Pro Val Ala Gly Asn Met Leu Gln
465                 470                 475                 480

Ile Gly Ala Ala Pro Ser Val Ala Asp Glu Met Glu Gly Gln Asp His
                485                 490                 495

Arg Val Gly Ser Gly Gly Cys Asp Val Ile Ser Arg Lys Ser Gly Gly
            500                 505                 510

Ile Gly Asp Asp Asp Asp Asp Lys Thr Asp Val Lys
        515                 520

<210> SEQ ID NO 29
<211> LENGTH: 1869
<212> TYPE: DNA
<213> ORGANISM: Ricinus communis
<220> FEATURE:
<221> NAME/KEY: misc_feature
<222> LOCATION: (0)...(0)
<223> OTHER INFORMATION: Ricinus communis TEL --Genomic

<400> SEQUENCE: 29
atggcagaaa ccggtattgc ccggtttcaa ggcagtttag acccaagagc ccaagaattc      60
agaccaagaa acaacagcct tcaccttaat acgccaacct taatccacca tcatcatcag     120
cagcagcagc agcagcagca gcagttacac atctttacgc ccccgccacc acctccacct     180
ccaccaccag cacagcaact ttattacccg tacgctcctc ctccttcgct cgggtttcct     240
caataccaac ttgcaccacc acaaccacaa gcgtacatta gcacaacagt accctcactg     300
ccaccacagt ccgcagcccc aacgcgaacg ctggttttaa gttcagtgcc aacggaagtg     360
agcgagtctg taattagacg agaattagaa gtgtttgggg aagtaagagg tgtacaaatg     420
gaaaggattt ctgatggaat cgtgaccgtt catttttatg atcttagaca tgcagagatt     480
gccttagtgg aaattagaga gaaacatatg cagcagcaat ccagacttcg aaacctttt     540 gctgctttag accaaaataa cttccttgca ccaccatctt tacctccatc accagcggca     600
gcggcggcgg cgcgtgggtt cattgctggg tgtgctgttt gggctcagtt cgtaatacca     660
tcttgtaacg ctgttcctga tggtcataac catgggacta tgttgttttt caatttagac     720
ccaaatgttt ctacttcttc tctcaaagaa atattccaag cttttggtgc tgttaaagaa     780
ttgagagaga caccattaaa gaagcaacaa aggtttgtgg agtttttatga tataagagat     840 gcagctaaag ctcttaaaga aatgaatggt aaagaaattc acgggaagca agttgtcatt     900
gagtttagtc gtccaggtgg ttttggtagg aagttcttca atggcagtag tacttctaag     960
gcctcgtctt tccacaacgc aatcaatatt aatccaaaaa tttcaagata tgcaccccca    1020
ccgcctccgc cgccgccacc agtgcgtcct aatatttctc cgcgcccatt tcttgcacaa    1080
```

-continued

```
actcactctt cctccgtcaa aagatcctcg aattccatca aaggaaaccc taacgagaat   1140
agtaatagca acaagggttc aattggatgt tgccgatga gtgatggaaa atatttccta    1200
actatttggg attcttttgc tttggccctt ttttttttt atattcatcg cagtcagaag    1260
ttactattga acatgctaga caaccactgc attcactgca atgagcagat tattgccgag   1320
ggcggcggcg gcgatgacca gccattgtct tcttatgatt tcgtctatct tcccattgat   1380
ttcaataaca agtgcaatgt gggatatggg ttcgtcaaca tgacatcctc acaggcaaca   1440
ttgaggctct ataaggcatt tcatcatcaa cattgggaag tctttaattc caggaaaatc   1500
tgtgaagtta cttatgcaag agttcaggga ttggaagcat taagagagca cttcaagaac   1560
tccaagtttc catgcgagat ggaccactat ttgccagtag tgttttctcc tccacgagat   1620
ggaaagcaac tacctgagcc actacccatc gttggccatg ccagaagca  accacagtca    1680 ctaatcattc ttggtctcca catgaaacgc accaacagta gtggtgagac tgacgaagaa   1740
gatcgagaag aagtagaaga tcaagaagaa gaagaaaatc tgaatcagag cagcagcaat   1800
aacagcagcc aaaacggctg cgatatcggt tatgatgaca agacagtag tagtggcagc    1860 ctggcctaa                                                            1869
```

<210> SEQ ID NO 30
<211> LENGTH: 622
<212> TYPE: PRT
<213> ORGANISM: Ricinus communis
<220> FEATURE:
<223> OTHER INFORMATION: Ricinus communis TEL

<400> SEQUENCE: 30

Met Ala Glu Thr Gly Ile Ala Arg Phe Gln Gly Ser Leu Asp Pro Arg
1 5 10 15

Ala Gln Glu Phe Arg Pro Arg Asn Asn Ser Leu His Leu Asn Thr Pro
20 25 30

Thr Leu Ile His His His His Gln Gln Gln Gln Gln Gln Gln Gln
35 40 45

Leu His Ile Phe Thr Pro Pro Pro Pro Pro Pro Pro Pro Pro Pro Ala
50 55 60

Gln Gln Leu Tyr Tyr Pro Tyr Ala Pro Pro Pro Ser Leu Gly Phe Pro
65 70 75 80

Gln Tyr Gln Leu Ala Pro Pro Gln Pro Gln Ala Tyr Ile Ser Thr Thr
85 90 95

Val Pro Ser Leu Pro Pro Gln Ser Ala Ala Pro Thr Arg Thr Leu Val
100 105 110

Leu Ser Ser Val Pro Thr Glu Val Ser Glu Ser Val Ile Arg Arg Glu
115 120 125

Leu Glu Val Phe Gly Glu Val Arg Gly Val Gln Met Glu Arg Ile Ser
130 135 140

Asp Gly Ile Val Thr Val His Phe Tyr Asp Leu Arg His Ala Glu Ile
145 150 155 160

Ala Leu Val Glu Ile Arg Glu Lys His Met Gln Gln Gln Ser Arg Leu
165 170 175

Arg Asn Leu Phe Ala Ala Leu Asp Gln Asn Asn Phe Leu Ala Pro Pro
180 185 190

Ser Leu Pro Pro Ser Pro Ala Ala Ala Ala Ala Ala Arg Gly Phe Ile
195 200 205

Ala Gly Cys Ala Val Trp Ala Gln Phe Val Ile Pro Ser Cys Asn Ala
210 215 220

```
Val Pro Asp Gly His Asn His Gly Thr Ile Val Phe Asn Leu Asp
225                 230                 235                 240

Pro Asn Val Ser Thr Ser Ser Leu Lys Glu Ile Phe Gln Ala Phe Gly
            245                 250                 255

Ala Val Lys Glu Leu Arg Glu Thr Pro Leu Lys Lys Gln Gln Arg Phe
                260                 265                 270

Val Glu Phe Tyr Asp Ile Arg Asp Ala Ala Lys Ala Leu Lys Glu Met
            275                 280                 285

Asn Gly Lys Glu Ile His Gly Lys Gln Val Val Ile Glu Phe Ser Arg
            290                 295                 300

Pro Gly Gly Phe Gly Arg Lys Phe Phe Asn Gly Ser Ser Thr Ser Lys
305                 310                 315                 320

Ala Ser Ser Phe His Asn Ala Ile Asn Ile Asn Pro Lys Ile Ser Arg
                325                 330                 335

Tyr Ala Pro Pro Pro Pro Pro Pro Pro Val Arg Pro Asn Ile
                340                 345                 350

Ser Pro Arg Pro Phe Leu Ala Gln Thr His Ser Ser Ser Val Lys Arg
        355                 360                 365

Ser Ser Asn Ser Ile Lys Gly Asn Pro Asn Glu Asn Ser Asn Ser Asn
370                 375                 380

Lys Gly Ser Ile Gly Cys Leu Pro Met Ser Asp Gly Lys Tyr Phe Leu
385                 390                 395                 400

Thr Ile Trp Asp Ser Phe Ala Leu Ala Leu Phe Phe Phe Tyr Ile His
                405                 410                 415

Arg Ser Gln Lys Leu Leu Leu Asn Met Leu Asp Asn His Cys Ile His
                420                 425                 430

Cys Asn Glu Gln Ile Ile Ala Glu Gly Gly Gly Gly Asp Asp Gln Pro
            435                 440                 445

Leu Ser Ser Tyr Asp Phe Val Tyr Leu Pro Ile Asp Phe Asn Asn Lys
450                 455                 460

Cys Asn Val Gly Tyr Gly Phe Val Asn Met Thr Ser Ser Gln Ala Thr
465                 470                 475                 480

Leu Arg Leu Tyr Lys Ala Phe His His Gln His Trp Glu Val Phe Asn
                485                 490                 495

Ser Arg Lys Ile Cys Glu Val Thr Tyr Ala Arg Val Gln Gly Leu Glu
            500                 505                 510

Ala Leu Arg Glu His Phe Lys Asn Ser Lys Phe Pro Cys Glu Met Asp
            515                 520                 525

His Tyr Leu Pro Val Val Phe Ser Pro Pro Arg Asp Gly Lys Gln Leu
            530                 535                 540

Pro Glu Pro Leu Pro Ile Val Gly His Gly Gln Lys Gln Pro Gln Ser
545                 550                 555                 560

Leu Ile Ile Leu Gly Leu His Met Lys Arg Thr Asn Ser Ser Gly Glu
                565                 570                 575

Thr Asp Glu Glu Asp Arg Glu Glu Val Glu Asp Gln Glu Glu Glu Glu
            580                 585                 590

Asn Leu Asn Gln Ser Ser Ser Asn Asn Ser Ser Gln Asn Gly Cys Asp
            595                 600                 605

Ile Gly Tyr Asp Asp Lys Asp Ser Ser Ser Gly Ser Leu Ala
            610                 615                 620

<210> SEQ ID NO 31
<211> LENGTH: 2761
```

<212> TYPE: DNA
<213> ORGANISM: Populus tremula x Populus alba
<220> FEATURE:
<221> NAME/KEY: misc_feature
<222> LOCATION: (0)...(0)
<223> OTHER INFORMATION: Populus tremula x Populus alba terminal ear1-like 1 protein (TEL1) gene

<400> SEQUENCE: 31

```
aaaccattct tccccgttct tttctttgtt ctcaccggtt taaaaaccac catggaagaa      60
accggttgtg tcccgtttcc gggaaaccta gaccctagag ctcaagagtt ccgacctcga     120
cataataatc ttcaagattt cactacaaaa tttcctcctt ttgggccgcc gcctccgccg     180
ccgccaccac aacttcctca gctcctgcac caagtctact acccctacac ccctcaagcg     240
gtgccgtttt gcgactttgt aggtttcacc cagtatcatc aacatgtgcc tccgatgtac     300
gataccgtga gtactcctct ccctcttcct cctactggcg cgcctactcg gactctggta     360
ctgagttcag tgccgggcga cgtgagtgag acattgatta ggagagaatt ggaggttttt     420
ggagaagtta gaggggtcca gatggaaaga gtaggtgatg ggatcgtgac cgttcatttc     480
tacgatctaa gacatgcaga gagagccttg aaggagatac gagagcagca catgctgcat     540
caagccaggc taaggaatct ctttattcaa aattgtgaga gcttgagctt gaatattgca     600
ccaccccccac cggcgcgtgg tttgattgcg ggttgtgtgg tttgggctca gtttattatc     660
ccgtcttgta aagcggtgcc cgacgggcaa atcaaggga cccttgtggt cttcaatttg      720
gaccccaatg tttctactaa atgtctcaaa gaaactttcc aagcttttgg taaattattt     780
gtcttgttct ggggttttttt tgaggttttg gtcttgttgg ttcaagtcag attgctcgaa     840
actttcgtgg actatttttct tcctgctaac tgttttttgt ttttgacatt ttctcattgg     900
gcaggtgctg ttaaggaatt gagagagact cctttgaaga ggcaccaaag gtttgtggag     960
ttttatgatg taagagatgc agccaaggca ctcggagaga tgaatggaaa ggaaatttac    1020
ggaaagcaag ttgatattga attcagtcgt cctggtgggt atggaaagaa gtttttcaat    1080
gccaacacca ccacttccaa gacctccttc tctgctcctg ccatcaactc cacaacaagc    1140
cttaaccgtt ccagaatttc aacttacgcc tctccaccat caccgccatt gcttcgtaga    1200
ttctcctccg gctgctcgtc tccgaatatc tccccccgct catttctgtc tgaaactcac    1260
tcctcagctg gaaagaaacc gtctggtaat cctggcaagg gaaaccctaa tgaggcttca    1320
aatgaagctg cttcatcggg gtgcttgtca ttgggtggtg gtgcagttgg agatggaatt    1380
gttgagaagg ttactgatca cgggcctccc aagaaaagct cgaaaagag ccagaacagc     1440
cagtccttca cagctacaaa gcatcaacag aagagtgcga agtcatggaa gggaacaagg    1500
caagcgaaga agttcgatac tcgttttctc ataagtggtg atgagtccat ggtggaaacc    1560
agtggtagtg attccagaac cactgtcatg atcaagaaca tacccaacaa gtataggttg    1620
gttttcttt ctgctaccat cattattatt ccttaaatag aactaatcac taaactaata    1680
ctgccgcgct cctttttta acactctaca tatatgagac tagagagatg ttttactaaa    1740
atctctgtta atttagaagc gtatatatgt tgaggtgatt cattaatgtt tattaatgaa    1800
taattgcagt cagaagctgt tgttgaatat gttggacaat cactgcattc actgcaacga    1860
gcagattgcc gatggggatg atgaccagcc cttgtcttct tatgacttt tataccttcc      1920
cattgatttc aagtgattcc ctctttcttc tttatccttc attattttcc tttctttctt    1980
tcgtttctgt gaggttaggt ttcttggca tataagtaga aacaaatatt cagacaattg      2040
aatttccatg tagtagttaa taaataagta cagagctgca cttgctgaat ttttcatgat    2100
```

```
ttgaaaatta aacagtaaca aatgcaatgt ggggtatggg ttcgtgaaca tgacgtcccc    2160
acaggcagca tggaggctct acaaggcctt ccataatcaa cactgggagg tcttcaactc    2220
tcgaaaaatc tgtgcagtca cttacgctag agttcaggta ttcccctat tttctctttc    2280 aacatcccca agcgtgagca atactgaagt ttgtattatt ttgttctggt tttaaagaaa    2340
atatttactc gtgcaaatga tgaagggatt ggaagcgttg aaggagcact ttaagaactc    2400
aaagttcccg tgcgagatgg accactatct tccagttgtt ttttctccgc ctcgagacgg    2460
gaggcaacag acggagcctc tccccattat tggcctcaag cagctccaac agcccatcaa    2520
tctaggtcac cgccccacc atgagattga agatggtgta gatgatagca gcctcaagat    2580
ttgcaacaaa ctatgtggcg acactgacca agaaggagag aaccagctcg agtgctgtag    2640
cagcatcagc agcagccaaa acggcggcga tgttggtgat gatgacaaag acagtagtgg    2700
cggcagcagc tagacgatag gagtatcata tagataatca tatatttact gcaaaaacca    2760
a                                                                   2761
```

<210> SEQ ID NO 32
<211> LENGTH: 534
<212> TYPE: PRT
<213> ORGANISM: Populus tremula x Populus alba
<220> FEATURE:
<223> OTHER INFORMATION: Populus tremula x Populus alba terminal ear1-
      like 1 protein (TEL1)

<400> SEQUENCE: 32

```
Met Glu Glu Thr Gly Cys Val Pro Phe Pro Gly Asn Leu Asp Pro Arg
 1               5                  10                  15

Ala Gln Glu Phe Arg Pro Arg His Asn Asn Leu Gln Asp Phe Thr Thr
            20                  25                  30

Lys Phe Pro Pro Phe Gly Pro Pro Pro Pro Pro Pro Gln Leu
        35                  40                  45

Pro Gln Leu Leu His Gln Val Tyr Tyr Pro Tyr Thr Pro Gln Ala Val
    50                  55                  60

Pro Phe Cys Asp Phe Val Gly Phe Thr Gln Tyr His Gln His Val Pro
65                  70                  75                  80

Pro Met Tyr Asp Thr Val Ser Thr Pro Leu Pro Leu Pro Pro Thr Gly
                85                  90                  95

Ala Pro Thr Arg Thr Leu Val Leu Ser Ser Val Pro Gly Asp Val Ser
            100                 105                 110

Glu Thr Leu Ile Arg Arg Glu Leu Glu Val Phe Gly Glu Val Arg Gly
        115                 120                 125

Val Gln Met Glu Arg Val Gly Asp Gly Ile Val Thr Val His Phe Tyr
    130                 135                 140

Asp Leu Arg His Ala Glu Arg Ala Leu Lys Glu Ile Arg Glu Gln His
145                 150                 155                 160

Met Leu His Gln Ala Arg Leu Arg Asn Leu Phe Ile Gln Asn Cys Glu
                165                 170                 175

Ser Leu Ser Leu Asn Ile Ala Pro Pro Pro Ala Arg Gly Leu Ile
            180                 185                 190

Ala Gly Cys Val Val Trp Ala Gln Phe Ile Ile Pro Ser Cys Lys Ala
        195                 200                 205

Val Pro Asp Gly Gln Asn Gln Gly Thr Leu Val Val Phe Asn Leu Asp
    210                 215                 220

Pro Asn Val Ser Thr Lys Cys Leu Lys Glu Thr Phe Gln Ala Phe Gly
```

```
                225                 230                 235                 240
Lys Leu Phe Val Leu Phe Trp Gly Phe Phe Glu Val Leu Val Leu Leu
                    245                 250                 255
Val Gln Val Arg Leu Leu Glu Thr Phe Val Asp Tyr Phe Leu Pro Ala
                260                 265                 270
Asn Cys Phe Leu Phe Leu Thr Phe Ser His Trp Ala Gly Ala Val Lys
            275                 280                 285
Glu Leu Arg Glu Thr Pro Leu Lys Arg His Gln Arg Phe Val Glu Phe
        290                 295                 300
Tyr Asp Val Arg Asp Ala Ala Lys Ala Leu Gly Glu Met Asn Gly Lys
305                 310                 315                 320
Glu Ile Tyr Gly Lys Gln Val Asp Ile Glu Phe Ser Arg Pro Gly Gly
                325                 330                 335
Tyr Gly Lys Lys Phe Phe Asn Ala Asn Thr Thr Thr Ser Lys Thr Ser
                340                 345                 350
Phe Ser Ala Pro Ala Ile Asn Ser Thr Thr Ser Leu Asn Arg Ser Arg
            355                 360                 365
Ile Ser Thr Tyr Ala Ser Pro Pro Ser Pro Pro Leu Leu Arg Arg Phe
        370                 375                 380
Ser Ser Gly Cys Ser Ser Pro Asn Ile Ser Pro Arg Ser Phe Leu Ser
385                 390                 395                 400
Glu Thr His Ser Ser Ala Gly Lys Lys Pro Ser Gly Asn Pro Gly Lys
                405                 410                 415
Gly Asn Pro Asn Glu Ala Ser Asn Glu Ala Ala Ser Ser Gly Cys Leu
            420                 425                 430
Ser Leu Gly Gly Gly Ala Val Gly Asp Gly Ile Val Glu Lys Val Thr
        435                 440                 445
Asp His Gly Pro Pro Lys Lys Ser Ser Lys Ser Gln Asn Ser Gln
        450                 455                 460
Ser Phe Thr Ala Thr Lys His Gln Gln Lys Ser Ala Lys Ser Trp Lys
465                 470                 475                 480
Gly Thr Arg Gln Ala Lys Lys Phe Asp Thr Arg Phe Leu Ile Ser Gly
                485                 490                 495
Asp Glu Ser Met Val Glu Thr Ser Gly Ser Asp Ser Arg Thr Thr Val
            500                 505                 510
Met Ile Lys Asn Ile Pro Asn Lys Tyr Arg Leu Val Phe Phe Ser Ala
        515                 520                 525
Thr Ile Ile Ile Ile Pro
    530
```

<210> SEQ ID NO 33
<211> LENGTH: 2816
<212> TYPE: DNA
<213> ORGANISM: Populus tremula x Populus alba
<220> FEATURE:
<221> NAME/KEY: misc_feature
<222> LOCATION: (0)...(0)
<223> OTHER INFORMATION: Populus tremula x Populus alba terminal ear1-
      like 2 protein (TEL2) gene

<400> SEQUENCE: 33

```
gaaacagtc tttcccgttg ttttccttaa gctaaccgct cttaaatcat cggaaaatca      60
ccatggaaga aaacggttct gttcagtttc cgggaaacct agacccaaga gcacaagagt    120
tcaggcctag acgtgataac cttcacaatt tctccccaaa gtttcttcct ttcggcccgc    180
cgactccgcc gctgccgcca ccaccaccac caccaagtca gcttccgcac caagtctact    240
```

```
accccctacac cccccaagtg ttgccgttta gcgactttgt aggtttcgct cagtatgatc      300
atcatatacc tccggcgtac gttagggtgg aaccttctcc ccctcttcct cctactgggg      360
cgccaactcg dacactggta ctgagttcgg tgccgagcga agtgaacgag tcattgatta      420
agagagaatt ggaggttttt ggagaggtta gaggggtcca gatggaaaga gttggttatg      480
ggactgtgac cgttcatttc tacgatctaa gacatgcaga gagagccttg agggagatac      540
gagagcagca catgctgcat caagccaggc taaggaactt ctttattcaa aattctgaga      600
gcattagctt caatattgca ccaacaccac caccgccggc gcgtggtgta attgctggtt      660
gtgtggtttg ggctcagttt attattccgt cgtgtaacga ggtgcctgat ggacagaatc      720
aagggaccct tgtggtcttc aatttggacc ccaatgtttc taccagaagc cttaaagaaa      780
ttttccaagc ttttggtaaa ttatttgtct tcctcggttt ccaaaataaa acagagattt      840
ttcctctcct ctggtcatgt ttcaagtcag tatgttaaat gtgatgggtc actttcctgg      900
attattttt atagctagca agctgatttt ttttggttaa tttcccgttt ggcaggtgct      960
gtcaaggagg tgagagagac acctttgaag aggcaccaaa ggtttgtaga gttttacgat      1020
gttagagatg cagccaaggc ccttagagag atgaatggaa aggaaattta tggaaagcaa      1080
gttgatattg aatttagtcg ccctggtggg catgggaaga ggttttttaa tgccaggccc      1140
aggaccactt ccaaaaactc ctttactact cctgtctttg actccacaac aaaccttcgc      1200
cattccaaag ttgcagcctt tgtgtctccg caacctccac cattgcttca tagattctcc      1260
tccggctgct cgcctccaaa tgtttcccct cgctcatttc tgtcggaaac tcaatcctca      1320
gctggaaaga aaccgtctgg tgatcctagc gagggaaacc ctattgaggc ttcaattgaa      1380
gcttctttgg ggtgtttgtc aatgggtgga gacgtaattg taggtaaggt tgcttatcgt      1440
ggccctccaa agagaagttt aaaaaagagc cagtctttta catctacaaa gcagcagcag      1500
aagagtgcta agtcttggaa gggatcaagg caagcgaaga agcttgatag tcgttttctt      1560
ataagtgatg aatccatggt ggaaactagc ggtagtgatt ccaggaccac tgtcatgatc      1620
aagaacatac ccaataagta caggttagct ttcttttcta ctacactatt caaataatca      1680
ataaactaat aatgttgaag ctcgttttca ttactatata ttttgagact ttgagagatt      1740
tctttactaa gatcttttaa ttaggagtat ttatatagag agaggtgatt catgaatttt      1800
ttattaatga attattgcag tcagaagctg ttgttgaata tgctggacaa tcactgcatt      1860
cactgcaacg agcagattgc caacggggat gaccagccct tgtcttctta tgattttta      1920
tatcttccaa ttgacttcaa gtgattccct tttacgttaa ccttcattta tttccttct      1980
ttcaattctt caattgtgcg aggctagggt tctttggcat tcaagtaaaa gcaaatgctc      2040
acgacaattg agtttcatat actcaggtac tggtgttgta ccattgctga atattttgt      2100
ttgtgaaaac agcaacaaat gcaatgtggg atatgggttc gtgaacatga catccccgca      2160
ggcagcatga aggctctaca aggcctttca taatcaacat tgggaggtct tcagctctag      2220
gaaaatctgt gcagtgactt atgctagagt tcaggtattt cctatttct ctttcaaaat      2280
ctctaagctt gagcaatatt ggagtgtgtt ttgctttgtc ctaattgtat tatattatgg      2340
ttccaaaaaa aataaaattc gtacaaatga tgaaagggat tggaagcgtt gaaggagcac      2400
tttaagaact caaagttccc atgcgagatg gaccaccatc tgccagttgt tttctctcct      2460
cctcgagacg ggaggcaaca gacggagcct cttcccatta ttggccacaa gcacaaccaa      2520
cagcccatca atattattct tggtgactcc atcgcatgca cccaccatga gatagacggt      2580
```

-continued

```
gtgaatgaaa gcctcaagac ctccaacaaa ttatttggtg acgctgacca agaaggagaa    2640
aaccagctca agtgcagcag cagcagcagc caaaatggcg gcgatactgg ggatgatgat    2700
aaagacagta gtagtggcag cagctagcac ggtggctttc taattaaagt tgagagggag    2760
ctccgcgatt gattctcttt ggataactga gaagatttga gtatcataca tccacc       2816
```

<210> SEQ ID NO 34
<211> LENGTH: 677
<212> TYPE: PRT
<213> ORGANISM: Populus tremula x Populus alba
<220> FEATURE:
<223> OTHER INFORMATION: Populus tremula x Populus alba terminal ear1-like 2 protein (TEL2)

<400> SEQUENCE: 34

```
Met Glu Glu Asn Gly Ser Val Gln Phe Pro Gly Asn Leu Asp Pro Arg
 1               5                  10                  15

Ala Gln Glu Phe Arg Pro Arg Asp Asn Leu His Asn Phe Ser Pro
            20                  25                  30

Lys Phe Leu Pro Phe Gly Pro Thr Pro Leu Pro Pro Pro
        35                  40                  45

Pro Pro Pro Ser Gln Leu Pro His Gln Val Tyr Tyr Pro Tyr Thr Pro
 50                  55                  60

Gln Val Leu Pro Phe Ser Asp Phe Val Gly Phe Ala Gln Tyr Asp His
 65                  70                  75                  80

His Ile Pro Pro Ala Tyr Val Arg Val Glu Pro Ser Pro Pro Leu Pro
                85                  90                  95

Pro Thr Gly Ala Pro Thr Arg Thr Leu Val Leu Ser Ser Val Pro Ser
            100                 105                 110

Glu Val Asn Glu Ser Leu Ile Lys Arg Glu Leu Glu Val Phe Gly Glu
        115                 120                 125

Val Arg Gly Val Gln Met Glu Arg Val Gly Tyr Gly Thr Val Thr Val
130                 135                 140

His Phe Tyr Asp Leu Arg His Ala Glu Arg Ala Leu Arg Glu Ile Arg
145                 150                 155                 160

Glu Gln His Met Leu His Gln Ala Arg Leu Arg Asn Phe Phe Ile Gln
                165                 170                 175

Asn Ser Glu Ser Ile Ser Phe Asn Ile Ala Pro Thr Pro Pro Pro Pro
            180                 185                 190

Ala Arg Gly Val Ile Ala Gly Cys Val Val Trp Ala Gln Phe Ile Ile
        195                 200                 205

Pro Ser Cys Asn Glu Val Pro Asp Gly Gln Asn Gln Gly Thr Leu Val
210                 215                 220

Val Phe Asn Leu Asp Pro Asn Val Ser Thr Arg Ser Leu Lys Glu Ile
225                 230                 235                 240

Phe Gln Ala Phe Gly Ala Val Lys Glu Val Arg Glu Thr Pro Leu Lys
                245                 250                 255

Arg His Gln Arg Phe Val Glu Phe Tyr Asp Val Arg Asp Ala Ala Lys
            260                 265                 270

Ala Leu Arg Glu Met Asn Gly Lys Glu Ile Tyr Gly Lys Gln Val Asp
        275                 280                 285

Ile Glu Phe Ser Arg Pro Gly Gly His Gly Lys Arg Phe Phe Asn Ala
290                 295                 300

Arg Pro Arg Thr Thr Ser Lys Asn Ser Phe Thr Thr Pro Val Phe Asp
305                 310                 315                 320
```

Ser Thr Thr Asn Leu Arg His Ser Lys Val Ala Ala Phe Val Ser Pro
            325                 330                 335

Gln Pro Pro Leu Leu His Arg Phe Ser Ser Gly Cys Ser Pro Pro
    340                 345                 350

Asn Val Ser Pro Arg Ser Phe Leu Ser Glu Thr Gln Ser Ser Ala Gly
            355                 360                 365

Lys Lys Pro Ser Gly Asp Pro Ser Glu Gly Asn Pro Ile Glu Ala Ser
370                 375                 380

Ile Glu Ala Ser Leu Gly Cys Leu Ser Met Gly Gly Asp Val Ile Val
385                 390                 395                 400

Gly Lys Val Ala Tyr Arg Gly Pro Pro Lys Arg Ser Leu Lys Ser
                405                 410                 415

Gln Ser Phe Thr Ser Thr Lys Gln Gln Gln Lys Ser Ala Lys Ser Trp
            420                 425                 430

Lys Gly Ser Arg Gln Ala Lys Lys Leu Asp Ser Arg Phe Leu Ile Ser
            435                 440                 445

Asp Glu Ser Met Val Glu Thr Ser Gly Ser Asp Ser Arg Thr Thr Val
    450                 455                 460

Met Ile Lys Asn Ile Pro Asn Lys Tyr Ser Gln Lys Leu Leu Leu Asn
465                 470                 475                 480

Met Leu Asp Asn His Cys Ile His Cys Asn Glu Gln Ile Ala Asn Gly
                485                 490                 495

Asp Asp Gln Pro Leu Ser Ser Tyr Asp Phe Leu Tyr Leu Pro Ile Asp
            500                 505                 510

Phe Asn Asn Lys Cys Asn Val Gly Tyr Gly Phe Val Asn Met Thr Ser
            515                 520                 525

Pro Gln Ala Ala Trp Arg Leu Tyr Lys Ala Phe His Asn Gln His Trp
    530                 535                 540

Glu Val Phe Ser Ser Arg Lys Ile Cys Ala Val Thr Tyr Ala Arg Val
545                 550                 555                 560

Gln Gly Leu Glu Ala Leu Lys Glu His Phe Lys Asn Ser Lys Phe Pro
                565                 570                 575

Cys Glu Met Asp His His Leu Pro Val Val Phe Ser Pro Pro Arg Asp
            580                 585                 590

Gly Arg Gln Gln Thr Glu Pro Leu Pro Ile Ile Gly His Lys His Asn
            595                 600                 605

Gln Gln Pro Ile Asn Ile Ile Leu Gly Asp Ser Ile Ala Cys Thr His
    610                 615                 620

His Glu Ile Asp Gly Val Asn Glu Ser Leu Lys Thr Ser Asn Lys Leu
625                 630                 635                 640

Phe Gly Asp Ala Asp Gln Glu Gly Glu Asn Gln Leu Lys Cys Ser Ser
                645                 650                 655

Ser Ser Ser Gln Asn Gly Gly Asp Thr Gly Asp Asp Lys Asp Ser
            660                 665                 670

Ser Ser Gly Ser Ser
            675

<210> SEQ ID NO 35
<211> LENGTH: 1590
<212> TYPE: DNA
<213> ORGANISM: Selaginella moellendorffii
<220> FEATURE:
<221> NAME/KEY: misc_feature
<222> LOCATION: (0)...(0)
<223> OTHER INFORMATION: Selaginella moellendorffii TEL

<400> SEQUENCE: 35

```
atgcatggcg ctccatcgcg agcattgctc gtctctggga tcccgcagca catcgtcgac    60
cctctggtga tgcaagatct ggaatcttgg ggtcccattc gatctttctt cctcggcgct   120
cgagcgcaag gctgtattac ggtctactac tacgatcttc gccacgcgca ggacgcgctt   180
ctctccatcc ggtcgcagta cttcttccag cacgatctca gctacagcga gggccgcgga   240
ttgatcggcg gatgcccagc atgggcggag ttcgtcacta tctctccctc gtatcccttg   300
atcgattcgc ccaaccaggg gaccttggtc gtgttctatc tccggatgaa cattactcac   360
gccgaactcg caagtatctt caagcaatac ggtgacgtga gagaaatccg cgaagccccc   420
agcaggagga gcagattcgt ggagttttac gacatacggg acgctgcccg ggccaaggaa   480
gctctggacg ggctcgaggt attgggacgg cggattaaga tcgaatttag caggccgtgt   540
caaccaagga acgcctacaa caccaccccg gccttatatc cttccttcgt cccgtactac   600
cccgtacctc gtggatatgg tcgggctgga ccagcggcgg cctcagtcac caccaggcgg   660
cgctttgaga tcagcgctta caatcagcag cagccagcgt cgctcagaac ccgggacgag   720
agcgctgcca gtgccagtgg caaccttggc gatggcagag gctgcattgt cagcttttct   780
tcggagcgta tctacgaaga atccaagtgg actggtagga agcacagggt ggtgagaagg   840
atcgcaaggg acgagtctca gtacgttttc aacacggggg aggaagagga aagcggacgt   900
accacgctga tgatcaggaa cattcccaat aaatacagcc ttcgcatagt gattcgggtg   960
ctggaccagc actgtatcac ctacaacaat ggcctgggag aggacgaaaa ggtttctgct  1020
tacgactttg tttatctccc agtggatttc atgaacagat ccaaccttgg atacgccttc  1080
gttaatttca ccacggtggt ggcaaccaaa aggctgcaca acgacttcca cggccgacgc  1140
tgggaggaat tcaagtcccg gaaagtctgt caggttgctt atgcccggct ccaggcgaaa  1200
caactagagg agcacttcaa gaactcccga tttgcctgtg acaccgacga gtacttgccg  1260
ctggtgttta gtcctccaag gacgggcttg cagtgttctt cgccaacggt ggtgtcctcc  1320
ttggccgcga gaaaggccgg gggcaagcgt ctggagatta agtcactcga gaatttgccg  1380
acaccagatc catcgcagga ggcgaccgaa gcgccacaga caagcattga tctcgagtcg  1440
ggatccgagc agccgtggga gggcgatcag attgacgacg acgacgacga gaactttgag  1500
tctgaggatc tggaagaaga gctggacgaa gacgatgacg atggtggatc ctcgcaggat  1560
aatgacgaag atggagaagg caaccagtga                                    1590
```

<210> SEQ ID NO 36
<211> LENGTH: 530
<212> TYPE: PRT
<213> ORGANISM: Selaginella moellendorffii
<220> FEATURE:
<223> OTHER INFORMATION: Selaginella moellendorffii TEL

<400> SEQUENCE: 36

Met His Gly Ala Pro Ser Arg Ala Leu Leu Val Ser Gly Ile Pro Gln
 1               5                  10                  15

His Ile Val Asp Pro Leu Val Met Gln Asp Leu Glu Ser Trp Gly Pro
            20                  25                  30

Ile Arg Ser Phe Phe Leu Gly Ala Arg Ala Gln Gly Cys Ile Thr Val
        35                  40                  45

Tyr Tyr Tyr Asp Leu Arg His Ala Gln Asp Ala Leu Leu Ser Ile Arg
    50                  55                  60

Ser Gln Tyr Phe Phe Gln His Asp Leu Ser Tyr Ser Glu Gly Arg Gly

```
                65                  70                  75                  80
Leu Ile Gly Gly Tyr Pro Ala Trp Ala Glu Phe Val Thr Ile Ser Pro
                    85                  90                  95

Ser Tyr Pro Leu Ile Asp Ser Pro Asn Gln Gly Thr Leu Val Val Phe
            100                 105                 110

Tyr Leu Arg Met Asn Ile Thr His Ala Glu Leu Ala Ser Ile Phe Lys
            115                 120                 125

Gln Tyr Gly Asp Val Arg Glu Ile Arg Glu Ala Pro Ser Arg Arg Ser
    130                 135                 140

Arg Phe Val Glu Phe Tyr Asp Ile Arg Asp Ala Ala Arg Ala Lys Glu
145                 150                 155                 160

Ala Leu Asp Gly Val Glu Val Leu Gly Arg Arg Ile Lys Ile Glu Phe
                165                 170                 175

Ser Arg Pro Cys Gln Pro Arg Asn Ser Tyr Asn Thr Thr Pro Ala Leu
            180                 185                 190

Tyr Pro Ser Phe Val Pro Tyr Tyr Pro Val Pro Arg Gly Tyr Gly Arg
            195                 200                 205

Ala Gly Pro Ala Ala Ala Ser Val Thr Thr Arg Arg Arg Phe Glu Ile
    210                 215                 220

Ser Ala Tyr Asn Gln Gln Ala Ala Ser Val Arg Thr Arg Asp Glu
225                 230                 235                 240

Ser Ala Ala Ser Ala Ser Gly Asn Leu Gly Asp Gly Arg Gly Cys Ile
                245                 250                 255

Val Ser Phe Ser Ser Glu Arg Ile Tyr Glu Glu Ser Lys Trp Thr Gly
            260                 265                 270

Arg Lys His Arg Val Val Arg Arg Ile Ala Arg Asp Glu Ser Gln Tyr
    275                 280                 285

Val Phe Asn Thr Gly Glu Asp Glu Glu Ser Gly Arg Thr Thr Leu Met
            290                 295                 300

Ile Arg Asn Ile Pro Asn Lys Tyr Ser Leu Arg Ile Val Ile Arg Val
305                 310                 315                 320

Leu Asp Gln His Cys Ile Thr Tyr Asn Asn Gly Leu Gly Glu Asp Glu
                325                 330                 335

Lys Val Ser Ala Tyr Asp Phe Val Tyr Leu Pro Val Asp Phe Met Asn
            340                 345                 350

Arg Ser Asn Leu Gly Tyr Ala Phe Val Asn Phe Thr Thr Val Val Ala
            355                 360                 365

Thr Lys Arg Leu His Lys Asp Phe His Gly Arg Arg Trp Glu Glu Phe
    370                 375                 380

Lys Ser Arg Lys Val Cys Gln Val Ala Tyr Ala Arg Leu Gln Ala Lys
385                 390                 395                 400

Gln Leu Glu Glu His Phe Lys Asn Ser Arg Phe Ala Cys Asp Thr Asp
                405                 410                 415

Glu Tyr Leu Pro Leu Val Phe Ser Pro Pro Arg Thr Gly Leu Gln Cys
            420                 425                 430

Ser Ser Pro Thr Val Val Ser Ser Leu Ala Ala Arg Lys Ala Gly Gly
            435                 440                 445

Lys Arg Leu Glu Ile Lys Ser Leu Asp Asn Ala Leu Pro Thr Pro Asp
    450                 455                 460

Pro Ser Gln Glu Ala Thr Glu Ala Pro Gln Thr Ser Ile Asp Leu Glu
465                 470                 475                 480

Ser Gly Ser Glu Gln Pro Trp Glu Gly Asp Gln Ile Asp Asp Asp Asp
                485                 490                 495
```

Asp Glu Asn Phe Glu Ser Glu Asp Leu Glu Glu Leu Asp Glu Asp
            500                 505                 510

Asp Asp Asp Gly Gly Ser Ser Gln Asp Asn Asp Glu Asp Gly Glu Gly
        515                 520                 525

Asn Gln
    530

<210> SEQ ID NO 37
<211> LENGTH: 2027
<212> TYPE: DNA
<213> ORGANISM: Vitis vinifera
<220> FEATURE:
<221> NAME/KEY: misc_feature
<222> LOCATION: (0)...(0)
<223> OTHER INFORMATION: Vitis vinifera TEL2 cDNA

<400> SEQUENCE: 37

| | | | |
|---|---|---|---|
| atgaaagaag caggagaagt tgccaagttt cagaaaaact tggacccaca agcccaagag | 60 |
| ttccgaccaa gaaacccttc atccaataac cagattggta ccccttttca accccatatt | 120 |
| tgctatgcct atccttttc ctatgtatct actccggtca tgtcgcagcc tagtctcgcc | 180 |
| gccggaaccc cgctgcctcc ggcggctccg gggcccacca gggtggtgct actgagttgt | 240 |
| gtgccgaccg atgtgagtga agcggcggtg aggatggaga tggaggggtt tggagaggtg | 300 |
| ggggctgttg agatggagag gttgagagat ggaatcgtga tcgttcattt ctatgacttg | 360 |
| aggcatgcgg aggaagcggt gatggagatt caagagcagt acatgcagca gcagagcagg | 420 |
| ttgaggaggt tttatgaata cgacgccatg ttgtttggcc atctggggtt ggagaggcag | 480 |
| agcttagttg ttccggttgc ttttccagca cgtggactca tcgccggcag ggctgtctgg | 540 |
| gctcagttct cggcgccgga gtccaccacc cccactcctg atgggcataa tcaggggaca | 600 |
| cttgtcattt ccaacttgga ttctaagctc tctgaaagca agctcaagga atcgtccaa | 660 |
| aactttgggc atgtgaagga attcagagaa atgacaccca acagcagaa gtggtttgta | 720 |
| gagttctttg ataccagaga cgctgctaga gcttttcag agctggatgg aaaggaaatt | 780 |
| tatgacaaaa aacttataat taaattcagc tgctcaggtg gctatggcag aataaagtcc | 840 |
| agtactgcag ctgcgacggc caccaccagt tacaatgaca ttaactcaag aaaaattatt | 900 |
| cattcaagaa cagccctatg ctcgccacat gttactggag gtatattaca agttgtcgc | 960 |
| tcaagctcag ttgctccttc tgcttcagta cacctttctc aagccttact gcctacaaaa | 1020 |
| agacccacct tcaggacaga gaacagtagt aggaagggca ttggaaggtc aaattgtgga | 1080 |
| tcaatagctc caatttcctc attgtccttg ggtgaagatg ggagtgaatg taccaaatcc | 1140 |
| agtgggaaat tcttgagaaa agtgaattac agccatcaaa aggtacccac agtcaagcaa | 1200 |
| cccaggaaga gggggcaaaa gaacccggat tctcactttt tgatcaatgt tgatgctata | 1260 |
| gctgagtcca attcgagaga caccccggacc actgtgatga tcaagaacat acccaacaag | 1320 |
| tacagtcaga aactgctttt gaatatgcta gacaatcact gcatcctctc taatgagaag | 1380 |
| attacaggag atgatgagcc cttgtcttcc tacgacttcg tctatcttcc tattgatttc | 1440 |
| cataacaaat gcaatgtggg atatggattt gtgaatctta cgtctcccca agctgcatgg | 1500 |
| agactctata aggctttcca tttgcaacag tgggaggtct ttaactccag aaaaatttgt | 1560 |
| gaagtcactt atgctcgctt gcagggtttg gaagctctga agcagcactt caagaactca | 1620 |
| aaatttgcat gcatggtgga cgactacctt ccagtcatgt tttctccacc ccagacggc | 1680 |
| aagcaaatgt ccgagccagt gcctgtggtt ggctgctcca tctctggcat cagccatgga | 1740 |

```
agacatgagg agaaggttga tggggaaatg gttgaggaag ttaatggtga taatggtgat   1800
tgtagctcaa atcccagcag caaacatgat gatgaatagt gaagccaatt cccatctcag   1860
attgacctca attacatgct ctactgcact tacttggtca tacaataggt cattaatgtt   1920
gggcacaagt gccggcattg gatctctgag ctgttactct ctcaacaatc gaatgctttc   1980
ttggttatgg cttctaatcg tgtaagataa gatctcttta ttttgta                 2027
```

<210> SEQ ID NO 38
<211> LENGTH: 612
<212> TYPE: PRT
<213> ORGANISM: Vitis vinifera
<220> FEATURE:
<223> OTHER INFORMATION: Vitis vinifera TE2

<400> SEQUENCE: 38

```
Met Lys Glu Ala Gly Glu Val Ala Lys Phe Gln Lys Asn Leu Asp Pro
 1               5                  10                  15

Gln Ala Gln Glu Phe Arg Pro Arg Asn Pro Ser Ser Asn Asn Gln Ile
            20                  25                  30

Gly Thr Pro Phe Gln Pro His Ile Cys Tyr Ala Tyr Pro Phe Ser Tyr
        35                  40                  45

Val Ser Thr Pro Val Met Ser Gln Pro Ser Leu Ala Ala Gly Thr Pro
    50                  55                  60

Leu Pro Pro Ala Ala Pro Gly Pro Thr Arg Val Val Leu Leu Ser Cys
65                  70                  75                  80

Val Pro Thr Asp Val Ser Glu Ala Ala Val Arg Met Glu Met Glu Gly
                85                  90                  95

Phe Gly Glu Val Gly Ala Val Glu Met Glu Arg Leu Arg Asp Gly Ile
           100                 105                 110

Val Ile Val His Phe Tyr Asp Leu Arg His Ala Glu Glu Ala Val Met
       115                 120                 125

Glu Ile Gln Glu Gln Tyr Met Gln Gln Gln Ser Arg Leu Arg Arg Phe
   130                 135                 140

Tyr Glu Tyr Asp Ala Met Leu Phe Gly His Leu Gly Leu Glu Arg Gln
145                 150                 155                 160

Ser Leu Val Val Pro Val Ala Phe Pro Ala Arg Gly Leu Ile Ala Gly
                165                 170                 175

Arg Ala Val Trp Ala Gln Phe Ser Ala Pro Glu Ser Thr Thr Pro Thr
            180                 185                 190

Pro Asp Gly His Asn Gln Gly Thr Leu Val Ile Ser Asn Leu Asp Ser
        195                 200                 205

Lys Leu Ser Glu Ser Lys Leu Lys Glu Ile Val Gln Asn Phe Gly His
    210                 215                 220

Val Lys Glu Phe Arg Glu Met Thr Pro Lys Gln Gln Lys Trp Phe Val
225                 230                 235                 240

Glu Phe Phe Asp Thr Arg Asp Ala Ala Arg Ala Phe Ser Glu Leu Asp
                245                 250                 255

Gly Lys Glu Ile Tyr Asp Lys Lys Leu Ile Ile Lys Phe Ser Cys Ser
            260                 265                 270

Gly Gly Tyr Gly Arg Ile Lys Ser Ser Thr Ala Ala Thr Ala Thr
        275                 280                 285

Thr Ser Tyr Asn Asp Ile Asn Ser Arg Lys Ile Ile His Ser Arg Thr
    290                 295                 300

Ala Leu Cys Ser Pro His Val Thr Gly Gly Ile Leu Gln Ser Cys Arg
```

```
                305                 310                 315                 320
Ser Ser Ser Val Ala Pro Ser Ala Ser Val His Leu Ser Gln Ala Leu
                    325                 330                 335

Leu Pro Thr Lys Arg Pro Thr Phe Arg Thr Glu Asn Ser Ser Arg Lys
                340                 345                 350

Gly Ile Gly Arg Ser Asn Cys Gly Ser Ile Ala Pro Ile Ser Ser Leu
                355                 360                 365

Ser Leu Gly Glu Asp Gly Ser Glu Cys Thr Lys Ser Ser Gly Lys Phe
            370                 375                 380

Leu Arg Lys Val Asn Tyr Ser His Gln Lys Val Pro Thr Val Lys Gln
385                 390                 395                 400

Pro Arg Lys Arg Gly Gln Lys Asn Pro Asp Ser His Phe Leu Ile Asn
                405                 410                 415

Val Asp Ala Ile Ala Glu Ser Asn Ser Arg Asp Thr Arg Thr Thr Val
                420                 425                 430

Met Ile Lys Asn Ile Pro Asn Lys Tyr Ser Gln Lys Leu Leu Leu Asn
                435                 440                 445

Met Leu Asp Asn His Cys Ile Leu Ser Asn Glu Lys Ile Thr Gly Asp
            450                 455                 460

Asp Glu Pro Leu Ser Ser Tyr Asp Phe Val Tyr Leu Pro Ile Asp Phe
465                 470                 475                 480

His Asn Lys Cys Asn Val Gly Tyr Gly Phe Val Asn Leu Thr Ser Pro
                485                 490                 495

Gln Ala Ala Trp Arg Leu Tyr Lys Ala Phe His Leu Gln Gln Trp Glu
                500                 505                 510

Val Phe Asn Ser Arg Lys Ile Cys Glu Val Thr Tyr Ala Arg Leu Gln
                515                 520                 525

Gly Leu Glu Ala Leu Lys Gln His Phe Lys Asn Ser Lys Phe Ala Cys
            530                 535                 540

Met Val Asp Asp Tyr Leu Pro Val Met Phe Ser Pro Pro Arg Asp Gly
545                 550                 555                 560

Lys Gln Met Ser Glu Pro Val Pro Val Val Gly Cys Ser Ile Ser Gly
                565                 570                 575

Ile Ser His Gly Arg His Glu Glu Lys Val Asp Gly Glu Met Val Glu
                580                 585                 590

Glu Val Asn Gly Asp Asn Gly Asp Cys Ser Ser Asn Pro Ser Ser Lys
            595                 600                 605

His Asp Asp Glu
    610

<210> SEQ ID NO 39
<211> LENGTH: 1977
<212> TYPE: DNA
<213> ORGANISM: Vitis vinifera
<220> FEATURE:
<221> NAME/KEY: misc_feature
<222> LOCATION: (0)...(0)
<223> OTHER INFORMATION: Vitis vinifera protein terminal ear1-like 1
      protein gene

<400> SEQUENCE: 39
atgggagaga cggggaccct caggtttctg ggaaacttag acccaagtgc gcaggagttc      60
aggccgagga acccatatat ccagaaccag atgagcttgt ctgtaccaac ccaaatttac     120
tatccataca cacatccaca cccacaattt gtagcttcat cggcgtacgt gagacctatc     180
gccggaaagc cgcctctctc tccgctgatg tcgcctttgt cggcaacacc tactagggcg     240
```

```
ctactattga gttcggtgcc gacggacgtg agcgaggtga cagtgagaag agaattggag      300
gcctttggag aggtgaggtc agtgcagatc gagagagtgt gtgatggaat tgtggctgtt      360
agtttctatg atctaaggca tgcacaagcg tgtttgacgg aggtacgaga acaacacatg      420
caacaacaaa gtaggctgaa gaagcactac gattccttgt taacacgaaa attagcttct      480
caagtggagc atttgcttgt cccactacca ccgccggcac gtgggcttat tgcaggtcgt      540
gcagtttggg ctcaattcat gattccagtg agcacttgca tgctggacga ctataatcaa      600
ggaactcttg tgattttcaa tttggactca gaggtctcca ccagcagtct gagggacata      660
ttcgagacat ttgggtcaat aaaggaattg agagagacac cattaaagcg gcaccagagg      720
tttgtggagt tttttgatat cagagatgca gctagggctc ttagagaaat gaatggcaag      780
aaaattcaag ggaaacgtgt ggtaatagaa tttagtcggc caggtggtca tggctggagg      840
ttcttcaatg ccattagtac taccgcccta tcaagtactt actctaccac caattcaact      900
gtaatctccc cctcaagact agcttaccac acagtcactt cgagatgccc accagcattg      960
ccttgtaaac taccagagaa aagctcacat ttcaatgtgc ctcctcattc ttatctctct     1020
caaacacatc attccacaaa aaagtccaat gttggtataa acaaaaggag ttcaaatgct     1080
gggaacatta agcttcaat gacatcactt cgtttgactg gttcagttgt taatggaatt      1140
gaagattcta aaggagttca taggtggaat ccaaagaaga gcccaaacgg ttcctcaaca     1200
acagaacaac aacaacaaca agctcaaaga aatcggccgt ggaagggaag acagaagaac     1260
atcgattcct gttttctaat aaacgaggat gccaaaacgg aatcccatta cagagattcc     1320
agaacaactg tcatgatcaa gaacataccc aacaagtaca gtcagaagct cctaatgaac     1380
atgttggata tcactgcat tgactgcaat aagcaggttc ccgacggagg ggaccaacca      1440
ttgtcctcct atgatttcat atacctcccc atcgatttca caacaagtg caatgtggga      1500 tatgggttcg tgaacatgac gtcccctcag gcgacatgga ggctctacaa ggcctttcat     1560
cttcaatctt ggaaggtttt caactccacc aaaatctgtg aagttactta tgctcgaatc     1620
cagggtttgg aagcattgaa agagcacttc aagaactcaa agttcctgtg cgacacgaag     1680
acatacctac cagtggtgtt ttcaccgcct cgagatggga gacaactgac agagcctcaa     1740
cccattgttg gcaacaataa gctcatcatc ggtatcatca ccaatgacac taaagcttct     1800
gatgacaacg atgatggtga tgaatgggag atgatgatgg acggtcctca taggctgaat     1860
aatggtggtc acgtccgcga ttatgatgat gatgttgagg attacaatga ccacaatcaa     1920
agtccaaacg atgacgatag tggcgatgat gatgatagca ctagtgttag tgcctaa        1977
```

<210> SEQ ID NO 40
<211> LENGTH: 658
<212> TYPE: PRT
<213> ORGANISM: Vitis vinifera
<220> FEATURE:
<223> OTHER INFORMATION: Vitis vinifera TE1

<400> SEQUENCE: 40

Met Gly Glu Thr Gly Thr Ser Arg Phe Leu Gly Asn Leu Asp Pro Ser
1               5                   10                  15

Ala Gln Glu Phe Arg Pro Arg Asn Pro Tyr Ile Gln Asn Gln Met Ser
            20                  25                  30

Leu Ser Val Pro Thr Gln Ile Tyr Tyr Pro Tyr Thr His Pro His Pro
        35                  40                  45

Gln Phe Val Ala Ser Ser Ala Tyr Val Arg Pro Ile Ala Gly Lys Pro

```
            50                  55                  60
Pro Leu Ser Pro Leu Met Ser Pro Leu Ser Ala Thr Pro Thr Arg Ala
 65                  70                  75                  80

Leu Leu Leu Ser Ser Val Pro Thr Asp Val Ser Glu Val Thr Val Arg
                 85                  90                  95

Arg Glu Leu Glu Ala Phe Gly Glu Val Arg Ser Val Gln Ile Glu Arg
                100                 105                 110

Val Cys Asp Gly Ile Val Ala Val Ser Phe Tyr Asp Leu Arg His Ala
                115                 120                 125

Gln Ala Cys Leu Thr Glu Val Arg Glu Gln His Met Gln Gln Gln Ser
130                 135                 140

Arg Leu Lys Lys His Tyr Asp Ser Leu Leu Thr Arg Lys Leu Ala Ser
145                 150                 155                 160

Gln Val Glu His Leu Leu Val Pro Leu Pro Pro Ala Arg Gly Leu
                165                 170                 175

Ile Ala Gly Arg Ala Val Trp Ala Gln Phe Met Ile Pro Val Ser Thr
                180                 185                 190

Cys Met Leu Asp Asp Tyr Asn Gln Gly Thr Leu Val Ile Phe Asn Leu
                195                 200                 205

Asp Ser Glu Val Ser Thr Ser Ser Leu Arg Asp Ile Phe Glu Thr Phe
210                 215                 220

Gly Ser Ile Lys Glu Leu Arg Glu Thr Pro Leu Lys Arg His Gln Arg
225                 230                 235                 240

Phe Val Glu Phe Phe Asp Ile Arg Asp Ala Ala Arg Ala Leu Arg Glu
                245                 250                 255

Met Asn Gly Lys Lys Ile Gln Gly Lys Arg Val Val Ile Glu Phe Ser
                260                 265                 270

Arg Pro Gly Gly His Gly Trp Arg Phe Phe Asn Ala Ile Ser Thr Thr
                275                 280                 285

Ala Leu Ser Ser Thr Tyr Ser Thr Thr Asn Ser Thr Val Ile Ser Pro
290                 295                 300

Ser Arg Leu Ala Tyr His Thr Val Thr Ser Arg Cys Pro Pro Ala Leu
305                 310                 315                 320

Pro Cys Lys Leu Pro Glu Lys Ser Ser His Phe Asn Val Pro Pro His
                325                 330                 335

Ser Tyr Leu Ser Gln Thr His His Ser Thr Lys Lys Ser Asn Val Gly
                340                 345                 350

Ile Asn Lys Arg Ser Ser Asn Ala Gly Asn Ile Lys Ala Ser Met Thr
                355                 360                 365

Ser Leu Arg Leu Thr Gly Ser Val Val Asn Gly Ile Glu Asp Ser Lys
370                 375                 380

Gly Val His Arg Trp Asn Pro Lys Lys Ser Pro Asn Gly Ser Ser Thr
385                 390                 395                 400

Thr Glu Gln Gln Gln Gln Ala Gln Arg Asn Arg Pro Trp Lys Gly
                405                 410                 415

Arg Gln Lys Asn Ile Asp Ser Cys Phe Leu Ile Asn Glu Asp Ala Lys
                420                 425                 430

Thr Glu Ser His Tyr Arg Asp Ser Arg Thr Thr Val Met Ile Lys Asn
                435                 440                 445

Ile Pro Asn Lys Tyr Ser Gln Lys Leu Leu Met Asn Met Leu Asp Asn
                450                 455                 460

His Cys Ile Asp Cys Asn Lys Gln Val Pro Asp Gly Gly Asp Gln Pro
465                 470                 475                 480
```

Leu Ser Ser Tyr Asp Phe Ile Tyr Leu Pro Ile Asp Phe Asn Asn Lys
            485                 490                 495

Cys Asn Val Gly Tyr Gly Phe Val Asn Met Thr Ser Pro Gln Ala Thr
        500                 505                 510

Trp Arg Leu Tyr Lys Ala Phe His Leu Gln Ser Trp Lys Val Phe Asn
        515                 520                 525

Ser Thr Lys Ile Cys Glu Val Thr Tyr Ala Arg Ile Gln Gly Leu Glu
    530                 535                 540

Ala Leu Lys Glu His Phe Lys Asn Ser Lys Phe Leu Cys Asp Thr Lys
545                 550                 555                 560

Thr Tyr Leu Pro Val Val Phe Ser Pro Pro Arg Asp Gly Arg Gln Leu
                565                 570                 575

Thr Glu Pro Gln Pro Ile Val Gly Asn Asn Lys Leu Ile Ile Gly Ile
            580                 585                 590

Ile Thr Asn Asp Thr Lys Ala Ser Asp Asp Asn Asp Gly Asp Glu
        595                 600                 605

Trp Glu Met Met Met Asp Gly Pro His Arg Leu Asn Asn Gly Gly His
        610                 615                 620

Val Arg Asp Tyr Asp Asp Asp Val Glu Asp Tyr Asn Asp His Asn Gln
625                 630                 635                 640

Ser Pro Asn Asp Asp Asp Ser Gly Asp Asp Asp Ser Thr Ser Val
                645                 650                 655

Ser Ala

<210> SEQ ID NO 41
<211> LENGTH: 4438
<212> TYPE: DNA
<213> ORGANISM: Physcomitrella patens
<220> FEATURE:
<221> NAME/KEY: misc_feature
<222> LOCATION: (0)...(0)
<223> OTHER INFORMATION: Physcomitrella patens terminal EAR1-like 1
      (TEL1) protein gene

<400> SEQUENCE: 41
cattgacgag tattggcgag cgcgcttatg ttgagaggac aataaagggg cgccttcatt    60
cttgcagcag ccaagcctca ccgttgacgc ttacagccct ttgtattagt gcctcggaag    120
gaatgggtgg tggaagaact gaaagtggcg gcacttccac tgtcaccaac gacacaagca    180
ccccttacga tgatgtagag attacacttg acgcttttca gaggatgagc tttgagtctg    240
gggaagtcac agattcagct ccagagggca ttgcaacagg tgaaactggg ttacaggcag    300
ttaagaaagg cgcattgtcc agccctcctg agctatcacg acaagctgac actaacattg    360
atgtggatta tgtgactaag cagcagcagc atcaacatgg acacggtcac gggcattgtg    420
gccaatatag gggggctccc agaggattcg acctgctgca gcagaagacg catgaatatc    480
ggcctccacc tgcattgcaa ctcccagacc agagaatgat ggacagtgag gtcgccgcct    540
tgcatgacga ggatcatcgc aagggagatt acgctcaggc tacgaatttc ggtctcccag    600
cctcccttgt cgtgtctcca gggtcatgcc atgtatcttg tcatgatgcc aaggcatcgc    660
ttgatcccaa cgcccgggag tacactccca acggcccgtc tccttgtatt tctccaggtg    720
tgccgccatc tgtagtgcag catcacgttg gtgtaccctc ttggtattct tttgagtcag    780
gccacatcta cgtttctggg atggacaata gtcgaatggt ttacagcccc agttatggat    840
cagagaccac aatgtcgcta tacggaagtg gtgcacaaat tgcgtatgct cccgtcacag    900

```
ccccaccatc ggctccctgg ggtggattag aacttcctga cctgagccaa caggcaactc    960
agagcgctgc gactggccaa cttttcaggaa ctcctgtagg tttgaccggg gtccagtcgt   1020
ctcatgcctt gcggtcgttt ggtattcctc cttttcaagc cgtaggtctt ccttcagttg   1080
gtatttccgg caacagtgta ttatctactc ccccaatttc aggtagagag catgtgtcac   1140
gggccatctt gctaaacggt gtaccggctt atgttagtga tgaccagttg aaggctgaga   1200
tggggaaatg gggcgatgtt aggactatag tttcggaccg caaacttact gagggattgg   1260
ttactgttaa cttctacgac cttcgctgcg ccaaggaggc tctgcgggat atacagcaac   1320
agcatctgaa taaacagcac cggatgcagc agcagtatca gttctctcaa aagctgcgag   1380
agggcagtag taacagctcg cgagatcacg tggaaatggc atatgagagg caggacgggg   1440
gcaagcgccc agatttgctc cctgacagca ttagttcctc gtccacacca actaattcag   1500
ggaaaggcct tgtttgtgga gtagtgatgt gggctcaata tacgctacct attggagctg   1560
ctgcaggtcc tgatagcctg aaccagggca cgcttgtcgt tttcaacctg gatgtcgaca   1620
caaccatgga gtgcttgaag tctatctttg aagttcacgg tatactcttg ttcctgtcaa   1680
aacctcattt acttttctct tcatgaaccc tgccaatgct ttacttggtt ttctcgtggt   1740
cttggtagga ggtattcatg cttgcttggt tacatggttg ggacagttgg taaacccgcc   1800
ctcatcaatt tcggagcagt aataaactag tctgtcaata gttttttcga ggtttcgtca   1860
gtccttgtag caaacacttg atgttgatat taaagaggtt tgatgtaatt agtggcatta   1920
gcgttgaaca tgcatttgat ttttgagcag aatgttttcg gatactgtgt tacaatattt   1980
tgcgtatccc gataagaaac tttgtaattg tgtcgctggt tacgatgttc tgccatggag   2040
gcgattgtgt cggatgctgt gaagttcgct ttgatttgta ctgtacgcct ggattaacct   2100
tattgaccaa acgcaccttt gacccatcga agtcaaggta tcgtagggta actgacgagg   2160
tagttcagga gtttgagatt gtatgtaatt tgtgcgctaa ttcctggtct ctgttgtggt   2220
gaatcaggtg atgtcaaaga actaagggaa acgcctgcta agaaacaaca caagtttgtg   2280
gaatttttcg atgtccgaga tgctgctaag gcactaaaag ccctggatgg tactgaaatt   2340
aatgaaagc gtgtaaaaat agagttcagt cgaccaggtg gacaagctca caaggctcgt    2400
gtacagctgc agcagcgagc gcagggaggt ccattgtaca attccttaac cagcagtctg   2460
ccctctctag caggggcagg tccaggttca gtagcgggtc aacctttcta cgcaatgggg   2520
acgtggagtg gagatgctgc atgcggatct gtaacaatgc cgggtcccca tggtggtcct   2580
tctgcatgcc tgtggacaag taacattgga actcctgtct ctcctttagg attgatgcag   2640
gcgccttgga gtagtggctc cagtcagctg caatcttaca attacgcatc tatgcaagaa   2700
ggcttggcaa gccctgccgg ccacttgtc gtaatgggaa atgtggatgc tttgcattac    2760
ggccgagctg gtggtagagc cttgatgatg tccttttcag gagcacaagg gtcaccgggg   2820
gaaaatcacc cttctcgagc gcagggatcc tctggaagga gaaatagcag cgctagtggg   2880
caaggtagag tggatggagt atcaagtcgc aggtcaaagc gcaatacatc tgtgaatgga   2940
aatgtttgtt tcggtaagct ggattccgcc aacgagttag tctccgggga caagagtgga   3000
gaaggtcctc gtgtgggcac gcgaatctcg acgaacaaat tagcttctcg tgcggatatt   3060
cctcctcagt atctgtttga tgaaactgga gtccagacca acgatactca acggacaaca   3120
cttatgatta agaatattcc taataagtac aggtagacag catttctttt cttttttctgc   3180
tttaagtgtt gccttactat gtcttagttg ccgaaaactt ggaccctgta agtactgata   3240
tacatcctgg agaagtaggg gccgagtacc tgttgtaggt ctctgttttt acattcgtcc   3300
```

```
cctcggtgta atctacgtct aggaactttc taattattgt tcttgttttt ccactacctg    3360
atgtagccag cagatgttac tttcgcttct ggatacacac tgcattgaat gtaataagcg    3420
tctggaggat ccgaatgaac caatttctgc atacgatttt gtttatcttc ccattgactt    3480
caagtaagtc cctgtttctc tagattgtct gaatcttgaa gtcttgacat tggtgtgtag    3540
gattgcccct atcacacatg atcaagttac cttgatgaag gtttggtatc tcatctactc    3600
gagttggact tacttttgat ttttctatga caggaatagg tgtaatctgg gatatgcatt    3660
tgtgaatttc actactgtcc aagcaacaat gagactgtat agggcttttc atcttcaaca    3720
gtgggaggag ttcaattcgc gcaaagtttg tcatgtgaca tatgctagag ttcaggcctg    3780
tttccgtctg cacatgcctt ttctatgctg acattcgtag tgtggatttg gtcccttcat    3840
taaacctttg caaatttatc atgcttggaa tatttgtcat gctttctaa cgtcagcagc    3900 tgtatcctct attgcaggga cgagccgctc ttgaggaaca ttttaagaat tcccgattcg    3960
cttgcgacac ggacgactac cttccactca tgtttcgacc ccctcggaat ggcgtggacc    4020
ccgtccaaac aattactgta gcagctgttc atcaatctag ccgtgtcgtg agcaatacct    4080
ctgtagagaa cagagagcat ggtaggggat cacgcaatgg agagaaaaat gatgagagaa    4140
gggtagtagc aaaaggtgtt agtggtcagg aattagaaat ggatcatttg ccgggtgggc    4200
agtccagagg aagttcgtca tcaggtggac ataagccaat tatgcttcag cagcattggt    4260
aagatatctc ttgggtgatg attggtcaaa gaggcagttg tttggaggtc gtttcacagg    4320
atggcagcgt gattgctgtg atagtgtgcc gtggcatctt taaggattta ggagtcattt    4380
cgagacgatg ccagtccagg aatcgaaacc ctaggctggt gttagtatac ttgacatt     4438
```

<210> SEQ ID NO 42
<211> LENGTH: 778
<212> TYPE: PRT
<213> ORGANISM: Physcomitrella patens
<220> FEATURE:
<223> OTHER INFORMATION: Physomitrella patens TE1

<400> SEQUENCE: 42

```
Met Ser Leu Tyr Gly Ser Gly Ala Gln Ile Ala Tyr Ala Pro Val Thr
 1               5                   10                  15

Ala Pro Pro Ser Ala Pro Trp Gly Gly Leu Glu Leu Pro Asp Leu Ser
                20                  25                  30

Gln Gln Ala Thr Gln Ser Ala Ala Thr Gly Gln Leu Ser Gly Thr Pro
            35                  40                  45

Val Gly Leu Thr Gly Val Gln Ser Ser His Ala Leu Arg Ser Phe Gly
        50                  55                  60

Ile Pro Pro Phe Gln Ala Val Gly Leu Pro Ser Val Gly Ile Ser Gly
65                  70                  75                  80

Asn Ser Val Leu Ser Thr Pro Pro Ile Ser Gly Arg Glu His Val Ser
                85                  90                  95

Arg Ala Ile Leu Leu Asn Gly Val Pro Ala Tyr Val Ser Asp Asp Gln
            100                 105                 110

Leu Lys Ala Glu Met Gly Lys Trp Gly Asp Val Arg Thr Ile Val Ser
        115                 120                 125

Asp Arg Lys Leu Thr Glu Gly Leu Val Thr Val Asn Phe Tyr Asp Leu
    130                 135                 140

Arg Cys Ala Lys Glu Ala Leu Arg Asp Ile Gln Gln Gln His Leu Asn
145                 150                 155                 160
```

```
Lys Gln His Arg Met Gln Gln Tyr Gln Phe Ser Gln Lys Leu Arg
                165                 170                 175

Glu Gly Ser Ser Asn Ser Ser Arg Asp His Val Glu Met Ala Tyr Glu
            180                 185                 190

Arg Gln Asp Gly Gly Lys Arg Pro Asp Leu Leu Pro Asp Ser Ile Ser
        195                 200                 205

Ser Ser Ser Thr Pro Thr Asn Ser Gly Lys Gly Leu Val Cys Gly Val
    210                 215                 220

Val Met Trp Ala Gln Tyr Thr Leu Pro Ile Ala Ala Gly Pro
225                 230                 235                 240

Asp Ser Leu Asn Gln Gly Thr Leu Val Val Phe Asn Leu Asp Val Asp
            245                 250                 255

Thr Thr Met Glu Cys Leu Lys Ser Ile Phe Glu Val His Gly Asp Val
        260                 265                 270

Lys Glu Leu Arg Glu Thr Pro Ala Lys Lys Gln His Lys Phe Val Glu
    275                 280                 285

Phe Phe Asp Val Arg Asp Ala Ala Lys Ala Leu Lys Ala Leu Asp Gly
    290                 295                 300

Thr Glu Ile Asn Gly Lys Arg Val Lys Ile Glu Phe Ser Arg Pro Gly
305                 310                 315                 320

Gly Gln Ala His Lys Ala Arg Val Gln Leu Gln Gln Arg Ala Gln Gly
            325                 330                 335

Gly Pro Leu Tyr Asn Ser Leu Thr Ser Ser Leu Pro Ser Leu Ala Gly
        340                 345                 350

Ala Gly Pro Gly Ser Val Ala Gly Gln Pro Phe Tyr Ala Met Gly Thr
    355                 360                 365

Trp Ser Gly Asp Ala Ala Cys Gly Ser Val Thr Met Pro Gly Pro His
370                 375                 380

Gly Gly Pro Ser Ala Cys Leu Trp Thr Ser Asn Ile Gly Thr Pro Val
385                 390                 395                 400

Ser Pro Leu Gly Leu Met Gln Ala Pro Trp Ser Ser Gly Ser Ser Gln
            405                 410                 415

Leu Gln Ser Tyr Asn Tyr Ala Ser Met Gln Glu Gly Leu Ala Ser Pro
        420                 425                 430

Ala Gly Pro Leu Val Val Met Gly Asn Val Asp Ala Leu His Tyr Gly
    435                 440                 445

Arg Ala Gly Gly Arg Ala Leu Met Met Ser Phe Ser Gly Ala Gln Gly
    450                 455                 460

Ser Pro Gly Glu Asn His Pro Ser Arg Ala Gln Gly Ser Ser Gly Arg
465                 470                 475                 480

Arg Asn Ser Ser Ala Ser Gly Gln Gly Arg Val Asp Gly Val Ser Ser
            485                 490                 495

Arg Arg Ser Lys Arg Asn Thr Ser Val Asn Gly Asn Val Cys Phe Gly
        500                 505                 510

Lys Leu Asp Ser Ala Asn Glu Leu Val Ser Gly Asp Lys Ser Gly Glu
    515                 520                 525

Gly Pro Arg Val Gly Thr Arg Ile Ser Thr Asn Lys Leu Ala Ser Arg
530                 535                 540

Ala Asp Ile Pro Pro Gln Tyr Leu Phe Asp Glu Thr Gly Val Gln Thr
545                 550                 555                 560

Asn Asp Thr Gln Arg Thr Thr Leu Met Ile Lys Asn Ile Pro Asn Lys
            565                 570                 575

Tyr Ser Gln Gln Met Leu Leu Ser Leu Leu Asp Thr His Cys Ile Glu
```

```
                580              585                590
Cys Asn Lys Arg Leu Glu Asp Pro Asn Glu Pro Ile Ser Ala Tyr Asp
            595                 600                 605
Phe Val Tyr Leu Pro Ile Asp Phe Lys Asn Arg Cys Asn Leu Gly Tyr
            610                 615                 620
Ala Phe Val Asn Phe Thr Thr Val Gln Ala Thr Met Arg Leu Tyr Arg
625                 630                 635                 640
Ala Phe His Leu Gln Gln Trp Glu Glu Phe Asn Ser Arg Lys Val Cys
                645                 650                 655
His Val Thr Tyr Ala Arg Val Gln Gly Arg Ala Ala Leu Glu Glu His
            660                 665                 670
Phe Lys Asn Ser Arg Phe Ala Cys Asp Thr Asp Tyr Leu Pro Leu
            675                 680                 685
Met Phe Arg Pro Pro Arg Asn Gly Val Asp Pro Val Gln Thr Ile Thr
            690                 695                 700
Val Ala Ala Val His Gln Ser Ser Arg Val Val Ser Asn Thr Ser Val
705                 710                 715                 720
Glu Asn Arg Glu His Gly Arg Gly Ser Arg Asn Gly Glu Lys Asn Asp
            725                 730                 735
Glu Arg Arg Val Val Ala Lys Gly Val Ser Gly Gln Glu Leu Glu Met
            740                 745                 750
Asp His Leu Pro Gly Gly Gln Ser Arg Gly Ser Ser Ser Gly Gly
            755                 760                 765
His Lys Pro Ile Met Leu Gln Gln His Trp
    770                 775

<210> SEQ ID NO 43
<211> LENGTH: 1485
<212> TYPE: DNA
<213> ORGANISM: Ostreococcus tauri
<220> FEATURE:
<221> NAME/KEY: misc_feature
<222> LOCATION: (0)...(0)
<223> OTHER INFORMATION: Ostreococcus tauri terminal ear1 cDNA

<400> SEQUENCE: 43
atgatgaaca tgcaaatgtc cgccatgcat caggacaga tgggtgcacc gattcagcca      60
gaatcgccca tgtcgcccat gtcaatgccg gcagtgtgga ccaacgacga tccgtctcgg     120
acggtttatc tcgttctggt cgacgcgtcc atgaacgacc agatgttgtg gtcgatcgcc     180
tcgcagttcg gagatattcg ttcaatcgcg aacgagctgc gacgaacgat gaacaccgtg     240
ttcgtgtctt actacgatat tcgagccgcc gagctcgcaa agttgacgct acaaatgtcc     300
acgcacatat tccacatggt ggcctactcc ggggcgtgtg attggatccc tgggatggag     360
aaccaaggcc gcttcctggc gtacgatatc ggcacggccg aagaagagcg cgacgcggag     420
tttcgagcgt tgttggattc gtttggtgag gtcaagcggt tgatgacgcc aaggggccac     480
gaaaatcata gattcataga gtactttgac gtgaggcacg cgcacacggc ggtgacagaa     540
ctgcagcaga gcgggttcag gagtaagccc cttttcagtgg actttcactc gcagtcttac    600
gctgcggact ccaccagca acacgcgttc tctccgccct cgccgtcctc catacatcag     660
tacatggggc aggccgcgat gatggcaaac atgtactggc catacggcgg tccggtcacg     720
acgatgccca tggttggcgc gcaagggtat ggtggttatc aaggatggtc gccggatcag     780
cagcactacg gttaccctgt acagagtgcg agtggccacg gttaccctgt acaaagtgcg     840
agtggccacg gcgggcatcg ctcgccccgt tcaagcggcg agtattcgcg atcgccgcga     900
```

```
acgagtgaaa gtatgggccg atctagatcg agtcacaata gtactttaga ggcgtttcag      960
aggacgaatc cggaagagtt catcttcagt atggaagaag cgaacgaggc ggggacgaag     1020
gataatccag agcacggaag gaccacgctc atgattcgca acatcccgaa caagtacaat     1080
caagctatgc tgttggatct cctcaatcga tcttacgaga accagtacga cttcttctac     1140
ttgcccatag acttcaaaaa caaatgcaac ttgggctacg cttttgtgaa cttcaagtgc     1200
gccaagacga cggcggcatt ttataaggag ttccacaagc agcgctggga agaattcaac     1260
tcccggaaag tgtgcgagat cacttacgct cgggtccaag gcaaggaggc catggttgag     1320
cacttcaaga acagtcgatt tccgtgtgag aacgaagagt tcttgccgct ggtcttcgat     1380
accgacggga acaaaactag ctaccatact ttaggacaca ccgtacatgg agcgactgga     1440
aggtttccag acacggcgag cgagaacgta accgacagtg tttaa                    1485
```

<210> SEQ ID NO 44
<211> LENGTH: 494
<212> TYPE: PRT
<213> ORGANISM: Ostreococcus tauri
<220> FEATURE:
<223> OTHER INFORMATION: Ostreococcus tauri Mei2

<400> SEQUENCE: 44

Met Met Asn Met Gln Met Ser Ala Met His Gln Gly Gln Met Gly Ala
1               5                   10                  15

Pro Ile Gln Pro Glu Ser Pro Met Ser Pro Met Ser Met Pro Ala Val
            20                  25                  30

Trp Thr Asn Asp Asp Pro Ser Arg Thr Val Tyr Leu Val Leu Val Asp
        35                  40                  45

Ala Ser Met Asn Asp Gln Met Leu Trp Ser Ile Ala Ser Gln Phe Gly
    50                  55                  60

Asp Ile Arg Ser Ile Ala Asn Glu Leu Arg Arg Thr Met Asn Thr Val
65                  70                  75                  80

Phe Val Ser Tyr Tyr Asp Ile Arg Ala Ala Glu Leu Ala Lys Leu Thr
                85                  90                  95

Leu Gln Met Ser Thr His Ile Phe His Met Val Ala Tyr Ser Gly Ala
            100                 105                 110

Cys Asp Trp Ile Pro Gly Met Glu Asn Gln Gly Arg Phe Leu Ala Tyr
        115                 120                 125

Asp Ile Gly Thr Ala Glu Glu Arg Asp Ala Glu Phe Arg Ala Leu
    130                 135                 140

Leu Asp Ser Phe Gly Glu Val Lys Arg Leu Met Thr Pro Arg Gly His
145                 150                 155                 160

Glu Asn His Arg Phe Ile Glu Tyr Phe Asp Val Arg His Ala His Thr
                165                 170                 175

Ala Val Thr Glu Leu Gln Gln Ser Gly Phe Arg Ser Lys Pro Leu Ser
            180                 185                 190

Val Asp Phe His Ser Gln Ser Tyr Ala Ala Asp Phe His Gln Gln His
        195                 200                 205

Ala Phe Ser Pro Pro Ser Pro Ser Ser Ile His Gln Tyr Met Gly Gln
    210                 215                 220

Ala Ala Met Met Ala Asn Met Tyr Trp Pro Tyr Gly Gly Pro Val Thr
225                 230                 235                 240

Thr Met Pro Met Val Gly Ala Gln Gly Tyr Gly Gly Tyr Gln Gly Trp
                245                 250                 255

-continued

```
Ser Pro Asp Gln Gln His Tyr Gly Tyr Pro Val Gln Ser Ala Ser Gly
            260                 265                 270

His Gly Tyr Pro Val Gln Ser Ala Ser Gly His Gly His Arg Ser
        275                 280                 285

Pro Arg Ser Ser Gly Glu Tyr Ser Arg Ser Pro Arg Thr Ser Glu Ser
    290                 295                 300

Met Gly Arg Ser Arg Ser Ser His Asn Ser Thr Leu Glu Ala Phe Gln
305                 310                 315                 320

Arg Thr Asn Pro Glu Glu Phe Ile Phe Ser Met Glu Glu Ala Asn Glu
                325                 330                 335

Ala Gly Thr Lys Asp Asn Pro Glu His Gly Arg Thr Thr Leu Met Ile
            340                 345                 350

Arg Asn Ile Pro Asn Lys Tyr Asn Gln Ala Met Leu Leu Asp Leu Leu
        355                 360                 365

Asn Arg Ser Tyr Glu Asn Gln Tyr Asp Phe Phe Tyr Leu Pro Ile Asp
    370                 375                 380

Phe Lys Asn Lys Cys Asn Leu Gly Tyr Ala Phe Val Asn Phe Lys Cys
385                 390                 395                 400

Ala Lys Thr Thr Ala Ala Phe Tyr Lys Glu Phe His Lys Gln Arg Trp
                405                 410                 415

Glu Glu Phe Asn Ser Arg Lys Val Cys Glu Ile Thr Tyr Ala Arg Val
            420                 425                 430

Gln Gly Lys Glu Ala Met Val Glu His Phe Lys Asn Ser Arg Phe Pro
        435                 440                 445

Cys Glu Asn Glu Glu Phe Leu Pro Leu Val Phe Asp Thr Asp Gly Asn
    450                 455                 460

Lys Thr Ser Tyr His Thr Leu Gly His Thr Val His Gly Ala Thr Gly
465                 470                 475                 480

Arg Phe Pro Asp Thr Ala Ser Glu Asn Val Thr Asp Ser Val
                485                 490

<210> SEQ ID NO 45
<211> LENGTH: 6192
<212> TYPE: DNA
<213> ORGANISM: Brassica Rapa
<220> FEATURE:
<221> NAME/KEY: misc_feature
<222> LOCATION: (0)...(0)
<223> OTHER INFORMATION: Brassica Rapa TEL1
      -- genomic sequence with promoter and terminator

<400> SEQUENCE: 45
aagcttgaac gattaggctg ttgtaggcat accattccca agacagactt ccataaatct    60
aagatttggt ttggttttac ccaaatttaa tcgaacctaa ccgaaaccat tttggctcgt   120
ttggttttat ggcaattcta ttcaggttag agtctagttc ggttcgatca tatcttacat   180
ttatttttat ttttattttt tttgtactaa atacatatat taaatttgat aaaaataaat   240
ttatatttta agtttgtgcc gtacgtaaaa aggcaaatcg tagcttattg caaatagatt   300
caaattatgt atattaaaaa gagaaattcc attagatagt catttttagt ttattttcac   360
aaaaataaat ttcagggaag aaaatgatcg aaacaagtgt tattaaagga taaatatgca   420
attatactca agagttaatt aatctagact tagggaaatt aaagttaaag gatggagttt   480
agggattcaa atttaaaaaa attaaaaatt aaaattaaa attttcaaaa caaaaggtg    540 ctattttagt cattttatt tttgagtgtt gttttttgtga caataactta aaaagtctat   600
ttgagagaat tgccttaaaa aaatcatta ctccttatgt tcctaaatgt aggatgtttc   660
```

```
aaaaaaaaaa acattgatgt tcaggaacag aggagtatat accagtgtat tatttcttag      720
aaacataata gtccacttac taactaaaat gagaattaaa aatgatcaca tattgtaaat      780
ttaaaataac aacagggttg gatttttttt ttttactat agggttttgt gggtttggtt      840
ttgaatttca gtttggataa atcaatttcg tttattgtaa aactaaaagt aaactataac      900 cgagttttg gttcaattcc gaaataaata tatacatgtc gattaacaat gataaagtaa      960
gaagatttag aattatggaa agaaagaaaa caatcaaaga atagtgatgc ctaaaagaga     1020
ttccatagca atgtcacaaa acgattttc ttatattttg accataactt ggtttgagtc     1080
tttgacattg tacggttgcc aagaagaatc atatttgtac aacaaataag aaaaataaac     1140
tgaagcaaac gtggtaagca agaagttgta ttactttagt aatttttta cctggtaata     1200 taaacgaagg acaagaatca agattatggt tttggtcgtt ggttttgagg agtcttcttc     1260
tcgaaccgag atttcatgc acgtgtgttt ggtcactact tcgtgtttaa caacactttc     1320
ttcaccatac caatatccgc ataaaacaaa cattttttct ttttgaaaa aaggcttttct     1380 aacataaaac aaaaattatt tgttaaaaca cacaaaatga ttgctttaa atccttgatc     1440 atctatcatt aaacctttt gttttattat aataagcaat atgcattta gttttatgtc     1500 ttgtgaataa atgtgtaatg taacccataa tcgctaaacg taccctcaaa gacttaaaag     1560
agttacatat gctacttatc acaaatatcg attggctttt tttttggtca aacaaatatc     1620
gataagctat cttcaatttg tttgatgagt gtgtgtgttt gtagaattgc catttaagac     1680
tatttgctaa aattatgtaa caaaggttac gactctagct aactattgcc gttctcaaat     1740
gttctacaga ttagaggttg taaataactt acatactcca tctgttttt aatgttacat     1800 attctagtat tttcacacat tttaataaaa cacattaaat ttacataatt ttttgtgttt     1860
atctttgttc cataatttta agctaataaa aattcagtac aattaaattt tttgaaattt     1920
gtaattagtt aataaaacat gtcttgaaaa tgtaaaaaat agatttttt taaaacaatt     1980 tttttctaa aatatataat attaaggaac agagtgagta tatatcaaaa aataaaaaaa     2040
tggtccatga tttattttt acgtttgttt ttccttcact gcaagttttt ctattcacag     2100
tttcgaatat ttttttttta aaacagttca caaaggatta acccaggtac tcagtattcc     2160
tgcctcgtaa accaagaacc caagcctaca aaagtgagt aggggtacta aggtaacttc     2220
agcaaaatga tagtataatc catttattta aaaacaacag tcattttcga gaaacataaa     2280
tgcgcttata aattggaaag acataaagaa ataaacaaa ataaacattt gttctcttcc     2340
actgtcttgt ctaatgtctg tagagtaaag agatagagcc gacgttacag ttatctctct     2400
cttctctctc acacgatcaa gaaaactttc acgttcaccg gagaaaacta ttactcctgt     2460
aagaaaacaa ttaaagacct attcaaatgg aaaattttag agcttttcct ttcgccggga     2520
atctagaccc tcgagctcaa gagttcgtac cactaaaccc tatgtcttca cgttttcact     2580
ttccgtacac ttctctcccg ccgccgccgc tgcctccacc tcctccgtcg tacgactat      2640 ctccatcgga tccaagaatg ttcacgttct ttaatatccc accacatccg atgatgtttc     2700
ctcctgctcc tcatcctcca cctccaccac caccaccacc tcgtccctgg tttaacggtt     2760
tttcagctgt tcaacggcca tctccgccgt cgaactcgcc gacgcgatca ctttctctga     2820
tctacgtacc gcgtgacgtc accgagtcta cggtgagacg tgacttggag gtgttcggcg     2880
acgtgcgtgg cgtgcagatg gagagaatct cggaaggagt cgtgaccgtc catttctacg     2940
atctccgtgg cgctaaaaga gctgttcgag agttttgcgg tagacacatg cagcaccaag     3000
```

```
aaaggctcgg tagcagcagt ggaggtggaa gcgtttggag atcaccttct tcatcggcgc    3060
gtgggtttgt ttctggtaga cctgtgtggg cccactttgt agttccggat acaaacgccg    3120
tacccggcgg ttgtaaccaa ggaacgttgg tgatatttaa cctagacccc gaagtctctt    3180
ccattgctct cagacagatt ttccaagttt acggtatatg tttttttact tatgtttcta    3240
tgtcttagat ttttgagttt cgtttcctcg atttgtggat atgtcaggaa ttaaaacatt    3300
ttacaaagac tgaaacattt tcacttaaat tattataatc atgccattta ctagcttttg    3360
aatttttgaa tatagaccat gtaagacagt ttggttatat ggaagcactt tataatattg    3420 tgaattttg tctccaggtt cgatcaaaga gttgagagag acaccataca agaaacatca     3480
aagattcatc gagttttacg atgtaagaga tgcagtgaat gcgtttgacc gaatgaatag    3540
tgaagaaatt tatgggaagc aagttgtgat cgaatttagc cgaccaggtg ggcttaagaa    3600
caagttcacg ccatttaggc aaccgcagtt accgtttcag ccgcgaccag ttttattgac    3660
tcctcctttg aagcagtctg ttattctgac caatggtaaa agcaagaatg tgagccctaa    3720
taatggagtt gatgttgttg aagcttctat gcgttcgttg tgtgacatcg atgatgaagc    3780
agaacctgaa acaaagagca agaacgtggc taagttgggg aggaaaaagc agatgaagag    3840
catggaacta agtcagtttc ttatcagtga agaaacaatg aatgatccaa gttgcagaga    3900
tccacgtacc actttgatga taaagaacat accaaacaag tacaggttcg gctttataat    3960
ctaattattc gtatttaaa ttttatagat ttaaagttgg acgattttt caaatttag       4020 gacggctaaa gattttagat ctttctaatc tttttattaa aatattcaca tggattcgtg    4080
tgttaagatg ctgtttatat atatttaaag atttatattc tagataaaat gctcttacgc    4140
tatgttccat caattcaagc ttttaattat cttcgtgttt gatattacaa ttagtcggct    4200 aacatttcc tggatgctct tatatttcag attcctatag gttttgttta tatgagattc     4260
caatttaatt ttatagttaa gtgtttttg gttttgtata gtcaaaagct gctgttgaat      4320
atgctggata atcactgcat tcacatcaac gaagctatca ccgaggagga gagggacgaa    4380
cacaaagctc atcatgatca gccaatttct tcttatgatt tcgtgtatct cccgatggat    4440
ttcaagtaat caaacaccgg actttattga ctatatagta ttactattat atataactaa    4500
aatcataact cctttttttg gctttgatat tagcaacaag tgcaatgttg ttatggatt     4560 tgtgaacatg acatcccgg aggcagcttg gaggctttac aaggcgtttc atcgccagcg     4620
ttgggagatt tttaattcgc ataagatttg ccaaatcaca tatgcgagag ttcaggtaga    4680
catagacatt agtgttttga aatcgcttac caaagtataa gctaaatttt ttaatgtcta    4740
tgataattgg gtgtcacaat atgattattt tgttacttt tcgtccaaa aacagggttt       4800 ggaggatcta aaggaacact tcaggagctc aaggtttccg tgcgaggccg aactgtacct    4860
tccggtggtt ttttcgcctc cacgagacgg gaagcagtta acggaacctg tttctatcaa    4920
catcaacgac tgcaccgggc tcaataatat tcatcatctc gagcctattg acggtccaga    4980
tcactctgtg ggtggttcat gttgcggtag tgacaatgat aacagtcagg aagatggatt    5040
atccggcaat aacatagatg gtggacggag tttcacggtg gtaggagcga catctttcta    5100
gaagttgttt gtaatgtaaa ccataaatat atgaaagtgt aattagacaa atcatgttgt    5160
ttatgtttta tgcgtgttat gttgtctcat tctaaattat attttcgacg cgatttactt    5220
atcaagcaaa gttctgaaaa gtgatagttt gggtgaatgt ctgaatgagc aaagtaacaa    5280
tgaattccaa cttgttattt ttctaaaact ttttgcatgc ggaatcgtca atatattttg    5340
tagtcatatt ttctctcttg gatagtgtga tgtaggatgg cataatatga ctaaattta    5400
```

-continued

```
ttaaatttaa gaataaaact tgcatcaaat gatgtcattg gagctaagaa taacaattac    5460
aacatgttgt tttcaaacac tctaattttt tgtttggtta caattgagaa tatgtccata    5520
acacaaccta tttgttgata tttattttac aaaatgaatt catggttata taatatatat    5580
caaatgatgt taaacgtcat aaccttattg tttcttgtag acaaatgat taagaaatta     5640 ataatattat gtcattaaaa ttcattattt ttaaatgata aggtggaaaa tgggtggtaa    5700
actagaaatg gttgacctag ggtaagagtt ccttttcagg caaagatact agtctttgtt    5760
ctagtgttta tagctgtctt attcagtgac ctgctgaaag ggacagcaga taactctgtg    5820
ctagtgatga tcacaatctg tatttccctc tggttcgtgg ggtttcgaca cgtgttgata    5880
tcttcaccgt tcgtatcgtt catggcagag ttgataggga tcgttgacta caagttgtaa    5940
gttgtaagtt gtaagttgta accttctgat gtatatttgc taattttta ttattttaaa    6000 gccttttag agtgacgaaa aagaacaatg caatccaagt agaattggaa atcatgctat     6060
tttagattta ttgggtctgt aaattttttt aaaatccatc cacttagaat tgaagatcat    6120
tttaacttct ctgtgtgttt ggttggtata aatgttatac caaatccaac aacacaaatt    6180
catttaggta cc                                                        6192
```

<210> SEQ ID NO 46
<211> LENGTH: 608
<212> TYPE: PRT
<213> ORGANISM: Brassica Rapa
<220> FEATURE:
<223> OTHER INFORMATION: Brassica Rapa TEL1

<400> SEQUENCE: 46

```
Met Glu Asn Phe Arg Ala Phe Pro Phe Ala Gly Asn Leu Asp Pro Arg
  1               5                  10                  15

Ala Gln Glu Phe Val Pro Leu Asn Pro Met Ser Ser Arg Phe His Phe
             20                  25                  30

Pro Tyr Thr Ser Leu Pro Pro Pro Leu Pro Pro Pro Pro Pro Pro Ser
         35                  40                  45

Tyr Gly Leu Ser Pro Ser Asp Pro Arg Met Phe Thr Phe Phe Asn Ile
     50                  55                  60

Pro Pro His Pro Met Met Phe Pro Pro Ala Pro His Pro Pro Pro Pro
 65                  70                  75                  80

Pro Pro Pro Pro Arg Pro Trp Phe Asn Gly Phe Ser Ala Val Gln
             85                  90                  95

Arg Pro Ser Pro Pro Ser Asn Ser Pro Thr Arg Ser Leu Ser Leu Ile
            100                 105                 110

Tyr Val Pro Arg Asp Val Thr Glu Ser Thr Val Arg Arg Asp Leu Glu
        115                 120                 125

Val Phe Gly Asp Val Arg Gly Val Gln Met Glu Arg Ile Ser Glu Gly
    130                 135                 140

Val Val Thr Val His Phe Tyr Asp Leu Arg Gly Ala Lys Arg Ala Val
145                 150                 155                 160

Arg Glu Phe Cys Gly Arg His Met Gln His Gln Glu Arg Leu Gly Ser
                165                 170                 175

Ser Ser Gly Gly Gly Ser Val Trp Arg Ser Pro Ser Ser Ser Ala Arg
            180                 185                 190

Gly Phe Val Ser Gly Arg Pro Val Trp Ala His Phe Val Pro Asp
        195                 200                 205

Thr Asn Ala Val Pro Gly Gly Cys Asn Gln Gly Thr Leu Val Ile Phe
```

```
            210                 215                 220
Asn Leu Asp Pro Glu Val Ser Ser Ile Ala Leu Arg Gln Ile Phe Gln
225                 230                 235                 240

Val Tyr Gly Ser Ile Lys Glu Leu Arg Glu Thr Pro Tyr Lys Lys His
                245                 250                 255

Gln Arg Phe Ile Glu Phe Tyr Asp Val Arg Asp Ala Val Asn Ala Phe
                260                 265                 270

Asp Arg Met Asn Ser Glu Glu Ile Tyr Gly Lys Gln Val Val Ile Glu
                275                 280                 285

Phe Ser Arg Pro Gly Gly Leu Lys Asn Lys Phe Thr Pro Phe Arg Gln
            290                 295                 300

Pro Gln Leu Pro Phe Gln Pro Arg Pro Val Leu Leu Thr Pro Pro Leu
305                 310                 315                 320

Lys Gln Ser Val Ile Leu Thr Asn Gly Lys Ser Lys Asn Val Ser Pro
                325                 330                 335

Asn Asn Gly Val Asp Val Val Glu Ala Ser Met Arg Ser Leu Cys Asp
                340                 345                 350

Ile Asp Asp Glu Ala Glu Pro Glu Thr Lys Ser Lys Asn Val Ala Lys
            355                 360                 365

Leu Gly Arg Lys Lys Gln Met Lys Ser Met Glu Leu Ser Gln Phe Leu
            370                 375                 380

Ile Ser Glu Glu Thr Met Asn Asp Pro Ser Cys Arg Asp Pro Arg Thr
385                 390                 395                 400

Thr Leu Met Ile Lys Asn Ile Pro Asn Lys Tyr Ser Gln Lys Leu Leu
                405                 410                 415

Leu Asn Met Leu Asp Asn His Cys Ile His Ile Asn Glu Ala Ile Thr
                420                 425                 430

Glu Glu Glu Arg Asp Glu His Lys Ala His His Asp Gln Pro Ile Ser
            435                 440                 445

Ser Tyr Asp Phe Val Tyr Leu Pro Met Asp Phe Asn Asn Lys Cys Asn
            450                 455                 460

Val Gly Tyr Gly Phe Val Asn Met Thr Ser Pro Glu Ala Ala Trp Arg
465                 470                 475                 480

Leu Tyr Lys Ala Phe His Arg Gln Arg Trp Glu Ile Phe Asn Ser His
                485                 490                 495

Lys Ile Cys Gln Ile Thr Tyr Ala Arg Val Gln Gly Leu Glu Asp Leu
                500                 505                 510

Lys Glu His Phe Arg Ser Ser Arg Phe Pro Cys Glu Ala Glu Leu Tyr
            515                 520                 525

Leu Pro Val Val Phe Ser Pro Pro Arg Asp Gly Lys Gln Leu Thr Glu
            530                 535                 540

Pro Val Ser Ile Asn Ile Asn Asp Cys Thr Gly Leu Asn Asn Ile His
545                 550                 555                 560

His Leu Glu Pro Ile Asp Gly Pro Asp His Ser Val Gly Gly Ser Cys
                565                 570                 575

Cys Gly Ser Asp Asn Asp Asn Ser Gln Glu Asp Gly Leu Ser Gly Asn
            580                 585                 590

Asn Ile Asp Gly Gly Arg Ser Phe Thr Val Val Gly Ala Thr Ser Phe
            595                 600                 605

<210> SEQ ID NO 47
<211> LENGTH: 11410
<212> TYPE: DNA
<213> ORGANISM: Artificial Sequence
```

<220> FEATURE:
<223> OTHER INFORMATION: modified pCambia1300 vector

<400> SEQUENCE: 47

```
cgtaatcatg gtcatagctg tttcctgtgt gaaattgtta tccgctcaca attccacaca      60
acatacgagc cggaagcata aagtgtaaag cctggggtgc ctaatgagtg agctaactca     120
cattaattgc gttgcgctca ctgcccgctt tccagtcggg aaacctgtcg tgccagctgc     180
attaatgaat cggccaacgc gcggggagag gcggtttgcg tattggctag agcagcttgc     240
caacatggtg gagcacgaca ctctcgtcta ctccaagaat atcaaagata cagtctcaga     300
agaccaaagg gctattgaga cttttcaaca agggtaata tcgggaaacc tcctcggatt      360
ccattgccca gctatctgtc acttcatcaa aaggacagta gaaaggaag gtggaccta      420
caaatgccat cattgcgata aggaaaggc tatcgttcaa gatgcctctg ccgacagtgg     480
tcccaaagat ggaccccac ccacgaggag catcgtggaa aagaagacg ttccaaccac      540
gtcttcaaag caagtggatt gatgtgataa catggtggag cacgcactc tcgtctactc      600
caagaatatc aaagatacag tctcagaaga ccaaggggct attgagactt tcaacaaag     660
ggtaatatcg ggaaacctcc tcggattcca ttgcccagct atctgtcact tcatcaaaag    720
gacagtagaa aaggaaggtg gcacctacaa atgccatcat tgcgataaag gaaaggctat    780
cgttcaagat gcctctgccg acagtggtcc caaagatgga cccccaccca cgaggagcat    840
cgtggaaaaa gaagacgttc caaccacgtc ttcaaagcaa gtggattgat gtgatatctc    900
cactgacgta agggatgacg cacaatccca ctatccttcg caagaccttc ctctatataa    960
ggaagttcat ttcatttgga gaggacacgc tgaaatcacc agtctctctc tacaaatcta   1020
tctctctcga cgcatgccta cagtgcagcg tgacccggtc gtgcccctct ctagagataa   1080
tgagcattgc atgtctaagt tataaaaaat taccacatat ttttttttgtc acacttgttt   1140
gaagtgcagt ttatctatct ttatacatat atttaaactt tactctacga ataatataat   1200
ctatagtact acaataatat cagtgtttta gagaatcata taaatgaaca gttagacatg   1260
gtctaaagga caattgagta ttttgacaac aggactctac agttttatct ttttagtgtg   1320
catgtgttct cctttttttt tgcaaatagc ttcacctata taatacttca tccattttat   1380
tagtacatcc attagggtt tagggttaat ggttttata gactaatttt tttagtacat      1440
ctattttatt ctattttagc ctctaaatta agaaaactaa aactctatt tagttttttt     1500
atttaataat ttagatataa aatagaataa aataaagtga ctaaaaatta aacaaatacc   1560
ctttaagaaa ttaaaaaaac taaggaaaca tttttcttgt ttcgagtaga taatgccagc   1620
ctgttaaacg ccgtcgacga gtctaacgga caccaaccag cgaaccagca gcgtcgcgtc   1680
gggccaagcg aagcagacgg cacggcatct ctgtcgctgc ctctggaccc ctctcgagag   1740
ttccgctcca ccgttggact tgctccgctg tcggcatcca gaaattgcgt ggcggagcgg   1800
cagacgtgag ccggcacggc aggcggcctc ctcctcctct cacggcacgg cagctacggg   1860
ggattccttt cccaccgctc cttcgctttc ccttcctcgc ccgccgtaat aaatagacac   1920
cccctccaca ccctctttcc caacctcgt gttgttcgga gcgcacacac acacaaccag   1980
atctccccca aatccacccg tcggcacctc cgcttcaagg tacgccgctc gtcctccccc   2040
cccccccctc tctaccttct ctagatcggc gttccggtcc atggttaggg cccggtagtt   2100
ctacttctgt tcatgtttgt gttagatccg tgtttgtgtt agatccgtgc tgctagcgtt   2160
cgtacacgga tgcgacctgt acgtcagaca cgttctgatt gctaacttgc cagtgtttct   2220
```

```
ctttggggaa tcctgggatg gctctagccg ttccgcagac gggatcgatt tcatgatttt    2280
ttttgtttcg ttgcataggg tttggtttgc ccttttcctt tatttcaata tatgccgtgc    2340
acttgtttgt cgggtcatct tttcatgctt ttttttgtct tggttgtgat gatgtggtct    2400
ggttgggcgg tcgttctaga tcggagtaga attctgtttc aaactacctg gtggatttat    2460
taattttgga tctgtatgtg tgtgccatac atattcatag ttacgaattg aagatgatgg    2520
atggaaatat cgatctagga taggtataca tgttgatgcg ggttttactg atgcatatac    2580
agagatgctt tttgttcgct tggttgtgat gatgtggtgt ggttgggcgg tcgttcattc    2640
gttctagatc ggagtagaat actgtttcaa actacctggt gtatttatta attttggaac    2700
tgtatgtgtg tgtcatacat cttcatagtt acgagtttaa gatggatgga aatatcgatc    2760
taggataggt atacatgttg atgtgggttt tactgatgca tatacatgat ggcatatgca    2820
gcatctattc atatgctcta accttgagta cctatctatt ataataaaca agtatgtttt    2880
ataattattt tgatcttgat atacttggat gatggcatat gcagcagcta tatgtggatt    2940
tttttagccc tgccttcata cgctatttat ttgcttggta ctgtttcttt tgtcgatgct    3000
caccctgttg tttggtgtta cttctgcagg tcgactctag aggatctacc atggccaccg    3060
ccgccgccgc gtctaccgcg ctcactggcg ccactaccgc tgcgcccaag gcgaggcgcc    3120
gggcgcacct cctggccacc cgccgcgccc tcgccgcgcc catcaggtgc tcagcggcgt    3180
cacccgccat gccgatggct cccccggcca ccccgctccg gccgtggggc cccaccgatc    3240
cccgcaaggg atccgacgcc ctgcccgcca ccttcgacgt gatcgtgcat ccagctcgcg    3300
aactccgcgc cgagcttcgc gctcagccat ccaagaacta caccactcgc tacctcctcg    3360
ccgctgccct cgctgagggc gagacccgcg tggtgggcgt ggctacctct gaggacgccg    3420
aggccatgct ccgctgcctc cgcgactggg gcgctggcgt ggagcttgtg ggcgatgacg    3480
ccgtgatccg cggtttcggc gctcgcccac aggccggtgt gaccctcaac ccaggcaacg    3540
ctggcgcagt ggcccgcttc ctcatgggcg tggccgctct cacctctggc accactttcg    3600
tgaccgacta cccggactcc ctcggcaagc gccctcaggg cgacctcctt gaggccctcg    3660
aacgcctcgg tgcctgggtg tcctccaacg acggtcgcct cccgatctcc gtgtccggcc    3720
cagtgcgcgg tggcaccgtg gaggtgtccg ccgagcgctc ctcccagtac gcctccgccc    3780
tcatgttcct cggccctctc ctcccggacg gactcgaact ccgcctcacc ggcgacatca    3840
agtcccacgc tccgctccgc cagacactcg acaccctctc tgacttcggc gtgcgcgcca    3900
ctgcctccga cgacctccgc cgcatctcca tcccgggtgg ccagaagtac cgcccaggcc    3960
gcgtgctcgt gccgggcgac tacccgggct ccgctgccat cctcaccgcc gctgccctcc    4020
tcccaggcga ggtgcgcctc tctaacctcc gcgagcacga cctccagggc gagaaggagg    4080
ccgtgaacgt gctccgcgag atgggcgctg acatcgtgcg cgagggcgat accctcaccg    4140
tgcgcggtgg ccgccctctc cacgccgtga ctcgcgacgg cgattccttc accgacgccg    4200
tgcaagccct caccgccgct gctgccttcg ccgagggcga caccacctgg gagaacgtgg    4260
ccactctccg cctcaaggag tgcgaccgca tctctgacac ccgcgctgag cttgagcgcc    4320
tcggcctccg cgcacgcgag accgccgact ctctctccgt gactggctct gctcacctcg    4380
ctggtggcat caccgccgac ggccacggcg accaccgcat gatcatgctc ctcaccctcc    4440
tcggcctccg cgcagacgct ccactccgca tcaccggcgc acaccacatc cgcaagtcct    4500
accctcagtt cttcgctcac ctcgaagccc tcggcgctcg cttcgagtac gctgaggcca    4560
ccgcctaata ggtcgagttt ctccataata atgtgtgagt agttcccaga taagggaatt    4620
```

```
agggttccta tagggtttcg ctcatgtgtt gagcatataa gaaaccctta gtatgtattt    4680
gtatttgtaa aatacttcta tcaataaaat ttctaattcc taaaaccaaa atccagtact    4740
aaaatccaga tcccccgaat taattcggcg ttaattcagt acattaaaaa cgtccgcaat    4800
gtgttattaa gttgtctaag cgtcaatttg tttacaccac aatatatcct gccaccagcc    4860
agccaacagc tccccgaccg gcagctcggc acaaaatcac cactcgatac aggcagccca    4920
tcagtccggg acggcgtcag cgggagagcc gttgtaaggc ggcagacttt gctcatgtta    4980
ccgatgctat tcggaagaac ggcaactaag ctgccgggtt tgaaacacgg atgatctcgc    5040
ggagggtagc atgttgattg taacgatgac agagcgttgc tgcctgtgat caccgcggtt    5100
tcaaaatcgg ctccgtcgat actatgttat acgccaactt gaaaacaac  tttgaaaaag    5160
ctgttttctg gtatttaagg ttttagaatg caaggaacag tgaattggag ttcgtcttgt    5220
tataattagc ttcttggggt atctttaaat actgtagaaa agaggaagga aataataaat    5280
ggctaaaatg agaatatcac cggaattgaa aaaactgatc gaaaaatacc gctgcgtaaa    5340
agatacggaa ggaatgtctc ctgctaaggt atataagctg gtgggagaaa atgaaaacct    5400
atatttaaaa atgacggaca gccggtataa agggaccacc tatgatgtgg aacgggaaaa    5460
ggacatgatg ctatggctgg aaggaaagct gcctgttcca aaggtcctgc actttgaacg    5520
gcatgatggc tggagcaatc tgctcatgag tgaggccgat ggcgtccttt gctcggaaga    5580
gtatgaagat gaacaaagcc ctgaaaagat tatcgagctg tatgcggagt gcatcaggct    5640
cttt cactcc atcgacatat cggattgtcc ctatacgaat agcttagaca gccgcttagc   5700
cgaattggat tacttactga ataacgatct ggccgatgtg gattgcgaaa actgggaaga    5760
agacactcca tttaaagatc cgcgcgagct gtatgatttt ttaaagacgg aaaagcccga    5820
agaggaactt gtcttttccc acggcgacct gggagacagc aacatctttg tgaaagatgg    5880
caaagtaagt ggctttattg atcttgggag aagcggcagg gcggacaagt ggtatgacat    5940
tgccttctgc gtccggtcga tcaggagga  tatcggggaa gaacagtatg tcgagctatt    6000
ttttgactta ctggggatca gcctgattg  ggagaaaata aaatattata ttttactgga    6060
tgaattgttt tagtacctag aatgcatgac caaaatccct taacgtgagt tttcgttcca    6120
ctgagcgtca gaccccgtag aaaagatcaa aggatcttct tgagatcctt ttttctgcg    6180
cgtaatctgc tgcttgcaaa caaaaaaacc accgctacca gcggtggttt gtttgccgga    6240
tcaagagcta ccaactcttt ttccgaaggt aactggcttc agcagagcgc agataccaaa    6300
tactgtcctt ctagtgtagc cgtagttagg ccaccacttc aagaactctg tagcaccgcc    6360
tacatacctc gctctgctaa tcctgttacc agtggctgct gccagtggcg ataagtcgtg    6420
tcttaccggg ttggactcaa gacgatagtt accggataag gcgcagcggt cgggctgaac    6480
gggggggttcg tgcacacagc ccagcttgga gcgaacgacc tacaccgaac tgagatacct    6540
acagcgtgag ctatgagaaa gcgccacgct tcccgaaggg agaaaggcgg acaggtatcc    6600
ggtaagcggc agggtcggaa caggagagcg cacgagggag cttccagggg gaaacgcctg    6660
gtatctttat agtcctgtcg ggtttcgcca cctctgactt gagcgtcgat ttttgtgatg    6720
ctcgtcaggg gggcggagcc tatggaaaaa cgccagcaac gcggcctttt tacggttcct    6780
ggccttttgc tggccttttg ctcacatgtt ctttcctgcg ttatcccctg attctgtgga    6840
taaccgtatt accgcctttg agtgagctga taccgctcgc cgcagccgaa cgaccgagcg    6900
cagcgagtca gtgagcgagg aagcggaaga gcgcctgatg cggtattttc tccttacgca    6960
```

```
tctgtgcggt atttcacacc gcatatggtg cactctcagt acaatctgct ctgatgccgc    7020
atagttaagc cagtatacac tccgctatcg ctacgtgact gggtcatggc tgcgccccga    7080
cacccgccaa cacccgctga cgcgccctga cgggcttgtc tgctcccggc atccgcttac    7140
agacaagctg tgaccgtctc cgggagctgc atgtgtcaga ggttttcacc gtcatcaccg    7200
aaacgcgcga ggcagggtgc cttgatgtgg gcgccggcgg tcgagtggcg acggcgcggc    7260
ttgtccgcgc cctggtagat tgcctggccg taggccagcc attttttgagc ggccagcggc    7320 cgcgataggc cgacgcgaag cggcggggcg tagggagcgc agcgaccgaa gggtaggcgc    7380
tttttgcagc tcttcggctg tgcgctggcc agacagttat gcacaggcca ggcgggtttt    7440
aagagtttta ataagttttta aagagtttta ggcggaaaaa tcgccttttt tctcttttat    7500
atcagtcact tacatgtgtg accggttccc aatgtacggc tttgggttcc caatgtacgg    7560
gttccggttc ccaatgtacg gctttgggtt cccaatgtac gtgctatcca caggaaagag    7620
accttttcga ccttttttccc ctgctagggc aatttgccct agcatctgct ccgtacatta    7680
ggaaccggcg gatgcttcgc cctcgatcag gttgcgtag cgcatgacta ggatcgggcc    7740
agcctgcccc gcctcctcct tcaaatcgta ctccggcagg tcatttgacc cgatcagctt    7800
gcgcacggtg aaacagaact tcttgaactc tccggcgctg ccactgcgtt cgtagatcgt    7860
cttgaacaac catctggctt ctgccttgcc tgcggcgcgg cgtgccaggc ggtagagaaa    7920
acggccgatg ccgggatcga tcaaaaagta atcggggtga accgtcagca cgtccgggtt    7980
cttgccttct gtgatctcgc ggtacatcca atcagctagc tcgatctcga tgtactccgg    8040
ccgcccggtt tcgctctttta cgatcttgta gcggctaatc aaggcttcac cctcggatac    8100
cgtcaccagg cggccgttct tggccttctt cgtacgctgc atggcaacgt gcgtggtgtt    8160
taaccgaatg caggtttcta ccaggtcgtc tttctgcttt ccgccatcgg ctcgccggca    8220
gaacttgagt acgtccgcaa cgtgtggacg gaacacgcgg ccgggcttgt ctcccttccc    8280
ttcccggtat cggttcatgg attcggttag atgggaaacc gccatcagta ccaggtcgta    8340
atcccacaca ctggccatgc cggccggccc tgcggaaacc tctacgtgcc cgtctggaag    8400
ctcgtagcgg atcacctcgc cagctcgtcg gtcacgcttc gacagacgga aaacggccac    8460
gtccatgatg ctgcgactat cgcgggtgcc cacgtcatag agcatcggaa cgaaaaaatc    8520
tggttgctcg tcgcccttgg gcggcttcct aatcgacggc gcaccggctg ccggcggttg    8580
ccgggattct ttgcggattc gatcagcggc cgcttgccac gattcaccgg ggcgtgcttc    8640
tgcctcgatg cgttgccgct gggcggcctg cgcggccttc aacttctcca ccaggtcatc    8700
acccagcgcc gcgccgattt gtaccgggcc ggatggtttg cgaccgtcac gccgattcct    8760
cgggcttggg ggttccagtg ccattgcagg gccggcagac aacccagccg cttacgcctg    8820
gccaaccgcc cgttcctcca cacatggggc attccacggc gtcggtgcct ggttgttctt    8880
gattttccat gccgcctcct ttagccgcta aaattcatct actcatttat tcatttgctc    8940
atttactctg gtagctgcgc gatgtattca gatagcagct cggtaatggt cttgccttgg    9000
cgtaccgcgt acatcttcag cttggtgtga tcctccgccg gcaactgaaa gttgacccgc    9060 ttcatgctg gcgtgtctgc caggctgcc aacgttgcag ccttgctgct gcgtgcgctc    9120
ggacggccgg cacttagcgt gtttgtgctt ttgctcattt tctctttacc tcattaactc    9180
aaatgagttt tgatttaatt tcagcggcca gcgcctggac ctcgcgggca gcgtcgccct    9240
cgggttctga ttcaagaacg gttgtgccgg cggcggcagt gcctgggtag ctcacgcgct    9300
gcgtgatacg ggactcaaga atgggcagct cgtacccggc cagcgcctcg gcaacctcac    9360
```

```
cgccgatgcg cgtgcctttg atcgcccgcg acacgacaaa ggccgcttgt agccttccat   9420
ccgtgacctc aatgcgctgc ttaaccagct ccaccaggtc ggcggtggcc catatgtcgt   9480
aagggcttgg ctgcaccgga atcagcacga agtcggctgc cttgatcgcg acacagcca    9540 agtccgccgc ctggggcgct ccgtcgatca ctacgaagtc gcgccggccg atggccttca   9600
cgtcgcggtc aatcgtcggg cggtcgatgc cgacaacggt tagcggttga tcttcccgca   9660
cggccgccca atcgcgggca ctgccctggg gatcggaatc gactaacaga acatcggccc   9720
cggcgagttg cagggcgcgg gctagatggg ttgcgatggt cgtcttgcct gacccgcctt   9780
tctggttaag tacagcgata accttcatgc gttccccttg cgtatttgtt tatttactca   9840
tcgcatcata tacgcagcga ccgcatgacg caagctgttt tactcaaata cacatcacct   9900
ttttagacgg cggcgctcgg tttcttcagc ggccaagctg gccggccagg ccgccagctt   9960
ggcatcagac aaaccggcca ggatttcatg cagccgcacg gttgagacgt gcgcgggcgg  10020
ctcgaacacg tacccggccg cgatcatctc cgcctcgatc tcttcggtaa tgaaaaacgg  10080
ttcgtcctgg ccgtcctggt gcggtttcat gcttgttcct cttggcgttc attctcggcg  10140
gccgccaggc cgtcggcctc ggtcaatgcg tcctcacgga aggcaccgcg ccgcctggcc  10200
tcggtgggcg tcacttcctc gctgcgctca agtgcgcggt acagggtcga gcgatgcacg  10260
ccaagcagtg cagccgcctc tttcacggtg cggccttcct ggtcgatcag ctcgcgggcg  10320
tgcgcgatct gtgccggggt gagggtaggg cggggggccaa acttcacgcc tcgggccttg  10380
gcggcctcgc gcccgctccg ggtgcggtcg atgattaggg aacgctcgaa ctcggcaatg  10440
ccggcgaaca cggtcaacac catgcggccg gccggcgtgg tggtgtcggc ccacggctct  10500
gccaggctac gcaggcccgc gccggcctcc tggatgcgct cggcaatgtc cagtaggtcg  10560
cgggtgctgc gggccaggcg gtctagcctg gtcactgtca caacgtcgcc agggcgtagg  10620
tggtcaagca tcctggccag ctccgggcgg tcgcgcctgg tgccggtgat cttctcggaa  10680
aacagcttgg tgcagccggc cgcgtgcagt tcggcccgtt ggttggtcaa gtcctggtcg  10740
tcggtgctga cgcgggcata gcccagcagg ccagcggcgg cgctcttgtt catggcgtaa  10800
tgtctccggt tctagtcgca agtattctac tttatgcgac taaaacacgc gacaagaaaa  10860
cgccaggaaa agggcagggc ggcagcctgt cgcgtaactt aggacttgtg cgacatgtcg  10920
ttttcagaag acgctgcac tgaacgtcag aagccgactg cactatagca gcggaggggt  10980
tggatcaaag tactttgatc ccgaggggaa ccctgtggtt ggcatgcaca tacaaatgga  11040
cgaacggata aaccttttca cgcccttta aatatccgtt attctaataa acgctctttt   11100
ctcttaggtt tacccgccaa tatatcctgt caaacactga tagtttaaac tgaaggcggg   11160
aaacgacaat ctgatccaag ctcaagctgc tctagcattc gccattcagg ctgcgcaact   11220
gttgggaagg gcgatcggtg cgggcctctt cgctattacg ccagctggcg aaagggggat   11280
gtgctgcaag gcgattaagt tgggtaacgc caggttttc ccagtcacga cgttgtaaaa   11340
cgacggccag tgccaagctt gcatgcctgc aggtcgactc tagaggatcc ccgggtaccg   11400
agctcgaatt                                                         11410
```

<210> SEQ ID NO 48
<211> LENGTH: 1324
<212> TYPE: DNA
<213> ORGANISM: Artificial Sequence
<220> FEATURE:
<223> OTHER INFORMATION: G10evo - EPSPS

<400> SEQUENCE: 48

```
ggatccgacg ccctgcccgc caccttcgac gtgatcgtgc atccagctcg cgaactccgc      60
ggcgagcttc gcgctcagcc atccaagaac tacaccactc gctacctcct cgccgctgcc     120
ctcgctgagg gcgagacccg cgtggtgggc gtggctacct ctgaggacgc cgaggccatg     180
ctccgctgcc tccgcgactg gggcgctggc gtggagcttg tgggcgatga cgccgtgatc     240
cgcggtttcg cgctcgccc acaggccggt gtgaccctca acccaggcaa cgctggcgca     300
gtggcccgct tcctcatggg cgtggccgct ctcacctctg caccactttt cgtgaccgac     360
tacccggact ccctcggcaa cgcccctcag ggcgacctcc ttgaggccct cgaacgcctc     420
ggtgcctggg tgtcctccaa cgacggtcgc ctcccgatct ccgtgtccgg cccagtgcgc     480
ggtggcaccg tggaggtgtc cgccgagcgc tcctcccagt acgcctccgc cctcatgttc     540
ctcggccctc tcctcccgga cggactcgaa ctccgcctca ccggcgacat caagtcccac     600
gctccgctcc gccagacact cgacacccte tctgacttcg gcgtgcgcgc cactgcctcc     660
gacgacctcc gccgcatctc catcccgggt ggccagaagt accgcccagg ccgcgtgctc     720
gtgccgggcg actacccggg ctccgctgcc atcctcaccg ccgctgccct cctcccaggc     780
gaggtgcgcc tctctaacct ccgcgagcac gacctccagg gcgagaagga ggccgtgaac     840
gtgctccgcg agatgggcgc tgacatcgtg cgcgagggcg ataccctcac cgtgcgcggt     900
ggccgccctc tccacgccgt gactcgcgac ggcgattcct tcaccgacgc cgtgcaagcc     960
ctcaccgccg ctgctgcctt cgccgagggc gacaccacct gggagaacgt ggccactctc    1020
cgcctcaagg agtgcgaccg catctctgac accgcgctg agcttgagcg cctcggcctc    1080
cgcgcacgcg agaccgccga ctctctctcc gtgactggct ctgctcacct cgctggtggc    1140
atcaccgccg acgccacgg cgaccaccgc atgatcatgc tcctcaccct cctcggcctc    1200
cgcgcagacg ctccactccg catcaccggc gcacaccaca tccgcaagtc ctaccctcag    1260
ttcttcgctc acctcgaagc cctcggcgct cgcttcgagt acgctgaggc caccgcctaa    1320
tagg                                                                  1324
```

<210> SEQ ID NO 49  
<211> LENGTH: 10386  
<212> TYPE: DNA  
<213> ORGANISM: Artificial Sequence  
<220> FEATURE:  
<223> OTHER INFORMATION: pCambia 1300-G10 (without p35S)

<400> SEQUENCE: 49

```
cctcgacgca tgcctacagt gcagcgtgac ccggtcgtgc ccctctctag agataatgag      60
cattgcatgt ctaagttata aaaaattacc acatattttt tttgtcacac ttgtttgaag     120
tgcagtttat ctatctttat acatatattt aaactttact ctacgaataa tataatctat     180
agtactacaa taatatcagt gttttagaga atcatataaa tgaacagtta gacatggtct     240
aaaggacaat tgagtatttt gacaacagga ctctacagtt ttatcttttt agtgtgcatg     300
tgttctcctt ttttttgca aatagcttca cctatataat acttcatcca ttttattagt     360
acatccattt aggtttagg gttaatggtt tttatagact aattttttta gtacatctat     420
tttattctat tttagcctct aaattaagaa aactaaaact ctattttagt ttttttattt     480
aataatttag atataaaata gaataaaata aagtgactaa aaattaaaca aatacccttt     540
aagaaattaa aaaaactaag gaaacatttt tcttgtttcg agtagataat gccagcctgt     600
taaacgccgt cgacgagtct aacggacacc aaccagcgaa ccagcagcgt cgcgtcgggc     660
```

```
caagcgaagc agacggcacg gcatctctgt cgctgcctct ggacccctct cgagagttcc      720
gctccaccgt tggacttgct ccgctgtcgg catccagaaa ttgcgtggcg gagcggcaga      780
cgtgagccgg cacggcaggc ggcctcctcc tcctctcacg gcacggcagc tacggggat       840
tcctttccca ccgctccttc gctttccctt cctcgcccgc cgtaataaat agacacccc       900
tccacaccct ctttccccaa cctcgtgttg ttcggagcgc acacacacac aaccagatct      960
ccccaaatc cacccgtcgg cacctccgct tcaaggtacg ccgctcgtcc tcccccccc      1020
cccctctcta ccttctctag atcggcgttc cggtccatgg ttagggcccg gtagttctac     1080
ttctgttcat gtttgtgtta gatcgtgtt tgtgttagat ccgtgctgct agcgttcgta     1140
cacggatgcg acctgtacgt cagacacgtt ctgattgcta acttgccagt gtttctcttt     1200
ggggaatcct gggatggctc tagccgttcc gcagacggga tcgatttcat gattttttt     1260
gtttcgttgc atagggtttg gtttgcccctt ttcctttatt tcaatatatg ccgtgcactt    1320
gtttgtcggg tcatcttttc atgcttttt ttgtcttggt tgtgatgatg tggtctggtt     1380
gggcggtcgt tctagatcgg agtagaattc tgtttcaaac tacctggtgg atttattaat   1440
tttggatctg tatgtgtgtg ccatacatat tcatagttac gaattgaaga tgatggatgg     1500
aaatatcgat ctaggatagg tatacatgtt gatgcgggtt ttactgatgc atatacagag    1560
atgcttttg ttcgcttggt tgtgatgatg tggtgtggtt gggcggtcgt tcattcgttc     1620
tagatcggag tagaatactg tttcaaacta cctggtgtat ttattaattt tggaactgta     1680
tgtgtgtgtc atacatcttc atagttacga gtttaagatg gatggaaata tcgatctagg    1740
ataggtatac atgttgatgt gggttttact gatgcatata catgatggca tatgcagcat    1800
ctattcatat gctctaacct tgagtaccta tctattataa taaacaagta tgttttataa    1860
ttattttgat cttgatatac ttggatgatg gcatatgcag cagctatatg tggattttttt 1920
tagccctgcc ttcatacgct atttatttgc ttggtactgt ttcttttgtc gatgctcacc    1980
ctgttgtttg gtgttacttc tgcaggtcga ctctagagga tctaccatgg ccaccgccgc    2040
cgccgcgtct accgcgctca ctggcgccac taccgctgcg cccaaggcga ggcgccgggc    2100
gcacctcctg gccacccgcc gcgccctcgc cgcgcccatc aggtgctcag cggcgtcacc    2160
cgccatgccg atggctcccc cggccacccc gctccggccg tggggcccca ccgatccccg    2220
caagggatcc gacgccctgc ccgccacctt cgacgtgatc gtgcatccag ctcgcgaact    2280
ccgcggcgag cttcgcgctc agccatccaa gaactacacc actcgctacc tcctcgccgc    2340
tgccctcgct gagggcgaga cccgcgtggt gggcgtggct acctctgagg acgccgaggc    2400
catgctccgc tgcctccgcg actggggcgc tggcgtggag cttgtgggcg atgacgccgt    2460
gatccgcggt ttcggcgctc gcccacaggc cggtgtgacc ctcaacccag gcaacgctgg    2520
cgcagtggcc cgcttcctca tgggcgtggc cgctctcacc tctggcacca ctttcgtgac    2580
cgactacccg gactccctcg gcaagcgccc tcagggcgac ctccttgagg ccctcgaacg    2640
cctcggtgcc tgggtgtcct ccaacgacgg tcgcctcccg atctccgtgt ccggcccagt    2700
gcgcggtggc accgtggagg tgtccgccga gcgctcctcc cagtacgcct ccgccctcat    2760
gttcctcggc cctctcctcc cggacggact cgaactccgc ctcaccggcg acatcaagtc    2820
ccacgctccg ctccgccaga cactcgacac cctctctgac ttcggcgtgc gcgccactgc    2880
ctccgacgac ctccgccgca tctccatccc gggtggccag aagtaccgcc caggccgcgt    2940
gctcgtgccg ggcgactacc cgggctccgc tgccatcctc accgccgctg ccctcctccc    3000
```

```
aggcgaggtg cgcctctcta acctccgcga gcacgacctc cagggcgaga aggaggccgt    3060
gaacgtgctc cgcgagatgg gcgctgacat cgtgcgcgag ggcgataccc tcaccgtgcg    3120
cggtggccgc cctctccacg ccgtgactcg cgacggcgat tccttcaccg acgccgtgca    3180
agccctcacc gccgctgctg ccttcgccga gggcgacacc acctgggaga acgtggccac    3240
tctccgcctc aaggagtgcg accgcatctc tgacacccgc gctgagcttg agcgcctcgg    3300
cctccgcgca cgcgagaccg ccgactctct ctccgtgact ggctctgctc acctcgctgg    3360
tggcatcacc gccgacggcc acggcgacca ccgcatgatc atgctcctca ccctcctcgg    3420
cctccgcgca gacgctccac tccgcatcac cggcgcacac cacatccgca agtcctaccc    3480
tcagttcttc gctcacctcg aagccctcgg cgctcgcttc gagtacgctg aggccaccgc    3540
ctaataggtc gagtttctcc ataataatgt gtgagtagtt cccagataag ggaattaggg    3600
ttcctatagg gtttcgctca tgtgttgagc atataagaaa cccttagtat gtatttgtat    3660
ttgtaaaata cttctatcaa taaaatttct aattcctaaa accaaaatcc agtactaaaa    3720
tccagatccc ccgaattaat tcggcgttaa ttcagtacat taaaaacgtc cgcaatgtgt    3780
tattaagttg tctaagcgtc aatttgttta caccacaata tatcctgcca ccagccagcc    3840
aacagctccc cgaccggcag ctcggcacaa aatcaccact cgatacaggc agcccatcag    3900
tccgggacgg cgtcagcggg agagccgttg taaggcggca gactttgctc atgttaccga    3960
tgctattcgg aagaacggca actaagctgc cgggtttgaa acacggatga tctcgcggag    4020
ggtagcatgt tgattgtaac gatgacagag cgttgctgcc tgtgatcacc gcggtttcaa    4080
aatcggctcc gtcgatacta tgttatacgc caactttgaa acaactttg aaaaagctgt     4140 tttctggtat ttaaggtttt agaatgcaag gaacagtgaa ttggagttcg tcttgttata    4200
attagcttct tggggtatct ttaaatactg tagaaaagag gaaggaaata ataaatggct    4260
aaaatgagaa tatcaccgga attgaaaaaa ctgatcgaaa aataccgctg cgtaaaagat    4320
acggaaggaa tgtctcctgc taaggtatat aagctggtgg gagaaaatga aaacctatat    4380
ttaaaaatga cggacagccg gtataaaggg accacctatg atgtggaacg ggaaaaggac    4440
atgatgctat ggctggaagg aaagctgcct gttccaaagg tcctgcactt tgaacggcat    4500
gatggctgga gcaatctgct catgagtgag gccgatggcg tcctttgctc ggaagagtat    4560
gaagatgaac aaagccctga aaagattatc gagctgtatg cggagtgcat caggctcttt    4620
cactccatcg acatatcgga ttgtccctat acgaatagct tagacagccg cttagccgaa    4680
ttggattact tactgaataa cgatctggcc gatgtggatt gcgaaaactg ggaagaagac    4740
actccattta aagatccgcg cgagctgtat gattttttaa agacggaaaa gcccgaagag    4800
gaacttgtct tttcccacgg cgacctggga gacagcaaca tctttgtgaa agatggcaaa    4860
gtaagtggct ttattgatct tgggagaagc ggcagggcgg acaagtggta tgacattgcc    4920
ttctgcgtcc ggtcgatcag ggaggatatc ggggaagaac agtatgtcga gctatttttt    4980
gacttactgg ggatcaagcc tgattgggag aaaataaaat attatatttt actggatgaa    5040
ttgttttagt acctagaatg catgaccaaa atcccttaac gtgagttttc gttccactga    5100
gcgtcagacc ccgtagaaaa gatcaaagga tcttcttgag atcctttttt tctgcgcgta    5160
atctgctgct tgcaaacaaa aaaaccaccg ctaccagcgg tggtttgttt gccggatcaa    5220
gagctaccaa ctctttttcc gaaggtaact ggcttcagca gagcgcagat accaaatact    5280
gtccttctag tgtagccgta gttaggccac cacttcaaga actctgtagc accgcctaca    5340
tacctcgctc tgctaatcct gttaccagtg gctgctgcca gtggcgataa gtcgtgtctt    5400
```

```
accgggttgg actcaagacg atagttaccg gataaggcgc agcggtcggg ctgaacgggg    5460
ggttcgtgca cacagcccag cttggagcga acgacctaca ccgaactgag atacctacag    5520
cgtgagctat gagaaagcgc cacgcttccc gaagggagaa aggcggacag gtatccggta    5580
agcggcaggg tcggaacagg agagcgcacg agggagcttc caggggggaaa cgcctggtat    5640 ctttatagtc ctgtcgggtt tcgccacctc tgacttgagc gtcgattttt gtgatgctcg    5700 tcagggggc ggagcctatg gaaaaacgcc agcaacgcgg cctttttacg gttcctggcc    5760
ttttgctggc cttttgctca catgttcttt cctgcgttat ccctgattc tgtggataac    5820 cgtattaccg cctttgagtg agctgatacc gctcgccgca gccgaacgac cgagcgcagc    5880
gagtcagtga gcgaggaagc ggaagagcgc ctgatgcggt attttctcct tacgcatctg    5940
tgcggtattt cacaccgcat atggtgcact ctcagtacaa tctgctctga tgccgcatag    6000
ttaagccagt atacactccg ctatcgctac gtgactgggt catggctgcg ccccgacacc    6060
cgccaacacc cgctgacgcg ccctgacggg cttgtctgct cccggcatcc gcttacagac    6120
aagctgtgac cgtctccggg agctgcatgt gtcagaggtt ttcaccgtca tcaccgaaac    6180
gcgcgaggca gggtgccttg atgtgggcgc cggcggtcga gtggcgacgg cgcggcttgt    6240
ccgcgccctg gtagattgcc tggccgtagg ccagccattt ttgagcggcc agcggccgcg    6300
ataggccgac gcgaagcggc ggggcgtagg gagcgcagcg accgaagggt aggcgctttt    6360
tgcagctctt cggctgtgcg ctggccagac agttatgcac aggccaggcg ggttttaaga    6420
gttttaataa gttttaaaga gttttaggcg gaaaaatcgc ctttttttctc ttttatatca    6480 gtcacttaca tgtgtgaccg gttcccaatg tacggctttg ggttcccaat gtacgggttc    6540
cggttcccaa tgtacggctt tgggttccca atgtacgtgc tatccacagg aaagagacct    6600
tttcgacctt ttttcccctgc tagggcaatt tgccctagca tctgctccgt acattaggaa    6660
ccggcggatg cttcgccctc gatcaggttg cggtagcgca tgactaggat cgggccagcc    6720
tgccccgcct cctccttcaa atcgtactcc ggcaggtcat ttgacccgat cagcttgcgc    6780
acggtgaaac agaacttctt gaactctccg gcgctgccac tgcgttcgta gatcgtcttg    6840
aacaaccatc tggcttctgc cttgcctgcg gcgcggcgtg ccaggcggta gagaaaacgg    6900
ccgatgccgg gatcgatcaa aaagtaatcg gggtgaaccg tcagcacgtc cgggttcttg    6960
ccttctgtga tctcgcggta catccaatca gctagctcga tctcgatgta ctccggccgc    7020
ccggtttcgc tctttacgat cttgtagcgg ctaatcaagg cttcaccctc ggataccgtc    7080
accaggcggc cgttcttggc cttcttcgta cgctgcatgg caacgtgcgt ggtgtttaac    7140
cgaatgcagg tttctaccag gtcgtctttc tgctttccgc catcggctcg ccggcagaac    7200
ttgagtacgt ccgcaacgtg tggacggaac acgcggccgg gcttgtctcc cttcccttcc    7260
cggtatcggt tcatggattc ggttagatgg gaaaccgcca tcagtaccag gtcgtaatcc    7320
cacacactgg ccatgccggc cggccctgcg gaaacctcta cgtgcccgtc tggaagctcg    7380
tagcggatca cctcgccagc tcgtcggtca cgcttcgaca gacggaaaac ggccacgtcc    7440
atgatgctgc gactatcgcg ggtgcccacg tcatagagca tcggaacgaa aaaatctggt    7500
tgctcgtcgc ccttgggcgg cttcctaatc gacggcgcac cggctgccgg cggttgccgg    7560
gattctttgc ggattcgatc agcggccgct tgccacgatt caccggggcg tgcttctgcc    7620
tcgatgcgtt gccgctgggc ggcctgcgcg gccttcaact tctccaccag gtcatcaccc    7680
agcgccgcgc cgatttgtac cgggccggat ggtttgcgac cgtcacgccg attcctcggg    7740
```

-continued

```
cttgggggtt ccagtgccat tgcagggccg gcagacaacc cagccgctta cgcctggcca   7800
accgcccgtt cctccacaca tggggcattc cacggcgtcg gtgcctggtt gttcttgatt   7860
ttccatgccg cctcctttag ccgctaaaat tcatctactc atttattcat ttgctcattt   7920
actctggtag ctgcgcgatg tattcagata gcagctcggt aatggtcttg ccttggcgta   7980
ccgcgtacat cttcagcttg gtgtgatcct ccgccggcaa ctgaaagttg accgcttca    8040
tggctggcgt gtctgccagg ctggccaacg ttgcagcctt gctgctgcgt gcgctcggac   8100
ggccggcact tagcgtgttt gtgcttttgc tcattttctc tttacctcat taactcaaat   8160
gagttttgat ttaatttcag cggccagcgc ctggacctcg cgggcagcgt cgccctcggg   8220
ttctgattca agaacggttg tgccggcggc ggcagtgcct gggtagctca cgcgctgcgt   8280
gatacgggac tcaagaatgg gcagctcgta cccggccagc gcctcggcaa cctcaccgcc   8340
gatgcgcgtg cctttgatcg cccgcgacac gacaaaggcc gcttgtagcc ttccatccgt   8400
gacctcaatg cgctgcttaa ccagctccac caggtcggcg gtgcccata tgtcgtaagg    8460
gcttggctgc accggaatca gcacgaagtc ggctgccttg atcgcggaca cagccaagtc   8520
cgccgcctgg ggcgctccgt cgatcactac gaagtcgcgc cggccgatgg ccttcacgtc   8580
gcggtcaatc gtcgggcggt cgatgccgac aacggttagc ggttgatctt cccgcacggc   8640
cgcccaatcg cgggcactgc cctggggatc ggaatcgact aacagaacat cggcccggc    8700
gagttgcagg gcgcgggcta gatgggttgc gatggtcgtc ttgcctgacc cgccttctg    8760
gttaagtaca gcgataacct tcatgcgttc cccttgcgta tttgtttatt tactcatcgc   8820
atcatatacg cagcgaccgc atgacgcaag ctgttttact caaatacaca tcaccttttt   8880
agacggcggc gctcggtttc ttcagcggcc aagctggccg gccaggccgc cagcttggca   8940
tcagacaaac cggccaggat ttcatgcagc cgcacggttg agacgtgcgc gggcggctcg   9000
aacacgtacc cggccgcgat catctccgcc tcgatctctt cggtaatgaa aaacggttcg   9060
tcctggccgt cctggtgcgg tttcatgctt gttcctcttg gcgttcattc tcggcggccg   9120
ccagggcgtc ggcctcggtc aatgcgtcct cacggaaggc accgcgccgc ctggcctcgg   9180
tgggcgtcac ttcctcgctg cgctcaagtg cgcggtacag ggtcgagcga tgcacgccaa   9240
gcagtgcagc cgcctctttc acggtgcggc cttcctggtc gatcagctcg cgggcgtgcg   9300
cgatctgtgc cggggtgagg gtagggcggg ggccaaactt cacgcctcgg gccttggcgg   9360
cctcgcgccc gctccgggtg cggtcgatga ttagggaacg ctcgaactcg gcaatgccgg   9420
cgaacacggt caacaccatg cggccggccg cgtggtggt gtcggcccac ggctctgcca    9480
ggctacgcag gcccgcgccg gcctcctgga tgcgctcggc aatgtccagt aggtcgcggg   9540
tgctgcgggc caggcggtct agcctggtca ctgtcacaac gtcgccaggg cgtaggtggt   9600
caagcatcct ggccagctcc gggcggtcgc gcctggtgcc ggtgatcttc tcggaaaaca   9660
gcttggtgca gccggccgcg tgcagttcgg cccgttggtt ggtcaagtcc tggtcgtcgg   9720
tgctgacgcg ggcatagccc agcaggccag cggcggcgct cttgttcatg gcgtaatgtc   9780
tccggttcta gtcgcaagta ttctacttta tgcgactaaa acacgcgaca agaaaacgcc   9840
aggaaaaggg cagggcggca gcctgtcgcg taacttagga cttgtgcgac atgtcgtttt   9900
cagaagacgg ctgcactgaa cgtcagaagc cgactgcact atagcagcgg aggggttgga   9960
tcaaagtact ttgatcccga ggggaaccct gtggttggca tgcacataca aatggacgaa  10020
cggataaacc ttttcacgcc cttttaaata tccgttattc taataaacgc tcttttctct  10080
taggtttacc cgccaatata tcctgtcaaa cactgatagt ttaaactgaa ggcgggaaac  10140
```

```
gacaatctga tccaagctca agctgctcta gcattcgcca ttcaggctgc gcaactgttg    10200
ggaagggcga tcggtgcggg cctcttcgct attacgccag ctggcgaaag ggggatgtgc    10260
tgcaaggcga ttaagttggg taacgccagg gttttcccag tcacgacgtt gtaaaacgac    10320
ggccagtgcc aagcttgcat gcctgcaggt cgactctaga ggatccccgg gtaccgagct    10380
cgaatt                                                               10386

<210> SEQ ID NO 50
<211> LENGTH: 152
<212> TYPE: DNA
<213> ORGANISM: Artificial Sequence
<220> FEATURE:
<223> OTHER INFORMATION: Left border sequence of T-DNA of HAS-20

<400> SEQUENCE: 50
gagagagaaa cagtttgagt catagagata gtagcaggga gcatgctatt atccggttag      60
aagggtgatc cggccatgca aagggtgatc cgtgtgcgg  acgaggcca  cgactgcgac     120 ggcaaaaaaa aatctcgaga ggggaagaa  aa                                   152

<210> SEQ ID NO 51
<211> LENGTH: 170
<212> TYPE: DNA
<213> ORGANISM: Artificial Sequence
<220> FEATURE:
<223> OTHER INFORMATION: Right border sequence of T-DNA of HAS-20

<400> SEQUENCE: 51
gcgcgaaaag gccaataaaa gaggagagag agagagatcg cgggagggcg caggttacga      60
ggaggaagag gagaagttga ggaggtggca gtggctgtag cctgccacgt aggacgatcg     120
gagccaatga cctggtggtc catggcgttg actgtatccg tacgtccacg                170

<210> SEQ ID NO 52
<211> LENGTH: 2142
<212> TYPE: DNA
<213> ORGANISM: Oryza sativa

<400> SEQUENCE: 52
aagctttata ctctacttct aatattcctt attttaatt  ccgaattta gctatttcta      60 aattgtattt ctatatggac tctacttttt cttttctcc gattaatgtg agaatttcta     120
gtccatgaga gcgaacgtgg aggctccttt ttctattcct ttaataatat aatagatggt     180
acggtagttg aaaactataa ttacgtaatt aagagttcgc taaaataaat cccatgttgt     240
agaggtcagg ataattatat tgtattagac cattcccaac ccaaaacact agacatagtt     300
tccataaact ccacatcatc aagaaactag tactagacat tactcttcca atgcaaacac     360
cactattcca tacttaaatt taatgctatt tatatcacat gatgtcttgg atgttgtgta     420
gaaactatat ctcatgcaag acatgatttc cttctctttc ctcatttatt tacttgccac     480
atcatttttc atcctaggtg acaacttatt taatgctatg gacactatcc tagtcattgg     540
gttgggaatg gccttactcc ctccattcca aaatagcaca actactctta acccaaaaaa     600
caaaaaataa ttattatcat attatagttt gaatgatcct aataaatata atgcatatat     660
ccaatatgat tagataacat gagagtgaag gatttaaaaa taataataat ttaatggaga     720
agatgccata gttaattgta tacttgcatg catgccttat attatggaac atctaagaaa     780
attggttgtg ctttatatta tgcaatggag ggagtgtctt aaaaaatata ctccagtttg     840
```

```
taattctaac atattaccat gttaattgga taaaaattat atatgttaga tggtggtgga    900
ttgaaattat aatggttgat ataattatat tcgaaacaca aatagcatat gtggagattg    960
aagctataag atgtatttca aatagaatcc tacttaaatc tactgtatgc aaatgtatct   1020
ttggaaaaag ctacgaatta cattaagaaa atgtattttc taatatacac tttctctatc   1080
gtaaaatata gctatctata gcatttaaaa attatcataa aatataacaa cttctatacc   1140
aatcacaacc ttcgacattc aaattctcca cctagtcctt cttaaccaaa catttctttt   1200
ctcatttaat tttatctact tttttaatcc cttatatcca aacttaaaac tttctattta   1260
gaatggaggt aattctgtat atagattacc aaaaggtaca agagctaaga atcgtgcatc   1320
aaattcactt cggaaaatta cataagaaaa acatttgcta gtttgttcta cataaatctc   1380
gagaattttc acaacggaac acgaagctag gagaatttca cattttataa aacttttata   1440
aaatgattaa aaaatattga aaaataaatt aaaaaaatct aaagtcaact tcaaattaaa   1500
aaattaaaat taaatttttg gctaataaac atagcaaaag ccgaaagatg agactgaaag   1560
ctacccagat caaacagttc tatcgctata gaggatccga gcaaaaaaca gggccggccg   1620
gccggcagaa gaacacacca caccactccc cagtccccag cccaccccca ccccccccc   1680
tcgtggcact gtagccagtg tactatactg ccctgccctt caccactttc acctccctcc   1740
tcgagtcttc tcctctcgtc tcccctctc cctctcctct ccgccaccac gccaccgtgc   1800
ttccctcccc tttgttcctg tagcgttccg aataaaagcc cacctgcttt cctttcccgc   1860
gaccattacc ataaaagag cttgctccca ccgcctctct ctctatctcc ccgtcgctag   1920
ctaccagcag caacaagtac actccccca ctcctccccc acacgccgcg tacaactagc   1980
taagcagagg agagggagag agagagaggt ggggttttga tggaagtaca attctagcta   2040
tgttcttgat cggggccatg atcgcggatc tctagaaagt tctagatctt ccgtgcgtgg   2100
tgggcgggtg ggggtgttct tggtagggta ggtaagggat cc                     2142

<210> SEQ ID NO 53
<211> LENGTH: 2017
<212> TYPE: DNA
<213> ORGANISM: Zea mays
<220> FEATURE:
<221> NAME/KEY: misc_feature
<222> LOCATION: 1477
<223> OTHER INFORMATION: n = A,T,C or G

<400> SEQUENCE: 53
aagcttaccg gtcgccgttg gcccggacgg tccgtgctca tgtgcggatg gtccggacat     60
gcgtagatcg acgaatttat caccgatgtg tggaggaggt tgcggttgcc cagggcatgt    120
gtctatcgac atcccataaa ggggttataa ctggtcgtga caacctgtag ccgatgaatt    180
acacgtgttt tccccaaatt catcctcgcg cgaaggaaaa tttgcaccag tagatttatc    240
aaacgcacgg tactagcctc ctataatcat tttgcatacc ccctatgata ttttgcattt    300
gttctcgctg ttcatctaca taattttaa gagattatag ctcgtttgtg ttgcttacct    360
cggggtagtc gtggtaggtc gaagtgaagt cagatccgtc gccagttgtc gaacgacctt    420
gttattcctg tccaccttga agttggccag gaactttgcc tttgcctctt ggatcagctg    480
ctccttgtgc tcctcgaact ggagctgttc gtcagccggc aaggtttccc aagtcgactc    540
tatgatattg ctgggggaga cttcagaact atcccttgaa tcggccattg agggccgatt    600
tgatgggtct atatgtgtcg tccccagcgg ggtcaccaaa aagtgtgttg gcgcttttc     660
tgagtgccaa tcactgcgtg agaaccggcg gcggtgctca ctgcacaggc gcggacggtc    720
```

```
cgcggccagg ggccggacgg tctgcgacct ggcgcagggc ttagggtttc ctgcttgacg    780
gtcggacgat ccgcgcctat aggccggacg tccgcacgt gtgcagggca gcgaaggtcg     840
tcggtggcgc ctggatctcg ctcccgggag ggaccccgtc ggggaggaga gatcctaggt    900
gttgtctagg cttggcaggc cgacctagac tcctatcgat atagagtcga agagaagcgg    960
agaatttggg gattggaagg ctaaactaga actactccta aatatacaag aaataaatac   1020
gagataaact ggtattgatt cgattgatgg tgtttaatcg gtcggtattc ctctgtattt   1080
atagaggagg ggggctggac ccgttacaaa catatttttc gagctaattc tgtgaatcta   1140
gccaacaact atagcaagaa actcagaatt ctaactggtt ctgcgcgcgc aaaccgtccg   1200 acccttttatt tgatgctcac cagaaccctg tcttaccaat gtattgaaat tgatttatgg   1260
tgaagataga aatctaaagt tgtaattctt aaaataaagc actcctaaac agaacattaa   1320
tctttataat tgatattcga atattttagt ccggtaaccg aacgcccagt aatttgaaga   1380
atatggtctt tatttgtagc cggcggcatc tcgaaaagct agatctaact ccgaaaacaa   1440
acacgcaaaa tctaccggaa aaatctcccc agcaaanaag cagacgtggg gcctgtcatg   1500
tacgcacggg gcatgactcg tgcaagagca acaagtgctg tcgttgcaga ggatccgagc   1560
taaaacaatc cagcacacgg ccactctcgt ctctcctctt cctcctcttc cctccgtacc   1620 gcccgcccctt cacctcctcg actcttctcc accgccccct ccctcctcgc gtctctctcc   1680 cccttttgtcc ctgtagagct ccaaataaaa ccccaccggt tttcttttcc cgcggcaatt   1740
accataaaaa gagctcccaa tctctctcct ctctccggcc cctctctctc gtttctggca   1800
gcagtggtgc ggtactacca ccgctctcac tccacacaca cacaccgagt atacggttaa   1860
gcaggagaga gaacgggaga gtgagactga gaccgggtcc caagtacaat tctcgcctgg   1920
ttcttgatcg aaggcatgat caagaatcac cagaaagttc tagatcttta gacggcagtc   1980
ttctttggac tcctcggttt cttttgttct gggatcc                              2017
```

<210> SEQ ID NO 54
<211> LENGTH: 1898
<212> TYPE: DNA
<213> ORGANISM: Triticum aestivum

<400> SEQUENCE: 54

```
aagcttgtgc agtgagttgg agagcaactt tgcagtccat cgtggcatgt tccactactg     60
atgccaatta tatggctatt tccgaggcat gcaagaagc tatttgattg tgaggtttat    120
acactcggct ttgtggagat tcatcttgcc ctactgtatt tagtggaagt gctatatatc    180
ttacaaaaaa tctaatgtat catgagacaa caaagcacat tgatatcaga tatcactata    240
ttcgagatgt tgctgaaggt tatttgaagg tatgaaagat aagtactcat aataatcctg    300
ctgatatgat gacaaagcca gtttctacca ataagtttga gcaaatgtag gcgctctcgc    360
tgcccagccg cctgcgccac ccaagcccgc aaccatgcag tgcgctttgc tgcaaagcac    420
cgctcacgcc ctcatccccg tccgcgcgcc cctgtgtgct cacgacgagt tgcgtcgttg    480
aggtatttgg ggaaccaatt gtaatctagc tatcgatttt agggtgtgtt gtgctatttt    540
gtatggacct tgttataaat tcaactagtg actagtgggc tgccgtgtga actggtcgt    600 aatggtagta tcatagttag tatcatgcat gccaactaga caatttttaat gaggtgtcat    660 agcattaaat aaagaaagag atgatagagc atcacatcat gacaccgtat cataataaat    720
gatactccct ccgtccgggt ttattaggcc taaagacaac ttttcttaga ccaagacaca    780
```

-continued

```
tagtaatttg atcacattaa ttcttccatt ccactcccaa tgcactctct cacatgcatg    840
cagccaatga aaaagcacac atgaagtgta ttaactttc agccatgca ccaacaacaa     900
tagcttcaa tacaaccaat gaaatggttg catgcatgca tccttccaac gccgggcctt    960
ataaaagggg gcatgcttgt gatgctgaga ggcctaataa acccggacgg agggagtatg   1020
ctactttgtg tcatgcatga caataaataa aatagtacat gatactaata tatgatacta   1080
tgcattagag aggtactatt attcactagt atcatatgca tgatactagc atatgatact   1140
ctccattaca accaggctga ccgaaatagt ctttacagga tcagtttcgc ccgatgccac   1200
atggtaccac aaatccattt tagggcgagc cgtatactgt ttttgtagag gcgttttttg   1260
cggtataacc tagagctgtc taaagttgca atatcgagct tttacatttt cccctaaaac   1320
agggtttgat ttttacagca gagagtttct tacagtgaac gtagtatcta agcagtggca   1380
gcagctagaa gatccgtgca acatgagaca caagagctct aacaaactcc cggaatcatc   1440
catgtccccg aaagatgaac acgttctggc gtcacagaag atccgagcca acagggccgg   1500
ccagccgcac aacacaacac cccgcagcgg gcgcaggagg cagcgcttct tcctcccgag   1560
accagccagc cgctctccct ccctcccct tgttcctgta gacttccaaa taaaagccca    1620
cctgctttct tttcccgcga ccatttccat aaaaagagct ccccgcccct ctctcctc     1680
ctccccccag ccccaggtac ccctccaccc aacccagtcc acagctaagc aagaagggc    1740
aggcgggcga gggagagaga gagagaggga ccgctcaagt acaattctag cctagtttct   1800
tgatcgcggt ttgcagccac gacccagaat taatcccaag aatgttctag atcttccgcc   1860
tagcgccgcc gccgccgctg ctccaattcg gcggatcc                           1898
```

<210> SEQ ID NO 55
<211> LENGTH: 2067
<212> TYPE: DNA
<213> ORGANISM: Sorghum Bicolor

<400> SEQUENCE: 55

```
aagcttagtt gtgtttcata atttttatgt ttttagaatt tggttcgttc atgtgtctgt     60
taatgacttc tgtgtttgca gttttggcac aagttagtta attcgttcct ttgtgtttaa   120
tgacttttta tacataaaag atgttttata actcctaaga ttttaagttt ttcgcataag    180
ttatattta taagcataag ttatatgatg taagttaata tacataaatt agtagcagaa    240
aaaataaatc ttcgaaacat gtgcaagtag ggtctagttt tgttttgtct cgtcgtgtaa    300
acaaatcagt gcagacgaaa ttaaaaaag atacgatacg ccgttcagaa gttatagtat    360
tttaaaataa atatatttct cttttctat gacgtcagtt atctttaaaa agcgcgcatg    420
aatgtggaag tgtggaagaa gcgctgcgta tgtgcggctg gttgccaaaa agagaaagag    480
gtggaatttt tttctaaata aaatatgcct taaattgatc gtttaatttg atatgggtga    540
acgttcgtaa tttagtaaga tcgattgtca cgtgcccta tcctttcctg cctatgccat    600
gggctctttt ctatcaatat tttggttggc gttaacggtg tttgcagata tcgttttcc    660
ttcatagagg tattgctttt gaaatcccct tggtagttgtt gctacattgg gctgggtggt   720
ttgtggttta gttgacaact ttgtttgtga agatctgtct ctgttatcat taaatgttga    780
ttttcggtag tgttggtaca tagaattttg tttttatatt tgtctatatt tatttacttc   840
ttcttatta acacatagac cgacaattta accgtcggc ttctcttaaa aaaaaactaa    900
gacagaattg aaaactactt ttggcgtcag ctaaaattgc agtcacgaga tcaggggcga    960
agctacgtag atgacagtgg gtgcagatgc accacccaaa attcatgaaa acaatagatt   1020
```

```
tttgtaaaat tcaccatat atgcaccccg tataatacaa atctatgcac ctacaaggca    1080
agtgtaccac cctctaattt gctctagctt cgccactgca cgagacagta ataataagga    1140
aaaaaagact agaaacatga caataccttg aagtcagagt tagagtcaat gccaatgggt    1200
agggtaaaga cacatcgaga taaaaacaat tagttatctt cgttaaagcg gagcttttgt    1260
atgcatacaa ttattatttt tgtattgtta taagaattct atagaaattt cgtaagacaa    1320
ttgtaggaac aagattgttt ccatattcca agatgcccta aataatgaaa atgtaataga    1380
tttgtagccg gaacgttaat gtatggcatc tcgaaaagct aaagctaact ccgaaaacaa    1440
acacacaaaa tccaccggaa aaatctcccc cagcaaagag gcagacgtgg ggcctgtcat    1500
gtacgcacgg ggcatgactc gtgcaagagc aacaagtgct gtcgttgcag aggatccgga    1560
gctaaacaat ccagcgcacg acggcctctc tcgtctctcc tcttccctcc tccgtaccgc    1620
ccgcccttcc tccacctcgc tccctcctcc tcgactcttc tccactcagg cctctccctt    1680
ctccttcctc tcgtctcgtc tctctcccct ttgtccctgt agagctagct ccaaataaaa    1740
ccccaccggt tttcttttcc cgcgacaatt accataaaaa gagctcccaa tctctctctc    1800
tctcctctct ccgcccccct ctctctccct cgtttctggc agcagtggtg cggtactacc    1860
acaccgctct cactccacac acaccgagta tacagctaag caggagagag aacgggccgg    1920
gagagagaga gagagacggg gtccccaagt acaattctcg cctggttctt gatcgaaggc    1980
atgatcaaga atcaccagaa agttctagat ctttagacgg ccgtctccct tggacgcctc    2040
ggtttctttt gttctgcagc tggatcc                                       2067
```

<210> SEQ ID NO 56
<211> LENGTH: 2052
<212> TYPE: DNA
<213> ORGANISM: Artificial Sequence
<220> FEATURE:
<223> OTHER INFORMATION: OsTEL cDNA

<400> SEQUENCE: 56

```
atggaggaag gaggtgggag tggcgtgggt gggatgcagg gagcggcgtc gaatcttctg     60
gacgccggag ctcaggcgtt ctaccctgcc gtcggcgcgc cgttcccgtt ccagcagctt    120
ccgcaccagc tgtactgccc gcagccgccg ccgccgccgt accaggtcat gccggtgccg    180
ccgccgccgc cgccggtggg cttgcctgta ccgccgctgc cggcgacgat ggcgccgcag    240
ccgggctact gcgtgccggc ggccgcgacg gtggtggacg gtccggccag ccgcgccgtc    300
gtgctgagcc tggtgccgcc gcacgcgccg gaggacgaga tcgcccgcgc gatggctccg    360
ttcggtgcgg tgcgcgccgt ggacgcgtcg gcggtggcgt ccgagggcgt cgcgaccgtc    420
tacttcttcg atctccgctc cgccgagcac gccgtcacgg gggtccgcga gcagcacatc    480
cggcagcagt gccggctcgg ccagctctac gccgccgccg ccgccgccgc cgcctcgtcc    540
ccgacctggc cccgccggc gtgggactgg ccccacgacg acaaccgcgg gctcgtcctc    600
ggccaggccg tctgggccca cttcgccgcc gcctccaccg tccccgacga cggcgccagc    660
cgcggctccc tcgtcgtgct caattccctc cccgccatgt ccgtgttcga actccgcgaa    720
atcttccaag catacggtga cgtgaaggac gtgagggagt cggcgctgcg gccgagcaac    780
aagttcgtcg agttcttcga cacgcgcgac gccgaccgcg cgctccacga gctcaacggc    840
aaggagctct cggccgccg cctcgtcgtc gagtacacgc gccttccct ccccggccca    900 cgcaggcgcg ggcacgtgtc gcaccagccc ttggccccga cgccgccgag gctgcaggcg    960
```

| | |
|---|---|
| gcttggcggc cggcgccggc gccgtcgcag tctgcgcagc cgtcgtcgtc tggctccggc | 1020 |
| aaggcgaggg aaggcgtggt gcttctgcgc aggagctccg ggaaaggtag ctcgggtagc | 1080 |
| cagtccaagg gcggtggcaa tgctggccac gagcggaaga gcaagggcgg caagagcgcc | 1140 |
| gcggcggcgt gttcgacggc ggcttcagca tcgtcgtcta ccgcaacggc gcccagcaag | 1200 |
| caaagccaga aaggcggcgg cggcggcggc ggccgtggcg ggagctggag aggccagaag | 1260 |
| agcgggtggg aggctcgctt cctgttcaaa gaacccgagg ccgcggccgc cgccgccggc | 1320 |
| gacgctgccg cctccgagac gcatgagccg gcgagctgca aggacgcgag aaccaccgtg | 1380 |
| atgatcagga acatcccaaa caagtacagc cagaagctgc tgctcaacat gctggacaac | 1440 |
| cactgcatcc tctccaacca gcagatcgag gcgagctgcg aagacgaagc ccagccattc | 1500 |
| tcctcctacg atttcctcta cctccccata gatttcaaca acaagtgcaa cgtgggctat | 1560 |
| ggcttcgtca acctcacctc gccggaggct gccgtgcggc tgtacaaggc gttccacaag | 1620 |
| caaccgtggg aggtgttcaa ctcgcgcaag atttgccaag tgacatacgc acgcgtgcaa | 1680 |
| ggcctggacg cgctcaagga gcacttcaag aactccaagt tcccgtgcga cagcgacgag | 1740 |
| tacctgcccg tggtgttctc gccgccgcgg gacggcaagc tgctcacgga gccggtgccg | 1800 |
| ctggtcggcc gctcgccggc accgtcgtcg gcgtccgggg cgtcgtcgcc gcccaagagc | 1860 |
| tgcgccgcga gcgtcgaccc actcgcgcag gagctcatga cagcgccgtc ttcctccggc | 1920 |
| gacggcgcct cctccgcctc ctcgtccaat gcccacgccg acgaggatga cgtccatggc | 1980 |
| gaaaccggtg gtgaccgtgg cgacgacgcg gggctcgatc tggagctaca gcgcctaggc | 2040 |
| tacactgact ag | 2052 |

<210> SEQ ID NO 57
<211> LENGTH: 1971
<212> TYPE: DNA
<213> ORGANISM: Artificial Sequence
<220> FEATURE:
<223> OTHER INFORMATION: ZmTE1 cDNA

<400> SEQUENCE: 57

| | |
|---|---|
| atgggtgggt tcccggaagc cacgggtaac cttctcgatg ccgcagctca ggagttccac | 60 |
| cctacggtct gtgcccccta tcctctacag ccgcttccgc aacagctata ctgccccac | 120 |
| ccatatccag ccatgccggt gcctccgccg ccgcaaatag ccatgttaca gccagtgcct | 180 |
| ccgatggcga tggccatggc gccgcagccg gggtacacct tgccaacgac gacgccggtg | 240 |
| gtcaatggcc cgtcgagccg cgtcgtggtg ctgggccttg tccgccgcca cgcgcaggag | 300 |
| gccgacgtgg cgcaggcgat ggcgccattc ggcgcgatcc gctcggtcga cgcgtgcgcg | 360 |
| gtggcgtccg agggcgtggc caccgtccat ttcttcgaca tccgcgccgc cgagctcgcc | 420 |
| ttgacctgtg tccgcgagca gcacatgcgc cagcagagcc gcctcgggca gctctacgcg | 480 |
| gcggccgccg tagcccccggc gtgggctcct gcaccgacgc cccaggcctg gactggccc | 540 |
| caccccaacg acgacggccg cggcctcgtc ctcgggcacg ccgtgtgggc ccacttcgcc | 600 |
| accggcgccg acgacggcga caaccgcggc tccctggtgg tcctgagccc cctgcccggc | 660 |
| gtctcggtcg ctgacctccg ccaagtcttc caggccttcg ggacttgaa ggatgtgagg | 720 |
| gagtcggcgc agcggcccag ccacaagttc gtggacttct tcgacacgcg cgacgccgcg | 780 |
| cgcgcgctcg ccgagctcaa cggccaggag cttttcggcc gccgcctcgt cgtcgagttc | 840 |
| acgcgccctt ccggccccgg gcccgcagg gcgggtacg cacccacca gcaccggccc | 900 |
| accgcgccga ctccgccgag gcttcaagcg acgtggcgac cgtcccaacc gacgtcgtct | 960 |

```
cagccgccgg catcctcgtc gtcgtccggt tccgtaaggg cgagggaagg agtggtgctt      1020
ctgaggagga gctcctgtaa gtctagcgcg ggcagcgacc agtcgtccaa gggaggcaat      1080
gccggaacga gccatgagcg caagaccaag ggcggcaaga tcgtggtggc ggcggcggcg      1140
gcatcctcgt cgaccccgac agcgtccggg aagcaaaccc agaaaggcgt cgggagcagc      1200
ggcggcggga gctggaaagg acgaaagagc gggtgggagg cgcgcttcct gttcaaggag      1260
cccgaggccg gcggcggcgc cgacacgcaa gcaacgccgg cttcggagat ggatacgagg      1320
accaccgtca tgatcaggaa cataccgaac aagtacagcc agaagctgct gctcaacatg      1380
ctggacaacc actgcatcca atccaacgag tggatcgtgg cgagcggcga ggagcagccc      1440
ttctccgcct acgatttcgt ctacctcccc atagatttca acaacaagtg taatgtgggc      1500
tacggcttcg tcaacctgac atcgccgag gctcgcgtgc ggctgtacaa ggcgttccac      1560
aagcagccat gggaggtgta caactcgcgc aagatctgcc aagtgacata cgcgcgcgta      1620
caaggcctgg aagcgctgaa ggagcacttc aagaactcca agttcccgtg cgacagcgac      1680
gagtacctgc ccgtggcgtt ctcgccggcg cgcgacggca aggagcttac ggatccagtg      1740
cccatcgtgg gccgctcgcc cgcggcgtcg tccgcgtcgt cgcctcccaa gagccgggcg      1800
gctagcgtgg accggcttgg gcaggagctg atgccggcgc cgtcgtcatc cgcggacggc      1860
gcgtcgtcga ccactacgtc cacccacgcg ccgtccgaac acgacgagga ggaggaggag      1920
ggagacatca ggctcgcagg cgagctgcgg cggcttggct acgacgacta g                1971

<210> SEQ ID NO 58
<211> LENGTH: 61
<212> TYPE: DNA
<213> ORGANISM: Artificial Sequence
<220> FEATURE:
<223> OTHER INFORMATION: Targeted sequence by TALEN

<400> SEQUENCE: 58
ctgtttatac aagagcccta tcaatgatgg cctaaatacg agactacta gatcaactaa       60 c                                                                     61

<210> SEQ ID NO 59
<211> LENGTH: 4968
<212> TYPE: DNA
<213> ORGANISM: Artificial sequence
<220> FEATURE:
<223> OTHER INFORMATION: Expression cassette of EPSPS with 35S promoter
      and flanked with corn sequence at each side

<400> SEQUENCE: 59
ctcgagagat ctccaggtat tgtatgaaga gaaaacttct caattctcag tttctcacgc       60
aagtcaagaa aacgctcgac ctctgccctg cactacacta cacactctca cgcaagtcaa      120
gaaaacttct gaacccttgc cctatccata ttattatatt aagaggcgta tcatgcaggt      180
cgagaaaaac cttagacata tgctttgact tgggatagac gaggtaattt tcttaacacc      240
aacctgagtt ttttaacac caacctaaga atcgctttcg caatgagtcg aacccaaaac      300
ttaagaagta ctactcaaac cacctaacta atccacctta tagagacata cgtatgcttt      360
aatcattatc taaacaaatt tgtcaatggg agattttgat aatttagaca gatttaagag      420
ggtatttaat ttttataata atgtaatgca gtttgagtta tgcaaattgt cgattataag      480
gctatctcta gcagatttct catctcgtct cctatttcaa acttcactat gtaaatattg      540
tcaaacaata tcatctacaa ttctacctcc cctatttgca ctacccgttg agacagtct       600
```

```
aataagagga tgttggtaac taaatacaaa tttagatcta ctttagatca ataagaaaac    660
atgagtgggt gatataaatc agtatattat ttcttaacaa catattgtaa gttagtttat    720
attgttatgc atcagcgcaa atgtggataa tgatttagaa aacggaaaag attcagtgta    780
taatgtaaat atgagtcctg agttagtata tattgtttta tacaatagca gaagtggata    840
attattttaa aaatagacta gatctaaatag ctattatatt atcaatagtg atgagatagt    900
cacagtacat ctaaggccct cttttgttag ggcttttttca aaggatgttt cgatagctcc    960
tttaaaaaat ttatcaaacg agggggctct tttactggct tctcggtgaa acagagagg   1020 agctgctcca agaaactacc gaagacgata gcccaaaaac tccctcataa aaataggagg   1080 aactacatttt ccgtccaaat gagagatcct tttcatagtc tcttcctgaa aaaagaatg   1140 aagttatttt atatgaggaa tcagaggtag agttgaagcg cgatggtgga gcacgacact   1200
ctcgtctact ccaagaatat caaagataca gtctcagaag accaaagggc tattgagact   1260
tttcaacaaa gggtaatatc gggaaacctc ctcggattcc attgcccagc tatctgtcac   1320
ttcatcaaaa ggacagtaga aaaggaaggt ggcacctaca aatgccatca ttgcgataaa   1380
ggaaaggcta tcgttcaaga tgcctctgcc gacagtggtc ccaaagatgg acccccaccc   1440
acgaggagca tcgtggaaaa agaagacgtt ccaaccacgt cttcaaagca gtggattga   1500 tgtgataaca tggtggagca cgacactctc gtctactcca agaatatcaa agatacagtc   1560
tcagaagacc aaagggctat tgagactttt caacaaaggg taatatcggg aaacctcctc   1620
ggattccatt gcccagctat ctgtcacttc atcaaaagga cagtagaaaa ggaaggtggc   1680
acctacaaat gccatcattg cgataaagga aaggctatcg ttcaagatgc ctctgccgac   1740
agtggtccca agatggaccc ccacccacg aggagcatcg tggaaaaaga agacgttcca   1800
accacgtctt caaagcaagt ggattgatgt gatatctcca ctgacgtaag ggatgacgca   1860
caatcccact atccttcgca agaccttcct ctatataagg aagttcattt catttggaga   1920
ggacacgctg aaatcaccag tctctctcta caaatctatc tcttggtact tagaggatct   1980
accatggcca ccgccgccgc cgcgtctacc gcgctcactg gcgccactac cgctgcgccc   2040
aaggcgaggc gccgggcgca cctcctggcc acccgccgcg ccctcgccgc gcccatcagg   2100
tgctcagcgg cgtcacccgc catgccgatg gctcccccgg ccaccccgct ccggccgtgg   2160
ggccccaccg atccccgcaa gggatccgac gccctgcccg ccaccttcga cgtgatcgtg   2220
catccagctc gcgaactccg cggcgagctt cgcgctcagc catccaagaa ctacaccact   2280
cgctacctcc tcgccgctgc cctcgctgag ggcgagaccc gcgtggtggg cgtggctacc   2340
tctgaggacg ccgaggccat gctccgctgc ctccgcgact ggggcgctgg cgtggagctt   2400
gtgggcgatg acgccgtgat ccgcggtttc ggcgctcgcc acaggccgg tgtgacccctc   2460 aacccaggca acgctggcgc agtggcccgc ttcctcatgg gcgtggccgc tctcacctct   2520
ggcaccactt tcgtgaccga ctaccccgac tccctcggca agcgccctca gggcgacctc   2580
cttgaggccc tcgaacgcct cggtgcctgg gtgtcctcca acgacggtcg cctcccgatc   2640
tccgtgtccg gccagtgcg cggtggcacc gtggaggtgt ccgccgagcg ctcctcccag   2700
tacgcctccg ccctcatgtt cctcggccct ctcctcccgg acggactcga actccgcctc   2760
accggcgaca tcaagtccca cgctccgctc cgccagacac tcgacaccct ctctgacttc   2820
ggcgtgcgcg ccactgcctc cgacgacctc gccgcatct ccatcccggg tggccagaag   2880
taccgcccag gccgcgtgct cgtgccgggc gactacccgg gctccgctgc catcctcacc   2940
```

```
gccgctgccc tcctcccagg cgaggtgcgc ctctctaacc tccgcgagca cgacctccag    3000
ggcgagaagg aggccgtgaa cgtgctccgc gagatgggcg ctgacatcgt gcgcgagggc    3060
gataccctca ccgtgcgcgg tggccgccct ctccacgccg tgactcgcga cggcgattcc    3120
ttcaccgacg ccgtgcaagc cctcaccgcc gctgctgcct cgccgagggg cgacaccacc    3180
tgggagaacg tggccactct ccgcctcaag gagtgcgacc gcatctctga cacccgcgct    3240
gagcttgagc gcctcggcct ccgcgcacgc gagaccgccg actctctctc cgtgactggc    3300
tctgctcacc tcgctggtgg catcaccgcc gacggccacg gcgaccaccg catgatcatg    3360
ctcctcaccc tcctcggcct ccgcgcagac gctccactcc gcatcaccgg cgcacaccac    3420
atccgcaagt cctaccctca gttcttcgct cacctcgaag ccctcggcgc tcgcttcgag    3480
tacgctgagg ccaccgccta ataggtcgag tttctccata ataatgtgtg agtagttccc    3540
agataaggga attagggttc ctatagggtt tcgctcatgt gttgagcata taagaaaccc    3600
ttagtatgta tttgtatttg taaaatactt ctatcaataa aatttctaat tcctaaaacc    3660
aaaatccagt actaaaatcc agatccccg  aattaattcg gcgttaattc agtacattaa    3720
aaacgtccgc aatgtgttat taagttgtct aagcgtcact aacttttagt tatgaccta    3780 acaactacaa taattagttc ggtggacatg cccagctaat cgtcccaaaa gtaaacttct    3840
tttttgaaaa ttttaacgta ctgtaagggt ttttgtacag tattttttatt tcagataaga    3900 gggacaagag aatttataga ttaaaaagag ggggaggatt tacaatgtct gatattctcg    3960
gctaacaaat cttttatcct gtcagtgttg gggagcaact cctttatgaa tatgcttttg    4020
catgagtgta ctattaatac atgacacact tctctcttat aaaatttctt cgttctttgt    4080
ccaagtcgac ttaagggcat gtacaaccta gacactacga ctatacagta ctctaagtat    4140
aagcacaaac taaaacagaa cataatacag tggtcatgtc taaaacatgt gtcttacaat    4200
attcattgta tcaatcagag cattcaataa attaaagtga ccaatcagct aatctcatgt    4260
ctcgaacata gagctaagac attatgtctt cgtcaagata catgtcttga gttttttac    4320 cttcaccccc tagacacaac ttaagacact cattatacat gacctaagtt tacaatctcc    4380
ttattctctc tcatctctct catccacctc tgcagttcgc atacttacaa ccctttatta    4440
tatttgttct aagctgtttt aactttgcta accaggcatt cttttactat aaatttaaat    4500
gcagattata tgtagataca taactagcta caagcaagcc cgtagtttgg gaaacgtgca    4560
tggtgaacat gtcaaggtta tttccaatcc atagtatata tatacttatt aatacttgcc    4620
gagaaaaaaa ctatatcttg agagagattt aaaacttgaa tcgtcctggt gactcacatc    4680
tcttactcta atataggcta gtatttaata ttctttagag gataaaaaat aatatgtgat    4740
accatatatt agtatagttg tatcttatat gatatgacac tttatttgat atgtgtccgt    4800
gctactatat attagtttag aaatgaaata gcgggcgaca aatattcgat aacgaagata    4860
gtaatataat ttgaataacc taaaaaaata ttaaaattcc agcgaaatcg tgtatatata    4920
tatatgtcga catgccagat attatctgaa tcgaactgtg ctggtacc              4968
```

<210> SEQ ID NO 60
<211> LENGTH: 5086
<212> TYPE: DNA
<213> ORGANISM: Artificial Sequence
<220> FEATURE:
<223> OTHER INFORMATION: TALEN-L (expression cassette) (35S promoter + CDS+35S terminator)

<400> SEQUENCE: 60

-continued

| | |
|---|---|
| aagcttatgg tggagcacga cactctcgtc tactccaaga atatcaaaga tacagtctca | 60 |
| gaagaccaaa gggctattga gacttttcaa caaagggtaa tatcgggaaa cctcctcgga | 120 |
| ttccattgcc cagctatctg tcacttcatc aaaaggacag tagaaaagga aggtggcacc | 180 |
| tacaaatgcc atcattgcga taaaggaaag gctatcgttc aagatgcctc tgccgacagt | 240 |
| ggtcccaaag atggaccccc acccacgagg agcatcgtgg aaaaagaaga cgttccaacc | 300 |
| acgtcttcaa agcaagtgga ttgatgtgat aacatggtgg agcacgacac tctcgtctac | 360 |
| tccaagaata tcaaagatac agtctcagaa gaccaaaggg ctattgagac ttttcaacaa | 420 |
| agggtaatat cgggaaacct cctcggattc cattgcccag ctatctgtca cttcatcaaa | 480 |
| aggacagtag aaaaggaagg tggcacctac aaatgccatc attgcgataa aggaaaggct | 540 |
| atcgttcaag atgcctctgc cgacagtggt cccaaagatg gaccccc acc cacgaggagc | 600 |
| atcgtggaaa aagaagacgt tccaaccacg tcttcaaagc aagtggattg atgtgatatc | 660 |
| tccactgacg taagggatga cgcacaatcc cactatcctt cgcaagacct tcctctatat | 720 |
| aaggaagttc atttcatttg gagaggacac gctgaaatca ccagtctctc tctacaaatc | 780 |
| tatctctatg gatcccattc gttcgcgcac gccaagtcct gcccgcgagc ttctgcccgg | 840 |
| accccaaccg datagggttc agccgactgc agatcggggg ggggctccgc ctgctggcgg | 900 |
| cccctggat ggcttgcccg ctcggcggac gatgtcccgg acccggctgc atctcccc | 960 |
| tgcgccctcg cctgcgttct cggcgggcag cttcagcgat ctgctccgtc agttcgatcc | 1020 |
| gtcgcttctt gatacatcgc ttcttgattc gatgcctgcc gtcggcacgc cgcatacagc | 1080 |
| ggctgcccca gcagagtggg atgaggtgca atcgggtctg cgtgcagccg atgacccgcc | 1140 |
| acccaccgtg cgtgtcgctg tcactgccgc gcggccgccg cgcgccaagc cggcccccgcg | 1200 |
| acggcgtgcg gcgcaacccct ccgacgcttc gccggccgcg caggtggatc tacgcacgct | 1260 |
| cggctacagt cagcagcagc aagagaagat caaaccgaag gtgcgttcga cagtggcgca | 1320 |
| gcaccacgag gcactggtgg gccatgggtt tacacacgcg cacatcgttg cgctcagcca | 1380 |
| acacccggca gcgttaggga ccgtcgctgt caagtatcag cacataatca cggcgttgcc | 1440 |
| agaggcgaca cacgaagaca tcgttggcgt cggcaaacag tggtccggcg cacgcgccct | 1500 |
| ggaggccttg ctcacgaagg cgggggagtt gagaggtccg ccgttacagt tggacacagg | 1560 |
| ccaacttctc aagattgcaa aacgtggcgg cgtgaccgca gtggaggcag tgcatgcatc | 1620 |
| gcgcaatgca ctgacgggtg ccccctgaa cctgaccccg gcacaggtgg tggccatcgc | 1680 |
| cagccacgat ggcggcaagc aggcgctgga cggtgcag cggctgttgc cggtgctgtg | 1740 |
| ccaggaccat ggcctgaccc cggaccaggt cgtggccatc gccagcaatg cggcggcaa | 1800 |
| gcaggccttg gagacggtgc agcggctgtt gccggtgctg tgccaggccc atggcctgac | 1860 |
| cccggaccag gtcgtggcca tcgccaacaa taacggcggc aagcaggctt tggagacggt | 1920 |
| acagcggctg ttgccggtgc tgtgccaggg ccatggcctg accccggccc aagtggtggc | 1980 |
| catcgccagc aatggcggcg gcaagcaggc tctggagacg gtacagcggc tgttgccggt | 2040 |
| gctgtgccag gaccatggcc tgaccccgga ccaggtcgtg gccatcgcca gcaatggcgg | 2100 |
| cggcaagcag gcattggaga cggtacagcg gctgttgccg gtgctgtgcc aggaccatgg | 2160 |
| cctgaccccg gaccaggtcg tggccatcgc cagcaatggc ggcggcaagc aggccctgga | 2220 |
| gacggtacag cggctgttgc cggtgctgtg ccaggaccat ggcctgaccc cggaccaggt | 2280 |
| ggtgccatc gccagcaata ttggcggcaa gcaggccttg gagacggtgc agcggctgtt | 2340 |
| gccggtgctg tgccaggccc atggcctgac cccgcccaa gtggtggcca tcgccagcaa | 2400 |

```
tggcggcggc aagcaggctc tggagacggt acagcggctg ttgccggtgc tgtgccagga   2460
ccatggcctg accccggacc aggtcgtggc catcgccagc aatattggcg gcaagcaggc   2520
gttggagacg gtacagcggc tgttgccggt gctgtgccag gaccatggcc tgacccagga   2580
ccaggtggtg gccatcgcca gccacgatgg cggcaagcag gcattggaga cggtacagcg   2640
gctgttgccg gtgctgtgcc aggaccatgg cctgaccccg gaccaggtgg tggccatcgc   2700
cagcaatatt ggcggcaagc aggccctgga gacggtacag cggctgttgc cggtgctgtg   2760
ccaggaccat ggcctgaccc ggaccaggt ggtggccatc gccagcaata ttggcggcaa   2820
gcaggctctg gagacggtac agcggctgtt gccggtgctg tgccaggacc atggcctgac   2880
cccggaccag gtcgtggcca tcgccaacaa taacggcggc aagcaggctt ggagacggt   2940
acagcggctg ttgccggtgc tgtgccaggg ccatggcctg accccggacc aggtggtggc   3000
catcgccagc aatattggcg gcaagcaggc cctggagacg gtacagcggc tgttgccggt   3060
gctgtgccag gaccatggcc tgaccccgga ccaggtcgtg gccatcgcca acaataacgg   3120
cggcaagcag gctttggaga cggtacagcg gctgttgccg gtgctgtgcc agggccatgg   3180
cctgacccag gaccaggtgg tggccatcgc cagccacgat ggcggcaagc aggcgttgga   3240
gacggtacag cggctgttgc cggtgctgtg ccaggaccat ggcctgaccc aggaccaggt   3300
ggtggccatc gccagccacg atggcggcaa gcaggcattg agacggtac agcggctgtt   3360
gccggtgctg tgccaggacc atggcctgac cccggaccag gtggtggcca tcgccagcca   3420
cgatggcggc aagcaggctt tggagacggt acagcggctg ttgccggtgc tgtgccagga   3480
ccatggcctg accccggacc aggtggtggc catcgccagc aatggcggcg gcaagcaggc   3540
actggagacg attgttgccc agttatctcg ccctgatccg gcgttggccg cgttgaccaa   3600
cgaccacctc gtcgccttgg cctgcctcgg cggacgtcct gccctggatg cagtgaaaaa   3660
gggattgccg cacgcgccgg aattgatcag aagaatcaat cgccgcattc ccgaacgcac   3720
gtcccatcgc gttcccgacc tcgcgcacgt ggttcgcgtg cttggttttt tccagagcca   3780
ctcccaccca gcgcaagcat tcgatgacgc catgacgcag ttcgagatga gcaggcacgg   3840
cttggtacag ctctttcgca gagtgggcgt caccgagttc gaagcccgct acggaacgct   3900
cccccagcc tcgcagcgtt gggaccgtat cctccaggca tcaggatga aagggccaa   3960
accgtccct acttcagctc aaacaccgga tcaggcgtct ttgcatgcag attcaagga   4020
cgacgacgac aagaaggatt acaaggacga cgacgacaag aagggtcgac ccagcccaat   4080
gcacgaggga atcagacag gggcaagcag ccgtaaacgg tcccgatcgg atcgtgctgt   4140
caccggcccc tccgcacagc aatctttcga ggtgcgcgtt cccgaacagc gcgatgcgct   4200
gcatttgccc ctcagctgga gggtaaaacg cccgcgtacc aggatcgggg gcggcctccc   4260
agatcctggt acgcccatcg ctgccgacct ggcagcgtcc agcaccgtga tcagatccca   4320
gctagtgaaa tctgaattgg aagagaagaa atctgaactt agacataaat tgaaatatgt   4380
gccacatgaa tatattgaat tgattgaaat cgcaagaaat tcaactcagg atagaatcct   4440
tgaaatgaag gtgatggagt tctttatgaa ggtttatggt tatcgtggta aacatttggg   4500
tggatcaagg aaaccagacg gagcaattta tactgtcgga tctcctattg attacggtgt   4560
gatcgttgat actaaggcat attcaggagg ttataatctt ccaattggtc aagcagatga   4620
aatgcaaaga tatgtcgaag agaatcaaac aagaaacaag catatcaacc ctaatgaatg   4680
gtggaaagtc tatccatctt cagtaacaga atttaagttc ttgtttgtga gtggtcattt   4740
```

```
caaaggaaac tacaaagctc agcttacaag attgaatcat atcactaatt gtaatggagc    4800
tgttcttagt gtagaagagc ttttgattgg tggagaaatg attaaagctg gtacattgac    4860
acttgaggaa gtgagaagga aatttaataa cggtgagata aactttttaac tcgagtttct    4920 ccataataat gtgtgagtag ttcccagata agggaattag ggttcctata gggtttcgct    4980
catgtgttga gcatataaga aacccttagt atgtatttgt atttgtaaaa tacttctatc    5040
aataaaattt ctaattccta aaaccaaaat ccagtactaa gaattc                   5086

<210> SEQ ID NO 61
<211> LENGTH: 5738
<212> TYPE: DNA
<213> ORGANISM: Artificial Sequence
<220> FEATURE:
<223> OTHER INFORMATION: TALEN-R (expression cassette) ( rice actin
      promoter + TALEN-R+35S terminator)

<400> SEQUENCE: 61
gaattcaggt cattcatatg cttgagaaga gtcgggatag tccaaaataa aacaaaggta      60
agattacctg gtcaaaagtg aaaacatcag ttaaaaggtg gtatgaagta aaatatcggt     120
aataaaaggt ggcccaaagt gaaatttact cttttctact attataaaaa ttgaggatgt     180
ttttgtcggt actttgatac gtcattttg tatgaattgg ttttttaagtt tattcgcttt     240 tgaaatgca tatctgtatt tgagtcgggt tttaagttcg tctgcttttg taaatacaga     300
gggatttgta taagaaatat cttttaaaaaa acccatatgc taatttgaca taattttttga    360 gaaaaaatata tattcaggcg cattctcaca atgaacaata ataagattaa aatagctttc     420
ccccgttgca gcgcatgggt atttttcta gtaaaaataa aagatagact tagactcaaa     480
acatttacaa aaacaacccc taagttcct aaagcccaaa gtgctatcca cgatccatag      540
caagcccagc ccaacccaac ccaacccaac ccaccccagt ccagccaact ggacaatagt     600
ctccacaccc ccccactatc accgtgagtt gttcgcacgc accgcacgtc tcgcagccaa     660
aaaaaaaaaa aagaaagaaa aaaagaaaa agaaaaaaca gcaggtgggt ccgggtcgtg     720
ggggccggaa acgcgaggag gatcgcgagc cagcgacgag gccggccctc cctccgcttc     780
caaagaaacg cccccccatcg ccactatata catacccccc cctctcctcc catccccca     840 accctaccac caccaccacc accacctcca cctcctcccc cctcgctgcc ggacgacgag     900
ctcctccccc ctccccctcc gccgccgcg cgccggtaac caccccgccc ctctcctctt     960
tctttctccg ttttttttt ccgtctcggt ctcgatcttt ggccttggta gtttgggtgg    1020
gcgagaggcg gcttcgtgcg cgcccagatc ggtgcgcggg aggggcggga tctcgcggct    1080
ggggctctcg ccggcgtgag tcggcccgaa tcctcgcggg gaatgggct ctcggatgta     1140 gatctgcgat ccgccgttgt tgggggagat gatgggggg ttaaaatttc cgccatgcta     1200
aacaagatca ggaagagggg aaaagggcac tatggtttat atttttatat atttctgctg    1260
cctcgtcagg cttagatctg ctagatcttt cttctcttctt tttgtgggta gaatttgaat     1320
ccctcagcat tgttcatcgg tagtttttct tttcatgatt tgtgacaaat gcagcctcgt     1380
gcggagcttt tttgtaggta gaagatggct gacgccgaat ggatccccatt cgttcgcgca    1440 cgccaagtcc tgcccgcgag cttctgcccg gaccccaacc ggatagggtt cagccgactg    1500
cagatcgggg gggggctccg cctgctggcg gcccctgga tggcttgccc gctcggcgga    1560
cgatgtcccg gacccggctg ccatctcccc ctgcgccctc gcctgcgttc tcggcgggca    1620
gcttcagcga tctgctccgt cagttcgatc cgtcgcttct tgatacatcg cttcttgatt    1680
```

```
cgatgcctgc cgtcggcacg ccgcatacag cggctgcccc agcagagtgg gatgaggtgc    1740
aatcgggtct gcgtgcagcc gatgacccgc cacccaccgt gcgtgtcgct gtcactgccg    1800
cgcggccgcc gcgcgccaag ccggccccgc gacggcgtgc ggcgcaaccc tccgacgctt    1860
cgccggccgc gcaggtggat ctacgcacgc tcggctacag tcagcagcag caagagaaga    1920
tcaaaccgaa ggtgcgttcg acagtggcgc agcaccacga ggcactggtg ggccatgggt    1980
ttacacacgc gcacatcgtt gcgctcagcc aacacccggc agcgttaggg accgtcgctg    2040
tcaagtatca gcacataatc acggcgttgc cagaggcgac acacgaagac atcgttggcg    2100
tcggcaaaca gtggtccggc gcacgcgccc tggaggcctt gctcacgaag gcggggagt     2160 tgagaggtcc gccgttacag ttggacacag gccaacttct caagattgca aaacgtggcg    2220
gcgtgaccgc agtggaggca gtgcatgcat cgcgcaatgc actgacgggt gcccccctga    2280
acctgacccc ggaccaggtc gtggccatcg ccagcaatgg cggcggcaag caggcgttgg    2340
agacggtaca gcggctgttg ccggtgctgt gccaggacca tggcctgacc ccggaccagg    2400
tggtggccat cgccaacaat aacggcggca agcaggcttt ggagacggta cagcggctgt    2460
tgccggtgct gtgccaggac catggcctga ccccggacca ggtcgtggcc atcgccagca    2520
atattggcgg caagcaggcc ctggagacgg tacagcggct gttgccggtg ctgtgccagg    2580
accatggcct gaccccggac caggtcgtgg ccatcgccag caatggcggc ggcaagcagg    2640
cactggagac tgtacagcgg ctgttgccgg tgctgtgcca ggaccatggc ctgaccccgg    2700
accaggtggt ggccatcgcc agccacgatg gcggcaagca ggcattggag acggtacagc    2760
ggctgttgcc ggtgctgtgc caggaccatg gcctgacccc ggaccaggtc gtggccaccg    2820
ccagcaatgg cggcggcaag caggcattgg agacggtaca gcggctgttg ccggtgctgt    2880
gccaggacca tggcctgacc ccggaccagg tcgtggccat cgccagcaat attggcggca    2940
agcaggccct ggagacggta cagcggctgt tgccggtgct gtgccaggac catggcctga    3000
ccccggacca ggtcgtggcc atcgccaaca ataacggcgg caagcaggca ctggaaacac    3060
tgcagcggct gttgccggtg ctgtgccagg accatggcct gaccccggac caggtcgtgg    3120
ccatcgccag caatggaggc ggcaagcagg ccttggagac ggtgcagcgg ctgttgccgg    3180
tgctgtgcca ggaccatggc ctgaccccgg accaggtcgt ggccatcgcc agcaatattg    3240
gcggcaagca ggcgttggag acggtacagc ggctgttgcc ggtgctgtgc caggaccatg    3300
gcctgacccc ggaccaggtg gtggccatcg ccaacaataa cggcggcaag caggcattgg    3360
agacggtaca gcggctgttg ccggtgctgt gccaggacca tggcctgacc ccggaccagg    3420
tcgtggccat cgccagcaat ggcggcggca agcaggcact ggagactgta cagcggctgt    3480
tgccggtgct gtgccaggac catggcctga ccccggacca ggtggtggcc atcgccagcc    3540
acgatggcgg caagcaggca ttggagacgg tacagcggct gttgccggtg ctgtgccagg    3600
accatggcct gaccccggac caggtggtgg ccatcgccag caatggcggc ggcaagcagg    3660
cgttggagac ggtacagcgg ctgttgccgg tgctgtgcca ggaccatggc ctgacccagg    3720
accaggtggt ggccatcgcc agccacgatg gcggcaagca ggctttggag acggtacagc    3780
ggctgttgcc ggtgctgtgc caggaccatg gcctgacccc ggaccaggtc gtggccatcg    3840
ccagccacga tggcggcaag caggccctgg agacggtaca gcggctgttg ccggtgctgt    3900
gccaggacca tggcctgacc ccggaccagg tcgtggccat cgccaacaat aacggcggca    3960
agcaggcctt ggagacggtg cagcggctgt tgccggtgct gtgccaggac catggcctga    4020
ccccggacca ggtcgtggcc atcgccagca atggtggcgg caagcaggca ctggagacga    4080
```

```
ttgttgccca gttatctcgc cctgatccgg cgttggccgc gttgaccaac gaccacctcg    4140
tcgccttggc ctgcctcggc ggacgtcctg ccctggatgc agtgaaaaag ggattgccgc    4200
acgcgccgga attgatcaga agaatcaatc gccgcattcc cgaacgcacg tcccatcgcg    4260
ttcccgacct cgcgcacgtg gttcgcgtgc ttggtttttt ccagagccac tcccacccag    4320
cgcaagcatt cgatgacgcc atgacgcagt tcgagatgag caggcacggc ttggtacagc    4380
tctttcgcag agtgggcgtc acccaattcg aagcccgcta cggaacgctc cccccagcct    4440
cgcagcgttg ggaccgtatc ctccaggcat cagggatgaa aagggccaaa ccgtcccccta   4500 cttcagctca aacaccggat caggcgtctt tgcatgcaga ttacaaggac gacgacgaca    4560
agaaggatta caaggacgac gacgacaaga agggtcgacc cagcccaatg cacgagggag    4620
atcagacgcg ggcaagcagc cgtaaacggt cccgatcgga tcgtgctgtc accggccccct  4680 ccacacagca atctttcgag gtgcgcgttc ccgaacagca agatgcgctg catttgcccc    4740
tcagctggag ggtaaaaacgc ccgcgtacca ggatcggggg cggcctcccg gatcctggta   4800
cgcccatcgc tgccgacctg gcagcgtcca gcaccgtgat gtgggaacaa gatgcggccc    4860
ccttcgcagg ggcagcggat gatttcccgg cattcaacga agaggagctc gcatggttga    4920
tggagctatt gcctcagtca ggctcagtcg gagggacgat ctctagacag ctagtgaaat    4980
ctgaattgga agagaagaaa tctgaactta gacataaatt gaaatatgtg ccacatgaat    5040
atattgaatt gattgaaatc gcaagaaatt caactcagga tagaatcctt gaaatgaagg    5100
tgatggagtt cttttatgaag gtttatggtt atcgtggtaa acatttgggt ggatcaagga    5160
aaccagacgg agcaatttat actgtcggat ctcctattga ttacggtgtg atcgttgata    5220
ctaaggcata ttcaggaggt tataatcttc caattggtca agcagatgaa atgcaaagat    5280
atgtcgaaga gaatcaaaca agaaacaagc atatcaaccc taatgaatgg tggaaagtct    5340
atccatcttc agtaacagaa tttaagttct tgtttgtgag tggtcatttc aaaggaaact    5400
acaaagctca gcttacaaga ttgaatcata tcactaattg taatggagct gttcttagtg    5460
tagaagagct tttgattggt ggagaaatga ttaaagctgg tacattgaca cttgaggaag    5520
tgagaaggaa atttaataac ggcgagataa acttttaata actcgagttt ctccataata    5580
atgtgtgagt agttcccaga taagggaatt agggttccta tagggtttcg ctcatgtgtt    5640
gagcatataa gaaacccctta gtatgtatttt gtatttgtaa aatacttcta tcaataaaat   5700
ttctaattcc taaaaccaaa atccagtact aaggtacc                             5738
```

<210> SEQ ID NO 62
<211> LENGTH: 147
<212> TYPE: PRT
<213> ORGANISM: Oryza sativa
<220> FEATURE:
<223> OTHER INFORMATION: Rice TEL functional motif

<400> SEQUENCE: 62

Asp Thr Arg Thr Thr Val Met Ile Arg Asn Ile Pro Asn Lys Tyr Ser
 1               5                  10                  15

Gln Lys Leu Leu Leu Asn Met Leu Asp Asn His Cys Ile Leu Ser Asn
            20                  25                  30

Gln Gln Ile Glu Ala Ser Cys Glu Asp Glu Ala Gln Pro Phe Ser Ser
        35                  40                  45

Tyr Asp Phe Leu Tyr Leu Pro Ile Asp Phe Asn Asn Lys Cys Asn Val
    50                  55                  60

```
Gly Tyr Gly Phe Val Asn Leu Thr Ser Pro Glu Ala Ala Val Arg Leu
 65                  70                  75                  80

Tyr Lys Ala Phe His Lys Gln Pro Trp Glu Val Phe Asn Ser Arg Lys
                 85                  90                  95

Ile Cys Gln Val Thr Tyr Ala Arg Val Gln Gly Leu Asp Ala Leu Lys
            100                 105                 110

Glu His Phe Lys Asn Ser Lys Phe Pro Cys Asp Ser Asp Glu Tyr Leu
        115                 120                 125

Pro Val Val Phe Ser Pro Pro Arg Asp Gly Lys Leu Leu Thr Glu Pro
    130                 135                 140

Val Pro Leu
145

<210> SEQ ID NO 63
<211> LENGTH: 4
<212> TYPE: PRT
<213> ORGANISM: Artficial

<400> SEQUENCE: 63

Asn His Cys Ile
 1

<210> SEQ ID NO 64
<211> LENGTH: 12
<212> TYPE: PRT
<213> ORGANISM: Artificial Sequence
<220> FEATURE:
<223> OTHER INFORMATION: Synthetic (consensus)
<220> FEATURE:
<221> NAME/KEY: VARIANT
<222> LOCATION: (0)...(0)
<223> OTHER INFORMATION: Xaa at position 1 can be Lys or Arg
<220> FEATURE:
<221> NAME/KEY: VARIANT
<222> LOCATION: (0)...(0)
<223> OTHER INFORMATION: Xaa at position 3 can be Pro or Ala
<220> FEATURE:
<221> NAME/KEY: VARIANT
<222> LOCATION: (0)...(0)
<223> OTHER INFORMATION: Xaa at position 5 can be Asp or Glu
<220> FEATURE:
<221> NAME/KEY: VARIANT
<222> LOCATION: (0)...(0)
<223> OTHER INFORMATION: Xaa at position 6 can be any residue
<220> FEATURE:
<221> NAME/KEY: VARIANT
<222> LOCATION: (0)...(0)
<223> OTHER INFORMATION: Xaa at position 7 can be Asp or Glu
<220> FEATURE:
<221> NAME/KEY: VARIANT
<222> LOCATION: (0)...(0)
<223> OTHER INFORMATION: Xaa at position 8 can be any residue
<220> FEATURE:
<221> NAME/KEY: VARIANT
<222> LOCATION: (0)...(0)
<223> OTHER INFORMATION: Xaa at position 12 can be Leu or Val

<400> SEQUENCE: 64

Xaa Phe Xaa Cys Xaa Xaa Xaa Xaa Tyr Leu Pro Xaa
 1               5                  10

<210> SEQ ID NO 65
<211> LENGTH: 38
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
```

```
<222> LOCATION: (1)...(38)
<223> OTHER INFORMATION: pOsTEL-F

<400> SEQUENCE: 65
aagcttgaaa ctagtactag acattactct tccaatgc                              38

<210> SEQ ID NO 66
<211> LENGTH: 32
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(32)
<223> OTHER INFORMATION: pOsTEL-R

<400> SEQUENCE: 66
ggatccactt acctacccta ccaagaacac cc                                    32

<210> SEQ ID NO 67
<211> LENGTH: 31
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(31)
<223> OTHER INFORMATION: pOsTEL-MF

<400> SEQUENCE: 67
atcgctatag agcatccgag caaaaaacag g                                     31

<210> SEQ ID NO 68
<211> LENGTH: 31
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(31)
<223> OTHER INFORMATION: pOsTEL-MR

<400> SEQUENCE: 68
cctgtttttt gctcggatgc tctatagcga t                                     31

<210> SEQ ID NO 69
<211> LENGTH: 32
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(32)
<223> OTHER INFORMATION: OsTELCod-F

<400> SEQUENCE: 69
caggatccaa caatggagga aggaggtggg ag                                    32

<210> SEQ ID NO 70
<211> LENGTH: 37
<212> TYPE: DNA
<213> ORGANISM: Artificial Sequence
<220> FEATURE:
<223> OTHER INFORMATION: Synthetic sequence
<220> FEATURE:
```

<221> NAME/KEY: misc_feature
<222> LOCATION: (1)..(37)
<223> OTHER INFORMATION: OsTELter-R

<400> SEQUENCE: 70
caggtaccac ctcatccttc aaccataaag aaatgct                              37

<210> SEQ ID NO 71
<211> LENGTH: 34
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(34)
<223> OTHER INFORMATION: ZmTE-A-F

<400> SEQUENCE: 71
ggaagcttgg cgcttttct gagtgccaat cact                                  34

<210> SEQ ID NO 72
<211> LENGTH: 30
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(30)
<223> OTHER INFORMATION: ZmTE-A-R

<400> SEQUENCE: 72
caggctggga agcttgtgtg tgttcttgca                                       30

<210> SEQ ID NO 73
<211> LENGTH: 30
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(30)
<223> OTHER INFORMATION: ZmTE-B-F

<400> SEQUENCE: 73
tgcaagaaca cacacaagct tcccagcctg                                       30

<210> SEQ ID NO 74
<211> LENGTH: 32
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(32)
<223> OTHER INFORMATION: ZmTE-B-R

<400> SEQUENCE: 74
gtgaaaagca tggccgaagt cactactgcc tc                                   32

<210> SEQ ID NO 75
<211> LENGTH: 30
<212> TYPE: DNA
<213> ORGANISM: Artificial Sequence
<220> FEATURE:
<223> OTHER INFORMATION: Synthetic sequence

```
<220> FEATURE:
<221> NAME/KEY: misc_feature
<222> LOCATION: (1)...(30)
<223> OTHER INFORMATION: ZmTE-C-F

<400> SEQUENCE: 75
cttcggccat gcttttcaca gatccgtagc                               30

<210> SEQ ID NO 76
<211> LENGTH: 36
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(36)
<223> OTHER INFORMATION: ZmTE-C-R

<400> SEQUENCE: 76
gtggtaccga ggtttgaatt accccctat ttaaga                         36

<210> SEQ ID NO 77
<211> LENGTH: 37
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(37)
<223> OTHER INFORMATION: GhTEL1-F

<400> SEQUENCE: 77
ctgcaggaca ttagagttag gaccttatgg aacatga                       37

<210> SEQ ID NO 78
<211> LENGTH: 34
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(34)
<223> OTHER INFORMATION: GhTEL1-R

<400> SEQUENCE: 78
ggtaccacga gctaatctct atctgttaac caga                          34

<210> SEQ ID NO 79
<211> LENGTH: 27
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(27)
<223> OTHER INFORMATION: GhTEL2-F

<400> SEQUENCE: 79
aagcttctaa gcacaaattt gacttag                                  27

<210> SEQ ID NO 80
<211> LENGTH: 34
<212> TYPE: DNA
<213> ORGANISM: Artificial Sequence
<220> FEATURE:
```

```
<223> OTHER INFORMATION: Synthetic sequence
<220> FEATURE:
<221> NAME/KEY: misc_feature
<222> LOCATION: (1)...(34)
<223> OTHER INFORMATION: GhTEL2-R

<400> SEQUENCE: 80
ggtacctcac caactagttg aattaatggt gaca                                      34

<210> SEQ ID NO 81
<211> LENGTH: 35
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(35)
<223> OTHER INFORMATION: AtTEL1-F

<400> SEQUENCE: 81
ggggtacccc cgaaaagaat catacttgta gaaca                                    35

<210> SEQ ID NO 82
<211> LENGTH: 41
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(41)
<223> OTHER INFORMATION: AtTEL1-R

<400> SEQUENCE: 82
ggggtaccat aagattaaag ttgtagtcaa ccatcactat c                              41

<210> SEQ ID NO 83
<211> LENGTH: 38
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(38)
<223> OTHER INFORMATION: AtTEL2-F

<400> SEQUENCE: 83
ggaagcttgg tcgagacatg gtactgagta aaaccta                                  38

<210> SEQ ID NO 84
<211> LENGTH: 38
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(38)
<223> OTHER INFORMATION: AtTEL2-R

<400> SEQUENCE: 84
ggaagcttaa cctgaacaag caaaaaaaca ctcacatc                                 38

<210> SEQ ID NO 85
<211> LENGTH: 27
<212> TYPE: DNA
<213> ORGANISM: Artificial Sequence
```

-continued

```
<220> FEATURE:
<223> OTHER INFORMATION: Synthetic sequence
<220> FEATURE:
<221> NAME/KEY: misc_feature
<222> LOCATION: (1)...(27)
<223> OTHER INFORMATION: BrTEL-F

<400> SEQUENCE: 85
aagcttgaac gattaggctg ttgtagg                                          27

<210> SEQ ID NO 86
<211> LENGTH: 28
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(28)
<223> OTHER INFORMATION: BrTEL-MR

<400> SEQUENCE: 86
ggatccgatg gagatagtcc gtacgacg                                         28

<210> SEQ ID NO 87
<211> LENGTH: 33
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(33)
<223> OTHER INFORMATION: BrTEL-MF

<400> SEQUENCE: 87
ggatccaaga atgttcacgt tctttaatat ccc                                   33

<210> SEQ ID NO 88
<211> LENGTH: 33
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(33)
<223> OTHER INFORMATION: BrTEL-R

<400> SEQUENCE: 88
ggtacctaaa tgaatttgtg ttgttggatt tgg                                   33

<210> SEQ ID NO 89
<211> LENGTH: 33
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(33)
<223> OTHER INFORMATION: TaTEL-F

<400> SEQUENCE: 89
aagcttgtgc agtgagttgg agagcaactt tgc                                   33

<210> SEQ ID NO 90
<211> LENGTH: 28
<212> TYPE: DNA
```

```
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(28)
<223> OTHER INFORMATION: TaTEL-MR

<400> SEQUENCE: 90
gaggtcaaag aagtgcactg tggccacg                                      28

<210> SEQ ID NO 91
<211> LENGTH: 28
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(28)
<223> OTHER INFORMATION: TaTEL-MF

<400> SEQUENCE: 91
cgtggccaca gtgcacttct ttgacctc                                      28

<210> SEQ ID NO 92
<211> LENGTH: 37
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(37)
<223> OTHER INFORMATION: TaTEL-R

<400> SEQUENCE: 92
ggtacccatc acccgcatga tatattttca tactacg                            37

<210> SEQ ID NO 93
<211> LENGTH: 34
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(34)
<223> OTHER INFORMATION: GmTEL1-F

<400> SEQUENCE: 93
gtcgacttaa caccaaaaca aacatgcagt atct                               34

<210> SEQ ID NO 94
<211> LENGTH: 36
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(36)
<223> OTHER INFORMATION: GmTEL1-R

<400> SEQUENCE: 94
gtcgaccatg tttattacct aaatctccta catcga                             36

<210> SEQ ID NO 95
<211> LENGTH: 34
```

```
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(34)
<223> OTHER INFORMATION: GmTEL2-F

<400> SEQUENCE: 95
aagcttggaa atggaaatct aagggataaa gcag                                    34

<210> SEQ ID NO 96
<211> LENGTH: 38
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(38)
<223> OTHER INFORMATION: GmTEL2-R

<400> SEQUENCE: 96
gtcgacgtga gaatcataat acagctagga tttctcta                                38

<210> SEQ ID NO 97
<211> LENGTH: 30
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(30)
<223> OTHER INFORMATION: OsTEL-f

<400> SEQUENCE: 97
ggatccatgg aggaaggagg tgggagtggc                                         30

<210> SEQ ID NO 98
<211> LENGTH: 34
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (10)...(34)
<223> OTHER INFORMATION: OsTEL-r

<400> SEQUENCE: 98
ctcgagctag tcagtgtagc ctaggcgctg tagc                                    34
```